(12) United States Patent
Brodney et al.

(10) Patent No.: US 10,112,958 B2
(45) Date of Patent: *Oct. 30, 2018

(54) N-[2-(2-AMINO-6,6-DISUBSTITUTED-4,4A,5,6-TETRAHYDROPYRANO[3,4-D][1,3]THIAZIN-8A(8H)-YL)-1,3-THIAZOL-4-YL] AMIDES

(71) Applicant: Pfizer Inc., New York, NY (US)

(72) Inventors: Michael Aaron Brodney, Newton, MA (US); Christopher Ryan Butler, Canton, MA (US); Lei Zhang, Auburndale, MA (US); Brian Thomas O'Neill, Haddam, CT (US); Patrick Robert Verhoest, Newton, MA (US); Peter Justin Mikochik, Pawcatuck, CT (US); John Charles Murray, East Lyme, CT (US); Xinjun Hou, Winchester, MA (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/646,572

(22) Filed: Jul. 11, 2017

(65) Prior Publication Data

US 2017/0305931 A1  Oct. 26, 2017

Related U.S. Application Data

(63) Continuation of application No. 15/272,501, filed on Sep. 22, 2016, now Pat. No. 9,751,895.

(60) Provisional application No. 62/232,037, filed on Sep. 24, 2015.

(51) Int. Cl.
| | | |
|---|---|---|
| C07D 513/04 | (2006.01) | |
| C07D 513/10 | (2006.01) | |
| C07D 513/20 | (2006.01) | |

(52) U.S. Cl.
CPC ......... *C07D 513/04* (2013.01); *C07D 513/10* (2013.01); *C07D 513/20* (2013.01)

(58) Field of Classification Search
CPC .................................................. C07D 513/04
USPC .......................................... 544/8; 514/224.2
See application file for complete search history.

(56) References Cited

U.S. PATENT DOCUMENTS

| | | | |
|---|---|---|---|
| 5,750,349 A | 5/1998 | Suzuki et al. | |
| 7,115,600 B2 | 10/2006 | Wager et al. | |
| 7,285,293 B2 | 10/2007 | Castillo et al. | |
| 7,975,664 B2 | 7/2011 | Himsel et al. | |
| 8,158,620 B2 | 4/2012 | Suzuki et al. | |
| 8,198,269 B2 | 6/2012 | Motoki et al. | |
| 8,278,441 B2 | 10/2012 | Mergott et al. | |
| 8,729,071 B2 | 5/2014 | Scott et al. | |
| 8,822,456 B2 | 9/2014 | Brodney et al. | |
| 8,865,706 B2 | 10/2014 | Brodney et al. | |
| 8,933,221 B2 | 1/2015 | Brodney et al. | |
| 8,962,616 B2 | 2/2015 | Brodney et al. | |
| 9,045,498 B2 | 6/2015 | Brodney et al. | |
| 9,045,499 B2 | 6/2015 | Brodney et al. | |
| 9,192,612 B2 | 11/2015 | Brodney et al. | |
| 9,198,917 B2 | 12/2015 | Brodney et al. | |
| 9,233,981 B1 | 1/2016 | Brodney et al. | |
| 9,260,455 B2 | 2/2016 | Brodney et al. | |
| 9,315,520 B2 * | 4/2016 | Brodney | C07D 513/04 |
| 9,403,846 B2 | 8/2016 | Brodney et al. | |
| 9,428,523 B2 * | 8/2016 | Brodney | C07D 519/00 |
| 9,605,007 B2 | 3/2017 | Brodney et al. | |
| 9,611,264 B1 | 4/2017 | Brodney et al. | |
| 9,751,895 B2 * | 9/2017 | Brodney | C07D 513/04 |
| 2003/0073655 A1 | 4/2003 | Shain | |
| 2003/0195205 A1 | 10/2003 | DeNinno et al. | |
| 2004/0192898 A1 | 9/2004 | Jia et al. | |
| 2004/0220186 A1 | 11/2004 | Bell et al. | |

(Continued)

FOREIGN PATENT DOCUMENTS

| | | |
|---|---|---|
| EP | 0994728 | 10/1998 |
| EP | 1257584 | 10/2004 |

(Continued)

OTHER PUBLICATIONS

Alberti, K.G. et al., "The Metabolic Syndrome—A New Worldwide Definition," Lancet, Sep. 24-30, 2005, pp. 1059-1062, 366(9491).

(Continued)

*Primary Examiner* — Kahsay Habte
(74) *Attorney, Agent, or Firm* — Lisa A. Samuels

(57) ABSTRACT

The present invention is directed to compounds, tautomers and pharmaceutically acceptable salts of the compounds which are disclosed, wherein the compounds have the structure of Formula I,

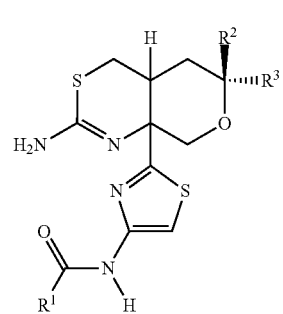

and the variables $R^1$, $R^2$ and $R^3$ are as defined in the specification. Corresponding pharmaceutical compositions, methods of treatment, methods of synthesis, and intermediates are also disclosed.

28 Claims, No Drawings

(56) References Cited

U.S. PATENT DOCUMENTS

| | | |
|---|---|---|
| 2005/0019328 A1 | 1/2005 | Schenk et al. |
| 2005/0043354 A1 | 2/2005 | Wager et al. |
| 2005/0048049 A1 | 3/2005 | Schenk et al. |
| 2005/0256135 A1 | 11/2005 | Lunn et al. |
| 2005/0267009 A1 | 12/2005 | Deagle |
| 2005/0267095 A1 | 12/2005 | Bernardelli et al. |
| 2005/0267100 A1 | 12/2005 | Elliott et al. |
| 2006/0057701 A1 | 3/2006 | Rosenthal et al. |
| 2006/0106035 A1 | 5/2006 | Hendrix et al. |
| 2006/0111372 A1 | 5/2006 | Hendrix et al. |
| 2006/0178501 A1 | 8/2006 | Summers et al. |
| 2007/0031416 A1 | 2/2007 | Shoji et al. |
| 2007/0160616 A1 | 7/2007 | Rosenthal et al. |
| 2007/0179175 A1 | 8/2007 | Lunn |
| 2008/0096955 A1 | 4/2008 | Wager et al. |
| 2008/0176925 A1 | 7/2008 | Butler et al. |
| 2009/0054482 A1 | 2/2009 | Chan et al. |
| 2010/0056618 A1 | 3/2010 | Mascitti et al. |
| 2010/0093999 A1 | 4/2010 | Motoki et al. |
| 2010/0285145 A1 | 11/2010 | Darout et al. |
| 2011/0009395 A1 | 1/2011 | Edmund et al. |
| 2011/0027279 A1 | 2/2011 | Chain |
| 2011/0038861 A1 | 2/2011 | Rosenthal |
| 2011/0046122 A1 | 2/2011 | Andreini et al. |
| 2011/0207723 A1 | 8/2011 | Motoki et al. |
| 2012/0245155 A1 | 9/2012 | Yoshida et al. |
| 2013/0053373 A1 | 2/2013 | Brodney et al. |
| 2013/0296308 A1 | 11/2013 | Brodney et al. |
| 2014/0128382 A1 | 5/2014 | Wu et al. |
| 2014/0163015 A1 | 6/2014 | Brodney et al. |
| 2014/0228356 A1 | 8/2014 | Brodney et al. |
| 2014/0323474 A1 | 10/2014 | Brodney et al. |
| 2014/0364426 A1 | 12/2014 | Brodney et al. |
| 2015/0087637 A1 | 3/2015 | Brodney et al. |
| 2015/0133438 A1 | 5/2015 | Brodney et al. |
| 2015/0224110 A1 | 8/2015 | Brodney et al. |
| 2015/0231144 A1 | 8/2015 | Brodney et al. |
| 2015/0239908 A1 | 8/2015 | Brodney et al. |
| 2015/0291621 A1 | 10/2015 | Brodney et al. |
| 2015/0376207 A1 | 12/2015 | Brodney et al. |
| 2016/0002264 A1 | 1/2016 | Brodney et al. |
| 2016/0152637 A1 | 6/2016 | Brodney et al. |
| 2017/0088558 A1 | 3/2017 | Brodney et al. |
| 2017/0151252 A1 | 6/2017 | Brodney et al. |

FOREIGN PATENT DOCUMENTS

| | | |
|---|---|---|
| EP | 2332943 | 6/2011 |
| EP | 2511269 | 10/2012 |
| WO | 1998044955 | 10/1998 |
| WO | 2002020521 | 3/2002 |
| WO | 2003072197 | 9/2003 |
| WO | 2004032868 | 4/2004 |
| WO | 2005025616 | 3/2005 |
| WO | 2005049616 | 11/2005 |
| WO | 2005116014 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007122466 | 11/2007 |
| WO | 2007122482 | 11/2007 |
| WO | 2007138431 | 12/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011009898 | 1/2011 |
| WO | 2011044181 | 4/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |
| WO | 2014045162 | 3/2014 |
| WO | 2014091352 | 6/2014 |
| WO | 2014097038 | 6/2014 |
| WO | 2014125394 | 8/2014 |
| WO | 2014125397 | 8/2014 |
| WO | 2015155626 | 10/2015 |
| WO | 2017051276 | 3/2017 |
| WO | 2017051294 | 3/2017 |
| WO | 2017051303 | 3/2017 |

OTHER PUBLICATIONS

Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).

Chao, Edward, et al., "SGLT2 Inhibition—A Novel Strategy for Diabetes Treatment", Nature Reviews Drug Discovery, Jul. 2010, pp. 551-559, 9(7).

Demong, D.E. et al., "Chapter 8, Glucagon Receptor Antagonists for Type II Diabetes", Annual Reports in Medicinal Chemistry 2008, pp. 119-137, vol. 43.

Denmark, S.E., et al., "Allylation of Carbonyls: Methodology and Stereochemistry", Modern Carbonyl Chemistry, 2000, Chapter 10, pp. 299-401.

England, et al., "An Improved Synthesis of a Novel α1A Partial Agonist Including a New Two-Step Synthesis of 4-Fluoropyrazole", Tetrahedron Letters, May 26, 2010, pp. 2849-2851, 51(21).

English equivalent U.S. Pat. No. 8,158,620; Suzuki, et al., filed Jan. 16, 2009 for WO 2009091016, published Jun. 23, 2007.

Esterhazy, Daria, et al., "BACE2 Is a β Cell-Enriched Protease that Regulates Pancreatic β Cell Function and Mass", Cell Metabolism, Sep. 2011, pp. 365-377, 14(3).

Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).

Finnin, Barrie, et al., "Transdermal Penetration Enhancers Applications, Limitations, and Potential", Journal Pharmaceutical Sciences, Oct. 1999, pp. 955-958, 88(10).

Flack, H.D., "On Enantiomorph-Polarity Estimation", Acta Cryst., 1983, pp. 876-881, vol. A39.

Glenner, G., et al., "Amyloidosis of the Nervous System", Journal of Neurological Science, 1989, pp. 1-28, vol. 94.

Guidance for Industry, Q3C-Tables and List, U.S. Department of Health and Human Services, Food and Drug Administration, Center for Drug Evaluation and Research (CDER), Center for Biologics Evaluation and Research (CBER), Nov. 2003, ICH, Revision I.

Haan, J., et al., "Amyloid in Central Nervous System Disease", Clinical Neurology and Neurosurgery, 1990, pp. 305-310, 92(4).

Haleblian, John K., "Characterization of Habits and Crystalline Modification of Solids and Their Pharmaceutical Applications", Journal Pharmaceutical Sciences, Aug. 1975, pp. 1269-1288, 64(8).

Hooft, Rob, et al., "Determination of Absolute Structure Using Bayesian Statistics on Bijvoet differences", Journal of Applied Crystallography, Feb. 2008, , pp. 96-103, 41(1).

(56) References Cited

OTHER PUBLICATIONS

International Application No. PCT/IB2012/054198, filed Aug. 17, 2012, International Search Report and Written Opinion, dated Jan. 23, 2013, 14 pages.
International Application No. PCT/IB2013/053178, filed Apr. 22, 2013, International Search Report & Written Opinion, dated Jul. 3, 2013, 10 pages.
International Application No. PCT/IB2013/058402, filed Sep. 9, 2013, International Search Report, dated Dec. 16, 2013, 11 pages.
International Application No. PCT/IB2013/060456, filed Nov. 27, 2013, International Preliminary Report on Patentability, dated Jun. 16, 2015, 5 pages.
International Application No. PCT/IB2013/060456, filed Nov. 27, 2013, International Search Report, dated Feb. 21, 2014, 8 pages.
International Application No. PCT/IB2013/060633, filed Dec. 4, 2013, International Preliminary Report on Patentability, dated Jun. 23, 2015.
International Application No. PCT/IB2013/060633, filed Dec. 4, 2013, International Search Report and Written Opinion, dated Mar. 24, 2014.
International Application No. PCT/IB2014/0558760 filed Feb. 3, 2014, International Preliminary Report on Patentability and Written Opinion dated Aug. 18, 2015, 7 pages.
International Application No. PCT/IB2014/0558760 filed Feb. 3, 2014, International Search Report and Written Opinion, dated Mar. 13, 2015, 10 pages.
International Application No. PCT/IB2014/0558777 filed Feb. 4, 2014, International Preliminary Report on Patentability, dated Aug. 18, 2015, 7 pages.
International Application No. PCT/IB2015/052279, filed Mar. 27, 2015, International Search Report and Written Opinion, dated Jun. 24, 2015, 10 pages.
International Patent Application No. PCT/IB2014/058777, filed Feb. 4, 2014, International Search Report and Written Opinion, dated Mar. 25, 2014, 11 pages.
Jones, R.M. et al., "Chapter 7, The Emergence of GPR119 Agonists as Anti-Diabetic Agents", Annual Reports in Medicinal Chemistry 2009, pp. 149-170, vol. 44.
Kharitonenkov, A. et al., "FGF21: A Novel Prospect for the Treatment of Metabolic Diseases", Current Opinion in Investigational Drugs, Apr. 2009, pp. 359-364, 10(4).
Macrae, Clare, et al., "Mercury: Visualization and Analysis of Crystal Structures", Journal of Applied Crystallography, Jun. 2006, pp. 453-457, 39(3).

Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).
Medina, J.C., et al., "Chapter 5, GPR40 (FFAR1) Modulators", Annual Reports in Medicinal Chemistry 2008, pp. 75-85, vol. 43.
Miyaura, N., et al., "Palladium-Catalyzed Cross-Coupling Reactions of Organobom Compounds", Chemical Review, Nov. 1995, pp. 2457-2483, 95(7).
Olson, R., et al., "Secretase Inhibitors and Modulators for the Treatment of Alzheimer's Disease", Annual Reports in Medicinal Chemistry, 2007, pp. 27-47, vol. 42.
Sheppeck, J.E. II, et al., "A Convenient and Scaleable Procedure for Removing the Fmoc Group in Solution", Tetrahedron Letters, 2000, pp. 5329-5333, vol. 41(28).
Spek, A.L., "Single-Crystal Structure Validation with the Program Platon", Journal of Applied Crystallography, Feb. 2003, pp. 7-13, 36(1).
Suzuki, Akira, "Recent advances in the cross-coupling reactions of organoboron derivatives with organic electrophiles 1995-1998", Journal Organometallic Chemistry, 1999, pp. 147-168, vol. 576.
Zhang, S. et al., "PTP1B as a Drug Target: Recent Developments in PTP1B Inhibitor Discovery", Drug Discovery Today, May 2007, pp. 373-381, 12(9/10).
Zhong, M., "TGR5 as a Therapeutic Target for Treating Obesity", Current Topics in Medicinal Chemistry, 2010, pp. 386-396, 10(4).
Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).
International Application No. PCT/IB2016/055399, filed Sep. 9, 2016, International Search Report and Written Opinion, dated Nov. 2, 2016, 14 pages.
International Application No. PCT/IB2016/055536, filed Sep. 19, 2016, International Search Report and Written Opinion, dated Oct. 25, 2016, 10 pages.
International Application No. PCT/IB2016/055580, filed Sep. 19, 2016, International Search Report and Written Opinion, dated Oct. 24, 2016, 12 pages.
Shimshek, Derya R., et al., "Pharmacological BACE1 and BACE2 inhibition induces hair depigmentation by inhibiting PMEL17 processing in mice", Scientific Reports, [6:21917] Feb. 25, 2016, pp. 1-13.

* cited by examiner

N-[2-(2-AMINO-6,6-DISUBSTITUTED-4,4A,5,6-TETRAHYDROPYRANO[3,4-D][1,3]THIAZIN-8A(8H)-YL)-1,3-THIAZOL-4-YL] AMIDES

This application is a continuation application under 35 U.S.C. § 120 of U.S. patent application Ser. No. 15/272,501, filed Sep. 22, 2016, which claims the benefit under 35 U.S.C. 119(e) of U.S. Provisional Patent Application No. 62/232,037, filed on Sep. 24, 2015, the disclosure of which is hereby incorporated by reference in its entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A-beta peptides that can contribute to the formation of neurological deposits of amyloid protein. The present invention also relates to the treatment of Alzheimer's disease (AD) and other neurodegenerative and/or neurological disorders, as well as the treatment of diabetes in mammals, including humans. More particularly, this invention relates to thioamidine compounds and pharmaceutically acceptable salts thereof useful for the treatment of neurodegenerative and/or neurological disorders, such as AD and Down's syndrome, related to A-beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4):305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's disease (AD), which is the most common cause of cognitive decline in the elderly (Hardy & Allsop, Trends Pharmacol. Sci., 1991; 12(10):383-8; Selkoe, Behav. Brain Res., 2008; 192 (1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 diabetes (de la Monte, J. Diabetes Sci. Technol., 2008; 2(6):1101-1113). Of special interest is the fact that AD and Type 2 diabetes share common pathogenic mechanisms and possibly treatments (Park S. A., J. Clin. Neurol., 2011; 7:10-18; Raffa, Br. J. Clin. Pharmacol 2011, 71(3):365-376). Elevated plasma levels of Aβ, the product of BACE activities, were recently associated with hyperglycemia and obesity in humans (see Meakin et al., Biochem J., 2012, 441(1):285-96; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme. Fused heterocyclic derivatives useful as inhibitors of the β-secretase enzyme are described in WO 2011071109 and corresponding US 2012245155. Co-pending PCT application, PCT/IB2012/054198, filed by Pfizer Inc on Aug. 17, 2012, also describes aminodihydrothiazine compounds that are useful inhibitors of the β-secretase enzyme. The present invention is directed to novel thioamidine compounds and their use in the treatment of neurodegenerative diseases, including AD, as well as the treatment of metabolic diseases and conditions such as diabetes and obesity.

SUMMARY OF THE INVENTION

A first embodiment of a first aspect of the present invention is a compound of Formula I

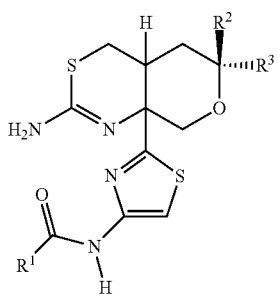

wherein $R^1$ is selected from the group consisting of: $C_{1-6}$alkyl optionally substituted with one to three fluoro or with $C_{1-3}$alkoxy; $C_{5-9}$bicycloalkyl optionally substituted with one to three $R^4$; and a 5- to 6-membered heteroaryl, having one to four heteroatoms independently selected from N, O or S, wherein at least one of the heteroatoms is N and wherein said N is optionally substituted with $R^5$; and wherein said 5- to 6-membered heteroaryl is optionally substituted on carbon with one to three $R^4$; $R^2$ and $R^3$ are each independently selected from $C_{1-6}$alkyl or $C_{3-7}$cycloalkyl; wherein the $C_{1-6}$alkyl is optionally substituted with one to three fluoro or $C_{1-3}$alkoxy; or $R^2$ and $R^3$ taken together with the carbon to which they are attached form a $C_{3-6}$cycloalkyl ring or a 4- to 6-membered heterocycloalkyl ring, each of which is optionally and independently substituted with one to three fluoro, $C_{1-3}$alkyl or $C_{1-3}$alkoxy; $R^4$ at each occurrence is independently selected from the group consisting of halogen, hydroxy, cyano, $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl; wherein said $C_{1-6}$alkyl, $C_{1-6}$alkoxy, $C_{3-6}$alkenyl, $C_{3-6}$alkenyloxy, $C_{3-6}$alkynyl, $C_{3-6}$alkynyloxy, $C_{1-6}$alkoxy-$C_{1-6}$alkyl, $C_{3-6}$cycloalkoxy, $C_{3-6}$cycloalkyl, $C_{3-6}$cycloalkyl-$C_{1-6}$alkyl, $C_{3-6}$cycloalkyl-$C_{1-6}$alkoxy, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; and $R^5$ is hydrogen, $C_{1-6}$alkyl, $C_{3-6}$alkenyl, $C_{3-6}$alkynyl, $C_{1-6}$alkoxy-$C_{1-6}$alkyl, $C_{3-6}$cycloalkyl, $C_{3-6}$cycloalkyl-$C_{1-6}$alkyl, 4- to 6-membered heterocycloalkyl and 4- to 6-membered heterocycloalkyl-$C_{1-6}$alkyl; wherein said $C_{1-6}$alkyl, $C_{3-6}$alkenyl, $C_{3-6}$alkynyl, $C_{1-6}$alkoxy-$C_{1-6}$alkyl, $C_{3-6}$cycloalkyl, $C_{3-6}$cycloalkyl-$C_{1-6}$alkyl, 4- to 6-membered heterocycloalkyl and 4- to 6-membered heterocycloalkyl-$C_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; or $R^4$ and $R^5$ taken together can be a $C_{3-5}$alkylene; or a tautomer thereof or a pharmaceutically acceptable salt of said compound or tautomer.

Another embodiment of the present invention is a pharmaceutical composition comprising compounds of Formula I, or a tautomer thereof or a pharmaceutically acceptable salt of said compound or tautomer, and a pharmaceutically acceptable vehicle, diluent or carrier. The pharmaceutical compositions described herein can be used for inhibiting production of amyloid-β protein and for inhibiting beta-site amyloid precursor protein cleaving enzyme 1 (BACE1); for treating a neurodegenerative disease and, in particular, Alzheimer's disease; for inhibiting BACE1 and/or BACE2 activity for the therapeutic and/or prophylactic treatment of diseases and disorders characterized by elevated β-amyloid levels, including diabetes or Type 2 diabetes; for increasing insulin sensitivity in skeletal muscle and liver in a mammal, including humans; and for treating and/or preventing obesity.

The present invention is also directed to methods of treatment employing the compounds of Formula I such as:

(1) Methods of inhibiting BACE enzyme activity, by administering a therapeutically effective amount of a thioamidine compound of any of the embodiments of Formula I or a pharmaceutically acceptable salt thereof, and a pharmaceutically acceptable carrier, to a mammal or a patient in need thereof.

(2) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(5) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005); and (6) Methods for the treatment of nonalcoholic fatty liver disease (NAFLD) and hepatic insulin resistance;

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendant claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like.

The term "alkenyl" refers to a linear or branched-chain hydrocarbyl substituent (i.e., a substituent obtained from a hydrocarbon by removal of a hydrogen) which contains at least one carbon-carbon double bond; in one embodiment containing from three to six carbon atoms. Non-limiting examples of such substituents include allyl, propenyl, butenyl, isobutenyl, butadienyl, pentenyl, pentadienyl, hexenyl, hexadienyl and the like. The term "alkenyloxy" refers to an alkenyl group attached to an oxygen radical.

The term "alkynyl" refers to a linear or branched-chain hydrocarbyl substituent (i.e., a substituent obtained from a hydrocarbon by removal of a hydrogen) which contains at least one carbon-carbon triple bond; in one embodiment containing from three to six carbon atoms. Non-limiting examples of such substituents include propynyl, butynyl, isobutynyl, pentynyl, hexynyl and the like. The term "alkynyloxy" refers to an alkynyl group attached to an oxygen radical.

The term "alkylene" refers to an alkanediyl group (i.e. a substituent obtained from a hydrocarbon by removal of two hydrogens); in one embodiment containing from three to five carbons. Non-limiting examples of such groups include propylene, butylene and pentylene.

In some instances, the number of carbon atoms in a hydrocarbyl substituent (i.e., alkyl, cycloalkyl, etc.) is indicated by the prefix "$C_x$-$C_y$-" or "$C_{x\text{-}y}$", wherein x is the minimum and y is the maximum number of carbon atoms in the substituent. Thus, for example, "$C_1$-$C_6$-alkyl" or "$C_{1\text{-}6}$ alkyl" refers to an alkyl substituent containing from 1 to 6 carbon atoms. Illustrating further, $C_3$-$C_6$cycloalkyl or $C_{3\text{-}6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to six carbon atoms or having three to nine carbon atoms. The term "cycloalkyl" includes mono-, bi- and tricyclic saturated carbocycles, as well as bridged and fused ring carbocycles and also spiro-fused carbocyclic ring systems. For example, the term "$C_{3\text{-}9}$cycloalkyl" means a radical of a three- to nine-membered ring system, which includes the groups cyclopropyl, cyclobutyl, cyclopentyl, cyclohexyl, cycloheptyl, cyclooctyl, cyclononyl, bicyclopentyl, bicyclohexyl, bicycloheptyl, bicyclooctyl, bicyclononyl, spiropentyl, spirohexyl, spiroheptyl, spirooctyl and spirononyl. The term "$C_{3\text{-}6}$cycloalkyl" means a radical of a three- to six-membered ring system, which includes the groups cyclopropyl, cyclobutyl, cyclopentyl, cyclohexyl, bicyclopentyl, bicyclohexyl, spiropentyl and spirohexyl. The term "$C_{3\text{-}6}$cycloalkoxy" refers to a three- to six-membered cycloalkyl group attached to an oxygen radical. Examples include cyclopropoxy, cyclobutoxy, cyclopentoxy and cyclohexoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent. Thus, for example, "4- to 6-membered heterocycloalkyl" refers to a heterocycloalkyl containing from 4 to 6 atoms, including one to three heteroatoms, in the cyclic moiety of the heterocycloalkyl. Likewise the phrase "5- to 6-membered heteroaryl" refers to a heteroaryl containing from 5 to 6 atoms, and "5- to 10-membered heteroaryl" refers to a heteroaryl containing from 5 to 10 atoms, each including one or more heteroatoms, in the cyclic moiety of the heteroaryl. Furthermore the phases "5-membered heteroaryl" and "6-membered heteroaryl" refer to a five-membered heteroaromatic ring system and a six-membered heteroaromatic ring system, respectively. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom.

The term "heteroaryl" refers to an aromatic ring structure containing the specified number of ring atoms in which at least one of the ring atoms is a heteroatom (i.e., oxygen, nitrogen, or sulfur), with the remaining ring atoms being independently selected from the group consisting of carbon, oxygen, nitrogen, and sulfur. Examples of heteroaryl substituents include 6-membered heteroaryl substituents such as pyridyl, pyrazyl, pyrimidinyl, and pyridazinyl; and 5-membered heteroaryl substituents such as triazolyl, imidazolyl, furanyl, thiophenyl, pyrazolyl, pyrrolyl, oxazolyl, isoxazolyl, thiazolyl, 1,2,3-, 1,2,4-, 1,2,5-, or 1,3,4-oxadiazolyl and isothiazolyl. The heteroaryl group can also be a bicyclic heteroaromatic group such as indolyl, benzofuranyl, benzothienyl, benzimidazolyl, benzothiazolyl, benzoxazolyl, benzoisoxazolyl, oxazolopyridinyl, imidazopyridinyl, imidazopyrimidinyl and the like. In a group that has a heteroaryl substituent, the ring atom of the heteroaryl substituent that is bound to the group may be a ring nitrogen atom, or it may be a ring carbon atom. Similarly, if the heteroaryl substituent is in turn substituted with a group or substituent, the group or substituent may be bound to a ring nitrogen atom, or it may be bound to a ring carbon atom. The term "heteroaryl" also includes pyridyl N-oxides and groups containing a pyridine N-oxide ring. In addition, the heteroaryl group may contain an oxo group such as the one present in a pyridone group. Further examples include furyl, thienyl, oxazolyl, thiazolyl, imidazolyl, pyrazolyl, triazolyl, tetrazolyl, isoxazolyl, isothiazolyl, oxadiazolyl, thiadiazolyl, pyridinyl, pyridazinyl, pyrimidinyl, pyrazinyl, pyridin-2(1H)-onyl, pyridazin-2(1H)-onyl, pyrimidin-2(1H)-onyl, pyrazin-2(1H)-onyl, imidazo[1,2-a]pyridinyl, and pyrazolo[1,5-a]pyridinyl. The heteroaryl can be further substituted as defined herein.

Examples of single-ring heteroaryls and heterocycloalkyls include furanyl, dihydrofuranyl, tetrahydrofuranyl, thiophenyl, dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiaoxadiazolyl, oxathiazolyl, oxadiazolyl (including oxadiazolyl, 1,2,4-oxadiazolyl, 1,2,5-oxadiazolyl, or 1,3,4-oxadiazolyl), pyranyl (including 1,2-pyranyl or 1,4-pyranyl), dihydropyranyl, pyridinyl, piperidinyl, diazinyl (including pyridazinyl, pyrimidinyl, piperazinyl, triazinyl (including s-triazinyl, as-triazinyl and v-triazinyl), oxazinyl (including 2H-1,2-oxazinyl, 6H-1,3-oxazinyl, or 2H-1,4-oxazinyl), isoxazinyl (including o-isoxazinyl or p-isoxazinyl), oxazolidinyl, isoxazolidinyl, oxathiazinyl (including 1,2,5-oxathiazinyl or 1,2,6-oxathiazinyl), oxadiazinyl (including 2H-1,2,4-oxadiazinyl or 2H-1,2,5-oxadiazinyl), morpholinyl.

The term "heteroaryl" can also include, when specified, ring systems having two rings wherein such rings may be fused and wherein one ring is aromatic and the other ring is not fully part of the conjugated aromatic system (i.e., the heteroaromatic ring can be fused to a cycloalkyl or heterocycloalkyl ring). Non-limiting examples of such ring systems include 5,6,7,8-tetrahydroisoquinolinyl, 5,6,7,8-tetrahydroquinolinyl, 6,7-dihydro-5H-cyclopenta[b]pyridinyl, 6,7-dihydro-5H-cyclopenta[c]pyridinyl, 1,4,5,6-tetrahydro-cyclopenta[c]pyrazolyl, 2,4,5,6-tetrahydrocyclopenta[c]pyrazolyl, 5,6-dihydro-4H-pyrrolo[1,2-b]pyrazolyl, 6,7-dihydro-5H-pyrrolo[1,2-b][1,2,4]triazinyl, 5,6,7,8-tetrahydro-[1,2,4]triazolo[1,5-a]pyridinyl, 4,5,6,7-tetrahydropyrazolo[1,5-a]pyridinyl, 4,5,6,7-tetrahydro-1H-indazolyl and 4,5,6,7-tetrahydro-2H-indazolyl. It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3- or 4-pyridyl, the term "thienyl" means 2- or 3-thienyl, and so forth.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (-), a solid wedge (━), or a dotted wedge (⋯). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. For example, the compounds of Formula I may exist in several tautomeric forms, including the 2-aminodihydrothiazine form, I, and the 2-imino-tetrahydrothiazine form, I'. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula I and I' and, collectively and generically, are referred to as compounds of Formula I.

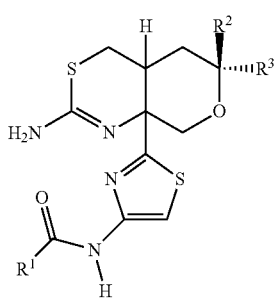

I

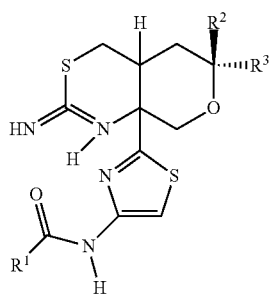

I'

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs" as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "pro-moieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

A second embodiment of a first aspect of the present invention is a compound of Formula Ia

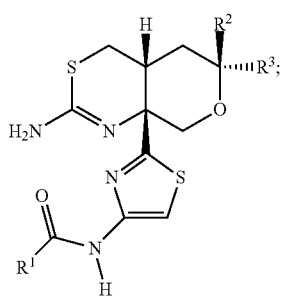

Ia or a tautomer thereof or a pharmaceutically acceptable salt of said compound or tautomer.

A third embodiment of a first aspect of the present invention is a compound of Formula Ib

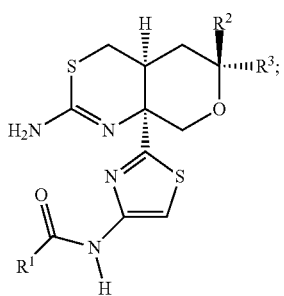

Ib or a tautomer thereof or a pharmaceutically acceptable salt of said compound or tautomer.

A fourth embodiment of a first aspect of the present invention is the compound of any one of the first through third embodiments of the first aspect wherein $R^1$ is a 5-membered heteroaryl selected from the group consisting of pyrazolyl and oxazolyl; each optionally substituted on carbon with one to two $R^4$; and wherein said pyrazolyl is substituted on N with $R^5$; $R^4$ at each occurrence is independently selected from the group consisting of halogen, $C_{1-3}$alkyl, $C_{3-6}$cycloalkyl, and $C_{1-3}$alkoxy-$C_{1-3}$alkyl; wherein said $C_{1-3}$alkyl is optionally substituted with one to three fluoro; and $R^5$ is $C_{1-3}$alkyl or $C_{3-6}$cycloalkyl, wherein said $C_{1-3}$alkyl is optionally substituted with one to three fluoro; or a tautomer thereof or a pharmaceutically acceptable salt of said compound or tautomer.

A fifth embodiment of a first aspect of the present invention is the compound of the fourth embodiment of the first aspect wherein $R^1$ is selected from the group consisting of

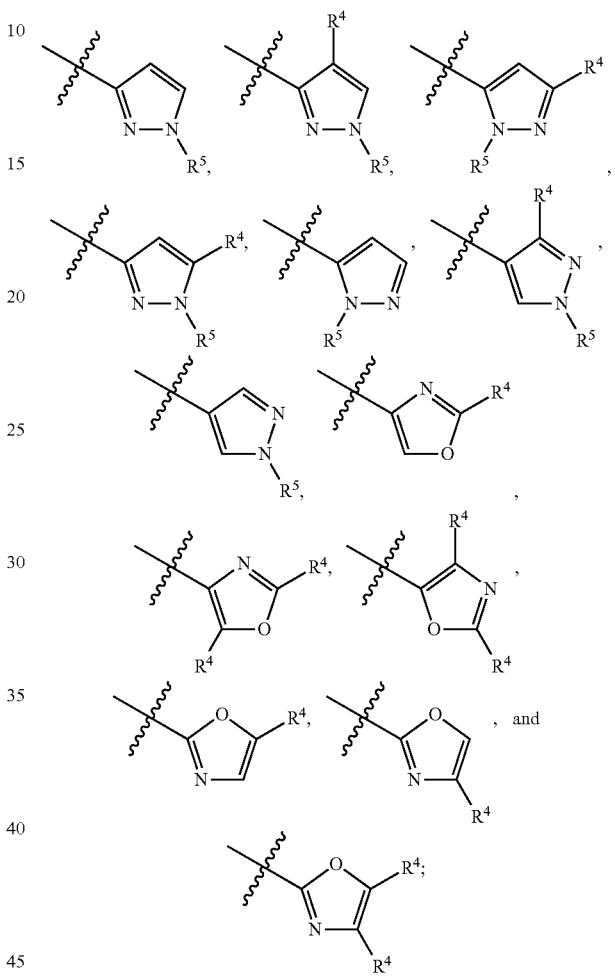

$R^4$ at each occurrence is independently selected from the group consisting of chloro, methyl, ethyl, isopropyl, isobutyl, fluoromethyl, difluoromethyl, trifluoromethyl, cyclopropyl, cyclobutyl and methoxymethyl; and $R^5$ is methyl, ethyl, isopropyl, difluoromethyl, cyclopropyl or cyclobutyl; or a tautomer thereof or a pharmaceutically acceptable salt of said compound or tautomer.

A sixth embodiment of the first aspect of the present invention is the compound of the fifth embodiment of the first aspect wherein $R^1$ is selected from the group consisting of

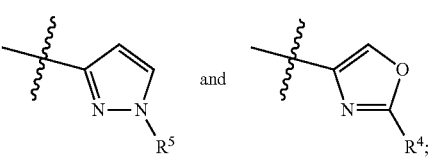

$R^2$ and $R^3$ are each methyl; $R^4$ is fluoromethyl; and $R^5$ is difluoromethyl; or a tautomer thereof or a pharmaceutically acceptable salt of said compound or tautomer.

A seventh embodiment of a first aspect of the present invention is the compound of any one of the first through third embodiments of the first aspect wherein $R^1$ is a 6-membered heteroaryl selected from the group consisting of pyridinyl and pyrazinyl; each optionally substituted on carbon with one to two $R^4$; and $R^4$ at each occurrence is independently selected from the group consisting of halogen, $C_{1-6}$alkyl, $C_{1-6}$alkoxy and $C_{3-6}$alkynyloxy; wherein said $C_{1-6}$alkyl and $C_{1-6}$alkoxy are optionally substituted with one to three fluoro; or a tautomer thereof or a pharmaceutically acceptable salt of said compound or tautomer.

An eighth embodiment of a first aspect of the present invention is the compound of the seventh embodiment of the first aspect wherein $R^1$ is selected from the group consisting of

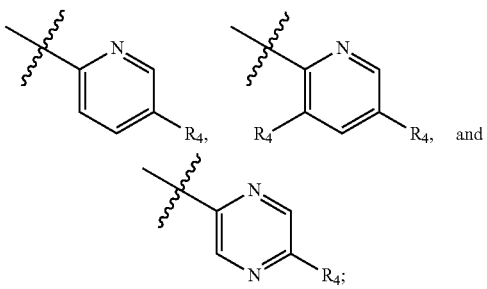

and
$R^4$ at each occurrence is independently selected from the group consisting of fluoro, chloro, methyl, fluoromethyl, difluoromethyl, trifluoromethyl, methoxy, fluoromethoxy, difluoromethoxy, trifluoromethoxy, difluoropropoxy and butynyloxy; or a tautomer thereof or pharmaceutically acceptable salt of said compound or tautomer.

A ninth embodiment of a first aspect of the present invention is the compound of the eighth embodiment of the first aspect wherein $R^1$ is

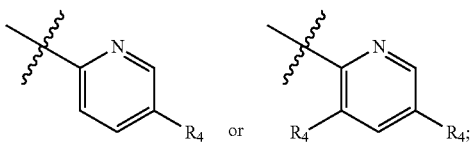

and
$R^4$ at each occurrence is independently selected from the group consisting of chloro, fluoro, methyl, but-2-ynyloxy, difluoromethoxy and 1,1-difluoroethoxy; or a tautomer thereof or a pharmaceutically acceptable salt of said compound or tautomer.

A tenth embodiment of a first aspect of the present invention is the compound of the ninth embodiment of the first aspect wherein $R^2$ and $R^3$ are each independently selected from the group consisting of methyl, fluoromethyl, methoxymethyl, ethyl and cyclopropyl; or a tautomer thereof or a pharmaceutically acceptable salt of said compound or tautomer.

An eleventh embodiment of a first aspect of the present invention is the compound of the ninth embodiment of the first aspect wherein $R^2$ and $R^3$ taken together with the carbon to which they are attached form a cyclopropyl, cyclobutyl or oxetanyl ring; or a tautomer thereof or a pharmaceutically acceptable salt of said compound or tautomer.

A twelfth embodiment of a first aspect of the present invention is the compound of the eighth embodiment of the first aspect wherein $R^1$ is

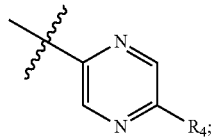

and
$R^4$ is selected from the group consisting of difluoromethoxy, 2,2-difluoropropoxy and but-2-ynyloxy; or a tautomer thereof or a pharmaceutically acceptable salt of said compound or tautomer.

A thirteenth embodiment of a first aspect of the present invention is the compound of the twelfth embodiment of the first aspect wherein $R^2$ and $R^3$ are each methyl; or a tautomer thereof or a pharmaceutically acceptable salt of said compound or tautomer.

A fourteenth embodiment of a first aspect of the present invention is the compound of the second embodiment of the first aspect wherein $R^1$ is a $C_{5-9}$bicycloalkyl; or a tautomer thereof or a pharmaceutically acceptable salt of said compound or tautomer.

A fifteenth embodiment of a first aspect of the present invention is the compound of the fourteenth embodiment of the first aspect wherein $R^1$ is bicyclo[1.1.1]pentan-1-yl or bicyclo[1.1.1]pentan-2-yl; and $R^2$ and $R^3$ are each independently methyl or ethyl; or a tautomer thereof or a pharmaceutically acceptable salt of said compound or tautomer.

A sixteenth embodiment of a first aspect of the present invention is the compound of the second embodiment of the first aspect wherein $R^1$ is $C_{1-6}$alkyl optionally substituted with one to three fluoro or $C_{1-3}$alkoxy; or a tautomer thereof or a pharmaceutically acceptable salt of said compound or tautomer.

A seventeenth embodiment of a first aspect of the present invention is the compound of the sixteenth embodiment of the first aspect wherein $R^1$ is 2-fluoropropan-2-yl or 2-methoxypropan-2-yl; and $R^2$ and $R^3$ are each methyl; or a tautomer thereof or a pharmaceutically acceptable salt of said compound or tautomer.

An eighteenth embodiment of the present invention is a compound of the first embodiment of the first aspect selected from the group consisting of:
N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyridine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyridine-2-carboxamide;
N-{2-[cis-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide;
N-{2-[(4a'S,8a'S)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide;
N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide;

N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-chloropyridine-2-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyridine-2-carboxamide;

N-{2-[(4aR,6S,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide N-{2-[(4aR,6R,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide;

N-{2-[(4aR,8aR)-2-amino-6,6-bis(fluoromethyl)-4,4a,5,6-tetrahydropyrano[3,4-d][1,3]thiazin-8a(8H)-yl]-1,3-thiazol-4-yl}-5-(difluoromethoxy)pyridine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-1-(difluoromethyl)-1H-pyrazole-3-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-1-(difluoromethyl)-1H-pyrazole-3-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyrazine-2-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyrazine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyridine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(1,1-difluoroethoxy)pyridine-2-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(1,1-difluoroethoxy)pyridine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(2,2-difluoropropoxy)pyrazine-2-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(2,2-difluoropropoxy)pyrazine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyrazine-2-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyrazine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4aS,6S,8aS)-2-amino-6-ethyl-6-methyl-4,4a,5,6-tetrahydropyrano[3,4-d][1, 3]thiazin-8a(8H)-yl]-1,3-thiazol-4-yl}-5-(difluoromethoxy)pyridine-2-carboxamide;

N-{2-[(4aR,6R,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide;

N-{2-[(4aS,6R,8aS)-2-amino-6-ethyl-6-methyl-4,4a,5,6-tetrahydropyrano[3,4-d][1, 3]thiazin-8a(8H)-yl]-1,3-thiazol-4-yl}-5-(difluoromethoxy)pyridine-2-carboxamide;

N-{2-[(4a'R,8a'R)-2'-amino-4a',5'-dihydro-4'H-spiro[oxetane-3,6'-pyrano[3,4-d][1,3]thiazin]-8a'(8'H)-yl]-1,3-thiazol-4-yl}-5-(difluoromethoxy)pyridine-2-carboxamide;

N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-3-chloro-5-(difluoromethoxy)pyridine-2-carboxamide;

N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-2-fluoro-2-methylpropanamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-2-methoxy-2-methylpropanamide;

N-{2-[(4aR,8aR)-2-amino-6,6-dimethyl-4,4a,5,6-tetrahydropyrano[3,4-d][1,3]thiazin-8a(8H)-yl]-1,3-thiazol-4-yl} bicyclo[1.1.1]pentane-1-carboxamide;

N-{2-[(4aR,6S,8aR)-2-amino-6-(fluoromethyl)-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide;

N-{2-[(4aR,6R,8aR)-2-amino-6-(fluoromethyl)-6-methyl-4,4a,5,6-tetrahydropyrano [3,4-d][1,3]thiazin-8a(8H)-yl]-1,3-thiazol-4-yl}-5-(difluoromethoxy)pyridine-2-carboxamide;

N-{2-[(4aR,6S,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide N-{2-[(4aR,6S,8aR)-2-amino-6-ethyl-6-methyl-4,4a,5,6-tetrahydropyrano[3,4-d][1,3]thiazin-8a(8H)-yl]-1,3-thiazol-4-yl}bicyclo[1.1.1]pentane-2-carboxamide;

N-{2-[(4a'S,8a'S)-2'-amino-4a',5'-dihydro-4'H-spiro[cyclopropane-1,6'-pyrano[3,4-d][1,3]thiazin]-8a'(8'H)-yl]-1,3-thiazol-4-yl}-5-(difluoromethoxy)pyridine-2-carboxamide;

N-{2-[(4a'R,8a'R)-2'-amino-4a',5'-dihydro-4'H-spiro[cyclopropane-1,6'-pyrano[3,4-d][1,3]thiazin]-8a'(8'H)-yl]-1,3-thiazol-4-yl}-5-(difluoromethoxy)pyridine-2-carboxamide;

N-{2-[(4aR,6S,8aR)-2-amino-6-(methoxymethyl)-6-methyl-4,4a,5,6-tetrahydropyrano[3,4-d][1,3]thiazin-8a (8H)-yl]-1,3-thiazol-4-yl}-5-(difluoromethoxy) pyridine-2-carboxamide; and N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-fluoropyridine-2-carboxamide;

or a tautomer thereof or a pharmaceutically acceptable salt of said compound or tautomer.

A nineteenth embodiment of a first aspect of the present invention is the compound N-{2-[(4a'R,8a'R)-2'-amino-4a',5'-dihydro-4'H-spiro[cyclobutane-1,6'-pyrano[3,4-d] [1,3]thiazin]-8a'(8'H)-yl]-1,3-thiazol-4-yl}-5-(difluoromethoxy)pyridine-2-carboxamide; or a tautomer thereof or a pharmaceutically acceptable salt of said compound or tautomer.

A twentieth embodiment of a first aspect of the present invention is the compound N-{2-[(4aR,8aR)-2-amino-6,6-dimethyl-4,4a,5,6-tetrahydropyrano[3,4-d][1,3]thiazin-8a (8H)-yl]-1,3-thiazol-4-yl}-5-(difluoromethoxy)pyridine-2-carboxamide; or a tautomer thereof or a pharmaceutically acceptable salt of said compound or tautomer.

A twenty-first embodiment of a first aspect of the present invention is the compound N-{2-[(4aR,6S,8aR)-2-amino-6-ethyl-6-methyl-4,4a,5,6-tetrahydropyrano[3,4-d] [1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

A twenty-second embodiment of a first aspect of the present invention is the compound N-{2-[(4aR,6R,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide; or a tautomer thereof or a pharmaceutically acceptable salt of said compound or tautomer.

A twenty-third embodiment of a first aspect of the present invention is the compound N-{2-[(4aS,6S,8aS)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

A twenty-fourth embodiment of a first aspect of the present invention is the compound N-{2-[(4aR,6R,8aR)-2-amino-6-(fluoromethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide; or a tautomer thereof or a pharmaceutically acceptable salt of said compound or tautomer.

A first embodiment of a second aspect of the present invention is a pharmaceutical composition comprising a therapeutically effective amount of a compound of any one of the first through twenty-fourth embodiments of the first aspect, or a tautomer thereof or a pharmaceutically acceptable salt of said compound or tautomer, and a pharmaceutically acceptable vehicle, diluent or carrier.

A first embodiment of a third aspect of the present invention is a method of inhibiting production of amyloid-β protein in a patient, the method comprising administering a therapeutically effective amount of a compound of any one of the first through twenty-fourth embodiments of the first aspect, or a tautomer thereof or a pharmaceutically acceptable salt of said compound or tautomer, to a patient in need of inhibition of production of amyloid-β protein.

A second embodiment of a third aspect of the present invention is a method of inhibiting beta-site amyloid precursor protein cleaving enzyme 1 (BACE1) in a patient, the method comprising administering a therapeutically effective amount of a compound of any one of the first through twenty-fourth embodiments of the first aspect, or a tautomer thereof or a pharmaceutically acceptable salt of said compound or tautomer, to a patient in need of inhibition of beta-site amyloid precursor protein cleaving enzyme 1 (BACE1).

A third embodiment of a third aspect of the present invention is a method for treating a neurodegenerative disease in a patient, the method comprising administering a therapeutically effective amount of a compound of any one of the first through twenty-fourth embodiments of the first aspect, or a tautomer thereof or a pharmaceutically acceptable salt of said compound or tautomer, to a patient in need of treatment thereof.

A fourth embodiment of a third aspect of the present invention is the method of the third embodiment of the third aspect wherein the neurodegenerative disease is Alzheimer's disease.

A fifth embodiment of a third aspect of the present invention is a method of treating or preventing diabetes in a patient, the method comprising administering a therapeutically effective amount of a compound of any one of the first through twenty-fourth embodiments of the first aspect, or a tautomer thereof or a pharmaceutically acceptable salt of said compound or tautomer, to a patient in need of treatment or prevention thereof.

A sixth embodiment of a third aspect of the present invention is the method of the fifth embodiment of the third aspect wherein the diabetes is Type 2 diabetes.

Further embodiments of the present invention include the use of a compound according to any one of first through twenty-fourth embodiments of the first aspect of the present invention in the preparation of a medicament useful for treating the conditions, diseases and disorders as described herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N.Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), include gut-selective MTP inhibitors (e.g., dirlotapide, mitratapide and implitapide, CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), $PYY_{3-36}$ (as used herein "$PYY_{3-36}$" includes analogs, such as peglated $PYY_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., Drug Discovery Today, 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high-affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g., SSTR1, SSTR2, SSTR3 and SSTR5), inhibitors or modulators of PDHK2 or PDHK4, inhibitors of MAP4K4, modulators of IL1 family including IL1beta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as Aβ$_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (1-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl)quinoline (PF-2545920);

(xiv) serotonin (5-hydroxytryptamine) 1A (5-$HT_{1A}$) receptor antagonists, such as spiperone, levo-pindolol, lecozotan;

(xv) serotonin (5-hydroxytryptamine) 2C (5-$HT_{2C}$) receptor agonists, such as vabicaserin, and zicronapine; serotonin (5-hydroxytryptamine) 4 (5-$HT_4$) receptor agonists/antagonists, such as PRX-03140 (Epix) and PF-04995274;

(xvi) serotonin (5-hydroxytryptamine) 3C (5-$HT_{3c}$) receptor antagonists, such as Ondansetron (Zofran);

(xvii) serotonin (5-hydroxytryptamine) 6 (5-$HT_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. Additionally, one skilled in the art will recognize that in many cases, these compounds will be mixtures and enantiomers that may be separated at various stages of the synthetic schemes using conventional techniques, such as, but not limited to, crystallization, normal-phase chromatography, reversed phase chromatography and chiral chromatography, to afford single enantiomers. The schemes are representative of methods useful in synthesizing the compounds of the present invention. They are not to constrain the scope of the invention in any way.

Scheme 1 refers to the preparation of compounds of Formula I or Formula Ia. Referring to Scheme 1, the compound of Formula I or Ia can be prepared through removal of protecting group $P^1$ from a compound of Formula II or II', respectively. $P^1$ in this case refers to groups well known to those skilled in the art for amine protection. For example, $P^1$ may be a benzoyl group (Bz), which can be cleaved via basic conditions, including but not limited to treatment with 1,8-diazabicyclo[5.4.0]undec-7-ene (DBU) in methanol. Alternatively, $P^1$ may be one of many other protecting group suitable for amines, including 9-fluorenylmethoxycarbonyl (Fmoc) or tert-butoxycarbonyl (BOC) and can be cleaved under standard conditions known to one skilled in the art.

Scheme 1

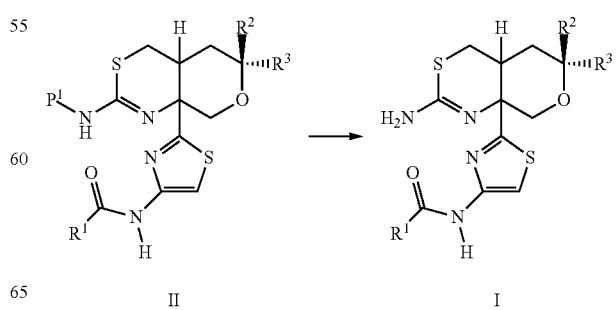

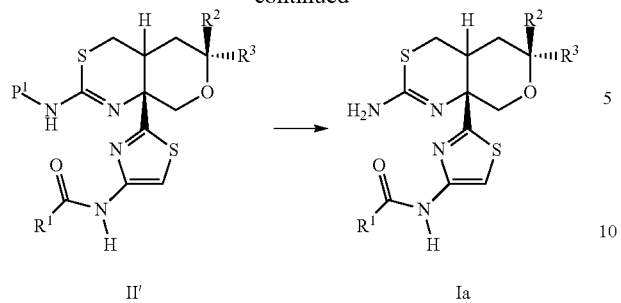

II'  Ia

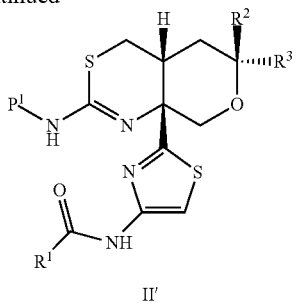

II'

Scheme 2 refers to the preparation of compounds II' wherein P¹ is Bz or Boc. Conversion of the bromothiazole of Formula III to the corresponding amine can be effected via a transition metal-catalyzed coupling reaction, such as palladium-mediated amination. An example includes using a protected ammonia source, such as, but not limited to, 1-(2,4-dimethoxyphenyl)methanamine and a suitable catalyst and ligand choice, for example, tris(dibenzylideneacetone)dipalladium(0) and di-tert-butyl[2',4',6'-tri(propan-2-yl)biphenyl-2-yl]phosphane. Alternatively, one can utilize a copper-mediated azide coupling method. One skilled in the art will recognize that the requisite protected ammonia source will need to be deprotected to afford compounds of Formula II'. In the example utilizing 1-(2,4-dimethoxyphenyl)methanamine, said deprotection can be effected via acidic hydrolysis, such as treatment with concentrated hydrochloric acid. The compound of Formula II' can be prepared from the compound of Formula IV via a standard peptide coupling with a carboxylic acid (R¹CO₂H), and a suitable coupling reagent, for example, but not limited to, O-(7-azabenzotriazol-1-yl)-N,N,N',N'-tetramethyluronium hexafluorophosphate (HATU). Compounds of Formula II' can be converted into a compound of Formula Ia according to the methods of Scheme 1. It is to be understood that the reactions depicted in the Schemes are representative and can be used to prepare compounds of Formulae I, Ia and Ib.

Scheme 3 refers to an alternative preparation of compounds II' wherein P¹ is Bz or Boc. Conversion of the bromothiazole of Formula III to a compound of Formula V can be effected via a transition metal-catalyzed coupling reaction, such as a palladium-mediated amination. An example includes using a protected ammonia source, such as, but not limited to, 1-(2,4-dimethoxyphenyl)methanamine and a suitable catalyst and ligand choice, for example, tris(dibenzylideneacetone)dipalladium(0) and di-tert-butyl [2',4',6'-tri(propan-2-yl)biphenyl-2-yl]phosphane. The compound of Formula VI can be prepared from the compound of Formula V via a standard peptide coupling with a carboxylic acid, and a suitable coupling reagent, for example but not limited to, O-(7-azabenzotriazol-1-yl)-N,N,N',N'-tetramethyluronium hexafluorophosphate (HATU). The compound of Formula II' can be prepared from the compound of Formula VI via a deprotection effected via acidic hydrolysis, such as treatment with concentrated trifluoroacetic acid. Compounds of Formula II' can be converted into a compound of Formula Ia according to the methods of Scheme 1.

Scheme 3

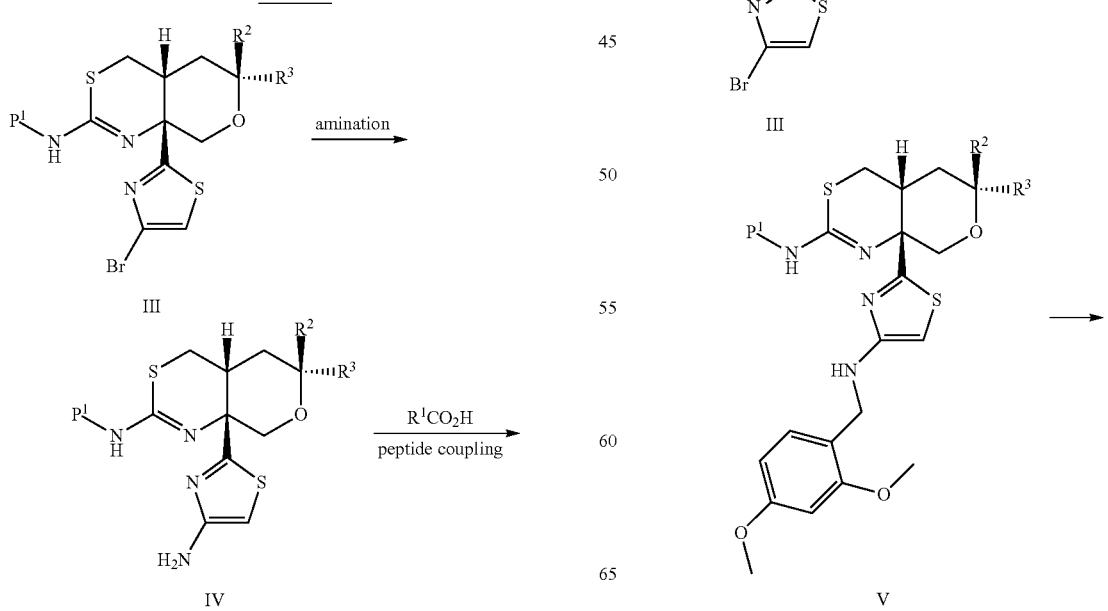

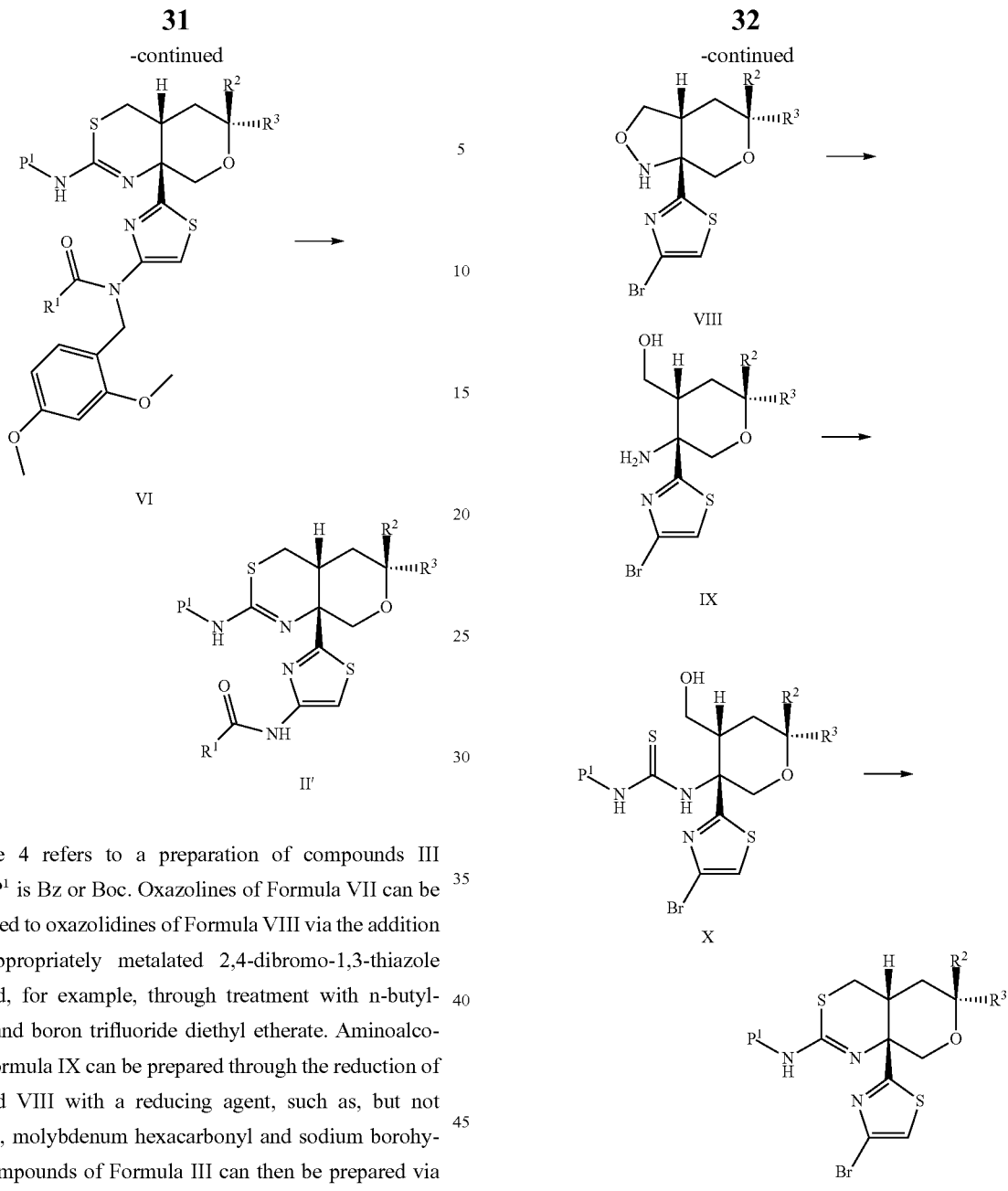

Scheme 4 refers to a preparation of compounds III wherein P¹ is Bz or Boc. Oxazolines of Formula VII can be transformed to oxazolidines of Formula VIII via the addition of an appropriately metalated 2,4-dibromo-1,3-thiazole (generated, for example, through treatment with n-butyllithium) and boron trifluoride diethyl etherate. Aminoalcohols of Formula IX can be prepared through the reduction of compound VIII with a reducing agent, such as, but not limited to, molybdenum hexacarbonyl and sodium borohydride. Compounds of Formula III can then be prepared via treatment with the appropriate isothiocyanate (such as benzoyl isothiocyanate), and subsequent ring closure using 1-chloro-N,N,2-trimethylprop-1-en-1-amine (Ghosez's reagent). Compounds of Formula III can be converted into a compound of Formula Ia according to the methods of Scheme 3, 2, and 1.

Scheme 5 refers to the preparation of compounds of Formula VII. The alkylation of compounds of Formula XI can be effected using 2-bromo-1,1-diethoxyethane and sodium hydride in tetrahydrofuran. Deprotection of the diethyl acetal of compounds of Formula XII can be achieved using acidic conditions; subsequent oxime formation occurs via treatment with hydroxylamine hydrochloride to afford compounds of Formula XIII. Treatment with sodium hypochlorite and triethylamine can then afford isoxazoline VII. A compound of Formula VII can be subsequently converted into a compound of Formula I according to the methods of Schemes 4, 3, 2 and 1.

Scheme 4

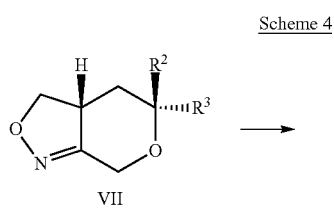

Scheme 5

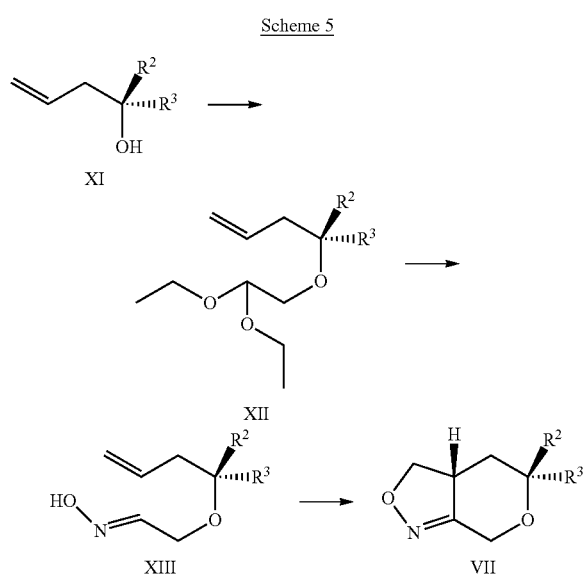

Scheme 6 refers to an alternative preparation of compounds of Formula VII. The alkylation of compounds of Formula XI can be effected using 2-nitroethanol and camphorsulfonic acid in dichloromethane. Treatment with di-tert-butyl dicarbonate and 4-(dimethylamino)pyridine (DMAP) in dichloromethane can afford isoxazolines of Formula VII. A compound of Formula VII can be converted into a compound of Formula I according to the methods of Schemes 4, 3, 2 and 1.

Scheme 6

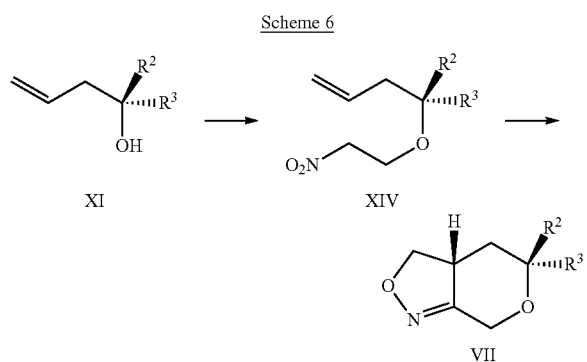

Scheme 7 refers to the preparation of compounds III from the diol compound of Formula XV, wherein $P^1$ is Bz or Boc. Methods for converting alcohols to compounds of Formula III wherein $R^2$ and $R^3$ are as defined herein are known to one skilled in the art. For example, one of the hydroxyl groups in compound XV can be protected as the tert-butyldimethylsilyl ether and the other hydroxyl can then be converted to the corresponding p-toluenesulfonate. The resulting compound can then be cyclized via treatment with tetrabutylammonium fluoride, to provide a compound of Formula III in which $R^2$ and $R^3$ taken together with the carbon to which they are attached form an oxetane ring. Alternatively, both hydroxyl groups in the compound XV can be converted to iodo and the resulting compound can undergo a benzoyl peroxide-induced radical cyclization to provide a compound of Formula III in which $R^2$ and $R^3$ together with the carbon to which they are attached form a cyclopropyl ring. Other reaction sequences employing differential protection and reaction of the hydroxyl groups in the compound XV can provide compounds of Formula III wherein $R^2$ and $R^3$ have been differentiated (e.g., one of $R^2$ and $R^3$ is methyl and the other is fluoromethyl or methoxymethyl). Alternatively, both of the hydroxyl groups in compound XV can be treated with an appropriate fluorinating reagent to provide a compound of Formula III in which both $R^2$ and $R^3$ are fluoromethyl. It is to be understood by one skilled in the art that there are numerous synthetic methodologies available for converting the diol XV to many varied $R^2$ and $R^3$ groups in the compound of Formula III. The resulting compounds of Formula III can be converted into a compound of Formula I according to the methods described herein.

Scheme 7

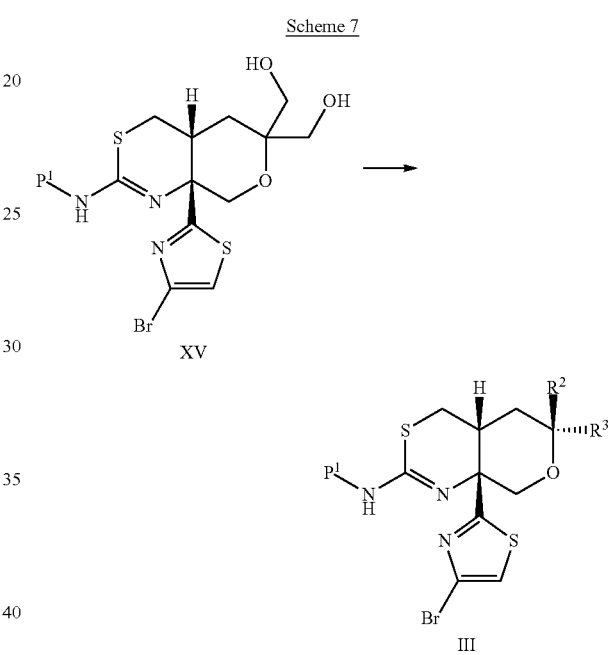

Scheme 8 refers to the preparation of compounds of Formula XV wherein $P^1$ is Bz or Boc. Oxazoline XVI (see C. R. Butler et al., *J. Med. Chem.* 2015, 58, 2678-2702) is transformed to the oxazolidine of Formula XVII via the addition of an appropriately metallated 2,4-dibromo-1,3-thiazole (generated, for example, through treatment with n-butyllithium) and boron trifluoride diethyl etherate. The aminoalcohol of Formula XVIII is prepared through the reduction of compound XVII with a reducing agent, such as, but not limited to, molybdenum hexacarbonyl and sodium borohydride. Compounds of Formula XX are then prepared via the treatment with the appropriate isothiocyanate (such as benzoyl isothiocyanate), and subsequent ring closure and benzyl deprotection using p-toluenesulfonic acid and methoxybenzene. Oxidation can be effected using 1,1,1-tris (acetyloxy)-1, 1-dihydro-1,2-benziodoxol-3-(1H)-one (Dess-Martin periodinane) to provide the corresponding aldehyde of Formula XXI. Subsequent treatment with formaldehyde and sodium hydroxide in 1,4-dioxane and water can then yield compounds of Formula XV. A compound of Formula XV can be converted into a compound of Formula I according to the methods of Schemes 7, 3, 2 and 1.

Scheme 8

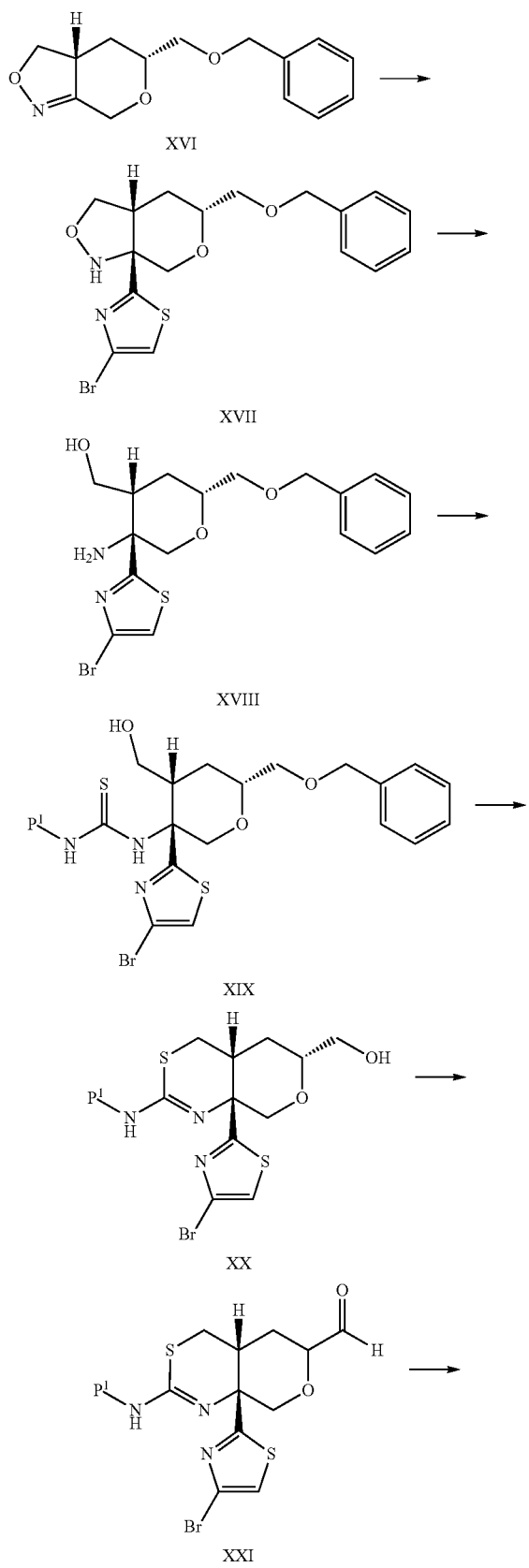

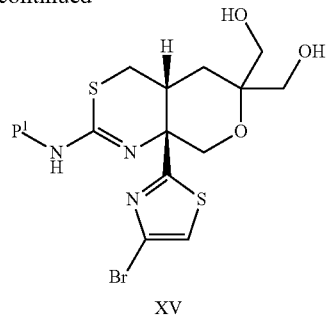

EXPERIMENTAL PROCEDURES

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification. Anhydrous solvents were employed where appropriate, generally AcroSeal® products from Acros Organics or DriSolv® products from EMD Chemicals. In other cases, commercial solvents were passed through columns packed with 4 Å molecular sieves, until the following QC standards for water were attained: a) <100 ppm for dichloromethane, toluene, N,N-dimethylformamide and tetrahydrofuran; b) <180 ppm for methanol, ethanol, 1,4-dioxane and diisopropylamine. For very sensitive reactions, solvents were further treated with metallic sodium, calcium hydride or molecular sieves, and distilled just prior to use. Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed. In some examples, chiral separations were carried out to separate enantiomers of certain compounds of the invention (in some examples, the separated enantiomers are designated as ENT-1 and ENT-2, according to their order of elution). In some examples, the optical rotation of an enantiomer was measured using a polarimeter. According to its observed rotation data (or its specific rotation data), an enantiomer with a clockwise rotation was designated as the (+)-enantiomer and an enantiomer with a counter-clockwise rotation was designated as the (−)-enantiomer. Racemic compounds are indicated by the presence of (+/−) adjacent to the structure; in these cases, indicated stereochemistry represents the relative (rather than absolute) configuration of the compound's substituents.

Reactions proceeding through detectable intermediates were generally followed by LCMS, and allowed to proceed to full conversion prior to addition of subsequent reagents. For syntheses referencing procedures in other Examples or Methods, reaction conditions (reaction time and temperature) may vary. In general, reactions were followed by thin-layer chromatography or mass spectrometry, and subjected to work-up when appropriate. Purifications may vary between experiments: in general, solvents and the solvent ratios used for eluents/gradients were chosen to provide appropriate R$_f$s or retention times. All starting materials in these Preparations and Examples are either commercially available or can be prepared by methods known in the art or as described herein.

The following are abbreviations which may appear in the experimental procedures described herein.

Abbreviations: br=broad; CDCl$_3$=deuteron-chloroform; CD$_3$OD=deuteron-methanol; d=doublet; dd=doublet of doublets; dddd=doublet of doublet of doublet of doublets; g=gram; h=hour; HPLC=high-performance liquid chromatography; Hz=hertz; L=liter; LCMS=liquid chromatography mass spectroscopy; min=minutes; m=multiplet; M=molar; MHz=megahertz; mmol=millimole; μmol=micromole; mL=milliliter; μL=microliter; mol=mole; NOE=Nuclear Overhauser effect; s=singlet; tr=triplet; q=quartet.

Preparation P1

N-[cis-8a-(4-Amino-1,3-thiazol-2-yl)-6,6-dimethyl-4,4a,5,6,8,8a-hexahydropyrano[3,4-d][1,3]thiazin-2-yl]benzamide (P1)

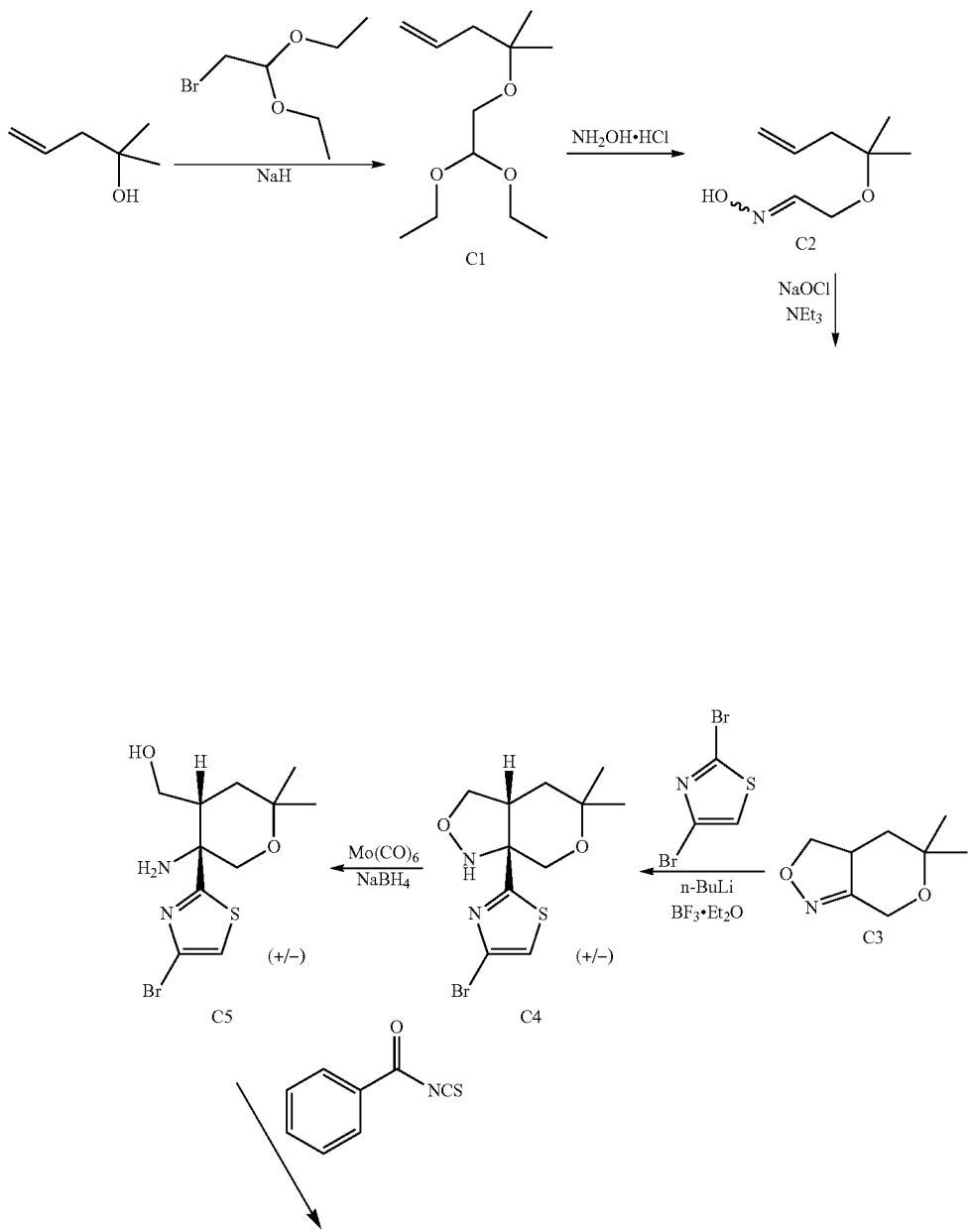

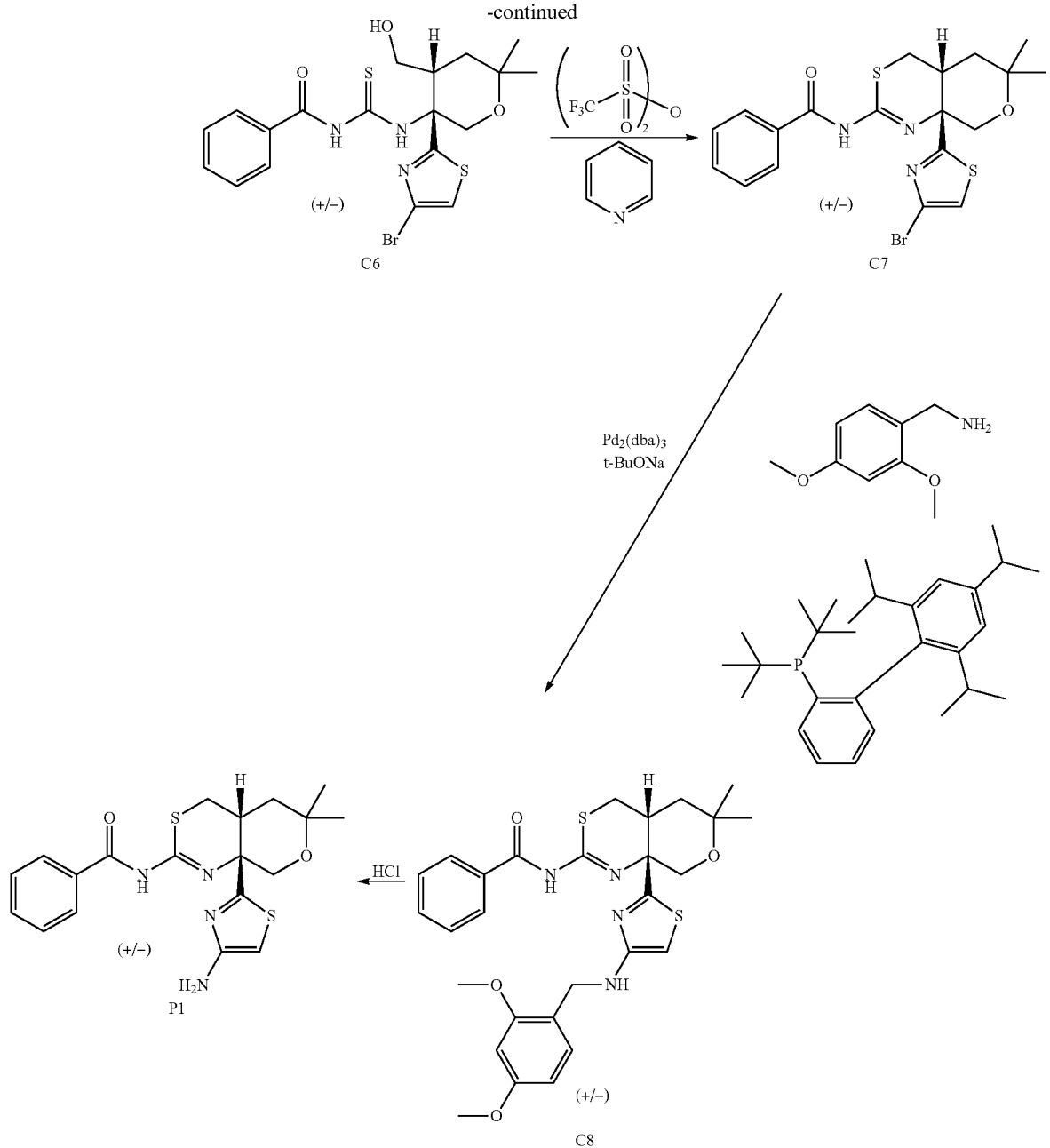

Step 1. Synthesis of 4-(2,2-diethoxyethoxy)-4-methylpent-1-ene (C1)

2-Methylpent-4-en-2-ol (89 g, 0.89 mol) was added dropwise to a suspension of sodium hydride (60% in mineral oil; 107 g, 2.67 mol) in tetrahydrofuran (1.5 L). The reaction mixture was stirred for 45 minutes at room temperature, whereupon 2-bromo-1,1-diethoxyethane (90%, 292 g, 1.33 mol) was slowly added. After the reaction mixture had been heated at reflux for 36 hours, it was poured into ice water (2 L) and extracted with ethyl acetate (3×1 L). The combined organic layers were washed with saturated aqueous sodium chloride solution (2×1.5 L), dried over sodium sulfate, filtered, and concentrated in vacuo. Purification via chromatography on alumina (Eluent: petroleum ether) afforded the product as a yellow oil. By $^1$H NMR, this material contained a significant percentage of 2-bromo-1,1-diethoxyethane; half of this material was taken directly to the following step.
$^1$H NMR (400 MHz, CDCl$_3$), characteristic product peaks: δ 5.92-5.78 (m, 1H), 5.06 (s, 1H), 5.05-5.01 (m, 1H), 4.68 (t, J=5.5 Hz, 1H), 3.43 (d, J=5.3 Hz, 2H), 2.24 (br d, J=7.3 Hz, 2H).

Step 2. Synthesis of N-hydroxy-2-[(2-methylpent-4-en-2-yl)oxy]ethanimine (C2)

To a solution of C1 (from the previous step; 85.0 g, ≤445 mmol) in ethanol (1.4 L) and water (700 mL) was added hydroxylamine hydrochloride (81.9 g, 1.18 mol) at room temperature. The reaction mixture was stirred at 50° C. for 15 hours, whereupon it was extracted with dichloromethane (2×100 mL). The combined organic layers were washed with saturated aqueous sodium chloride solution (2×1 L), dried over sodium sulfate, filtered, and concentrated in vacuo. Silica gel chromatography (Gradient: 0% to 10% ethyl acetate in petroleum ether) provided the product as a colorless oil. By $^1$H NMR, this product was somewhat impure, and consisted of a mixture of geometric isomers around the oxime. Yield: 40.0 g, <254 mmol, <57% over 2 steps. $^1$H NMR (400 MHz, CDCl$_3$), product peaks only: δ [7.47 (t, J=5.4 Hz) and 6.88 (t, J=3.4 Hz), total 1H], 5.90-5.76 (m, 1H), 5.09 (br s, 1H), 5.08-5.03 (m, 1H), [4.31 (d, J=3.6 Hz) and 4.05 (d, J=5.5 Hz), total 2H], 2.27 (d, J=7.2 Hz, 2H), 1.19 (s, 6H).

Step 3. Synthesis of 5,5-dimethyl-3,3a,4,5-tetrahydro-7H-pyrano[3,4-c][1,2]oxazole (C3)

Triethylamine (1.93 g, 19.1 mmol) was added to a solution of C2 (40.0 g, 254 mmol) in dichloromethane (1.2 L) at room temperature (~15° C.). Aqueous sodium hypochlorite solution (5%, 1.2 L) was then slowly added via syringe while the internal reaction temperature was maintained between 22° C. and 25° C. After completion of the addition, the organic layer of the reaction was washed with saturated aqueous sodium chloride solution (2×500 mL), dried over sodium sulfate, filtered, and concentrated in vacuo. Silica gel chromatography (Gradient: 0% to 10% ethyl acetate in petroleum ether) afforded the product as a colorless oil. Yield: 18 g, 120 mmol, 47%. LCMS m/z 155.7 [M+H]$^+$. $^1$H NMR (400 MHz, CDCl$_3$) δ 4.59 (dd, J=9.9, 7.9 Hz, 1H), 4.52 (d, half of AB quartet, J=14.0 Hz, 1H), 4.36 (br dd, half of ABX pattern, J=14.0, 0.8 Hz, 1H), 3.75 (dd, J=11.6, 7.8 Hz, 1H), 3.62-3.50 (m, 1H), 2.05 (dd, J=13.0, 6.3 Hz, 1H), 1.61 (dd, J=12, 12 Hz, 1H), 1.33 (s, 3H), 1.28 (s, 3H).

Step 4. Synthesis of cis-7a-(4-bromo-1,3-thiazol-2-yl)-5,5-dimethylhexahydro-1H-pyrano[3,4-c][1,2]oxazole (C4)

Boron trifluoride diethyl etherate (12.9 mL, 102 mmol) was added to a −70° C. solution of 2,4-dibromo-1,3-thiazole (26.0 g, 107 mmol) in toluene (360 mL) and tetrahydrofuran (36 mL). n-Butyllithium (2.5 M solution in hexanes; 40 mL, 100 mmol) was then added slowly, and stirring was continued for 30 minutes at −70° C., whereupon a solution of C3 (12.8 g, 82.5 mmol) in toluene (40 mL) and tetrahydrofuran (4 mL) was added drop-wise. After an additional 15 minutes at −70° C., the reaction was quenched, still at −70° C., via addition of saturated aqueous ammonium chloride solution (200 mL). The resulting mixture was extracted with ethyl acetate (2×200 mL), and the combined organic layers were washed with saturated aqueous sodium chloride solution (2×200 mL), dried over sodium sulfate, filtered, and concentrated in vacuo. Silica gel chromatography (Gradient: 0% to 15% ethyl acetate in petroleum ether) provided the product as a yellow solid. Yield: 9.8 g, 31 mmol, 38%. $^1$H NMR (400 MHz, CDCl$_3$) δ 7.21 (s, 1H), 6.42 (br s, 1H), 4.10 (d, J=13.2 Hz, 1H), 3.80-3.68 (m, 3H), 3.47-3.35 (m, 1H), 1.76 (dd, J=14, 6.5 Hz, 1H), 1.66-1.51 (m, 1H, assumed; partially obscured by water peak), 1.42 (s, 3H), 1.31 (s, 3H).

Step 5. Synthesis of [rel-(4R,5R)-5-amino-5-(4-bromo-1,3-thiazol-2-yl)-2,2-dimethyltetrahydro-2H-pyran-4-yl]methanol (C5)

Molybdenum hexacarbonyl (5.71 g, 21.6 mmol) was added to a solution of C4 (13.8 g, 43.2 mmol) in acetonitrile (300 mL) and water (15 mL), and the reaction mixture was heated at reflux for 1 hour. It was then cooled to 0° C., and treated portion-wise with sodium borohydride (3.27 g, 86.4 mmol). After completion of the addition, the reaction mixture was warmed to 60° C. and stirred for 1 hour, whereupon it was filtered. The filtrate was concentrated under reduced pressure, and the residue was treated with methanol (200 mL). This mixture was again concentrated in vacuo, treated once more with methanol (200 mL), and concentrated again. The residue was dissolved in dichloromethane (300 mL), washed sequentially with aqueous sodium hydroxide solution (1 M, 2×250 mL) and saturated aqueous sodium chloride solution (2×300 mL), dried over sodium sulfate, filtered, and concentrated in vacuo to afford the product (13.9 g) as a brown solid, which was used directly in the next step.

Step 6. Synthesis of N-{[rel-(3R,4R)-3-(4-bromo-1,3-thiazol-2-yl)-4-(hydroxymethyl)-6,6-dimethyltetrahydro-2H-pyran-3-yl]carbamothioyl}benzamide (C6)

To a room temperature (15° C.) solution of C5 (from the previous step; 13.9 g, ≤43.2 mmol) in dichloromethane (300 mL) was added benzoyl isothiocyanate (9.18 g, 56.3 mmol), and the reaction mixture was stirred overnight at room temperature. After removal of solvent in vacuo, the residue was recrystallized from dichloromethane/petroleum ether (5:1) to provide the product as a brown solid. Yield: 12.0 g, 24.8 mmol, 57% over 2 steps. LCMS m/z 483.8 [M+H]$^+$. $^1$H NMR (400 MHz, CDCl$_3$) δ 11.76 (br s, 1H), 8.95 (br s, 1H), 7.92-7.86 (m, 2H), 7.68-7.62 (m, 1H), 7.54 (br dd, J=8.0, 7.4 Hz, 2H), 7.28 (s, 1H), 5.05 (d, J=12.4 Hz, 1H), 4.07 (d, J=12.3 Hz, 1H), 3.88-3.82 (m, 2H), 2.67-2.59 (m, 1H), 2.46-2.36 (m, 1H), 2.01 (dd, J=13.8, 13.8 Hz, 1H), 1.69 (dd, J=14.1, 3.7 Hz, 1H), 1.39 (s, 3H), 1.39 (s, 3H).

Step 7. Synthesis of N-[cis-8a-(4-bromo-1,3-thiazol-2-yl)-6,6-dimethyl-4,4a,5,6,8,8a-hexahydropyrano[3,4-d][1,3]thiazin-2-yl]benzamide (C7)

Pyridine (100 mL) was added to a solution of C6 (10.0 g, 20.6 mmol) in dichloromethane (200 mL), and the mixture was cooled to −30° C. Trifluoromethanesulfonic anhydride (17.5 g, 62.0 mmol) was slowly added; on completion of the addition, the reaction mixture was warmed to 0° C. over 10 minutes, and then poured into saturated aqueous ammonium chloride solution (300 mL). The resulting mixture was extracted with dichloromethane (3×200 mL), and the combined organic layers were washed sequentially with water (3×200 mL) and saturated aqueous sodium chloride solution (2×300 mL), dried over sodium sulfate, filtered, and concentrated in vacuo to afford the product as a yellow solid. Yield: 9.0 g, 19 mmol, 92%. $^1$H NMR (400 MHz, CDCl$_3$) δ 8.15-8.02 (m, 2H), 7.59-7.51 (m, 1H), 7.51-7.41 (m, 2H), 7.23 (s, 1H), 4.15 (d, J=12 Hz, 1H), 3.71 (d, J=12 Hz, 1H), 3.28-3.12 (m, 2H), 2.62-2.52 (m, 1H), 2.09-1.96 (m, 1H), 1.6-1.48 (m, 1H, assumed; partially obscured by water peak), 1.45 (s, 3H), 1.32 (s, 3H).

Step 8. Synthesis of N-[cis-8a-{4-[(2,4-dimethoxybenzyl)amino]-1,3-thiazol-2-yl}-6,6-dimethyl-4,4a,5,6,8,8a-hexahydropyrano[3,4-d][1,3]thiazin-2-yl]benzamide (C8)

A mixture of tris(dibenzylideneacetone)dipalladium(0) (1.12 g, 1.22 mmol), di-tert-butyl[2',4',6'-tri(propan-2-yl)biphenyl-2-yl]phosphane (1.56 g, 3.67 mmol), and sodium tert-butoxide (2.90 g, 30.2 mmol) in 1,4-dioxane (100 mL)

was stirred in a 95° C. bath for 12 minutes, until the internal reaction temperature reached 87° C. to 88° C. A solution of C7 (5.70 g, 12.2 mmol) and 1-(2,4-dimethoxyphenyl)methanamine (4.09 g, 24.5 mmol) in 1,4-dioxane (100 mL) was then added in one portion, and the reaction mixture was stirred for 1.5 hours at an internal temperature of 88° C. to 92° C. After removal of solvent in vacuo, the residue was purified by silica gel chromatography (Gradient: 15% to 50% ethyl acetate in petroleum ether) to provide the product as a yellow solid. Yield: 4.40 g, 7.96 mmol, 65%. LCMS m/z 553.1 [M+H]$^+$.

Step 9. Synthesis of N-[cis-8a-(4-amino-1,3-thiazol-2-yl)-6,6-dimethyl-4,4a,5,6,8,8a-hexahydropyrano[3,4-d][1,3]thiazin-2-yl]benzamide (P1)

Concentrated hydrochloric acid (25 mL) was slowly added to an 8° C. solution of C8 (4.40 g, 7.96 mmol) in ethyl acetate (20 mL); once the addition was complete, the reaction mixture was warmed to room temperature (20° C.) and stirred for 4 hours. It was then poured into water (120 mL) and extracted with dichloromethane (3×150 mL). The combined organic layers were extracted with aqueous hydrochloric acid (2.5 M, 3×50 mL), and the combined acidic aqueous layers were slowly poured into aqueous sodium hydroxide solution (5 M, 150 mL) at 0° C. This resulted in a final pH of approximately 11-12. The aqueous solution was saturated with solid sodium chloride and then extracted with dichloromethane (3×200 mL). These three dichloromethane layers were combined and washed sequentially with aqueous citric acid solution (4.5% by weight, 2×80 mL), saturated aqueous sodium bicarbonate solution (200 mL), and saturated aqueous sodium chloride solution (200 mL), dried over sodium sulfate, filtered, and concentrated in vacuo, affording the product as a yellow solid. Yield: 2.5 g, 6.2 mmol, 78%. LCMS m/z 402.9 [M+H]$^+$. $^1$H NMR (400 MHz, CDCl$_3$) δ 8.26-8.08 (m, 2H), 7.56-7.48 (m, 1H), 7.48-7.41 (m, 2H), 5.94 (s, 1H), 4.17 (d, J=12.6 Hz, 1H), 4.07 (br s, 2H), 3.70 (d, J=12.6 Hz, 1H), 3.25 (dd, J=13, 4 Hz, 1H), 3.16 (br d, J=13 Hz, 1H), 2.54 (dd, J=12.9, 2.1 Hz, 1H), 2.04 (dd, J=13, 13 Hz, 1H), 1.49 (dd, J=13.7, 4.0 Hz, 1H), 1.44 (s, 3H), 1.32 (s, 3H).

Preparation P2

N-[(4aR,8aR)-8a-(4-Amino-1,3-thiazol-2-yl)-6,6-dimethyl-4,4a, 5,6,8,8a-hexahydropyrano[3,4-d]1,3]thiazin-2-yl benzamide (P2)

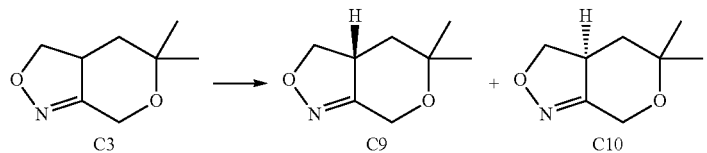

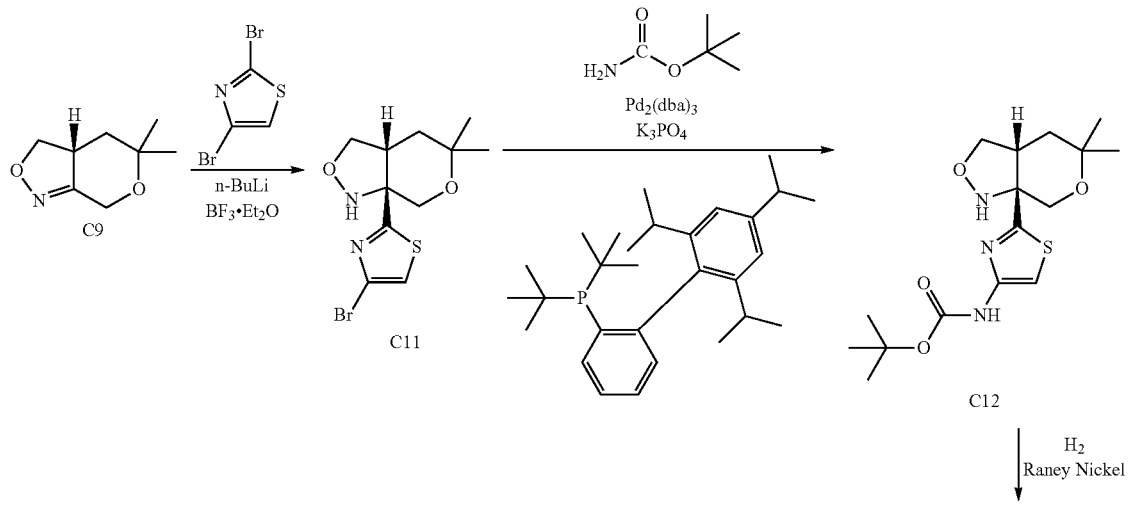

-continued

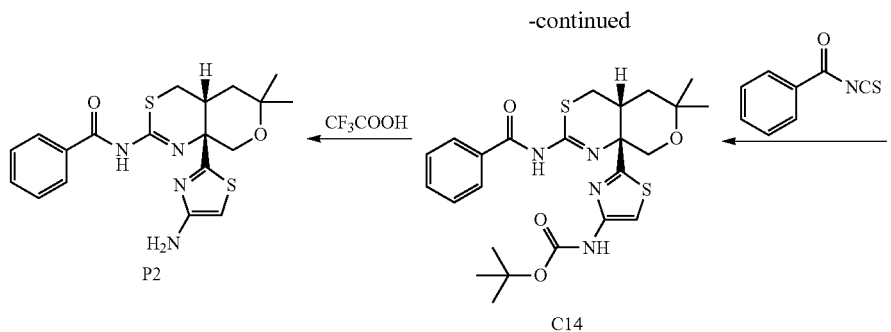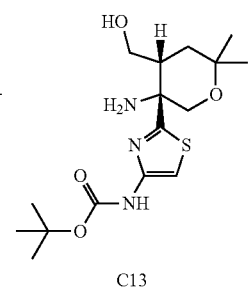

Step 1. Isolation of (3aR)-5,5-dimethyl-3,3a,4,5-tetrahydro-7H-pyrano[3,4-c][1,2]oxazole (C9) and (3aS)-5,5-dimethyl-3,3a,4,5-tetrahydro-7H-pyrano[3,4-c][1,2]oxazole (C10)

Separation of C3 (710 g) into its component enantiomers was carried out via supercritical fluid chromatography (Column: Chiral Technologies Chiralpak IC, 10 μm; Mobile phase: 7:3 carbon dioxide/2-propanol). Compound C9 was the first-eluting enantiomer from the column, isolated as a brown solid. Yield: 270 g, 38% for the isolation. Compound C10 was the second-eluting enantiomer from the column, also isolated as a brown solid. Yield: 270 g, 38% for the isolation.

The indicated absolute stereochemistry for these two products was assigned on the following basis. Compound C9 was used in the synthesis of 2 (note use of P2 in Alternate Synthesis of Example 2 below); this material was correlated with the more potent enantiomer from Examples 1 and 2 below via its biological activity. The absolute configuration of the potent enantiomer, and thereby C9, was assigned in analogy with the work reported by C. R. Butler et al., *J. Med. Chem.* 2015, 58, 2678-2702, and M. A. Brodney, *J. Med. Chem.* 2015, 58, 3223-3252.

C9: LCMS m/z 155.8 [M+H]$^+$. $^1$H NMR (400 MHz, CDCl$_3$) δ 4.59 (dd, J=9.9, 7.9 Hz, 1H), 4.51 (d, half of AB quartet, J=14.0 Hz, 1H), 4.36 (dd, half of ABX pattern, J=14.0, 1.2 Hz, 1H), 3.74 (dd, J=11.6, 7.8 Hz, 1H), 3.62-3.49 (m, 1H), 2.05 (dd, J=12.9, 6.3 Hz, 1H), 1.60 (dd, J=12.4, 12.3 Hz, 1H), 1.33 (s, 3H), 1.28 (s, 3H).

C10: LCMS m/z 155.8 [M+H]$^+$. $^1$H NMR (400 MHz, CDCl$_3$) δ 4.60 (dd, J=10.0, 7.8 Hz, 1H), 4.52 (d, half of AB quartet, J=14.0 Hz, 1H), 4.36 (dd, half of AB quartet, J=14.0, 1.4 Hz, 1H), 3.75 (dd, J=11.6, 7.8 Hz, 1H), 3.63-3.49 (m, 1H), 2.06 (dd, J=12.8, 6.3 Hz, 1H), 1.61 (dd, J=12.3, 12.3 Hz, 1H), 1.34 (s, 3H), 1.28 (s, 3H).

Step 2. Synthesis of (3aR,7aR)-7a-(4-bromo-1,3-thiazol-2-yl)-5,5-dimethylhexahydro-1H-pyrano[3,4-c][1,2]oxazole (C11)

Boron trifluoride diethyl etherate (3.00 mL, 23.7 mmol) was added to a −65° C. slurry of 2,4-dibromo-1,3-thiazole (5.63 g, 23.2 mmol) in toluene (50 mL). n-Butyllithium (2.5 M solution in hexanes; 10 mL, 25 mmol) was then slowly added, and the reaction mixture was allowed to stir at −65° C. for 10 minutes. A solution of C9 (3.0 g, 19 mmol) in tetrahydrofuran (5 mL) was added drop-wise, and stirring was continued for 30 minutes at −65° C., whereupon the reaction was quenched via addition of saturated aqueous ammonium chloride solution (150 mL) and the mixture was warmed to −10° C. to 0° C. The aqueous layer was extracted with ethyl acetate (2×100 mL), and the combined organic layers were washed with saturated aqueous sodium chloride solution (2×100 mL), dried over sodium sulfate, filtered, and concentrated in vacuo. Silica gel chromatography (Gradient: 0% to 10% ethyl acetate in petroleum ether) afforded the product as a yellow solid. Yield: 4.3 g, 13 mmol, 68%. $^1$H NMR (400 MHz, CDCl$_3$) δ 7.21 (s, 1H), 6.42 (s, 1H), 4.09 (d, J=13.0 Hz, 1H), 3.79-3.68 (m, 3H), 3.47-3.36 (m, 1H), 1.76 (dd, J=14.0, 6.6 Hz, 1H), 1.57 (br dd, J=13, 13 Hz, 1H), 1.42 (s, 3H), 1.30 (s, 3H).

Step 3. Synthesis of tert-butyl {2-[(3aR,7aR)-5,5-dimethyltetrahydro-1H-pyrano[3,4-c][1,2]oxazol-7a(7H)-yl]-1,3-thiazol-4-yl}carbamate (C12)

A mixture of C11 (4.30 g, 13.5 mmol), tert-butyl carbamate (2.37 g, 20.2 mmol), potassium phosphate (10 g, 47 mmol), tris(dibenzylideneacetone)dipalladium(0) (2.47 g, 2.70 mmol), and di-tert-butyl[2',4',6'-tri(propan-2-yl)biphenyl-2-yl]phosphane (572 mg, 1.35 mmol) in toluene (100 mL) was stirred at 115° C. for 18 hours. After the reaction mixture had cooled to room temperature, it was filtered through diatomaceous earth; the filter pad was washed with ethyl acetate (200 mL), and the combined filtrates were concentrated under reduced pressure. Chromatography on silica gel (Gradient: 0% to 25% ethyl acetate in petroleum ether) provided the product as a yellow foam. Yield: 2.95 g, 8.30 mmol, 61%. $^1$H NMR (400 MHz, CDCl$_3$), characteristic peaks: δ 7.24 (br s, 1H), 7.15 (brs, 1H), 6.36 (s, 1H), 4.03 (d, J=13.0 Hz, 1H), 3.79-3.69 (m, 3H), 3.33-3.23 (m, 1H), 1.72 (dd, half of ABX pattern, J=13.9, 6.5 Hz, 1H), 1.52 (s, 9H), 1.38 (s, 3H), 1.30 (s, 3H).

Step 4. Synthesis of tert-butyl {2-[(3R,4R)-3-amino-4-(hydroxymethyl)-6,6-dimethyltetrahydro-2H-pyran-3-yl]-1,3-thiazol-4-yl}carbamate (C13)

Raney nickel (1.94 g, 33.0 mmol) was added to a solution of C12 (4.70 g, 13.2 mmol) in 2-propanol (30 mL) and tetrahydrofuran (30 mL). The resulting mixture was subjected to three cycles of degassing and being charged with hydrogen, and then stirred at 50° C. under a hydrogen balloon for 4 hours. After the reaction mixture had cooled to room temperature, it was combined with a similar reaction mixture carried out using C12 (2.0 g, 5.6 mmol) and filtered through a pad of diatomaceous earth. The filter cake was washed with ethyl acetate (200 mL), and the combined filtrates were concentrated in vacuo to provide the product as a yellow gum. Yield: 6.8 g, 19 mmol, quantitative. LCMS m/z 358.1 [M+H]$^+$.

Step 5. Synthesis of tert-butyl {2-[(4aR,8aR)-2-(benzoylamino)-6,6-dimethyl-4,4a,5,6-tetrahydropyrano[3,4-d][1,3]thiazin-8a(8H)-yl]-1,3-thiazol-4-yl}carbamate (C14)

Benzoyl isothiocyanate (8.0 g, 49 mmol) was added in one portion to a solution of C13 (5.50 g, 15.4 mmol) in ethyl acetate (80 mL), and the reaction mixture was stirred at room temperature for 2 hours. It was then slowly warmed to 90° C. and stirred at that temperature for 16 hours. After cooling to room temperature, the reaction mixture was concentrated in vacuo and subjected to two chromatographic purifications on silica gel (Column #1 gradient: 0% to 100% ethyl acetate in petroleum ether; Column #2 gradients: 0% to 15% ethyl acetate in petroleum ether, followed by 0% to 10% ethyl acetate in dichloromethane) to afford the product as a pale yellow solid (2.7 g). Mixed fractions were rechromatographed on silica gel (Gradient: 0% to 10% ethyl acetate in dichloromethane) to provide additional product as a pale yellow solid (2.0 g). Combined yield: 4.70 g, 9.35 mmol, 61%. LCMS m/z 525.2 [M+Na⁺]. ¹H NMR (400 MHz, CDCl₃) δ 8.19-8.08 (m, 2H), 7.56-7.50 (m, 1H), 7.45 (br dd, J=7.8, 7.3 Hz, 2H), 7.18 (br s, 1H), 4.11 (d, J=12.3 Hz, 1H), 3.71 (d, J=12.3 Hz, 1H), 3.18 (dd, J=12.8, 4.3 Hz, 1H), 3.12-3.03 (m, 1H), 2.54 (dd, J=12.9, 2.4 Hz, 1H), 2.04 (dd, J=13.6, 13.4 Hz, 1H), 1.52 (s, 9H), 1.52-1.46 (m, 1H), 1.42 (s, 3H), 1.32 (s, 3H).

Step 6. Synthesis of N-[(4aR,8aR)-8a-(4-amino-1,3-thiazol-2-yl)-6,6-dimethyl-4,4a,5,6,8,8a-hexahydropyrano[3,4-d][1,3]thiazin-2-yl]benzamide (P2)

To a solution of C14 (535 mg, 1.06 mmol) in dichloromethane (4 mL) was added trifluoroacetic acid (3 mL). The reaction mixture was stirred at 45° C. for 25 minutes, whereupon it was diluted with dichloromethane (30 mL) and poured into saturated aqueous sodium bicarbonate solution (60 mL) at room temperature. The resulting mixture was stirred for 5 minutes, and the aqueous phase (pH 8) was extracted with dichloromethane (3×30 mL). The combined organic layers were dried over sodium sulfate, filtered, and concentrated in vacuo. The residue was treated with a mixture of ethyl acetate and dichloromethane (1:1, 4 mL), stirred at room temperature for 10 minutes, and left standing at room temperature overnight. The solid was collected via filtration, afforded the product as a pale yellow solid. Yield: 360 mg, 0.894 mmol, 84%. LCMS m/z 403.2 [M+H]⁺.

Preparation P3

N-[(4aR,8aR)-8a-{4-[(2,4-Dimethoxybenzyl)amino]-1,3-thiazol-2-yl}-6,6-dimethyl-4,4a, 5,6,8,8a-hexahydropyrano[3,4-d][1,3]thiazin-2-yl]benzamide (P3)

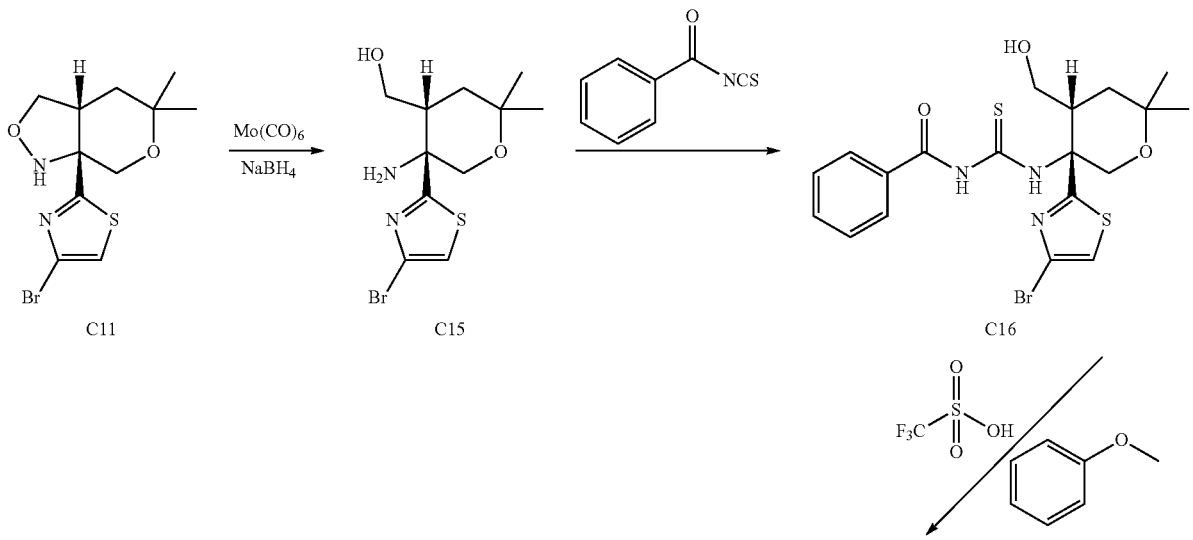

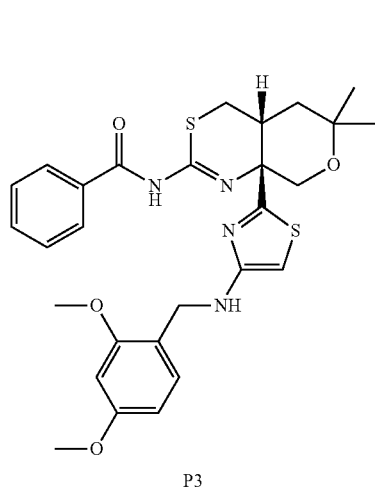

P3

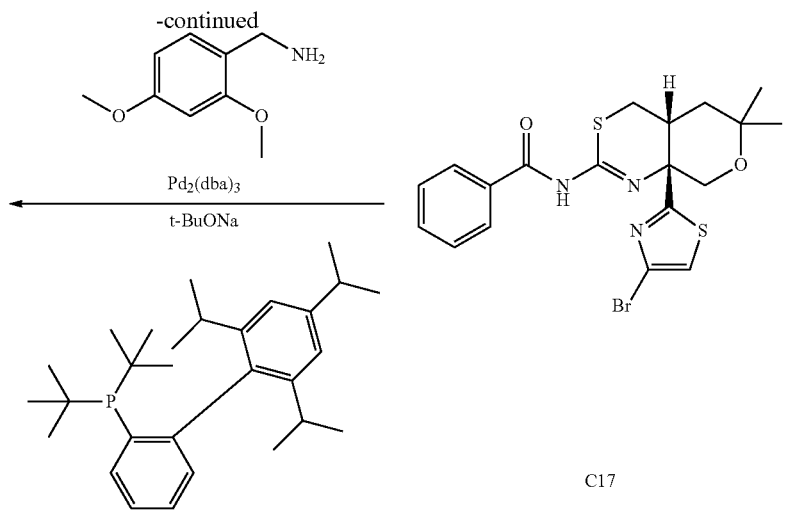

C17

Step 1. Synthesis of [(4R,5R)-5-amino-5-(4-bromo-1,3-thiazol-2-yl)-2,2-dimethyltetrahydro-2H-pyran-4-yl]methanol (C15)

Molybdenum hexacarbonyl (98%, 16.8 g, 62.4 mmol) was added to a solution of C11 (39.76 g, 124.6 mmol) in a mixture of acetonitrile and water (20:1, 1 L). The reaction mixture was heated to reflux in a preheated oil bath (100° C.) for 2 hours, whereupon it was cooled to room temperature and cooled in an ice bath. Sodium borohydride (9.42 g, 249 mmol) was added portion-wise, and stirring was continued for 1 hour at 0° C. The mixture was then filtered through diatomaceous earth, and the filter pad was washed three times with dichloromethane; the combined organic filtrates were washed with saturated aqueous sodium chloride solution, dried over sodium sulfate, filtered, and concentrated in vacuo. After addition of methanol to the residue, the mixture was concentrated under reduced pressure. This methanol treatment and concentration was repeated, and the resulting material was dissolved in dichloromethane and washed twice with 1 M aqueous sodium hydroxide solution, once with saturated aqueous sodium chloride solution, and concentrated in vacuo, providing the product as a light brown solid, which was used directly in the following step. $^1$H NMR (400 MHz, CDCl$_3$) δ 7.20 (s, 1H), 3.98 (d, J=11.8 Hz, 1H), 3.69 (dd, J=11.4, 3.6 Hz, 1H), 3.48 (dd, J=11.4, 4.0 Hz, 1H), 3.30 (d, J=11.8 Hz, 1H), 2.57 (dddd, J=13.4, 3.8, 3.8, 3.8 Hz, 1H), 2.6-2.2 (br s, 2H), 1.97 (dd, J=13.8, 13.7 Hz, 1H), 1.55 (dd, J=13.9, 4.0 Hz, 1H, assumed; partially obscured by water peak), 1.37 (s, 3H), 1.36 (s, 3H).

Step 2. Synthesis of N-{[(3R,4R)-3-(4-bromo-1,3-thiazol-2-yl)-4-(hydroxymethyl)-6,6-dimethyltetrahydro-2H-pyran-3-yl]carbamothioyl}benzamide (C16)

Benzoyl isothiocyanate (16.7 mL, 124 mmol) was added to a solution of C15 (material from the preceding step; ≤124.6 mmol) in dichloromethane (1.25 L), and the reaction mixture was stirred at room temperature overnight. After the reaction mixture had been concentrated in vacuo, chromatography on silica gel (Gradient: 0% to 100% ethyl acetate in heptane) afforded the product as a pale yellow foam (40.6 g).

Somewhat impure C15 (8.0 g) was also recovered from the column. Yield: 40.6 g, 84.3 mmol, 68% over 2 steps. LCMS m/z 484.2 [M+H]$^+$. $^1$H NMR (400 MHz, CDCl$_3$) δ 11.74 (br s, 1H), 8.91 (br s, 1H), 7.91-7.85 (m, 2H), 7.68-7.62 (m, 1H), 7.57-7.50 (m, 2H), 7.26 (s, 1H), 5.04 (d, J=12.3 Hz, 1H), 4.07 (d, J=12.3 Hz, 1H), 3.85 (dd, J=5.9, 4.6 Hz, 2H), 2.63 (dddd, J=13, 4, 4, 4 Hz, 1H), 2.32 (t, J=6.0 Hz, 1H), 2.00 (dd, J=13.8, 13.8 Hz, 1H), 1.68 (dd, J=14.1, 3.9 Hz, 1H), 1.39 (s, 3H), 1.38 (s, 3H).

Step 3. Synthesis of N-[(4aR,8aR)-8a-(4-bromo-1,3-thiazol-2-yl)-6,6-dimethyl-4,4a,5,6,8,8a-hexahydropyrano[3,4-d][1,3]thiazin-2-yl]benzamide (C17)

Trifluoromethanesulfonic acid (11.6 mL, 131 mmol) was rapidly added to a solution of C16 (21.54 g, 44.46 mmol) in 1,2-dichloroethane (300 mL) and methoxybenzene (14.5 mL, 133 mmol), and the reaction mixture was stirred at room temperature for 30 minutes. It was then diluted with dichloromethane and basified via addition of 1 M aqueous sodium hydroxide solution. The aqueous layer was extracted three times with dichloromethane, and the combined dichloromethane layers were washed with saturated aqueous sodium chloride solution, dried over sodium sulfate, filtered, and concentrated in vacuo. The residue was triturated in heptane for 30 minutes to provide the product as a white solid. Yield: 18.18 g, 39.06 mmol, 88%. LCMS m/z 466.3, 468.2 [M+H]$^+$. $^1$H NMR (400 MHz, CD$_3$OD) δ 8.15-7.95 (br m, 2H), 7.61-7.53 (m, 2H), 7.52-7.44 (m, 2H), 4.15 (d, J=11.9 Hz, 1H), 3.75 (br d, J=11.8 Hz, 1H), 3.20-3.10 (m, 1H), 3.04 (dd, J=13.2, 4.2 Hz, 1H), 2.67 (br dd, J=13, 2.5 Hz, 1H), 1.93 (dd, J=13.4, 13.3 Hz, 1H), 1.61 (dd, J=13.7, 4.0 Hz, 1H), 1.46 (s, 3H), 1.30 (s, 3H).

Step 4. Synthesis of N-[(4aR,8aR)-8a-{4-[(2,4-dimethoxybenzyl)amino]-1,3-thiazol-2-yl}-6,6-dimethyl-4,4a,5,6,8,8a-hexahydropyrano[3,4-d][1,3]thiazin-2-yl]benzamide (P3)

A mixture of tris(dibenzylideneacetone)dipalladium(0) (96%, 2.07 g, 2.17 mmol), di-tert-butyl[2',4',6'-tri(propan-2-yl)biphenyl-2-yl]phosphane (2.77 g, 6.52 mmol), and sodium tert-butoxide (10.5 g, 109 mmol) in 1,4-dioxane (150 mL) was subjected to three cycles of evacuation followed by nitrogen fill; the resulting solution was heated at an internal temperature of 85° C. to 90° C. (bath temperature 100° C.) for 5 minutes. A solution of C17 (20.29 g, 43.50 mmol) and 1-(2,4-dimethoxyphenyl)methanamine (11.1 mL, 73.9 mmol) in 1,4-dioxane (48 mL) was added, and the reaction mixture was heated at an internal temperature of approximately 90° C. for 10 minutes, whereupon it was cooled and partitioned between saturated aqueous sodium bicarbonate solution and dichloromethane. The aqueous layer was extracted twice with dichloromethane, and the combined organic layers were washed with saturated aqueous sodium chloride solution, dried over sodium sulfate, filtered, and concentrated in vacuo. Silica gel chromatography (Eluent: 1:1 ethyl acetate/heptane) afforded the product as an amber foam. By $^1$H NMR, this material contained a small amount of ethyl acetate. Yield: 25.0 g, quantitative. LCMS m/z 553.2 [M+H]$^+$. $^1$H NMR (400 MHz, CDCl$_3$), characteristic peaks: δ 8.17 (br d, J=7.5 Hz, 2H), 7.55-7.48 (m, 1H), 7.47-7.41 (m, 2H), 7.21 (d, J=8.2 Hz, 1H), 6.48 (d, half of AB quartet, J=2.4 Hz, 1H), 6.45 (dd, half of ABX pattern, J=8.3, 2.4 Hz, 1H), 5.73 (s, 1H), 4.21 (brs, 2H), 4.17 (d, J=12.6 Hz, 1H), 3.85 (s, 3H), 3.81 (s, 3H), 3.26 (dd, J=12.9, 4.2 Hz, 1H), 3.19-3.12 (m, 1H), 2.52 (dd, J=12.9, 2.7 Hz, 1H), 2.05 (dd, J=13.5, 13.4 Hz, 1H), 1.48 (dd, J=13.8, 4.2 Hz, 1H), 1.42 (s, 3H), 1.31 (s, 3H).

Preparation P4

N-[cis-8a'-{4-[(2,4-Dimethoxybenzyl)amino]-1,3-thiazol-2-yl}-4a',5,8,8a'-tetrahydro-4'H-spiro[cyclobutane-1,6'-pyrano[3,4-d][1,3]thiazin]-2'-yl]benzamide (P4)

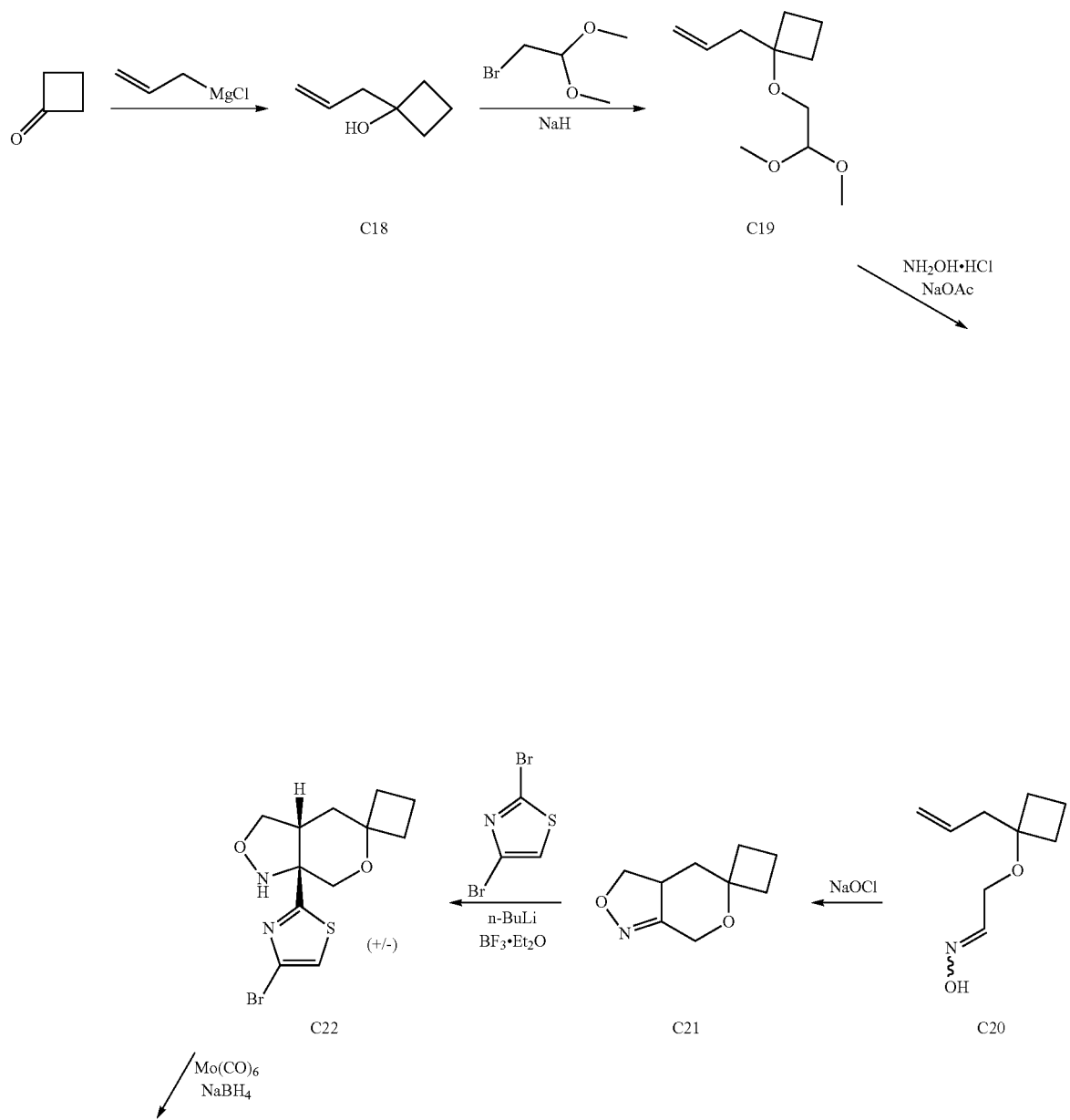

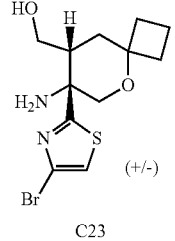 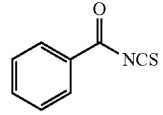 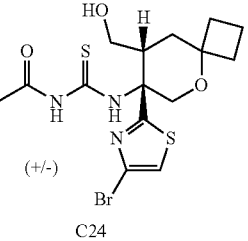 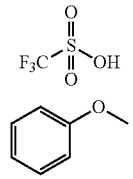 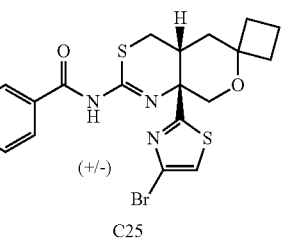

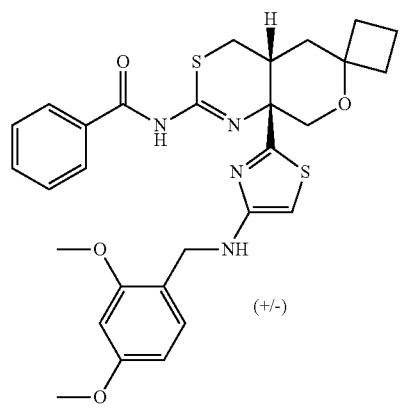

Step 1. Synthesis of 1-(prop-2-en-1-yl)cyclobutanol (C18)

Allylmagnesium chloride (2.0 M solution in tetrahydrofuran; 85.6 mL, 171 mmol) was added in a drop-wise manner to a 0° C. solution of cyclobutanone (6.00 g, 85.6 mmol) in tetrahydrofuran (60 mL). The reaction mixture was stirred at 0° C. for 1 hour and then at room temperature for 1 hour, whereupon saturated aqueous ammonium chloride solution (150 mL) was added, followed by aqueous hydrochloric acid (6 M, 25 mL). The resulting mixture was extracted with ethyl acetate (3×100 mL), and the combined organic layers were washed with saturated aqueous sodium bicarbonate solution (3×150 mL) until a basic pH was observed for the aqueous layer. The organic layer was washed with saturated aqueous sodium chloride solution (150 mL), dried over sodium sulfate, filtered, concentrated in vacuo, and adsorbed onto silica gel. Chromatography on silica gel (Gradient: 0% to 60% ethyl acetate in heptane) provided the product as a colorless oil. Yield: 5.13 g, 45.7 mmol, 53%. $^1$H NMR (400 MHz, CDCl$_3$) δ 5.94-5.83 (m, 1H), 5.22-5.20 (m, 1H), 5.20-5.16 (m, 1H), 2.39 (br d, J=7.2 Hz, 2H), 2.10-2.04 (m, 4H), 1.81-1.71 (m, 1H), 1.61-1.49 (m, 1H).

Step 2. Synthesis of 1-(2,2-dimethoxyethoxy)-1-(prop-2-en-1-yl)cyclobutane (C19)

To a suspension of sodium hydride (60% in mineral oil; 3.84 g, 96.0 mmol) in 1,4-dioxane (60 mL) was added C18 (5.13 g, 45.7 mmol) in a drop-wise manner. After the reaction mixture had been stirred for 45 minutes at room temperature, 2-bromo-1,1-dimethoxyethane (10.8 mL, 91.4 mmol) was slowly added, and the reaction mixture was heated at 100° C. for 16 hours, whereupon it was cooled and poured into ice water (800 mL). The resulting mixture was extracted with ethyl acetate (3×150 mL), and the combined organic layers were washed with saturated aqueous sodium chloride solution (2×200 mL), dried over sodium sulfate, filtered, and concentrated in vacuo. Chromatography on silica gel (Gradient: 0% to 70% ethyl acetate in heptane) afforded the product as a colorless oil. Yield: 3.45 g, 17.2 mmol, 38%. $^1$H NMR (400 MHz, CDCl$_3$) δ 5.91-5.80 (m, 1H), 5.17-5.12 (m, 1H), 5.12-5.08 (m, 1H), 4.46 (t, J=5.2

Hz, 1H), 3.40 (s, 6H), 3.36 (d, J=5.2 Hz, 2H), 2.41 (br d, J=7.0 Hz, 2H), 2.17-2.07 (m, 2H), 1.97-1.89 (m, 2H), 1.80-1.70 (m, 1H), 1.61-1.48 (m, 1H).

Step 3. Synthesis of N-hydroxy-2-{[1-(prop-2-en-1-yl)cyclobutyl]oxy}ethanimine (C20)

Hydroxylamine hydrochloride (1.72 g, 24.8 mmol) was added to a solution of C19 (3.45 g, 17.2 mmol) in ethanol (28 mL) and water (5 mL). The reaction mixture was heated to 70° C. for 90 minutes, whereupon it was cooled to room temperature and treated with a solution of sodium acetate (97%, 2.91 g, 34.4 mmol) in water (5 mL). The resulting mixture was stirred at room temperature for 10 minutes and concentrated in vacuo; the residue was partitioned between dichloromethane (100 mL) and water (150 mL). The aqueous layer was extracted with dichloromethane (2×150 mL), and the combined organic layers were washed with saturated aqueous sodium chloride solution (300 mL), dried over sodium sulfate, filtered, and concentrated under reduced pressure to afford the product as a colorless oil. By $^1$H NMR, this material was judged to be a mixture of geometric isomers around the oxime. Yield: 2.72 g, 16.1 mmol, 94%. $^1$H NMR (400 MHz, CDCl$_3$) δ [7.49 (t, J=5.6 Hz) and 6.90 (br t, J=3 Hz), total 1H], 5.90-5.77 (m, 1H), 5.18-5.14 (m, 1H), 5.14-5.10 (m, 1H), [4.23 (br d, J=3.5 Hz) and 3.99 (d, J=5.5 Hz), total 2H], 2.43 (br d, J=7 Hz, 2H), 2.18-2.07 (m, 2H), 2.00-1.92 (m, 2H), 1.83-1.73 (m, 1H), 1.65-1.51 (m, 1H).

Step 4. Synthesis of 3a',4'-dihydro-3'H, 7'H-spiro[cyclobutane-1,5'-pyrano[3,4-c][1,2]oxazole] (C21)

Sodium hypochlorite solution (5.6-6%, 21.2 mL, 18 mmol) was added in a drop-wise manner to a solution of C20 (2.72 g, 16.1 mmol) in dichloromethane (76 mL) at an internal temperature of −10° C., at a rate such that the internal temperature of the reaction never rose above 0° C. After completion of the addition, the reaction mixture was stirred at −10° C. for 3 hours, whereupon it was allowed to warm slowly to room temperature over 16 hours. The reaction mixture was diluted with water (500 mL), and the aqueous layer was extracted with dichloromethane (2×250 mL). The combined organic layers were washed with saturated aqueous sodium chloride solution (500 mL), dried over sodium sulfate, filtered, and adsorbed onto silica gel. Chromatography on silica gel (Gradient: 0% to 80% ethyl acetate in heptane) provided the product as a colorless oil. Yield: 2.06 g, 12.3 mmol, 76%. $^1$H NMR (400 MHz, CDCl$_3$) δ 4.60 (dd, J=10.2, 7.9 Hz, 1H), 4.52 (d, J=13.6 Hz, 1H), 4.20 (dd, J=13.6, 1.3 Hz, 1H), 3.80 (dd, J=11.6, 7.9 Hz, 1H), 3.52-3.40 (m, 1H), 2.40 (dd, J=12.9, 6.3 Hz, 1H), 2.30-2.20 (m, 1H), 2.19-2.02 (m, 2H), 2.00-1.83 (m, 2H), 1.76-1.57 (m, 2H).

Step 5. Synthesis of cis-7a'-(4-bromo-1,3-thiazol-2-yl)tetrahydro-1'H, 3'H-spiro[cyclobutane-1,5'-pyrano[3,4-c][1,2]oxazole] (C22)

To a −76° C. (internal temperature) solution of 2,4-dibromo-1,3-thiazole (3.78 g, 15.6 mmol) in a mixture of toluene and tetrahydrofuran (10:1, 80 mL) was added boron trifluoride diethyl etherate (1.85 mL, 14.6 mmol), followed by drop-wise addition of n-butyllithium (2.5 M solution in hexanes; 5.74 mL, 14.4 mmol). The internal temperature of the reaction mixture was maintained below −70° C. throughout both of these additions. The reaction mixture was then stirred at −76° C. (internal temperature) for 30 minutes, whereupon a solution of C21 (2.0 g, 12.0 mmol) in a mixture of toluene and tetrahydrofuran (10:1, 6 mL) was added. Additional toluene/tetrahydrofuran (10:1, 6 mL) was used to rinse the C21 flask; this was also added to the reaction mixture. Stirring was continued at −76° C. for 1 hour, at which time the reaction was quenched via addition of saturated aqueous ammonium chloride solution (200 mL) and then allowed to warm to room temperature. The resulting mixture was partitioned between ethyl acetate (200 mL) and water (500 mL); the organic layer was washed with saturated aqueous sodium chloride solution (300 mL), dried over sodium sulfate, filtered, and concentrated under reduced pressure. Chromatography on silica gel (Gradient: 0% to 80% ethyl acetate in heptane) afforded the product as a yellow solid. Yield: 3.32 g, 10.0 mmol, 83%. LCMS m/z 331.3, 333.2 [M+H]$^+$. $^1$H NMR (400 MHz, CDCl$_3$) δ 7.21 (s, 1H), 3.96 (d, J=12.8 Hz, 1H), 3.76-3.70 (m, 3H), 3.41-3.34 (m, 1H), 2.31-2.09 (m, 4H), 2.02-1.93 (m, 1H), 1.91-1.80 (m, 1H), 1.74-1.59 (m, 2H).

Step 6. Synthesis of [rel-(7R,8R)-7-amino-7-(4-bromo-1,3-thiazol-2-yl)-5-oxaspiro[3.5]non-8-yl]methanol (C23)

Conversion of C22 to C23 was carried out according to the procedure described for synthesis of C15 from C11 in Preparation P3. The product was isolated as an orange solid. Yield: 3.2 g, 9.6 mmol, 96%. $^1$H NMR (400 MHz, CDCl$_3$), characteristic peaks: β 7.20 (s, 1H), 3.75 (d, J=11.5 Hz, 1H), 3.70 (dd, J=11.4, 3.7 Hz, 1H), 3.51 (dd, J=11.4, 3.9 Hz, 1H), 3.30 (d, J=11.5 Hz, 1H), 2.49-2.41 (m, 1H), 2.27-1.80 (m, 6H), 1.74-1.61 (m, 1H).

Step 7. Synthesis of N-{[rel-(7R,8R)-7-(4-bromo-1,3-thiazol-2-yl)-8-(hydroxymethyl)-5-oxaspiro[3.5]non-7-yl]carbamothioyl}benzamide (C24)

To a solution of C23 (2.2 g, 6.6 mmol) in dichloromethane (100 mL) was added benzoyl isothiocyanate (0.938 mL, 6.98 mmol). The reaction mixture was stirred at room temperature for 16 hours, whereupon it was concentrated in vacuo to provide the product as a yellow solid (3.3 g). This material was used directly in the following step.

Step 8. Synthesis of N-[cis-8a'-(4-bromo-1,3-thiazol-2-yl)-4a',5',8,8a'-tetrahydro-4'H-spiro[cyclobutane-1,6'-pyrano[3,4-d][1,3]thiazin]-2'-yl]benzamide (C25)

Trifluoromethanesulfonic acid (1.74 mL, 19.7 mmol) was rapidly added to a mixture of C24 (from the previous step, 3.3 g, 56.6 mmol) and methoxybenzene (2.17 mL, 20.0 mmol) in 1,2-dichloroethane (44 mL). The reaction mixture was stirred at room temperature for 30 minutes, whereupon it was diluted with dichloromethane (100 mL) and treated with 1 M aqueous sodium hydroxide solution (150 mL). The resulting biphasic mixture was stirred at room temperature for 15 minutes, at which time the aqueous layer was extracted with dichloromethane (2×100 mL); the combined organic layers were washed with saturated aqueous sodium chloride solution (250 mL), dried over sodium sulfate, filtered, and concentrated in vacuo. The resulting yellow solid was triturated with heptane (15 mL) to afford the product (1.08 g) as a white solid. The filtrate from the trituration was concentrated under reduced pressure, dissolved in a mixture of dichloromethane and methanol (9:1), and adsorbed onto silica gel. Chromatography on silica gel (Gradient: 0% to 70% ethyl acetate in heptane) provided an off-white solid, which was triturated with heptane to provide additional product (0.77 g) as a white solid. Combined yield: 1.85 g, 3.87 mmol, 59% over 2 steps. $^1$H NMR (400 MHz, CDCl$_3$) δ 8.24-7.88 (br s, 2H), 7.60-7.52 (m, 1H), 7.52-7.40 (m, 2H), 7.23 (s, 1H), 3.82 (AB quartet, downfield doublet is broadened, $J_{AB}$=11.6 Hz, $\Delta v_{AB}$=85.4 Hz, 2H), 3.23-3.14 (m, 1H), 3.14-3.02 (m, 1H), 2.61 (br d, J=12.5 Hz, 1H), 2.31-2.11 (m, 3H), 2.11-1.95 (m, 2H), 1.93-1.80 (m, 2H), 1.75-1.61 (m, 1H).

Step 9. Synthesis of N-[cis-8a'-{4-[(2,4-dimethoxybenzyl)amino]-1,3-thiazol-2-yl}-4a',5',8',8a'-tetrahydro-4'H-spiro[cyclobutane-1,6'-pyrano[3,4-d][1,3]thiazin]-2'-yl]benzamide (P4)

A mixture of tris(dibenzylideneacetone)dipalladium(0) (96%, 99.7 mg, 0.105 mmol), di-tert-butyl[2',4',6'-tri(propan-2-yl)biphenyl-2-yl]phosphane (0.133 g, 0.313 mmol), and sodium tert-butoxide (0.502 g, 5.22 mmol) was purged twice with nitrogen; 1,4-dioxane (9.5 mL) was then added, and the resulting solution was heated to an internal temperature of 85° C. for 5 minutes. A solution of C25 (1.00 g, 2.09 mmol) in 1,4-dioxane (5 mL) was then added, as was 1-(2,4-dimethoxyphenyl)methanamine (0.534 mL, 3.55 mmol), and the reaction mixture was heated at an internal temperature of 85° C. for 10 minutes. It was then removed from the oil bath and quickly cooled to room temperature by immersion of the reaction flask in a water bath. Diatomaceous earth (4 spoonfuls) was added to the reaction mixture, followed by addition of water (50 mL), and the resulting mixture was filtered through a pad of diatomaceous earth using dichloromethane to transfer the mixture. The filter pad was washed with additional dichloromethane (3×100 mL); the resulting aqueous layer exhibited a pH of 12. The organic layer of the filtrate was washed with water (2×300 mL) until the aqueous wash was found to have a neutral pH. At this point, the organic layer was washed sequentially with aqueous citric acid (5%, 2×300 mL), saturated aqueous sodium bicarbonate solution (2×300 mL), and saturated aqueous sodium chloride solution (500 mL), dried over sodium sulfate, and filtered. The filtrate was adsorbed onto silica gel and subjected to chromatography on silica gel [Gradient: 20% to 100% (5% triethylamine in ethyl acetate) in heptane], affording the product as an orange solid. Yield: 651 mg, 1.15 mmol, 55%. LCMS m/z 565.5 [M+H]$^+$. $^1$H NMR (400 MHz, CDCl$_3$) δ 8.15 (br d, J=7 Hz, 2H), 7.55-7.47 (m, 1H), 7.47-7.40 (m, 2H), 7.20 (d, J=8.2 Hz, 1H), 6.48 (d, half of AB quartet, J=2.3 Hz, 1H), 6.45 (dd, half of ABX pattern, J=8.2, 2.4 Hz, 1H), 5.73 (s, 1H), 4.75-4.60 (br s, 1H), 4.20 (br s, 2H), 3.94 (d, J=12.1 Hz, 1H), 3.85 (s, 3H), 3.81 (s, 3H), 3.70 (br d, J=12 Hz, 1H), 3.27 (br dd, J=13, 4 Hz, 1H), 3.06-2.97 (m, 1H), 2.56 (br dd, J=13, 2.5 Hz, 1H), 2.29-1.94 (m, 5H), 1.92-1.78 (m, 2H), 1.73-1.60 (m, 1H).

Preparation P5

N-[(4a'R,8a'R)-8a'-{4-[(2,4-Dimethoxybenzyl)amino]-1,3-thiazol-2-yl}-4a',5,8,8a'-tetrahydro-4'H-spiro[cyclobutane-1,6'-pyrano[3,4-d][1,3]thiazin]-2'-yl]benzamide (P5)

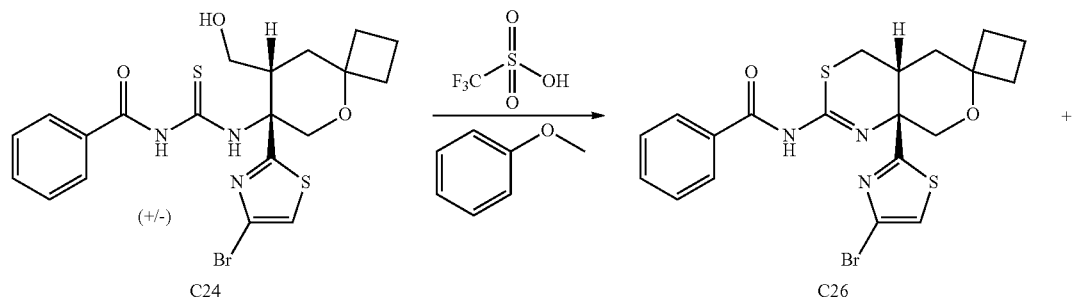

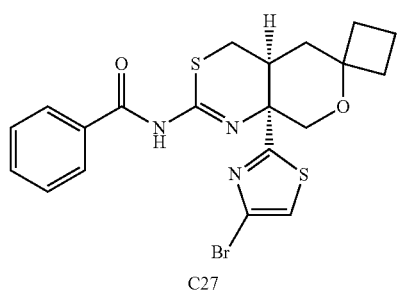

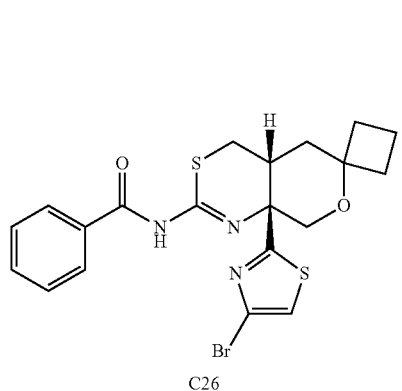

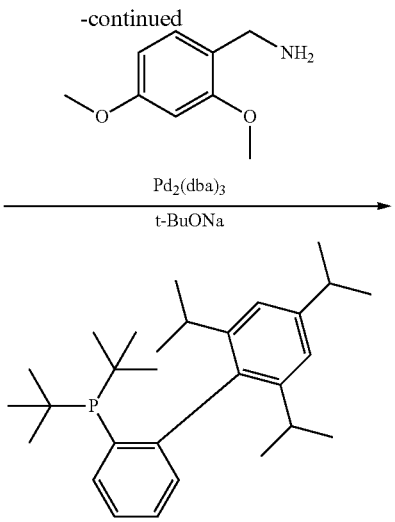

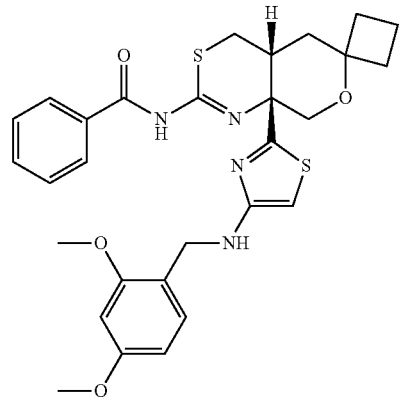

P5

Step 1. Synthesis of N-[(4a'R,8a'R)-8a'-(4-bromo-1,3-thiazol-2-yl)-4a',5',8',8a'-tetrahydro-4'H-spiro[cyclobutane-1,6'-pyrano[3,4-d][1,3]thiazin]-2'-yl]benzamide (C26) and N-[(4a'S,8a'S)-8a'-(4-bromo-1,3-thiazol-2-yl)-4a',5',8',8a'-tetrahydro-4'H-spiro[cyclobutane-1,6'-pyrano[3,4-d][1,3]thiazin]-2'-yl]benzamide (C27)

A solution of C24 (1.50 g, 3.02 mmol) in 1,2-dichloroethane (20 mL) was treated with methoxybenzene (0.984 mL, 9.05 mmol), followed by addition of trifluoromethanesulfonic acid (0.791 mL, 8.93 mmol) in one portion. A gum-like solid formed around the bottom of the flask, and stirring had to be monitored; it is best to use a large stir bar and a slow rate of stirring. The reaction mixture was allowed to stir at room temperature for 30 minutes, whereupon it was diluted with dichloromethane (100 mL) and treated with aqueous sodium hydroxide solution (1 M, 150 mL). The resulting biphasic solution was stirred at room temperature for 15 minutes, at which time the aqueous layer, which was found to exhibit a pH of 12, was extracted with dichloromethane (2×100 mL). The combined organic layers were washed with saturated aqueous sodium chloride solution (250 mL), dried over sodium sulfate, filtered, and concentrated in vacuo. The residue was triturated with heptane (15 mL); the resulting material was washed with heptane (2×10 mL) to provide the racemic product as a white solid. Yield: 1.07 g, 2.24 mmol, 74%. NMR of racemic material (C25): $^1$H NMR (400 MHz, CDCl$_3$) δ 8.14-7.99 (br s, 2H), 7.59-7.51 (m, 1H), 7.51-7.42 (m, 2H), 7.23 (s, 1H), 3.82 (AB quartet, $J_{AB}$=11.8 Hz, $\Delta\nu_{AB}$=85.4 Hz, 2H), 3.18 (br dd, J=13, 4 Hz, 1H), 3.14-3.04 (m, 1H), 2.65-2.57 (m, 1H), 2.31-1.95 (m, 5H), 1.92-1.81 (m, 2H), 1.74-1.61 (m, 1H).

This racemic product was separated into its component enantiomers via supercritical fluid chromatography (Column: Phenomenex Lux Cellulose-3, 5 μm; Mobile phase: 4:1 carbon dioxide/methanol). The first-eluting enantiomer was assigned as C26; yield: 348 mg, 33% for chiral separation. The second-eluting enantiomer was assigned as C27; yield: 480 mg, 45% for chiral separation. The indicated absolute stereochemistry was assigned on the basis of the conversion of C26 (via P5) to Example 6; the potent biological activity of this compound (see Table 2) was consistent with the given structure (see discussion under Isolation of C9 and C10 in Preparation P2 above.

Step 2. Synthesis of N-[(4a'R,8a'R)-8a'-{4-[(2,4-dimethoxybenzyl)amino]-1,3-thiazol-2-yl}-4a',5',8',8a'-tetrahydro-4'H-spiro[cyclobutane-1,6'-pyrano[3,4-d][1,3]thiazin]-2'-yl]benzamide (P5)

Conversion of C26 to P5 was effected via the method described for synthesis of P4 from C25 in Preparation P4. The product was isolated as an orange solid. Yield: 361 mg, 0.639 mmol, 90%. $^1$H NMR (400 MHz, CDCl$_3$) δ 8.15 (d, J=7.2 Hz, 2H), 7.54-7.48 (m, 1H), 7.47-7.40 (m, 2H), 7.20 (d, J=8.2 Hz, 1H), 6.48 (d, half of AB quartet, J=2.4 Hz, 1H), 6.45 (dd, half of ABX pattern, J=8.3, 2.4 Hz, 1H), 5.73 (s, 1H), 4.74-4.60 (br s, 1H), 4.21 (br s, 2H), 3.94 (d, J=12.1 Hz, 1H), 3.85 (s, 3H), 3.81 (s, 3H), 3.70 (d, J=12.2 Hz, 1H), 3.27 (dd, J=12.9, 4.1 Hz, 1H), 3.06-2.97 (m, 1H), 2.56 (dd, J=12.9, 2.7 Hz, 1H), 2.29-2.03 (m, 4H), 2.03-1.95 (m, 1H), 1.91-1.78 (m, 2H), 1.73-1.60 (m, 1H).

Preparation P6, P7, P8, and P9

N-[(4aR,6S,8aR)-8a-{4-[(2,4-Dimethoxybenzyl)amino]-1,3-thiazol-2-yl}-6-ethyl-6-methyl-4,4a,5,6,8,8a-hexahydropyrano[3,4-d][1,3]thiazin-2-yl]benzamide (P6), N-[(4aS,6S,8aS)-8a-{4-[(2,4-Dimethoxybenzyl)amino]-1,3-thiazol-2-yl}-6-ethyl-6-methyl-4,4a,5,6,8,8a-hexahydropyrano[3,4-d][1,3]thiazin-2-yl]benzamide (P7), N-[(4aR,6R,8aR)-8a-{4-[(2,4-Dimethoxybenzyl)amino]-1,3-thiazol-2-yl}-6-ethyl-6-methyl-4,4a, 5,6,8,8a-hexahydropyrano[3,4-d][1,3]thiazin-2-yl]benzamide (P8), and N-[(4aS,6R,8aS)-8a-{4-[(2,4-Dimethoxybenzyl)amino]-1,3-thiazol-2-yl}-6-ethyl-6-methyl-4,4a, 5,6,8,8a-hexahydropyrano[3,4-d][1,3]thiazin-2-yl]benzamide (P9)

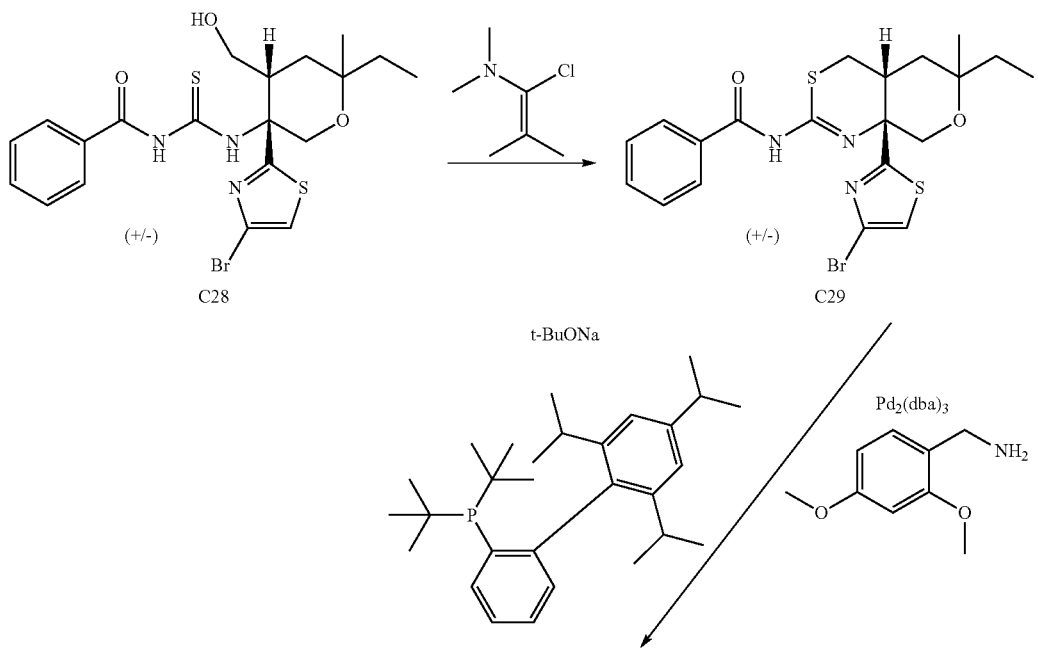

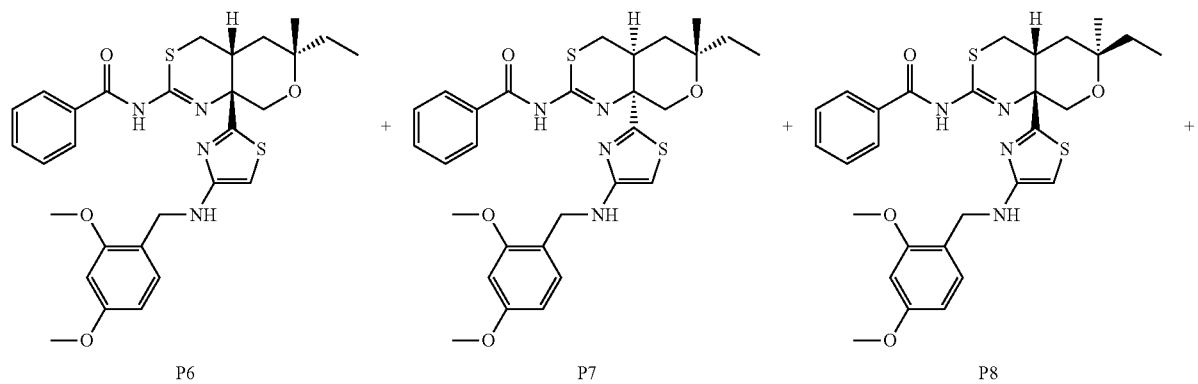

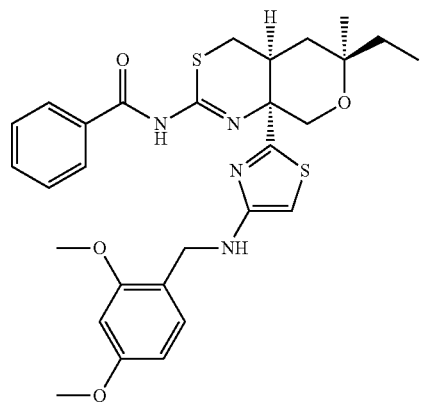

P9

Step 1. Synthesis of N-[cis-8a-(4-bromo-1,3-thiazol-2-yl)-6-ethyl-6-methyl-4,4a,5,6,8,8a-hexahydropyrano[3,4-d][1,3]thiazin-2-yl]benzamide (C29)

1-Chloro-N,N,2-trimethylprop-1-en-1-amine (197 mg, 1.47 mmol) was added in a drop-wise manner to a solution of C28 [rel-N-{[(3R,4R)-3-(4-bromo-1,3-thiazol-2-yl)-6-ethyl-4-(hydroxymethyl)-6-methyltetrahydro-2H-pyran-3-yl]carbamothioyl}benzamide; synthesized in analogous fashion to C6 in Preparation P1, by using 3-methylhex-5-en-3-ol and 1,1-diethoxy-2-iodoethane in the first step, rather than 2-methylpent-4-en-2-ol and 2-bromo-1,1-diethoxyethane] (245 mg, 0.492 mmol) in dichloromethane (5 mL). After the reaction mixture had stirred at room temperature for 1 hour, it was partitioned between dichloromethane and saturated aqueous sodium bicarbonate solution. The organic layer was washed with saturated aqueous sodium chloride solution, dried over sodium sulfate, filtered, and adsorbed onto silica gel. Chromatography on silica gel (Gradient: 0% to 100% ethyl acetate in heptane) provided the product. By $^1$H NMR analysis, this material consisted of a mixture of diastereomers, and contained some impurities. Yield: 145 mg, <0.302 mmol, <61%. LCMS m/z 482.0 (bromine isotope pattern observed) [M+H]$^+$. $^1$H NMR (400 MHz, CDCl$_3$), characteristic product peaks: δ 8.09 (br d, J=7.6 Hz, 2H), 7.56-7.50 (m, 1H), 7.49-7.41 (m, 2H), 7.23-7.21 (m, 1H), [4.13 (d, J=12.3 Hz) and 4.03 (d, J=12.3 Hz), total 1H], 3.73-3.64 (m, 1H), 3.27-3.09 (m, 2H), 2.61-2.52 (m, 1H), 2.02-1.90 (m, 1H), 1.65-1.50 (m, 2H), [1.37 (s) and 1.21 (s), total 3H].

Step 2. Synthesis of N-[(4aR,6S,8aR)-8a-{4-[(2,4-dimethoxybenzyl)amino]-1,3-thiazol-2-yl}-6-ethyl-6-methyl-4,4a,5,6,8,8a-hexahydropyrano[3,4-d][1,3]thiazin-2-yl]benzamide (P6), N-[(4aS,6S,8aS)-8a-{4-[(2,4-dimethoxybenzyl)amino]-1,3-thiazol-2-yl}-6-ethyl-6-methyl-4,4a,5,6,8,8a-hexahydropyrano[3,4-d][1,3]thiazin-2-yl]benzamide (P7), N-[(4aR,6R,8aR)-8a-{4-[(2,4-dimethoxybenzyl)amino]-1,3-thiazol-2-yl}-6-ethyl-6-methyl-4,4a,5,6,8,8a-hexahydropyrano[3,4-d][1,3]thiazin-2-yl]benzamide (P8), and N-[(4aS,6R,8aS)-8a-{4-[(2,4-dimethoxybenzyl)amino]-1,3-thiazol-2-yl}-6-ethyl-6-methyl-4,4a,5,6,8,8a-hexahydropyrano[3,4-d][1,3]thiazin-2-yl]benzamide (P9)

Conversion of C29 to a mixture of the products was carried out using the method described for synthesis of P4 from C25 in Preparation P4. The chromatographed product was subjected to supercritical fluid chromatography (Column: Phenomenex Lux Cellulose-3, 5 μm; Mobile phase: 65:35 carbon dioxide/(methanol containing 0.2% ammonium hydroxide) to separate the isomers of the product. In order of elution from the supercritical fluid chromatography:

P6: Yield: 60 mg, 0.11 mmol, 5%.
P7: Yield: 50 mg, 88 μmol, 4%.
P8: Yield: 90 mg, 0.16 mmol, 8%.
P9: Yield: 93 mg, 0.16 mmol, 8%.

The indicated absolute stereochemistry was assigned after each of these products was converted to the corresponding Example (i.e., Examples 8, 26, 27, and 28). See Example 8 for discussion.

Preparation P10

N-[(4aR,8aR)-8a-(4-Bromo-1,3-thiazol-2-yl)-6,6-bis(hydroxymethyl)-4,4a,5,6,8,8a-hexahydropyrano[3,4-d][1,3]thiazin-2-yl]benzamide (P10)

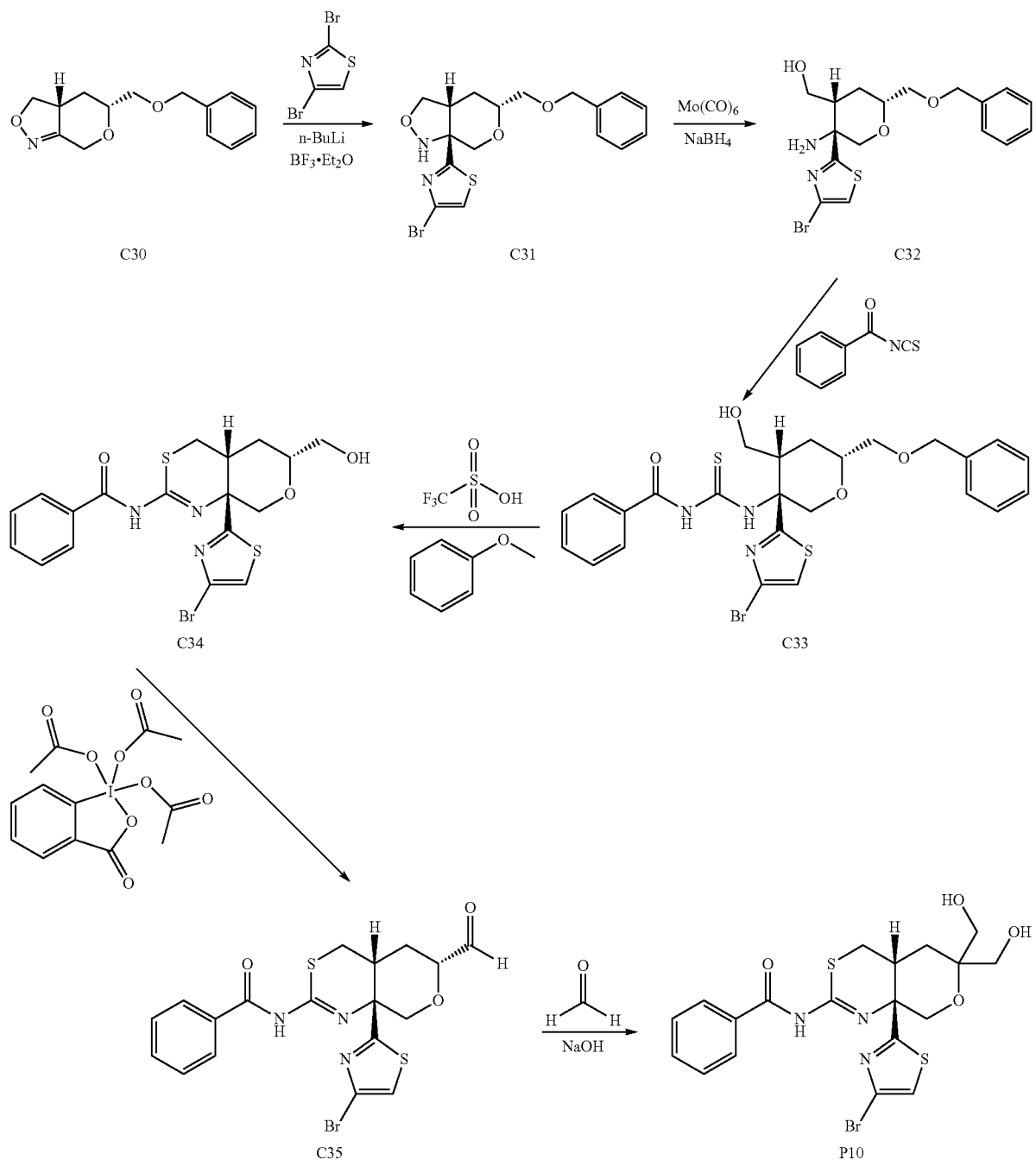

Step 1. Synthesis of (3aR,5R,7aR)-5-[(benzyloxy)methyl]-7a-(4-bromo-1,3-thiazol-2-yl)hexahydro-1H-pyrano[3,4-c][1,2]oxazole (C31)

To a −70° C. solution of 2,4-dibromo-1,3-thiazole (57.5 g, 237 mmol) in toluene (1 L) and tetrahydrofuran (100 mL) was added boron trifluoride diethyl etherate (28.6 mL, 226 mmol, followed by slow addition of n-butyllithium (2.5 M solution in hexanes; 87.3 mL, 218 mmol). After the reaction mixture had stirred for 30 minutes at −70° C., a solution of C30 [(3aR,5R)-5-[(benzyloxy)methyl]-3,3a,4,5-tetrahydro-7H-pyrano[3,4-c][1,2]oxazole; this material was prepared using the method of C. R. Butler et al., *J. Med. Chem.* 2015, 58, 2678-2702] (45.0 g, 182 mmol) in toluene (100 mL) and tetrahydrofuran (10 mL) was added drop-wise, and stirring was continued for 40 minutes at −70° C. Saturated aqueous ammonium chloride solution (200 mL) was added to the −70° C. reaction mixture, which was then allowed to warm to room temperature over 16 hours. The aqueous layer was extracted with ethyl acetate (2×200 mL), and the combined organic layers were washed with saturated aqueous sodium chloride solution (2×1 L), dried over sodium sulfate, and concentrated under reduced pressure. The residue was combined with the crude products from two similar reactions carried out using C30 (30 g, 120 mmol and 45.0 g, 182 mmol) and purified via chromatography on silica gel (Gradient: 10% to 100% ethyl acetate in petroleum ether), providing the product (100 g) as a yellow solid. Yield: 100 g, 243 mmol, 50%. Also isolated from the column was an impure batch of the product: 60 g, 60% purity by $^1$H NMR, 88 mmol. $^1$H NMR (400 MHz, CDCl$_3$) δ 7.41-7.28 (m, 5H), 7.23 (s, 1H), 4.59 (AB quartet, $J_{AB}$=12.3 Hz, $\Delta v_{AB}$=10.7 Hz, 2H), 4.07-3.97 (m, 2H), 3.88-3.79 (m, 1H), 3.76 (br d, half of AB quartet, J=7.5 Hz, 1H), 3.73-3.67 (m, 1H), 3.59-3.46 (m, 2H), 3.44-3.36 (m, 1H), 1.88 (br dd, J=13.5, 7 Hz, 1H), 1.61-1.47 (m, 1H).

Step 2. Synthesis of [(2R,4R,5R)-5-amino-2-[(benzyloxy)methyl]-5-(4-bromo-1,3-thiazol-2-yl)tetrahydro-2H-pyran-4-yl]methanol (C32)

Molybdenum hexacarbonyl (11.6 g, 43.9 mmol) was added to a solution of C31 (60 g, 60% purity by $^1$H NMR, 88 mmol) in acetonitrile (500 mL) and water (25 mL). The reaction mixture was heated at reflux for two hours, then cooled to 0° C. and treated with sodium borohydride (6.62 g, 175 mmol). The mixture was stirred at room temperature for 16 hours, whereupon it was filtered; the filtrate was concentrated under reduced pressure, dissolved in methanol (500 mL), stirred for 10 minutes, and concentrated once again. The residue was again dissolved in methanol (500 mL), stirred for 10 minutes, and concentrated. The resulting material was dissolved in dichloromethane (1.5 L), washed sequentially with aqueous sodium hydroxide solution (1 M, 1.0 L) and saturated aqueous sodium chloride solution (2×1 L), dried over sodium sulfate, filtered, and concentrated in vacuo, providing the product (36.2 g) as a brown solid. This material was taken directly to the following step.

Step 3. Synthesis of N-{[(3R,4R,6R)-6-[(benzyloxy)methyl]-3-(4-bromo-1,3-thiazol-2-yl)-4-(hydroxymethyl)tetrahydro-2H-pyran-3-yl]carbamothioyl}benzamide (C33)

Benzoyl isothiocyanate (15.7 g, 96.2 mmol) was added to a solution of C32 (from the previous step, ≤88 mmol) in dichloromethane (800 mL), and the mixture was stirred for 16 hours at 20° C. The reaction mixture was then concentrated in vacuo, and the residue was combined with the crude product from a similar two-step reaction sequence carried out using C31 (100 g, 243 mmol). Silica gel chromatography (Gradient: 15% to 100% ethyl acetate in petroleum ether) provided the product as a brown solid. Yield: 120 g, 208 mmol, 63% over 2 steps. $^1$H NMR (400 MHz, CDCl$_3$) δ 11.72 (br s, 1H), 8.93 (br s, 1H), 7.85 (br d, J=8.5 Hz, 2H), 7.65 (br dd, J=7.4, 7.4 Hz, 1H), 7.53 (br dd, J=8.0, 7.4 Hz, 2H), 7.38-7.28 (m, 5H), 7.25 (s, 1H), 5.55 (d, J=12.0 Hz, 1H), 4.59 (AB quartet, $J_{AB}$=12.0 Hz, $\Delta v_{AB}$=19.4 Hz, 2H), 3.94 (d, J=11.9 Hz, 1H), 3.94-3.86 (m, 1H), 3.86-3.78 (m, 2H), 3.67 (dd, half of ABX pattern, J=10.3, 6.2 Hz, 1H), 3.54 (dd, half of ABX pattern, J=10.4, 4.3 Hz, 1H), 2.52-2.43 (m, 1H), 2.25-2.15 (br s, 1H), 2.00-1.83 (m, 2H).

Step 4. Synthesis of N-[(4aR,6R,8aR)-8a-(4-bromo-1,3-thiazol-2-yl)-6-(hydroxymethyl)-4,4a,5,6,8,8a-hexahydropyrano[3,4-d][1,3]thiazin-2-yl]benzamide (C34)

A solution of C33 (80.0 g, 139 mmol) in 1,2-dichloroethane (1.2 L) was treated with methoxybenzene (45 mL, 410 mmol) and heated to 60° C. Trifluoromethanesulfonic acid (36 mL, 410 mmol) was added, and stirring was continued at 60° C. for 1 hour. The reaction mixture was then cooled to 22° C. and partitioned between dichloromethane (1 L) and saturated aqueous sodium bicarbonate solution (1.5 L); the organic layer was washed with saturated aqueous sodium chloride solution (2×1 L), dried over sodium sulfate, filtered, and concentrated in vacuo. Silica gel chromatography (Gradient: 25% to 75% ethyl acetate in petroleum ether) afforded the product as a yellow solid. Yield: 45.5 g, 97.1 mmol, 70%. $^1$H NMR (400 MHz, CDCl$_3$) δ 8.12-7.97 (m, 2H), 7.57 (br dd, J=7.3, 7.3 Hz, 1H), 7.48 (br dd, J=7.8, 7.2 Hz, 2H), 7.25 (s, 1H), 3.99 (AB quartet, $J_{AB}$=11.7 Hz, $\Delta v_{AB}$=7.4 Hz, 2H), 3.86-3.77 (m, 1H), 3.70 (br dd, half of ABX pattern, J=11.7, 2.9 Hz, 1H), 3.64 (dd, half of ABX pattern, J=11.8, 7.2 Hz, 1H), 3.19-3.09 (m, 2H), 2.67-2.60 (m, 1H), 2.00-1.87 (m, 1H), 1.65-1.55 (m, 1H, assumed; partially obscured by water peak).

Step 5. Synthesis of N-[(4aR,6R,8aR)-8a-(4-bromo-1,3-thiazol-2-yl)-6-formyl-4,4a,5,6,8,8a-hexahydropyrano[3,4-d][1,3]thiazin-2-yl]benzamide (C35)

Dess-Martin periodinane [1,1,1-tris(acetyloxy)-1,1-dihydro-1,2-benziodoxol-3-(1H)-one] (34.9 g, 82.3 mmol) was added in one portion to a solution of C34 (35.0 g, 74.7 mmol) in dichloromethane (750 mL), and the reaction mixture was stirred at room temperature (20° C.) for 2 hours. Dichloromethane (600 mL) and saturated aqueous sodium bicarbonate solution (600 mL) were then added, and the resulting mixture was stirred for 10 minutes. The aqueous layer was extracted with dichloromethane (2×300 mL), and the combined organic layers were washed with saturated aqueous sodium thiosulfate solution (400 mL), dried over sodium sulfate, filtered, and concentrated under reduced pressure to provide the product (46.9 g) as a light brown foam. This material was impure by $^1$H NMR, and was taken to the following step without additional purification. $^1$H NMR (400 MHz, CDCl$_3$), product peaks only: δ 9.70 (s, 1H), 8.03-7.96 (m, 2H), 7.58 (br dd, J=7.4, 7.3 Hz, 1H), 7.49 (br dd, J=7.8, 7.3 Hz, 2H), 7.26 (s, 1H), 4.16-4.06 (m, 2H), 4.02 (d, half of AB quartet, J=11.5 Hz, 1H), 3.20-3.09 (m, 2H), 2.71-2.63 (m, 1H), 2.07-1.91 (m, 2H).

Step 6. Synthesis of N-[(4aR,8aR)-8a-(4-bromo-1,3-thiazol-2-yl)-6,6-bis(hydroxymethyl)-4,4a,5,6,8,8a-hexahydropyrano[3,4-d][1,3]thiazin-2-yl]benzamide (P10)

A solution of C35 (from the previous step; 46.9 g, 574.7 mmol) in 1,4-dioxane (235 mL) and water (165 mL) was cooled to 0° C. Formaldehyde (37% solution in water; 44 mL, 590 mmol) was added, followed by addition of aqueous sodium hydroxide solution (1 M, 327 mL, 327 mmol), and stirring was continued at 0° C. for 1 hour. The reaction mixture was then allowed to warm to room temperature (18° C.), and was stirred at 18° C. for 15 hours, whereupon it was acidified to a pH of approximately 4 via addition of 1 M aqueous hydrochloric acid. The resulting mixture was partitioned between saturated aqueous sodium chloride solution (400 mL) and dichloromethane (400 mL), and the aqueous layer was extracted with dichloromethane (2×200 mL). The combined organic layers were washed with saturated aqueous sodium chloride solution (2×150 mL), dried over sodium sulfate, filtered, and concentrated in vacuo. Silica gel chromatography (Gradient, 0% to 4% methanol in dichloromethane) provided the product as a pale yellow solid. Yield: 23.2 g, 46.5 mmol, 62% over 2 steps. LCMS m/z 521.7 (bromine isotope pattern observed) [M+Na$^+$]. $^1$H NMR (400 MHz, CDCl$_3$) δ 8.04 (d, J=7.5 Hz, 2H), 7.56 (br dd, J=7.4, 7.3 Hz, 1H), 7.47 (br dd, J=7.8, 7.3 Hz, 2H), 7.22 (s, 1H), 4.20 (d, J=11.8 Hz, 1H), 4.11 (d, J=12.0 Hz, 1H), 3.81 (d, J=11.8 Hz, 1H), 3.77 (d, J=12.0 Hz, 1H), 3.65 (AB quartet, $J_{AB}$=11.5 Hz, $\Delta v_{AB}$=59.4 Hz, 2H), 3.20-3.08 (m, 2H), 2.60-2.53 (m, 1H), 2.02 (dd, J=13.9, 13.2 Hz, 1H), 1.58-1.50 (m, 1H).

Preparation P11
N-[(4a'R,8a'R)-8a'-{4-[(2,4-Dimethoxybenzyl)amino]-1,3-thiazol-2-yl}-4a',5,8,8a'-tetrahydro-4'H-spiro[oxetane-3,6'-pyrano[3,4-d][1,3]thiazin]-2'-yl]benzamide (P11)
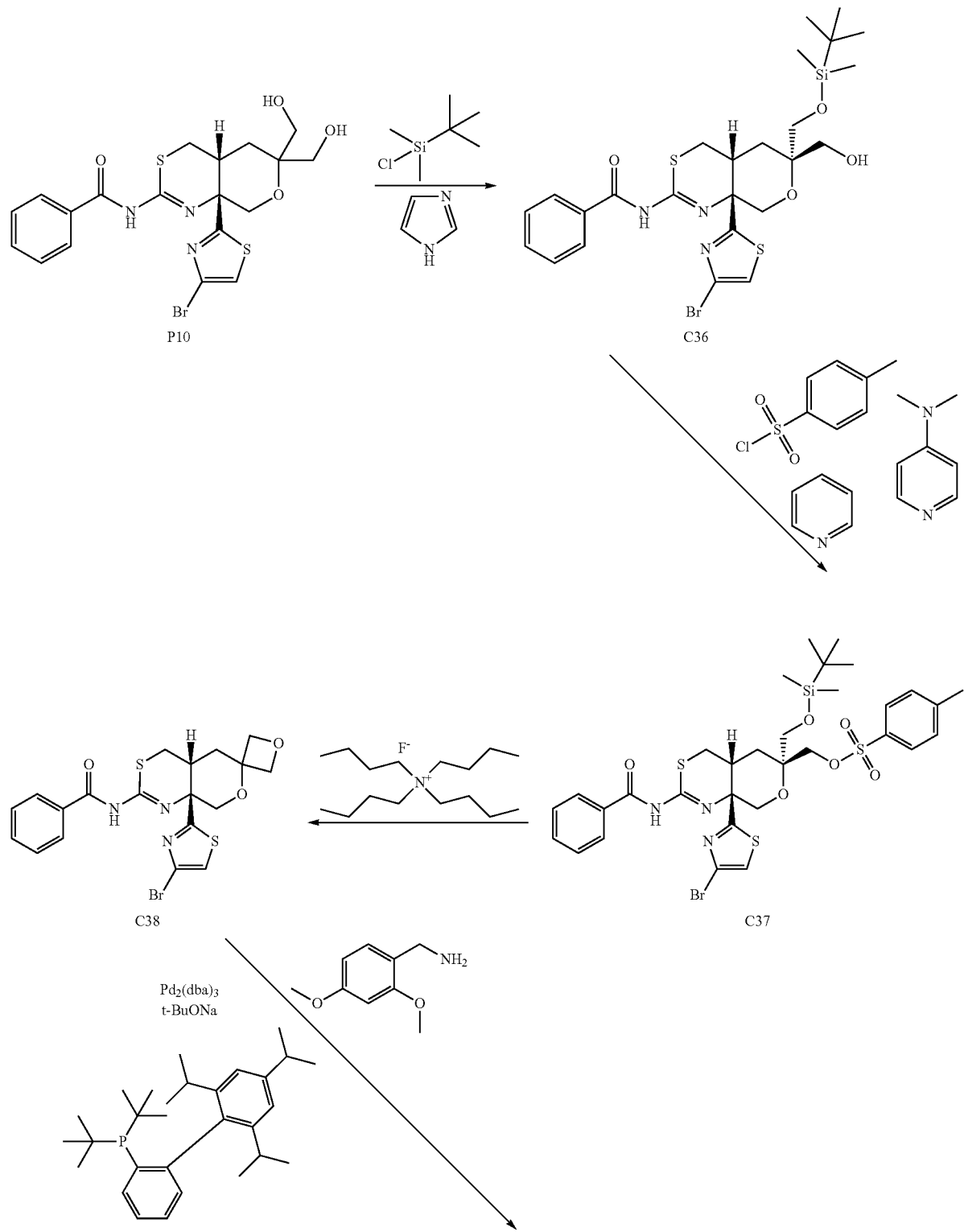

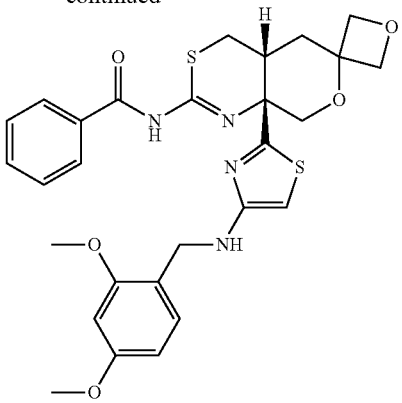

P11

Step 1. Synthesis of N-[(4aR,6S,8aR)-8a-(4-bromo-1,3-thiazol-2-yl)-6-({[tert-butyl(dimethyl)silyl]oxy}methyl)-6-(hydroxymethyl)-4,4a,5,6,8,8a-hexahydropyrano[3,4-d][1,3]thiazin-2-yl]benzamide (C36)

A solution of P10 (2.00 g, 4.01 mmol) and 1H-imidazole (0.546 g, 8.03 mmol) in dichloromethane (40 mL) was cooled to 0° C., and a solution of tert-butyl(dimethyl)silyl chloride (1.21 g, 8.03 mmol) in dichloromethane (20 mL) was added in a drop-wise manner. The reaction mixture was stirred at 0° C. for 1 hour and then, without removing the ice bath, it was allowed to slowly warm up for an additional hour. The reaction mixture was then partitioned between dichloromethane (100 mL) and water (100 mL); the aqueous layer was extracted with dichloromethane (2×50 mL) and the combined organic layers were washed with saturated aqueous sodium chloride solution (200 mL), dried over sodium sulfate, filtered, and concentrated in vacuo. Silica gel chromatography (Gradient: 0% to 70% ethyl acetate in heptane) provided the product as a white solid. The indicated regiochemistry of silylation was established via NOE study of C40, which was synthesized from C36 (see Preparation P12 below). Yield: 1.42 g, 2.30 mmol, 57%. LCMS m/z 614.4 (bromine isotope pattern observed) [M+H]$^+$. $^1$H NMR (400 MHz, CDCl$_3$) δ 8.06 (br s, 2H), 7.53-7.59 (m, 1H), 7.44-7.51 (m, 2H), 7.22 (s, 1H), 4.10-4.18 (m, 2H), 3.80-3.87 (m, 1H), 3.72-3.79 (m, 2H), 3.50-3.54 (m, 1H), 3.14-3.22 (m, 2H), 2.57-2.64 (m, 1H), 2.39-2.45 (m, 1H), 1.89-1.99 (m, 1H), 1.64-1.72 (m, 1H), 0.85-0.90 (m, 9H), 0.07 (d, J=2.9 Hz, 6H).

Step 2. Synthesis of [(4aR,6R,8aR)-2-(benzoylamino)-8a-(4-bromo-1,3-thiazol-2-yl)-6-({[tert-butyl(dimethyl)silyl]oxy}methyl)-4,4a, 5,6,8,8a-hexahydropyrano[3,4-d][1,3]thiazin-6-yl]methyl methanesulfonate (C37)

A solution of C36 (94.3 mg, 0.154 mmol) was dissolved in pyridine (1.9 mL) and sequentially treated with 4-(dimethylamino)pyridine (5.41 mg, 44.3 μmol) and p-toluenesulfonyl chloride (127 mg, 0.664 mmol). After 30 minutes, more p-toluenesulfonyl chloride (127 mg, 0.664 mmol) was added, and stirring was continued at room temperature for 16 hours. The reaction mixture was then partitioned between aqueous sodium bisulfate solution (1 M, 150 mL) and dichloromethane (50 mL); the aqueous layer was extracted with dichloromethane (2×50 mL), and the combined organic layers were washed with aqueous sodium chloride solution, dried over sodium sulfate, filtered, and concentrated in vacuo. Silica gel chromatography (Gradient: 0% to 70% ethyl acetate in heptane) provided the product. Yield: 109 mg, 0.141 mmol, 92%. $^1$H NMR (400 MHz, CDCl$_3$) δ 8.02 (br s, 2H), 7.87 (d, J=8.2 Hz, 2H), 7.54 (m, J=7.0 Hz, 1H), 7.42-7.51 (m, 2H), 7.39 (d, J=7.8 Hz, 2H), 7.21 (s, 1H), 4.44 (d, J=10.5 Hz, 1H), 4.22 (d, J=10.5 Hz, 1H), 3.66-3.75 (m, 1H), 3.55-3.65 (m, 2H), 3.39 (d, J=10.1 Hz, 1H), 3.03-3.12 (m, 1H), 2.84-2.97 (m, 1H), 2.51 (d, J=12.8 Hz, 1H), 2.42 (s, 3H), 1.88-2.01 (m, 1H), 1.60-1.66 (m, 1H), 0.81 (s, 9H), 0.00 (s, 6H).

Step 3. Synthesis of N-[(4a'R,8a'R)-8a'-(4-bromo-1,3-thiazol-2-yl)-4a',5',8',8a'-tetrahydro-4'H-spiro[oxetane-3,6'-pyrano[3,4-d][1,3]thiazin-2'-yl]benzamide (C38)

A mixture of C37 (165.0 mg, 0.205 mmol) and tetrabutylammonium fluoride (1.0 M solution in tetrahydrofuran; 2.05 mL, 2.05 mmol) was heated at 50° C. for 4 hours, then at 70° C. for 3 days. The reaction mixture was partitioned between 5% aqueous sodium bicarbonate solution (50 mL) and ethyl acetate (50 mL); the aqueous layer was extracted with ethyl acetate (3×50 mL) and the combined organic layers were washed with saturated aqueous sodium chloride solution, dried over sodium sulfate, filtered, and concentrated in vacuo. Silica gel chromatography (Gradient: 0% to 100% ethyl acetate in heptane) provided the product. LCMS m/z 482.3 (bromine isotope pattern observed) [M+H]$^+$.

Step 4. Synthesis of N-[(4a'R,8a'R)-8a'-{4-[(2,4-dimethoxybenzyl)amino]-1,3-thiazol-2-yl}-4a',5',8',8a'-tetrahydro-4'H-spiro[oxetane-3,6'-pyrano[3,4-d][1,3]thiazin]-2'-yl]benzamide (P11)

A flask charged with tris(dibenzylideneacetone)dipalladium(0) (11.4 mg, 12.5 μmol), di-tert-butyl[2',4',6'-tri(propan-2-yl)biphenyl-2-yl]phosphane (16.4 mg, 38.7 μmol), and sodium tert-butoxide (60.0 mg, 0.624 mmol) was purged three times with nitrogen, subsequently evacuating with vacuum after each purge. 1,4-Dioxane (0.7 mL) was added, and the flask was purged three times with nitrogen, subsequently evacuating with vacuum after each purge. The reaction mixture was heated to 95° C. for 5 minutes, whereupon a solution of C38 (120 mg, 0.250 mmol) and 1-(2,4-dimethoxyphenyl)methanamine (63.8 µL, 0.425 mmol) in 1,4-dioxane was added, and heating was continued at 95° C. for 15 minutes. The reaction mixture was then cooled to room temperature using a water bath. Diatomaceous earth and water were added, and the resulting mixture was filtered through a pad of diatomaceous earth, washing with dichloromethane. The organic layer of the filtrate was washed three times with water (until the aqueous wash exhibited a neutral pH), twice with 5% aqueous citric acid solution, twice with saturated aqueous sodium bicarbonate solution, and once with saturated aqueous sodium chloride solution. It was then dried over sodium sulfate, filtered, and concentrated in vacuo. Silica gel chromatography [Gradient: 10% to 100% (5% triethylamine in ethyl acetate) in heptane] provided the product. Yield: 25 mg, 44.1 µmol, 18%. LCMS m/z 567.5 [M+H$^+$].

Preparation P12

N-[(4aR,6R,8aR)-8a-(4-Bromo-1,3-thiazol-2-yl)-6-(methoxymethyl)-6-methyl-4,4a, 5,6,8,8a-hexahydropyrano[3,4-d][1,3]thiazin-2-yl]benzamide (P12)

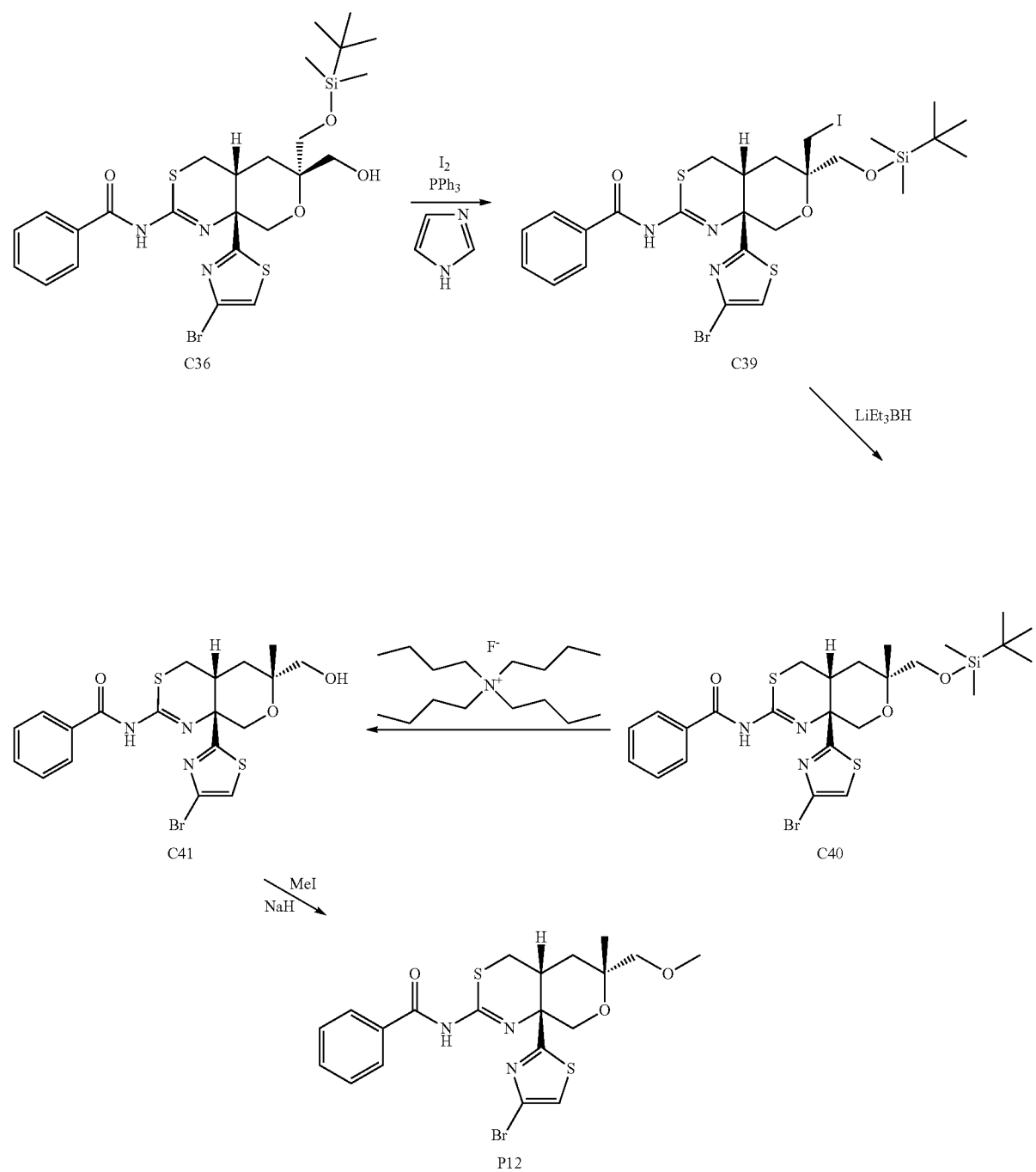

Step 1. Synthesis of N-[(4aR,6R,8aR)-8a-(4-bromo-1,3-thiazol-2-yl)-6-({[tert-butyl(dimethyl)silyl]oxy}methyl)-6-(iodomethyl)-4,4a,5,6,8,8a-hexahydropyrano[3,4-d][1,3]thiazin-2-yl]benzamide (C39)

To a solution of C36 (216 mg, 0.35 mmol) in tetrahydrofuran (12 mL) were added imidazole (96 mg, 1.4 mmol), triphenylphosphine (370, 1.4 mmol), and iodine (179 mg, 0.71 mmol). The reaction mixture was heated at reflux for 2.5 hours, whereupon it was allowed to cool to near room temperature. The reaction mixture was then partitioned between saturated aqueous sodium thiosulfate solution (30 mL) and diethyl ether (2×30 mL); the combined organic layers were dried over sodium sulfate, filtered, and concentrated in vacuo. Silica gel chromatography (Gradient: 0% to 75% ethyl acetate in heptane) provided the product as a white solid. Yield: 188.3 mg, 0.26 mmol, 74%. LCMS m/z 724.3 [M+H]$^+$. $^1$H NMR (400 MHz, CDCl$_3$) δ 7.95 (br m, 2H), 7.44-7.49 (m, 1H), 7.35-7.42 (m, 2H), 7.14 (s, 1H), 3.89 (d, J=12.4 Hz, 1H), 3.75 (d, J=10.5 Hz, 1H), 3.59-3.69 (m, 2H), 3.55 (d, J=10.9 Hz, 1H), 3.34 (d, J=9.7 Hz, 1H), 3.05-3.12 (m, 2H), 2.52 (d, J=11.7 Hz, 1H), 2.11 (t, J=13.5 Hz, 1H), 1.83 (dd, J=14.2, 4.1 Hz, 1H), 0.80 (s, 9H), −0.01 (d, J=9.4 Hz, 5H).

Step 2. Synthesis of N-[(4aR,6R,8aR)-8a-(4-bromo-1,3-thiazol-2-yl)-6-({[tert-butyl(dimethyl)silyl]oxy}methyl)-6-methyl-4,4a,5,6,8,8a-hexahydropyrano[3,4-d][1,3]thiazin-2-yl]benzamide (C40)

A solution of lithium triethylborohydride in tetrahydrofuran (1.0 M, 2.5 mL, 2.5 mmol) was added drop-wise to a 0° C. solution of C39 (180.5 mg, 0.25 mmol) in tetrahydrofuran (12 mL). The ice bath was removed at the completion of the addition, and the reaction mixture was allowed to warm to room temperature over 20 minutes. It was then heated at reflux for 1 hour, whereupon it was allowed to cool to room temperature. After careful addition of saturated aqueous sodium bicarbonate solution (25 mL), the mixture was extracted with diethyl ether (3×25 mL). The combined diethyl ether layers were dried over sodium sulfate, filtered, and concentrated in vacuo; silica gel chromatography (Gradient: 0% to 40% ethyl acetate in heptane) afforded the product as a colorless solid. NOE studies on this compound confirmed the indicated relative stereochemistry: irradiation of the quaternary methyl group provided an enhancement of the signal for the methine proton at the ring fusion. Yield: 117.1 mg, 0.20 mmol, 79%. LCMS m/z 598.3 [M+H]$^+$. $^1$H NMR (400 MHz, CDCl$_3$) δ 7.89-8.23 (br m, 2H), 7.35-7.58 (m, 3H), 7.19 (s, 1H), 4.14 (d, J=11.3 Hz, 1H), 3.69 (d, J=12.1 Hz, 1H), 3.39-3.52 (m, 2H), 3.13-3.21 (m, 2H), 2.56 (d, J=12.1 Hz, 1H), 1.91-2.16 (m, 1H), 1.48 (dd, J=14.1, 3.9 Hz, 1H), 1.37 (s, 3H), 0.82 (s, 9H), −0.05-0.07 (m, 6H).

Step 3. Synthesis of N-[(4aR,6R,8aR)-8a-(4-bromo-1,3-thiazol-2-yl)-6-(hydroxymethyl)-6-methyl-4,4a,5,6,8,8a-hexahydropyrano[3,4-d][1,3]thiazin-2-yl]benzamide (C41)

A solution of tetrabutylammonium fluoride in tetrahydrofuran (1.0 M, 1.73 mL, 1.73 mmol) was added to a solution of C40 (344 mg, 0.58 mmol) in tetrahydrofuran (10 mL). The reaction mixture was stirred at room temperature for 16 hours, whereupon it was concentrated in vacuo. Purification via silica gel chromatography (Gradient: 0% to 100% ethyl acetate in heptane) provided the product as a white solid. Yield: 286 mg, 0.58 mmol, 100%. LCMS m/z 484.3 [M+H]$^+$. $^1$H NMR (400 MHz, CDCl$_3$) δ 8.00-8.12 (br m, 2H), 7.51-7.59 (m, 1H), 7.42-7.49 (m, 2H), 7.23 (s, 1H), 4.15 (d, J=12.1 Hz, 1H), 3.75 (d, J=12.1 Hz, 1H), 3.41-3.56 (m, 2H), 3.27 (d, J=11.7 Hz, 1H), 3.18 (dd, J=13.0, 4.0 Hz, 1H), 2.59 (dd, J=12.8, 1.7 Hz, 1H), 2.19-2.35 (m, 1H), 1.41 (s, 3H), 1.35 (dd, J=13.7, 4.5 Hz, 1H).

Step 4. Synthesis of N-[(4aR,6R,8aR)-8a-(4-bromo-1,3-thiazol-2-yl)-6-(methoxymethyl)-6-methyl-4,4a,5,6,8,8a-hexahydropyrano[3,4-d][1,3]thiazin-2-yl]benzamide (P12)

A solution of C41 (34.8 mg, 72 μmol) in tetrahydrofuran (1 mL) was added drop-wise to a suspension of sodium hydride (60% dispersion in mineral oil; 8.7 mg, 0.22 mmol) in tetrahydrofuran (0.5 mL) at 0° C. The ice bath was removed and the reaction mixture was stirred at room temperature for 30 minutes, whereupon it was cooled to 0° C. Iodomethane (6.7 μL, 0.11 mmol) was added, and the ice bath was removed; the reaction mixture was stirred at room temperature for 2 hours, at which time more iodomethane (6.7 μL, 0.11 mmol) was added. After an additional 2.5 hours, the reaction mixture was diluted with saturated aqueous ammonium chloride solution (15 mL) and extracted with diethyl ether (3×15 mL). The combined organic layers were dried over sodium sulfate, filtered, and concentrated in vacuo. Silica gel chromatography (Gradient: 0% to 70% ethyl acetate in heptane) afforded the product as a white solid. Yield: 25.6 mg, 52 μmol, 72%. LCMS m/z 498.3 [M+H]$^+$. $^1$H NMR (400 MHz, CDCl$_3$) δ 7.91 (d, J=7.4 Hz, 2H), 7.35-7.41 (m, 1H), 7.27-7.34 (m, 2H), 7.06 (s, 1H), 3.99 (d, J=12.1 Hz, 1H), 3.59 (d, J=12.5 Hz, 1H), 3.21 (s, 3H), 3.10-3.20 (m, 2H), 3.06-3.09 (m, 1H), 3.02 (dd, J=12.9, 4.3 Hz, 1H), 2.42 (dd, J=13.1, 2.5 Hz, 1H), 1.89 (t, J=13.5 Hz, 1H), 1.34 (d, J=4.3 Hz, 1H), 1.31 (s, 3H)

Preparation P13

N-[(4aR,6S,8aR)-8a-(4-Bromo-1,3-thiazol-2-yl)-6-(fluoromethyl)-6-methyl-4,4a,5,6,8,8a-hexahydropyrano[3,4-d][1,3]thiazin-2-yl]benzamide (P13)

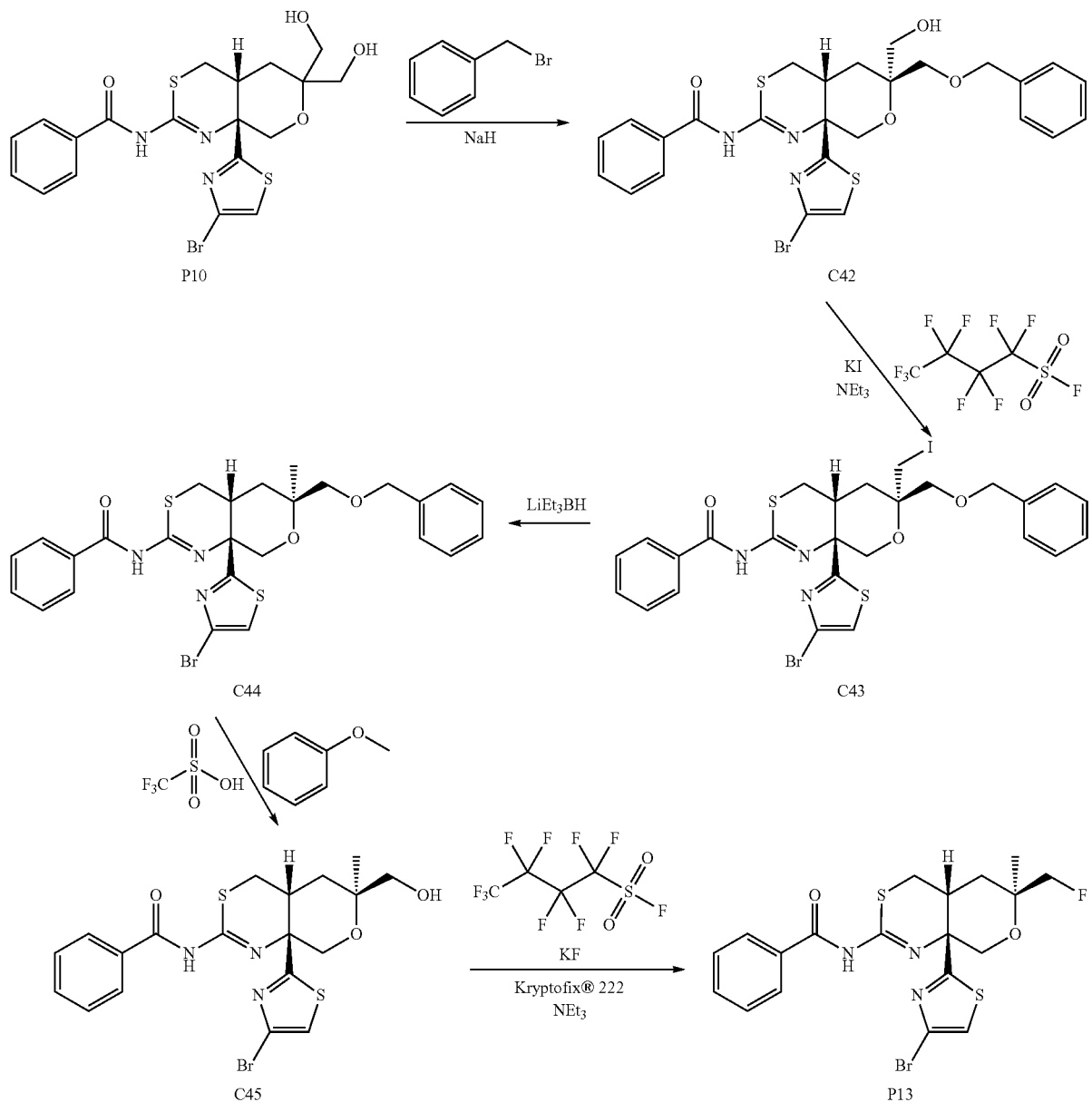

Step 1. Synthesis of N-[(4aR,6R,8aR)-6-[(benzyloxy)methyl]-8a-(4-bromo-1,3-thiazol-2-yl)-6-(hydroxymethyl)-4,4a,5,6,8,8a-hexahydropyrano[3,4-d][1,3]thiazin-2-yl]benzamide (C42)

Sodium hydride (60% in mineral oil; 98 mg, 2.4 mmol) was added to a solution of P10 (0.611 g, 1.23 mmol) in tetrahydrofuran (17.5 mL); the reaction mixture was stirred at room temperature for 10 minutes, and then it was cooled to 0° C. Benzyl bromide (0.238 mL, 1.96 mmol) was added in a drop-wise manner, the ice bath was removed, and the reaction mixture was stirred at room temperature until complete consumption of starting material was observed by LCMS analysis. The reaction mixture was partitioned between saturated aqueous ammonium chloride solution (20 mL) and ethyl acetate (20 mL); the organic layer was washed with saturated aqueous sodium chloride solution, dried over sodium sulfate, filtered, and concentrated in vacuo. Silica gel chromatography (Gradient: 20% to 100% ethyl acetate in heptane) provided the product as a white solid. Yield: 0.207 g, 0.352 mmol, 29%. LCMS m/z 590.4 (bromine isotope pattern observed) [M+H]$^+$. $^1$H NMR (400 MHz, CDCl$_3$), characteristic product peaks: δ: 8.07 (d, J=6.6 Hz, 2H), 7.53-7.58 (m, 1H), 7.37-7.50 (m, 6H), 7.31-7.36 (m, 1H), 7.23 (s, 1H), 4.62 (s, 2H), 4.15-4.23 (m, 1H), 3.88 (d, J=9.8 Hz, 1H), 3.73-3.81 (m, 2H), 3.68 (d, J=11.3 Hz, 1H), 3.52 (d, J=11.3 Hz, 1H), 3.20 (d, J=12.9 Hz, 1H), 3.12 (dd, J=12.9, 4.3 Hz, 1H), 2.57 (dd, J=13.3, 2.3 Hz, 1H), 2.06-2.15 (m, 1H), 1.73 (dd, J=14.0, 4.3 Hz, 1H).

Step 2. Synthesis of N-[(4aR,6S,8aR)-6-[(benzyloxy)methyl]-8a-(4-bromo-1,3-thiazol-2-yl)-6-(iodomethyl)-4,4a,5,6,8,8a-hexahydropyrano[3,4-d][1,3]thiazin-2-yl]benzamide (C43)

Triethylamine (0.146 mL, 1.05 mmol) was added to a solution of C42 (154 mg, 0.262 mmol) in acetonitrile (4.5 mL), and the solution was cooled to 0° C. 1,1,2,2,3,3,4,4,4-Nonafluorobutane-1-sulfonyl fluoride (0.214 mL, 1.22 mmol) was added in a drop-wise manner, and the reaction mixture was allowed to warm room temperature. After 2.2 hours, potassium iodide (0.434 g, 2.61 mmol) was added and the reaction mixture was heated to 45° C. for 16 hours. Additional potassium iodide (100 mg, 0.60 mmol) was added to the reaction mixture and heating was continued at 52° C. for 2 hours. The reaction mixture was cooled to room temperature, concentrated under reduced pressure, and partitioned between water (25 mL) and diethyl ether (30 mL). The aqueous layer was extracted with diethyl ether (30 mL), and the combined organic layers were washed with saturated aqueous sodium thiosulfate solution (10 mL), dried over sodium sulfate, filtered, and concentrated in vacuo. Silica gel chromatography (Gradient: 0% to 60% ethyl acetate in heptane) provided the product as a white solid. Yield: 0.126 g, 0.180 mmol, 69%. LCMS m/z 700.2 (bromine isotope pattern observed) [M+H]$^+$. $^1$H NMR (400 MHz, CDCl$_3$), characteristic product peaks: δ: 7.82-8.35 (m, 2H), 7.30-7.62 (m, 8H), 7.25 (s, 1H), 4.65 (d, J=3.1 Hz, 2H), 4.03-4.20 (m, 1H), 3.97 (d, J=9.8 Hz, 1H), 3.74-3.87 (m, 2H), 3.35-3.51 (m, 2H), 3.04-3.21 (m, 2H), 2.52-2.61 (m, 1H), 2.01-2.13 (m, 1H), 1.87-1.99 (m, 1H).

Step 3. Synthesis of N-[(4aR,6S,8aR)-6-[(benzyloxy)methyl]-8a-(4-bromo-1,3-thiazol-2-yl)-6-methyl-4,4a,5,6,8,8a-hexahydropyrano[3,4-d][1,3]thiazin-2-yl]benzamide (C44)

To a 0° C. solution of C43 (0.124 g, 0.178 mmol) in tetrahydrofuran (7.5 mL) was added lithium triethylborohydride (1 M in tetrahydrofuran, 1.95 mL, 1.95 mmol). The reaction mixture was allowed to warm to room temperature over 10 minutes, and was then heated at reflux for 5 hours. After cooling to room temperature, it was treated with methanol (15 mL), heated at reflux for 1 hour, and concentrated in vacuo. Silica gel column chromatography (Gradient: 0% to 100% ethyl acetate in heptane) provided the product as a white solid. NOE studies supported the quaternary methyl group being on the alpha face of the molecule: irradiation of that methyl group provided no enhancement of the signal for the methine proton at the ring fusion. Yield: 28 mg, 49 μmol, 28%. LCMS m/z 574.4 (bromine isotope pattern observed) [M+H]$^+$. $^1$H NMR (400 MHz, CDCl$_3$), characteristic product peaks: β 7.97-8.22 (m, 2H), 7.53-7.62 (m, 1H), 7.49 (d, J=7.0 Hz, 2H), 7.42 (d, J=4.7 Hz, 4H), 7.30-7.37 (m, 1H), 7.24 (s, 1H), 4.64 (s, 2H), 4.17-4.29 (m, 1H), 3.65-3.81 (m, 3H), 3.17-3.29 (m, 1H), 3.13 (d, J=12.9 Hz, 1H), 2.56 (br s, 1H), 1.89-2.01 (m, 1H), 1.74-1.85 (m, 1H), 1.32 (s, 3H).

Step 4. Synthesis of N-[(4aR,6S,8aR)-8a-(4-bromo-1,3-thiazol-2-yl)-6-(hydroxymethyl)-6-methyl-4,4a,5,6,8,8a-hexahydropyrano[3,4-d][1,3]thiazin-2-yl]benzamide (C45)

To a solution of C44 (52 mg, 91 μmol) in 1,2-dichloroethane (4 mL, 0.02 M) was added methoxybenzene (30 μL, 0.27 mmol), and the reaction mixture was heated to 60° C., followed by addition of trifluoromethanesulfonic acid (24 μL, 0.27 mmol). Heating was continued at 60° C. for 1.5 hours, whereupon the reaction mixture was cooled to room temperature and partitioned between dichloromethane (20 mL) and saturated aqueous sodium bicarbonate solution (15 mL). The aqueous layer was extracted with dichloromethane (2×20 mL), and the combined organic layers were dried over sodium sulfate, filtered, and concentrated in vacuo. Silica gel chromatography (Gradient: 0% to 100% ethyl acetate in heptane) provided the product as a white solid. Yield: 32 mg, 66 μmol, 73%. LCMS m/z 484.3 (bromine isotope pattern observed) [M+H]$^+$. $^1$H NMR (400 MHz, CDCl$_3$), characteristic product peaks: δ: 7.99-8.16 (m, 2H), 7.57 (d, J=7.8 Hz, 1H), 7.46-7.54 (m, 2H), 7.24 (s, 1H), 4.24 (d, J=11.3 Hz, 1H), 4.08-4.14 (m, 1H), 3.77 (d, J=12.1 Hz, 1H), 3.53 (d, J=10.5 Hz, 1H), 3.12-3.25 (m, 2H), 2.59 (d, J=11.3 Hz, 1H), 2.03-2.13 (m, 1H), 1.69-1.77 (br m, 1H), 1.60-1.69 (m, 1H), 1.33 (s, 3H).

Step 5. Synthesis of N-[(4aR,6S,8aR)-8a-(4-bromo-1,3-thiazol-2-yl)-6-(fluoromethyl)-6-methyl-4,4a,5,6,8,8a-hexahydropyrano[3,4-d][1,3]thiazin-2-yl]benzamide (P13)

To a solution of C45 (79 mg, 0.16 mmol) in acetonitrile (4 mL) was added triethylamine (91 μL, 0.66 mmol), followed by addition of 1,1,2,2,3,3,4,4,4-nonafluorobutane-1-sulfonyl fluoride (0.101 mL, 0.57 mmol) in a drop-wise manner, and the reaction mixture was stirred at room temperature for 1 hour. Additional 1,1,2,2,3,3,4,4,4-nonafluorobutane-1-sulfonyl fluoride (50 μL, 0.28 mmol) was added, and the reaction mixture was stirred at room temperature for 1 hour. Potassium fluoride (0.143 g, 2.46 mmol) and Kryptofix® 222 (4,7,13,16,21,24-hexaoxa-1,10-diazabicyclo[8.8.8]hexacosane; 0.566 g, 1.47 mmol) were then added to the reaction mixture, which was immediately concentrated in vacuo and re-dissolved in tetrahydrofuran (5 mL). The reaction mixture was stirred at room temperature for 30 minutes, and heated to 30° C. for 65 minutes, whereupon it was diluted with saturated aqueous sodium bicarbonate solution (5 mL) and water (5 mL). The aqueous layer was extracted with diethyl ether (3×15 mL), and the combined organic layers were dried over sodium sulfate, filtered, and concentrated under reduced pressure. Silica gel chromatography (Gradient: 0% to 70% ethyl acetate in heptane) provided the product as a white solid. Yield: 42 mg, 87 μmol, 54%. LCMS m/z 486.2 (bromine isotope pattern observed) [M+H]$^+$. $^1$H NMR (400 MHz, CDCl$_3$), characteristic product peaks: δ: 7.79-8.17 (m, 2H), 7.46-7.54 (m, 1H), 7.41 (br s, 2H), 7.15 (s, 1H), 4.47-4.68 (m, 2H), 4.08-4.25 (m, 1H), 3.71 (d, J=12.1 Hz, 1H), 3.02-3.25 (m, 2H), 2.47-2.58 (m, 1H), 1.91-2.06 (m, 1H), 1.65-1.75 (m, 1H), 1.24 (s, 3H).

Preparation P14
Di-tert-butyl [(4aR,6R,8aR)-8a-(4-bromo-1,3-thiazol-2-yl)-6-(fluoromethyl)-6-methyl-4,4a,5,6,8,8a-hexahydropyrano[3,4-d][1,3]thiazin-2-yl]imidodicarbonate (P14)
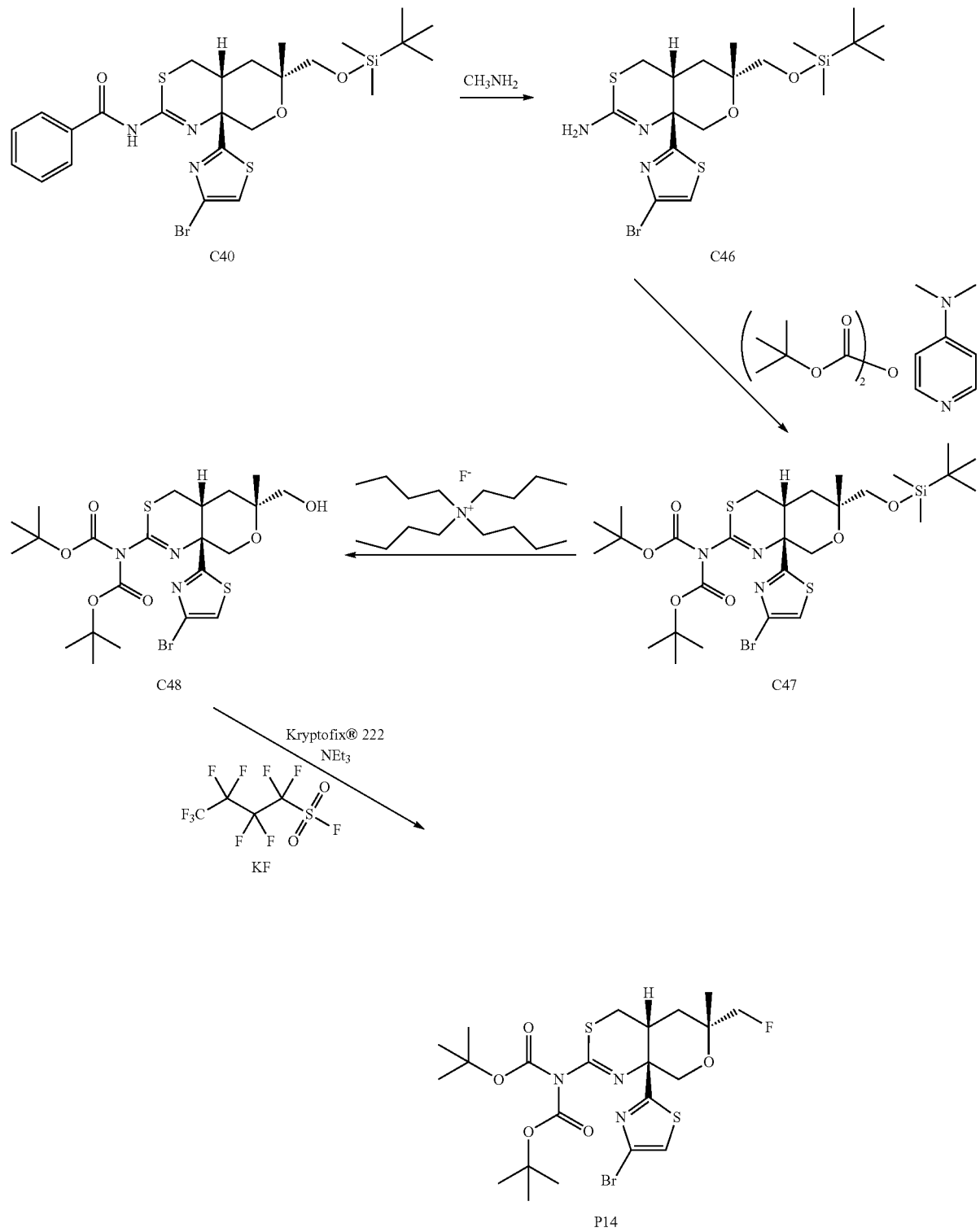

Step 1. Synthesis of (4aR,6R,8aR)-8a-(4-bromo-1, 3-thiazol-2-yl)-6-({[tert-butyl(dimethyl)silyl]oxy}methyl)-6-methyl-4,4a,5,6,8,8a-hexahydropyrano[3,4-d][1,3]thiazin-2-amine (C46)

A mixture of C40 (1.209 g, 2.026 mmol), ethanol (10 mL) and methylamine solution (33% by weight in ethanol; 10 mL) was stirred at room temperature for 6 hours, whereupon it was concentrated in vacuo. Purification via silica gel chromatography (Gradient: 0% to 100% ethyl acetate in heptane) afforded the product as a white solid. Yield: 895 mg, 1.82 mmol, 90%. LCMS m/z 494.3 (bromine isotope pattern observed) [M+H]$^+$. $^1$H NMR (400 MHz, CDCl$_3$) δ 7.17 (s, 1H), 4.57 (br s, 2H), 4.08 (d, J=11.3 Hz, 1H), 3.68 (d, J=11.3 Hz, 1H), 3.49 (s, 2H), 3.17-3.23 (m, 1H), 2.98-3.06 (m, 1H), 2.59 (dd, J=12.5, 2.7 Hz, 1H), 1.93 (t, J=13.5 Hz, 1H), 1.40-1.45 (m, 1H), 1.40 (s, 3H), 0.91 (s, 9H), 0.07 (s, 6H).

Step 2. Synthesis of di-tert-butyl [(4aR,6R,8aR)-8a-(4-bromo-1,3-thiazol-2-yl)-6-({[tert-butyl(dimethyl)silyl]oxy}methyl)-6-methyl-4,4a,5,6,8,8a-hexahydropyrano[3,4-d][1,3]thiazin-2-yl]imidodicarbonate (C47)

To a mixture of C46 (890 mg, 1.81 mmol) in tetrahydrofuran (40 mL) was added di-tert-butyl-dicarbonate (2.17 g, 9.94 mmol) followed by 4-(dimethylamino)pyridine (662 mg, 5.42 mmol). The reaction mixture was stirred at room temperature for 3 hours, whereupon it was concentrated in vacuo. Silica gel chromatography (Gradient: 0% to 80% ethyl acetate in heptane) provided the product as a white solid. Yield: 1.188 g, 1.71 mmol, 95%. $^1$H NMR (400 MHz, CDCl$_3$) δ 7.21 (s, 1H), 4.04 (d, J=11.7 Hz, 1H), 3.85 (d, J=11.7 Hz, 1H), 3.51 (s, 2H), 3.34 (dd, J=12.9, 3.9 Hz, 1H), 3.15-3.22 (m, 1H), 2.66 (dd, J=12.9, 2.7 Hz, 1H), 1.99 (t, J=13.5 Hz, 1H), 1.53 (s, 18H), 1.47-1.52 (m, 1H), 1.42 (s, 3H), 0.91 (s, 9H), 0.07 (s, 6H).

Step 3. Synthesis of di-tert-butyl [(4aR,6R,8aR)-8a-(4-bromo-1,3-thiazol-2-yl)-6-(hydroxymethyl)-6-methyl-4,4a,5,6,8,8a-hexahydropyrano[3,4-d][1,3]thiazin-2-yl]imidodicarbonate (C48)

To a mixture of C47 (1.18 g, 1.70 mmol) in tetrahydrofuran was added tetrabutylammonium fluoride solution (1 M in tetrahydrofuran; 4.26 mL, 4.26 mmol). The reaction mixture was stirred at room temperature for 4 hours, concentrated in vacuo, and subjected to two purifications via silica gel chromatography (Gradient: 0% to 100% ethyl acetate in heptane); the product was isolated as a white solid. Yield: 694 mg, 1.20 mmol, 70%. LCMS m/z 580.2 (bromine isotope pattern observed) [M+H]$^+$. $^1$H NMR (400 MHz, CDCl$_3$) δ 7.22 (s, 1H), 4.08 (d, J=11.3 Hz, 1H), 3.89 (d, J=11.3 Hz, 1H), 3.43-3.61 (m, 2H), 3.33 (dd, J=12.9, 3.9 Hz, 1H), 3.21-3.28 (m, 1H), 2.66 (dd, J=12.9, 2.7 Hz, 1H), 2.45 (t, J=13.5 Hz, 1H), 2.39 (dd, J=8.0, 4.5 Hz, 1H), 1.54 (s, 18H), 1.38 (s, 3H)

Step 4. Synthesis of di-tert-butyl [(4aR,6R,8aR)-8a-(4-bromo-1,3-thiazol-2-yl)-6-(fluoromethyl)-6-methyl-4,4a,5,6,8,8a-hexahydropyrano[3,4-d][1,3]thiazin-2-yl]imidodicarbonate (P14)

To a mixture of C48 (66 mg, 0.11 mmol) in acetonitrile (3 mL) was added triethylamine (64 µL, 0.46 mmol), followed by drop-wise addition of 1,1,2,2,3,3,4,4,4-nonafluorobutane-1-sulfonyl fluoride (70 µL, 0.40 mmol). The reaction mixture was stirred at room temperature for 50 minutes, during which time a white precipitate formed. After an additional 90 minutes, the mixture was concentrated to a white solid. This solid was dissolved in tetrahydrofuran (4 mL) and treated with potassium fluoride (99.4 mg, 1.71 mmol), followed by Kryptofix® 222 (438 mg, 1.14 mmol). The reaction mixture was stirred at 55° C. for 3 hours, then at 65° C. for another 1 hour and 45 minutes. It was then allowed to cool to room temperature, whereupon saturated aqueous sodium bicarbonate solution (10 mL) and water (5 mL) were added. The resulting mixture was extracted with diethyl ether (3×20 mL), and the combined organic layers were dried over sodium sulfate, filtered, and concentrated in vacuo. Silica gel chromatography (Gradient: 0% to 55% ethyl acetate in heptane) afforded the product as a white solid. Yield: 55.2 mg, 95 µmol, 83%. LCMS m/z 582.3 (bromine isotope pattern observed) [M+H]$^+$. $^1$H NMR (400 MHz, CDCl$_3$) δ 7.22 (s, 1H), 4.16-4.39 (m, 2H), 3.87-4.08 (m, 2H), 3.34 (dd, J=12.9, 3.9 Hz, 1H), 3.20-3.28 (m, 1H), 2.65 (dd, J=12.9, 2.7 Hz, 1H), 2.10 (t, J=13.3 Hz, 1H), 1.53 (s, 18H), 1.51 (d, J=1.6 Hz, 3H), 1.42 (dd, J=13.3, 4.3 Hz, 1H).

Preparation P15 di-tert-Butyl [(4aR,8aR)-8a-(4-amino-1,3-thiazol-2-yl)-6,6-bis(fluoromethyl)-4,4a, 5,6,8,8a-hexahydropyrano[3,4-d][1,3]thiazin-2-yl]imidodicarbonate (P15)

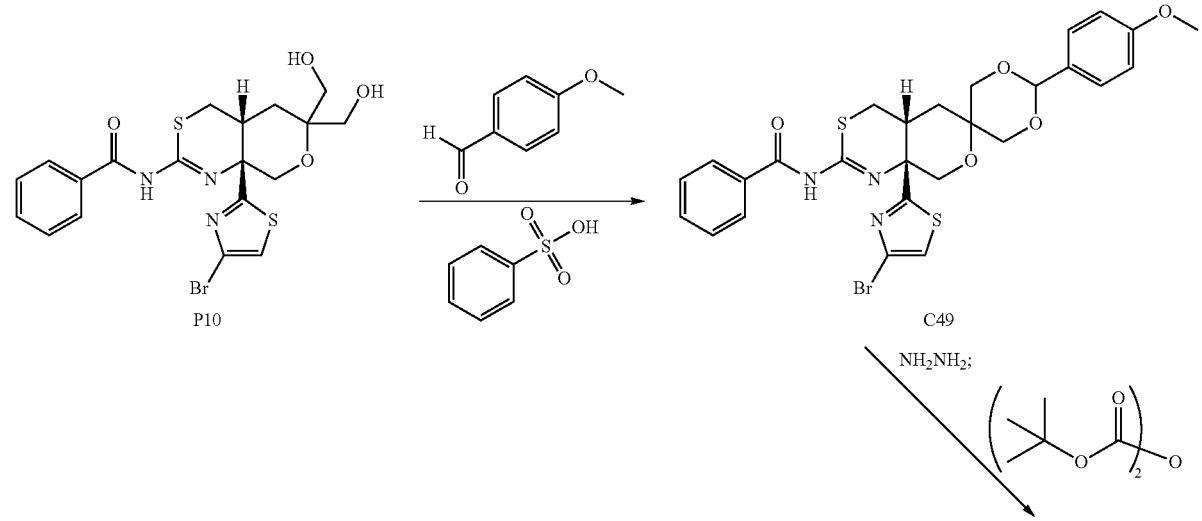

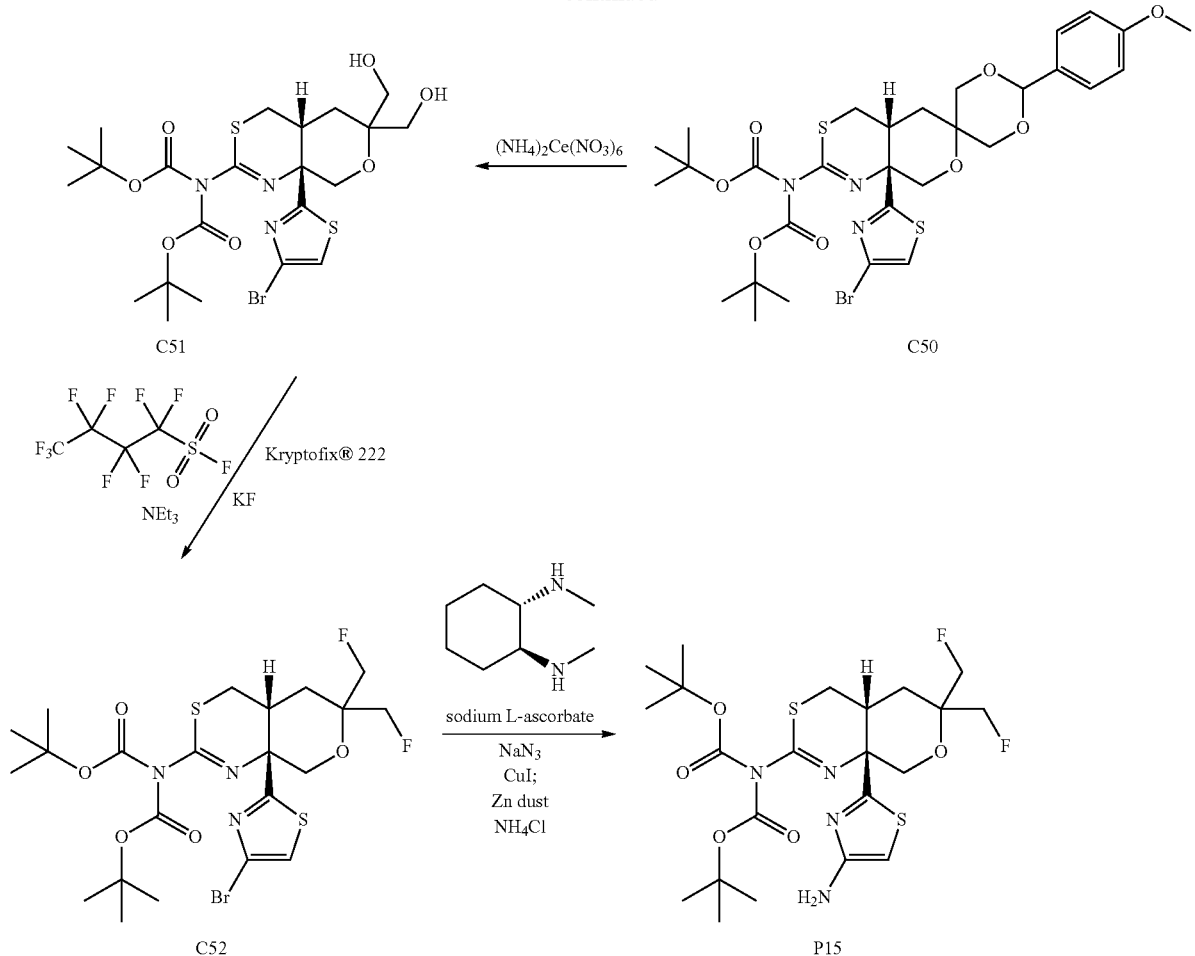

Step 1. Synthesis of N-[(4a'R,8a'R)-8a'-(4-bromo-1,3-thiazol-2-yl)-2-(4-methoxyphenyl)-4a',5',8',8a'-tetrahydro-4'H-spiro[1,3-dioxane-5,6'-pyrano[3,4-d][1,3]thiazin]-2'-yl]benzamide (C49)

4-Methoxybenzaldehyde (0.29 mL, 2.39 mmol), P10 (0.298 g, 0.598 mmol), sodium sulfate (1.0 g), and benzenesulfonic acid (9.46 mg, 59.8 μmol) were combined in toluene (30 mL), and heated to reflux. After 20 hours, the reaction mixture was cooled to ambient temperature and partitioned between saturated aqueous sodium bicarbonate solution (50 mL) and ethyl acetate (50 mL). The aqueous layer was extracted with ethyl acetate (2×50 mL), and the combined organic layers were washed with saturated aqueous sodium chloride solution, dried over sodium sulfate, filtered, and concentrated in vacuo. Chromatography on silica gel (Gradient: 0% to 80% ethyl acetate in heptane) afforded two diastereomers, which were separated for characterization purposes, then recombined for the subsequent reaction. Major diastereomer: Yield: 0.216 g, 0.350 mmol, 59%. $^1$H NMR (400 MHz, CDCl$_3$), characteristic peaks: δ 7.86-8.24 (m, 2H), 7.56 (m, 1H), 7.45-7.52 (m, 2H), 7.38-7.44 (m, 2H), 7.24 (s, 1H), 6.88-6.94 (m, 2H), 5.44 (s, 1H), 4.82 (dd, J=10.9, 2.3 Hz, 1H), 4.09 (d, J=12.5 Hz, 1H), 3.97 (dd, J=10.9, 2.3 Hz, 1H), 3.71-3.85 (m, 6H), 3.14-3.30 (m, 2H), 2.69 (m, 1H), 2.54 (dd, J=14.0, 4.3 Hz, 1H), 2.01 (m, 1H).

Minor diastereomer: Yield: 57 mg, 92 μmol, 15%. $^1$H NMR (400 MHz, CDCl$_3$), characteristic peaks: β 8.05 (m, 2H), 7.54-7.62 (m, 1H), 7.41-7.53 (m, 4H), 7.24 (s, 1H), 6.85-6.92 (m, 2H), 5.50 (s, 1H), 4.97 (dd, J=12.9, 2.7 Hz, 1H), 4.26 (d, J=12.5 Hz, 1H), 4.07 (dd, J=11.9, 2.9 Hz, 1H), 3.93 (d, J=12.5 Hz, 1H), 3.73-3.87 (m, 5H), 3.04-3.26 (m, 2H), 2.57 (d, J=10.9 Hz, 1H), 1.89 (t, J=13.5 Hz, 1H), 1.42 (dd, J=13.9, 4.1 Hz, 1H).

Step 2. Synthesis of di-tert-butyl [(4a'R,8a'R)-8a'-(4-bromo-1,3-thiazol-2-yl)-2-(4-methoxyphenyl)-4a',5',8',8a'-tetrahydro-4'H-spiro[1,3-dioxane-5,6'-pyrano[3,4-d][1,3]thiazin]-2'-yl]imidodicarbonate (C50)

To a mixture of C49 (0.273 g, 0.443 mmol) in ethanol (6.7 mL) and dichloromethane (8.7 mL) was added hydrazine monohydrate (0.235 mL, 3.10 mmol), and the reaction mixture was stirred for 3 hours. Concentration in vacuo provided a white solid, which was suspended in acetonitrile (8 mL), and treated with 4-(dimethylamino)pyridine (10 mg) and di-tert-butyl dicarbonate (0.30 g, 1.37 mmol). After 15 minutes, a fine white solid precipitated out of solution; this was collected via filtration to afford the product as an inseparable mixture (1.00:0.16) of diastereomers. Yield: 0.119 g, 0.167 mmol, 38%. LCMS m/z 714.3 (bromine isotope pattern observed) [M+H]$^+$. $^1$H NMR (400 MHz, CDCl$_3$), characteristic peaks: β 7.43 (m, 2.3H), 7.22 (s, 1H), 6.91 (m, 2.3H), 5.51-5.48 (m, 0.16H), 5.43 (s, 1H), 4.76-4.83 (m, 1.2H), 4.08-4.03 (m, 1.2H), 3.97 (m, 2.2H), 3.90 (d, 2.2H), 3.84-3.73 (m, 5.8H), 3.36-3.29 (m, 1.2H), 3.27-3.18 (m, 1.2H), 2.79-2.70 (m, 1.2H), 2.48-2.38 (m, 1.2H), 2.23-2.10 (m, 1.2H), 1.56 (s, 2.8H), 1.53 (s, 18H).

Step 3. Synthesis of di-tert-butyl [(4aR,8aR)-8a-(4-bromo-1,3-thiazol-2-yl)-6,6-bis(hydroxymethyl)-4,4a,5,6,8,8a-hexahydropyrano[3,4-d][1,3]thiazin-2-yl]imidodicarbonate (C51)

Ceric ammonium nitrate (0.445 g, 0.811 mmol) was added to a 0° C. solution of C50 (119 mg, 0.167 mmol) in acetonitrile (3.4 mL) and water (0.34 mL). The reaction mixture was allowed to warm to room temperature and stirred for 30 minutes, whereupon it was diluted with ethyl acetate (50 mL) and treated with saturated aqueous sodium bicarbonate solution (40 mL), then with water (100 mL). The resulting mixture was extracted with ethyl acetate (2×40 mL), and the combined organic layers were dried over sodium sulfate, filtered, and concentrated in vacuo. Chromatography on silica gel (Gradient: 0% to 100% ethyl acetate in heptane) afforded the product as a viscous oil. Yield: 73 mg, 0.123 mmol, 74%. $^1$H NMR (400 MHz, CDCl$_3$), characteristic peaks: δ 7.22 (s, 1H), 4.20 (dd, J=11.9, 3.7 Hz, 1H), 4.07-4.01 (m, 1H), 3.92 (d, J=11.3 Hz, 1H), 3.76 (m, 2H), 3.61 (dd, J=11.3, 6.6 Hz, 1H), 3.29 (dd, J=13.3, 3.9 Hz, 1H), 3.19 (dd, J=13.1, 2.9 Hz, 1H), 2.67 (m, 1H), 2.34 (m, 1H), 2.28 (t, J=13.9 Hz, 1H), 2.17 (m, 1H), 1.54 (s, 18H), 1.47 (m, 1H).

Step 4. Synthesis of di-tert-butyl [(4aR,8aR)-8a-(4-bromo-1,3-thiazol-2-yl)-6,6-bis(fluoromethyl)-4,4a,5,6,8,8a-hexahydropyrano[3,4-d][1,3]thiazin-2-yl]imidodicarbonate (C52)

Triethylamine (0.169 mL, 1.21 mmol) and 1,1,2,2,3,3,4,4-nonafluorobutane-1-sulfonyl fluoride (0.187 mL, 1.06 mmol) were sequentially added to a 0° C. solution of C51 (90 mg, 0.15 mmol) in tetrahydrofuran (5 mL). After 3 hours, LCMS showed formation of an intermediate corresponding to the bis-sulfonate intermediate {m/z 1159.8 (bromine isotope pattern observed) [M+H]$^+$}. At this time, potassium fluoride (0.132 g, 2.27 mmol) and Kryptofix® 222 (0.582 g, 1.51 mmol) were added to the reaction mixture, which was then stirred at 55° C. for 1 hour. The reaction mixture was cooled, and diluted with aqueous sodium bicarbonate solution (50 mL) and ethyl acetate (50 mL). The aqueous layer was extracted with ethyl acetate (3×25 mL), and the combined organic layers were washed with saturated aqueous sodium chloride solution, dried over sodium sulfate, filtered, and concentrated under reduced pressure. Silica gel chromatography (Gradient: 0% to 60% ethyl acetate in heptane) afforded the product as a yellow gum. Yield: 35 mg, 58 μmol, 39%. LCMS m/z 600.2 (bromine isotope pattern observed) [M+H]$^+$. $^1$H NMR (400 MHz, CDCl$_3$), characteristic peaks: β 7.23 (s, 1H), 4.96-4.24 (m, 4H), 4.11-3.91 (m, 2H), 3.32 (dd, J=12.9, 3.9 Hz, 1H), 3.26-3.17 (m, 1H), 2.74-2.66 (m, 1H), 2.24-2.06 (m, 1H), 1.76-1.65 (m, 1H), 1.56-1.50 (m, 18H).

Step 5. Synthesis of di-tert-butyl [(4aR,8aR)-8a-(4-amino-1,3-thiazol-2-yl)-6,6-bis(fluoromethyl)-4,4a,5,6,8,8a-hexahydropyrano[3,4-d][1,3]thiazin-2-yl]imidodicarbonate (P15)

A solution of C52 (35 mg, 58 μmol) and trans-N,N'-dimethylcyclohexane-1,2-diamine (10 mg, 70 μmol) in ethanol (1 mL) was treated with sodium azide (36 mg, 0.56 mmol), and with a solution of sodium L-ascorbate (6 mg, 30 μmol) in water (0.15 mL). The reaction mixture was briefly evacuated under high vacuum and then refilled with nitrogen (3 cycles). It was then stirred under nitrogen at ambient temperature for 15 minutes, followed by the addition of copper(I) iodide (5 mg, 30 μmol). The resulting blue solution was heated to 70° C. for 20 minutes, whereupon the reaction mixture was removed from the heat and partitioned between saturated aqueous sodium bicarbonate solution (25 mL), water (25 mL), and ethyl acetate (25 mL). The aqueous layer was extracted with ethyl acetate (2×25 mL), and the combined organic layers were dried over sodium sulfate, filtered, and concentrated in vacuo. To this residue was added ethanol (2.0 mL), water (0.30 mL), ammonium chloride (10 mg, 0.187 mmol) and zinc dust (10 mg, 0.15 mmol). The resulting suspension was heated to 60° C. for 25 minutes, at which time it was cooled, and worked up as described above. Chromatography on silica gel (Gradient: 0% to 100% ethyl acetate in heptane) afforded the product as a white solid. Yield: 7 mg, 13 μmol, 20%. LCMS m/z 535.4 [M+H]$^+$.

Preparation P16

Di-tert-butyl [(4aR,6S,8aR)-8a-(4-amino-1,3-thiazol-2-yl)-6-ethyl-6-methyl-4,4a,5,6,8,8a-hexahydropyrano[3,4-d][1,3]thiazin-2-yl]imidodicarbonate (P16)

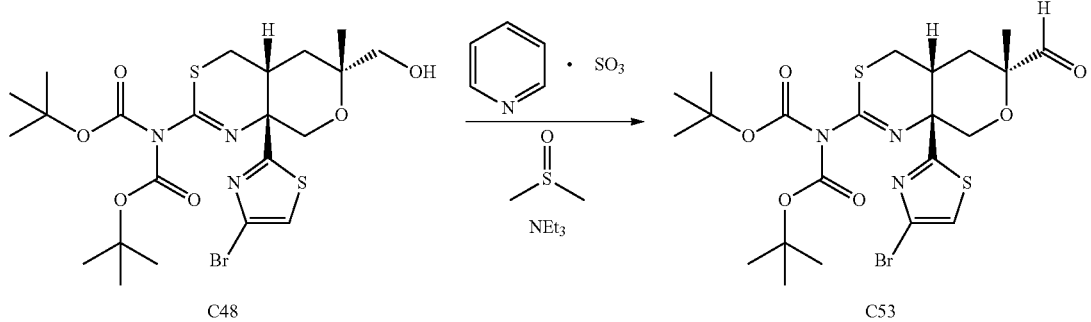

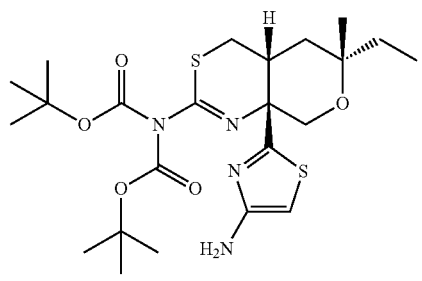

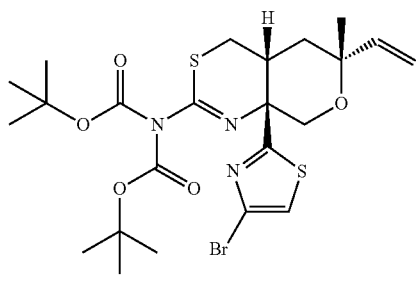

Step 1. Synthesis of di-tert-butyl [(4aR,6R,8aR)-8a-(4-bromo-1,3-thiazol-2-yl)-6-formyl-6-methyl-4,4a,5,6,8,8a-hexahydropyrano[3,4-d][1,3]thiazin-2-yl]imidodicarbonate (C53)

A solution of C48 (485 mg, 0.838 mmol) in dichloromethane (15 mL) was treated with triethylamine (0.7 mL, 5 mmol) and dimethyl sulfoxide (0.71 mL, 10 mmol), and cooled to 0° C. Pyridine-sulfur trioxide complex (820 mg, 5.0 mmol) was then added and the reaction mixture was stirred at room temperature for 18 hours, whereupon it was quenched with saturated aqueous ammonium chloride solution (30 mL) and water (15 mL), and diluted with dichloromethane (20 mL). The aqueous layer was extracted with dichloromethane (2×40 mL), and the combined organics layers were washed with saturated aqueous sodium chloride solution (30 mL), dried over sodium sulfate, filtered, and concentrated in vacuo. Silica gel chromatography (Gradient: 0% to 95% ethyl acetate in heptane) provided the product as a white solid. Yield: 267 mg, 0.463 mmol, 55%. LCMS m/z 578.2 (bromine isotope pattern observed) [M+H]$^+$. $^1$H NMR (400 MHz, CDCl$_3$) δ 9.62 (s, 1H), 7.25 (s, 1H), 4.10-4.18 (m, 1H), 4.00-4.07 (m, 1H), 3.35 (dd, J=12.9, 3.9 Hz, 1H), 3.23-3.31 (m, 1H), 2.70 (dd, J=12.9, 2.7 Hz, 1H), 2.16-2.26 (m, 1H), 1.49-1.55 (m, 21H), 1.48 (d, J=4.29 Hz, 1H)

Step 2. Synthesis of di-tert-butyl [(4aR,6R,8aR)-8a-(4-bromo-1,3-thiazol-2-yl)-6-formyl-6-methyl-4,4a,5,6,8,8a-hexahydropyrano[3,4-d][1,3]thiazin-2-yl]imidodicarbonate (C54)

Potassium tert-butoxide (1.0 M solution in tetrahydrofuran; 0.77 mL, 0.77 mmol) was added drop-wise to a suspension of methyltriphenylphosphomium bromide (338 mg, 0.926 mmol) in tetrahydrofuran (10 mL), and the reaction mixture was stirred at room temperature for 15 minutes before being cooled to 0° C. A solution of C53 (178 mg, 0.309 mmol) in tetrahydrofuran (2 mL) was added drop-wise and stirring was continued at room temperature for 2 hours. The reaction was then quenched via addition of saturated aqueous ammonium chloride solution (10 mL) and water (5 mL), and the mixture was extracted with diethyl ether (3×15 mL). The combined organic layers were dried over sodium sulfate, filtered, and concentrated in vacuo; silica gel chromatography (Gradient: 0% to 70% ethyl acetate in heptane) afforded the product as a white solid. Yield: 141 mg, 0.245 mmol, 79%. LCMS m/z 576.3 (bromine isotope pattern observed) [M+H]$^+$. $^1$H NMR (400 MHz, CDCl$_3$) δ 7.23 (s, 1H), 5.91-6.03 (m, 1H), 5.21-5.33 (m, 1H), 5.07 (dd, J=10.9, 1.2 Hz, 1H), 4.10 (d, J=11.7 Hz, 1H), 3.94 (d, J=11.7 Hz, 1H), 3.36 (dd, J=12.9, 3.9 Hz, 1H), 3.22-3.31 (m, 1H), 2.68 (dd, J=12.9, 2.7 Hz, 1H), 2.07-2.26 (m, 1H), 1.55-1.59 (m, 3H), 1.52 (s, 18H), 1.48-1.51 (m, 1H).

Step 3. Synthesis of di-tert-butyl [(4aR,6S,8aR)-8a-(4-amino-1,3-thiazol-2-yl)-6-ethyl-6-methyl-4,4a,5,6,8,8a-hexahydropyrano[3,4-d][1,3]thiazin-2-yl]imidodicarbonate (P16)

Compound C54 (137 mg, 0.238 mmol) was dissolved in a mixture of ethanol and water (6:1, 3 mL, which had been sparged with argon); trans-N,N'-dimethylcyclohexane-1,2-diamine (41 mg, 0.28 mmol) was then added, followed by sodium azide (147 mg, 2.27 mmol) and sodium L-ascorbate (24.1 mg, 0.119 mmol). The resulting mixture was purged in vacuo and refilled with nitrogen (three cycles), then the reaction mixture was stirred at room temperature for 15 minutes. Copper(I) iodide (22.7 mg, 0.119 mmol) was added and the resulting blue solution was heated to 70° C. for 4 hours, whereupon it was cooled to room temperature, concentrated in vacuo, and treated with half-saturated aqueous sodium bicarbonate solution (20 mL). The aqueous layer was extracted with ethyl acetate (2×25 mL), and the combined organic layers were dried over sodium sulfate, filtered, and concentrated under reduced pressure. The residue (130 mg) was dissolved in methanol (10 mL) and treated with 10% palladium on carbon (50 mg). The reaction mixture was pressurized with 75 psi nitrogen and evacuated (three cycles), then placed under 50 psi hydrogen and evacuated (three cycles). It was then stirred under 50 psi hydrogen for 7 hours. 10% Palladium on carbon (100 mg) was added and the reaction mixture was stirred for 18 hours under 65 psi hydrogen, whereupon it was filtered through diatomaceous earth, and the filtrate was concentrated in vacuo. Silica gel chromatography (Gradient: 0% to 100% ethyl acetate in heptane) provided the product as a white solid. Yield: 43 mg, 84 μmol, 35%. LCMS m/z 513.4 [M+H]$^+$. $^1$H NMR (400 MHz, CDCl$_3$) δ 5.86 (s, 1H), 3.87-4.00 (m, 3H), 3.78 (d, J=11.7 Hz, 1H), 3.32 (dd, J=12.9, 3.9 Hz, 1H), 2.98-3.09 (m, 1H), 2.52 (dd, J=12.7, 2.5 Hz, 1H), 1.88-2.00 (m, 1H), 1.48-1.54 (m, 3H), 1.41-1.47 (m, 18H), 1.25-1.31 (m, 3H), 0.86 (t, J=7.6 Hz, 3H).

Preparation P17
N-[cis-8a'-{4-[(2,4-Dimethoxybenzyl)amino]-1,3-thiazol-2-yl}-4a',5',8',8a'-tetrahydro-4'H-spiro[cyclopropane-1,6'-pyrano[3,4-d][1,3]thiazin]-2'-yl]benzamide (P17)
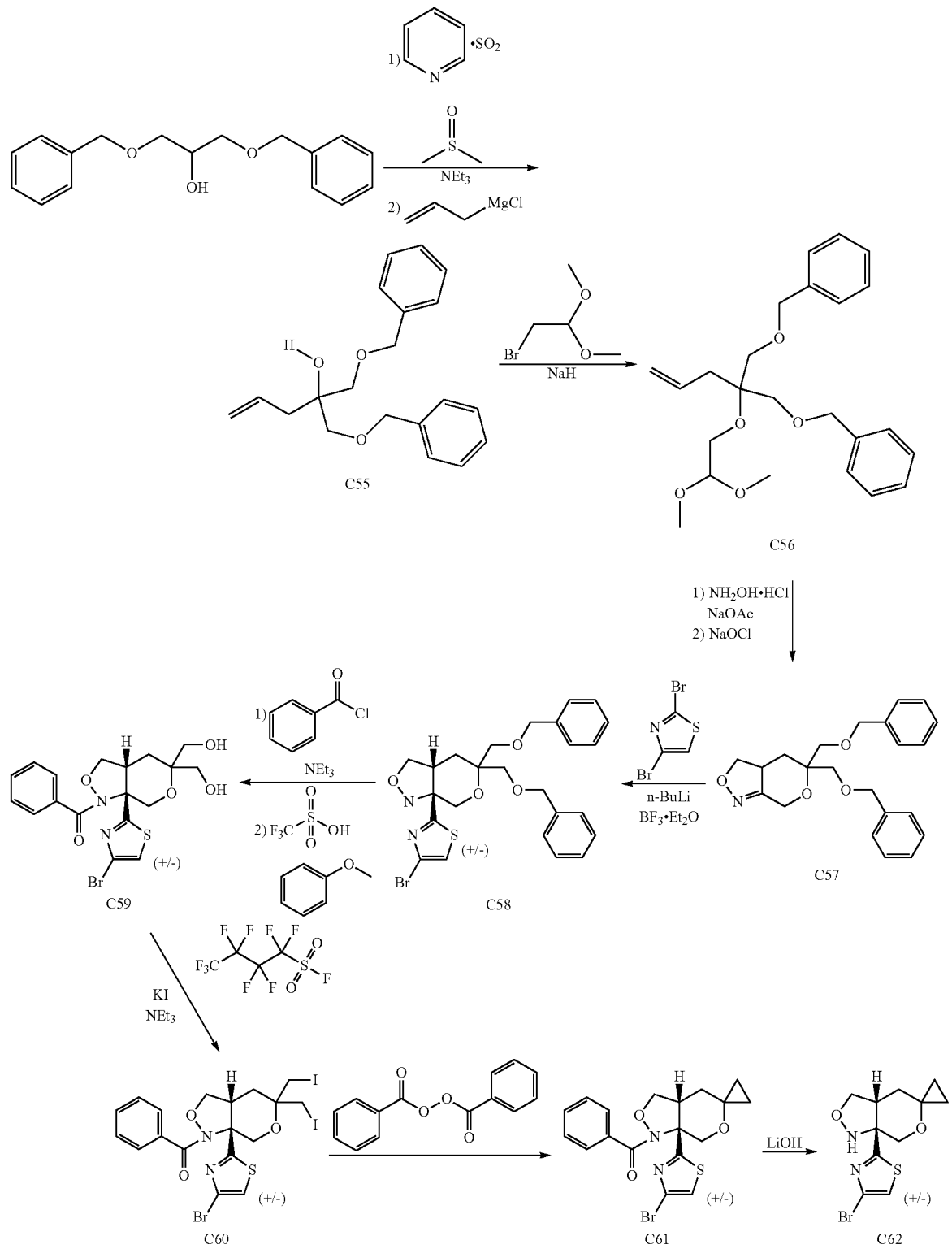

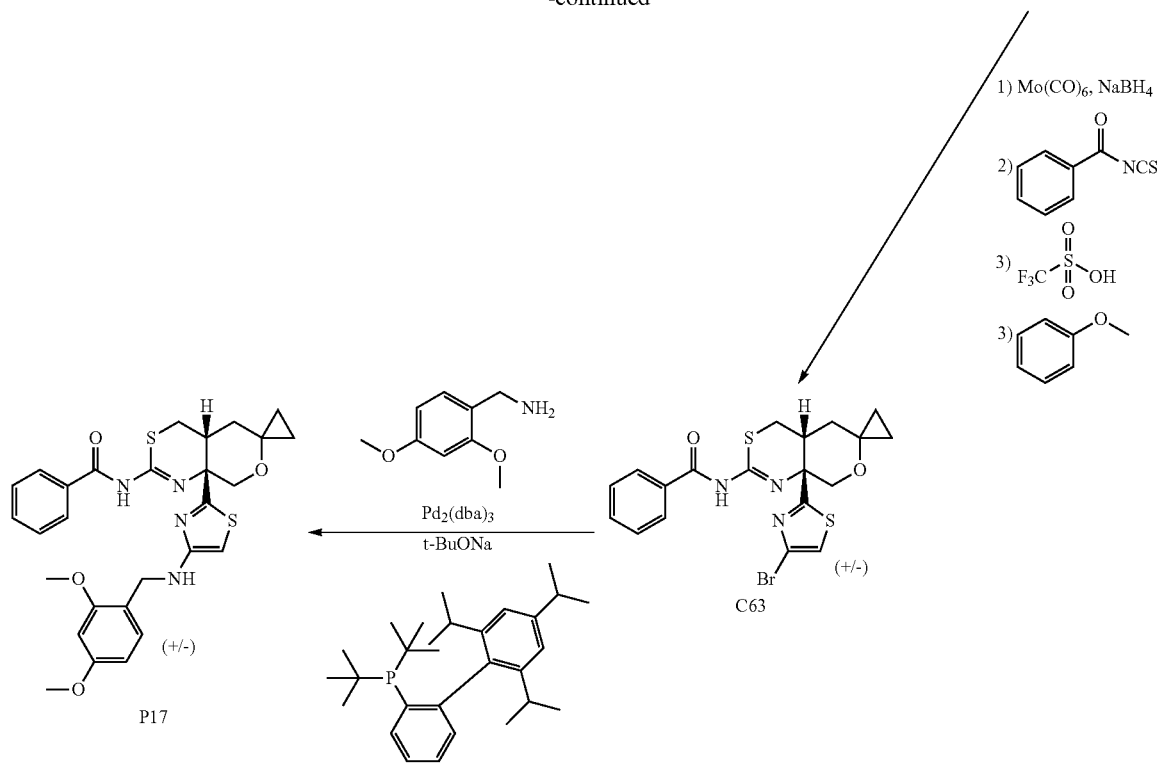

Step 1. Synthesis of 1-(benzyloxy)-2-(phenoxymethyl)pent-4-en-2-ol (C55)

Pyridine-sulfur trioxide complex (51.3 g, 316 mmol) was added to a 0° C. solution of 1,3-bis(benzyloxy)propan-2-ol (20.0 g, 73.4 mmol), triethylamine (49.8 mL, 358 mmol), and dimethyl sulfoxide (25.0 mL, 352 mmol) in dichloromethane (77 mL). The resulting solution was allowed to warm to room temperature and stir for 2 hours. The reaction mixture was then partitioned between ethyl acetate (250 mL) and water (500 mL); the organic layer was washed sequentially with aqueous hydrochloric acid (2 M, 2×250 mL), water (2×200 mL), and saturated aqueous sodium chloride solution (500 mL). It was then dried over sodium sulfate, filtered, and concentrated under reduced pressure to yield intermediate 1,3-bis(benzyloxy)propan-2-one as an orange oil (20.8 g, 77.0 mmol). This material was dissolved in tetrahydrofuran (77 mL) and cooled to 0° C.; allylmagnesium chloride (2.0 M solution in tetrahydrofuran, 38.5 mL, 77.0 mmol) was slowly added to this solution. The reaction mixture was allowed to warm to room temperature and stir at room temperature for 16 hours, whereupon it was quenched via slow addition of aqueous hydrochloric acid (1 M, 500 mL). The resulting biphasic solution was extracted with diethyl ether (3×200 mL). The combined organic layers were washed with water (2×150 mL), dried over magnesium sulfate, filtered, and concentrated under reduced pressure. Silica gel chromatography (Gradient: 0% to 80% ethyl acetate in heptane) afforded the product as a colorless oil. Yield: 17.0 g, 54.4 mmol, 74%. LCMS m/z 335.4 [M+Na⁺]. $^1$H NMR (400 MHz, CDCl$_3$), characteristic product peaks: β 7.27-7.38 (m, 10H), 5.78-5.93 (m, 1H), 5.04-5.14 (m, 2H), 4.54 (s, 4H), 3.39-3.52 (m, 4H), 2.36 (dt, J=7.4, 1.1 Hz, 2H).

Step 2. Synthesis of ({2-[(benzyloxy)methyl]-2-(2,2-dimethoxyethoxy)pent-4-en-1-yl}oxy)benzene (C56)

To a suspension of sodium hydride (60% dispersion in mineral oil, 4.30 g, 108 mmol) in 1,4-dioxane (68 mL) was added C55 (16.0 g, 51.2 mmol) in a drop-wise manner. After the addition was completed, the reaction mixture was stirred at room temperature for 45 minutes, whereupon 2-bromo-1,1-dimethoxyethane (12.1 mL, 102 mmol) was slowly added. The reaction mixture was heated to 100° C. for 4 days, and then cooled to room temperature and poured into ice water (1 L). The aqueous layer was extracted with ethyl acetate (3×250 mL), and the combined organic layers were washed with saturated aqueous sodium chloride solution (500 mL), dried over sodium sulfate, filtered, and concentrated in vacuo. Silica gel chromatography (Gradient: 0% to 20% ethyl acetate in heptane) afforded the product as a yellow oil. Yield: 11.6 g, 29 mmol, 57%. LCMS m/z 423.5 [M+Na⁺]. $^1$H NMR (400 MHz, CDCl$_3$), characteristic product peaks: β 7.26-7.35 (m, 10H), 5.75-5.90 (m, 1H), 5.03-5.12 (m, 2H), 4.51 (s, 4H), 4.44 (t, J=5.2 Hz, 1H), 3.60 (d, J=5.3 Hz, 2H), 3.46-3.55 (m, 4H), 3.36 (s, 6H), 2.35-2.40 (m, 2H).

Step 3. Synthesis of 5,5-bis[(benzyloxy)methyl]-3,3a,4,5-tetrahydro-7H-pyrano[3,4-c][1,2]oxazole (C57)

Hydroxylamine hydrochloride (2.89 g, 41.6 mmol) was added to a solution of C56 (11.6 g, 28.9 mmol) in ethanol (56 mL) and water (10 mL). The reaction mixture was heated to 70° C. for 2.5 hours, whereupon it was cooled to room temperature. Sodium acetate (4.89 g, 57.8 mmol) and water (10 mL) were added, and the reaction mixture was allowed to stir at room temperature for 10 minutes. It was then concentrated under reduced pressure to remove ethanol, and the residue was partitioned between dichloromethane (100 mL) and water (150 mL). The aqueous layer was extracted with dichloromethane (2×150 mL), and the combined organic layers were washed with saturated aqueous sodium chloride solution (300 mL), dried over sodium sulfate, filtered, and concentrated in vacuo to provide intermediate 2-({1-(benzyloxy)-2-[(benzyloxy)methyl]pent-4-en-2-yl}oxy)-N-hydroxyethanimine as a colorless oil (12.5 g). This material was dissolved in dichloromethane (160 mL), cooled to −10° C. (internal temperature, ice-methanol bath), and treated with aqueous sodium hypochlorite solution (5.65-6%, 44.9 mL, 37.5 mmol) in a drop-wise manner, such that the temperature of the reaction mixture did not exceed 0° C. throughout the addition. The reaction mixture was stirred at −10° C. for 3 hours and then allowed to warm to room temperature and stir for 16 hours, whereupon it was diluted with water (500 mL) and the aqueous layer was extracted with dichloromethane (2×250 mL). The combined organic layers were washed with saturated aqueous sodium chloride solution (500 mL), dried over sodium sulfate, filtered, and concentrated in vacuo. Silica gel chromatography (Gradient: 0% to 80% ethyl acetate in heptane) afforded the product as a colorless oil. Yield: 8.91 g, 24.2 mmol, 71%. LCMS m/z 368.4 [M+H]$^+$. $^1$H NMR (400 MHz, CDCl$_3$), characteristic product peaks: β 7.27-7.39 (m, 10H), 4.52-4.63 (m, 6H), 4.44-4.50 (m, 1H), 3.66-3.78 (m, 3H), 3.54-3.62 (m, 1H), 3.51 (d, J=9.8 Hz, 1H), 3.40 (d, J=9.6 Hz, 1H), 2.31 (dd, J=13.2, 6.7 Hz, 1H), 1.59 (dd, J=13.3, 11.9 Hz, 1H).

Step 4. Synthesis of cis-5,5-bis[(benzyloxy)methyl]-7a-(4-bromo-1,3-thiazol-2-yl)hexahydro-1H-pyrano[3,4-c][1,2]oxazole (C58)

Conversion of C57 to C58 was effected using the method described for synthesis of C22 from C21 in Preparation P4. The product was isolated as a yellow oil. Yield: 9.80 g, 18.4 mmol, 76%. LCMS m/z 533.3 (bromine isotope pattern observed) [M+H]$^+$. $^1$H NMR (400 MHz, CDCl$_3$), characteristic product peaks: δ: 7.27-7.38 (m, 10H), 7.19 (s, 1H), 4.51-4.62 (m, 4H), 4.08 (d, J=12.9 Hz, 1H), 3.77-3.86 (m, 2H), 3.67-3.77 (m, 2H), 3.37-3.66 (m, 3H), 3.23-3.32 (m, 1H), 1.96 (dd, J=14.6, 6.7 Hz, 1H), 1.68 (dd, J=14.5, 11.2 Hz, 1H)

Step 5. Synthesis of [cis-7a-(4-bromo-1,3-thiazol-2-yl)-5,5-bis(hydroxymethyl)hexahydro-1H-pyrano[3,4-c][1,2]oxazol-1-yl](phenyl)methanone (C59)

Benzoyl chloride (0.961 mL, 8.28 mmol) was added to a 0° C. solution of C58 (2.20 g, 4.14 mmol) and triethylamine (1.15 mL, 8.28 mmol) in tetrahydrofuran (41 mL). The reaction mixture was allowed to warm to room temperature and stir for 16 hours, whereupon it was partitioned between ethyl acetate (150 mL) and water (150 mL). The organic layer was washed sequentially with water (2×150 mL) and with saturated aqueous sodium chloride solution (300 mL), dried over sodium sulfate, filtered, and concentrated in vacuo. Silica gel chromatography (Gradient: 0% to 50% ethyl acetate in heptane) afforded intermediate [cis-5,5-bis[(benzyloxy)methyl]-7a-(4-bromo-1,3-thiazol-2-yl)hexahydro-1H-pyrano[3,4-c][1,2]oxazol-1-yl](phenyl)methanone as a light yellow oil (2.44 g, 3.84 mmol). This material was dissolved in 1,2-dichloroethane (26 mL) and treated with methoxybenzene (2.08 mL, 19.2 mmol), followed by trifluoromethanesulfonic acid (1.67 mL, 19.2 mmol). The reaction mixture was stirred at room temperature for 15 minutes, at which time aqueous sodium hydroxide solution (1 M, 100 mL) was added, followed by dichloromethane (100 mL). The resulting mixture was stirred vigorously at room temperature for 10 minutes. The aqueous layer was then extracted with dichloromethane (2×150 mL), and the combined organic layers were dried over sodium sulfate, filtered, and concentrated under reduced pressure. Silica gel chromatography (Gradient: 40% to 100% ethyl acetate in heptane) afforded the product as a white solid. Yield: 1.27 g, 2.79 mmol, 73%. LCMS m/z 457.2 (bromine isotope pattern observed) [M+H]$^+$. $^1$H NMR (400 MHz, CDCl$_3$), characteristic product peaks: δ 7.78-7.85 (m, 2H), 7.48-7.54 (m, 1H), 7.39-7.47 (m, 2H), 7.22 (s, 1H), 4.81 (d, J=12.7 Hz, 1H), 4.44 (dd, J=8.1, 6.2 Hz, 1H), 4.28 (d, J=12.7 Hz, 1H), 3.64-3.90 (m, 5H), 3.54-3.62 (m, 1H), 3.00 (dd, J=8.6, 4.3 Hz, 1H), 1.98-2.03 (m, 1H), 1.94 (dd, J=8.2, 4.5 Hz, 1H), 1.83-1.92 (m, 1H).

Step 6. Synthesis of [cis-7a-(4-bromo-1,3-thiazol-2-yl)-5,5-bis(iodomethyl)hexahydro-1H-pyrano[3,4-c][1,2]oxazol-1-yl](phenyl)methanone (C60)

To a 0° C. solution of C59 (3.07 g, 6.74 mmol) in acetonitrile (135 mL), was added triethylamine (3.76 mL, 27.0 mmol), followed by drop-wise addition of 1,1,2,2,3,3,4,4,4-nonafluorobutane-1-sulfonyl fluoride (4.15 mL, 23.6 mmol). Once the addition was completed, the reaction mixture was allowed to warm to room temperature and stir for 3 hours. Potassium iodide (11.2 g, 67.4 mmol) was then added, and the reaction mixture was heated to 45° C. for 16 hours, whereupon it was concentrated in vacuo and partitioned between diethyl ether (300 mL) and water (500 mL). The aqueous layer was extracted with diethyl ether (2×150 mL), and the combined organic layers were washed with saturated aqueous sodium thiosulfate solution (200 mL) and with saturated aqueous sodium chloride solution (300 mL), dried over sodium sulfate, filtered and concentrated in vacuo. Silica gel chromatography (Gradient: 0% to 70% ethyl acetate in heptane) afforded the product as a white solid. Yield: 3.88 g, 5.75 mmol, 85%. LCMS m/z 677.0 (bromine isotope pattern observed) [M+H]$^+$. $^1$H NMR (400 MHz, CDCl$_3$), characteristic product peaks: δ: 7.78-7.83 (m, 2H), 7.46-7.53 (m, 1H), 7.38-7.44 (m, 2H), 7.26 (s, 1H, assumed; partially obscured by solvent peak), 4.66 (d, J=13.3 Hz, 1H), 4.43-4.51 (m, 2H), 3.93 (dd, J=8.2, 2.3 Hz, 1H), 3.54-3.64 (m, 4H), 3.45-3.51 (m, 1H), 2.39 (dd, J=14.5, 5.5 Hz, 1H), 2.05-2.14 (m, 1H).

Step 7. Synthesis of [cis-7a'-(4-bromo-1,3-thiazol-2-yl)tetrahydro-1'H,3'H-spiro[cyclopropane-1,5'-pyrano[3,4-c][1,2]oxazol]-1'-yl](phenyl) methanone (C61)

Benzoyl peroxide (2.87 g, 11.8 mmol) was added to a solution of C60 (4.00 g, 5.92 mmol) in benzene (40 mL) in a microwave vial. The vial was capped, purged twice with nitrogen, and heated to 105° C. for 2 hours in a microwave reactor. The reaction mixture was then cooled to room temperature, diluted with dichloromethane (100 mL) and washed with saturated aqueous sodium bicarbonate solution (2×100 mL). The combined aqueous layers were extracted with dichloromethane (2×50 mL), and the combined organic layers were dried over sodium sulfate, filtered, and concentrated in vacuo. Silica gel chromatography (Gradient: 0% to 50% ethyl acetate in heptane) provided the product as a white solid. Yield: 1.78 g, 4.22 mmol, 71%. LCMS m/z 423.2 (bromine isotope pattern observed) [M+H]$^+$. $^1$H NMR (400 MHz, CDCl$_3$), characteristic product peaks: δ: 7.81-7.87 (m, 2H), 7.45-7.51 (m, 1H), 7.38-7.45 (m, 2H), 7.24-7.28 (m, 1H), 4.91 (d, J=12.1 Hz, 1H), 4.39 (d, J=12.5 Hz, 1H), 4.19 (dd, J=7.8, 4.7 Hz, 1H), 3.99 (dd, J=7.8, 3.9 Hz, 1H), 3.56-3.65 (m, 1H), 2.18 (ddd, J=13.9, 8.8, 1.2 Hz, 1H), 1.76 (dd, J=13.9, 6.5 Hz, 1H), 0.85-0.92 (m, 2H, partially obscured by heptane peaks), 0.52-0.62 (m, 2H).

Step 8. Synthesis of cis-7a'-(4-bromo-1,3-thiazol-2-yl)tetrahydro-1'H, 3'H-spiro[cyclopropane-1,5'-pyrano[3,4-c][1,2]oxazole] (C62)

Lithium hydroxide monohydrate (22.4 g, 507 mmol) was added to a solution of C61 (1.78 g, 4.22 mmol) in ethanol (125 mL) and water (76 mL). The reaction mixture was heated at reflux for 24 hours, whereupon it was cooled to room temperature, diluted with saturated aqueous sodium bicarbonate solution (100 mL), and extracted with dichloromethane (3×100 mL). The combined organic layers were dried over sodium sulfate, filtered, and concentrated under reduced pressure to afford the product as a crystalline solid. Yield: 1.06 g, 3.34 mmol, 79%. LCMS m/z 319.1 (bromine isotope pattern observed) [M+H]$^+$. $^1$H NMR (400 MHz, CDCl$_3$), characteristic product peaks: δ: 7.22 (s, 1H), 6.35-6.61 (br s, 1H), 4.03 (d, J=12.1 Hz, 1H), 3.82 (d, J=12.1 Hz, 1H), 3.69-3.80 (m, 2H), 3.40-3.50 (m, 1H), 2.21 (d, J=12.5 Hz, 1H), 1.38-1.49 (m, 1H), 0.91-0.98 (m, 1H), 0.80-0.87 (m, 1H), 0.53-0.66 (m, 2H).

Step 9. Synthesis of N-[cis-8a'-(4-bromo-1,3-thiazol-2-yl)-4a',5',8',8a'-tetrahydro-4'H-spiro[cyclopropane-1,6'-pyrano[3,4-d][1,3]thiazin]-2'-yl]benzamide (C63)

A mixture of C62 (1.00 g, 3.15 mmol) and molybdenum hexacarbonyl (0.425 g, 1.58 mmol) in acetonitrile (17 mL) and water (1 mL) was heated to 90° C. for 2 hours, whereupon it was cooled to 0° C. and treated with sodium borohydride (0.477 g, 12.6 mmol). After the reaction mixture had stirred at 0° C. for 1.5 hours, it was filtered through a pad of diatomaceous earth. The filter pad was washed with dichloromethane (3×100 mL), and the combined filtrates were washed with saturated aqueous sodium chloride solution (300 mL), dried over sodium sulfate, filtered, and concentrated in vacuo. The residue was dissolved in methanol (50 mL), stirred for 10 minutes, and concentrated under reduced pressure; this process was repeated two more times. The residue was mixed with dichloromethane (100 mL) and aqueous sodium hydroxide solution (1 M, 100 mL), and the biphasic solution was vigorously stirred at room temperature for 15 minutes. The organic layer was washed with aqueous sodium hydroxide solution (1 M, 100 mL) and with saturated aqueous sodium chloride solution (100 mL), dried over sodium sulfate, filtered, and concentrated under reduced pressure to provide intermediate [rel-(6R,7R)-6-amino-6-(4-bromo-1,3-thiazol-2-yl)-4-oxaspiro[2.5]oct-7-yl]methanol as a colorless oil (0.96 g). This material was dissolved in dichloromethane (20 mL) and treated with benzoyl isothiocyanate (0.424 mL, 3.16 mmol); the reaction mixture was stirred at room temperature for 16 hours, whereupon it was concentrated in vacuo, providing a yellow solid (1.45 g). This material was dissolved in 1,2-dichloroethane (30 mL) and treated with methoxybenzene (0.979 mL, 9.02 mmol), followed by trifluoromethanesulfonic acid (0.787 mL, 9.02 mmol). The reaction mixture was stirred at room temperature for 45 minutes, whereupon it was diluted with dichloromethane (100 mL) and basified with aqueous sodium hydroxide solution (1 M, 250 mL). The biphasic solution was allowed to stir at room temperature for 15 minutes, at which time the aqueous layer was extracted with dichloromethane (2×100 mL). The combined organic layers were washed with saturated aqueous sodium chloride solution (250 mL), dried over sodium sulfate, filtered, and concentrated in vacuo. Silica gel chromatography (Gradient: 0% to 70% ethyl acetate in heptane) provided the product as a white solid. Yield: 0.984 g, 2.12 mmol, 67%. LCMS m/z 466.1 (bromine isotope pattern observed) [M+H]$^+$. $^1$H NMR (400 MHz, CDCl$_3$), characteristic product peaks: δ: 8.05 (d, J=5.9 Hz, 2H), 7.52-7.59 (m, 1H), 7.43-7.50 (m, 2H), 7.24 (s, 1H), 4.02 (d, J=11.3 Hz, 1H), 3.82 (d, J=11.3 Hz, 1H), 3.21-3.29 (m, 1H), 3.16 (dd, J=12.9, 3.9 Hz, 1H), 2.71 (s, 1H), 2.61 (dd, J=12.9, 2.7 Hz, 1H), 1.09 (dd, J=13.7, 4.7 Hz, 1H), 0.94-1.03 (m, 1H), 0.78-0.89 (m, 1H), 0.59-0.69 (m, 1H), 0.48-0.58 (m, 1H).

Step 10. Synthesis of N-[cis-8a'-{4-[(2,4-dimethoxybenzyl)amino]-1,3-thiazol-2-yl}-4a',5',8',8a'-tetrahydro-4'H-spiro[cyclopropane-1,6'-pyrano[3,4-d][1,3]thiazin]-2'-yl]benzamide (P17)

A mixture of tris(dibenzylideneacetone)dipalladium(0) (0.101 g, 0.106 mmol), di-tert-butyl[2',4',6'-tri(propan-2-yl)biphenyl-2-yl]phosphane (0.135 g, 0.318 mmol), and sodium tert-butoxide (0.509 g, 5.29 mmol) was purged twice with nitrogen. 1,4-Dioxane (9.6 mL) was added, and the reaction mixture was heated to 85° C. (internal) for 5 minutes. A solution of C63 (0.98 g, 2.12 mmol) and 1-(2,4-dimethoxyphenyl)methanamine (0.541 mL, 3.60 mmol) in 1,4-dioxane (9.6 mL) was then added to the reaction mixture, and heating was continued at 85° C. (internal) for 25 minutes. The reaction mixture was quickly cooled to room temperature using a water bath, treated with water (30 mL) and diatomaceous earth, and filtered through a pad of diatomaceous earth. The filter pad was washed with dichloromethane (3×100 mL), and the organic layer from the combined filtrates was washed sequentially with water (2×300 mL), aqueous citric acid solution (5%, 2×300 mL), saturated aqueous sodium bicarbonate solution (2×300 mL), and saturated aqueous sodium chloride solution (500 mL), dried over sodium sulfate, filtered, and concentrated in vacuo. Silica gel chromatography [Gradient: 20% to 100% (5% triethylamine in ethyl acetate) in heptane] provided the product as an orange solid. Yield: 0.577 g, 1.05 mmol, 50%. LCMS m/z 551.4 [M+H]$^+$; $^1$H NMR (400 MHz, CDCl$_3$), characteristic product peaks: β 8.14 (d, J=7.4 Hz, 2H), 7.48-7.54 (m, 1H), 7.39-7.46 (m, 2H), 7.20 (d, J=8.2 Hz, 1H), 6.42-6.49 (m, 2H), 5.74 (s, 1H), 4.62-4.77 (br s, 1H), 4.20 (s, 2H), 4.02 (d, J=11.7 Hz, 1H), 3.78-3.85 (m, 7H), 3.25 (dd, J=12.9, 3.9 Hz, 1H), 3.11-3.20 (m, 1H), 2.73 (s, 1H), 2.57 (dd, J=12.7, 2.9 Hz, 1H), 1.06 (dd, J=13.7, 4.7 Hz, 1H), 0.95-1.03 (m, 1H), 0.83 (s, 1H), 0.60-0.67 (m, 1H), 0.47-0.54 (m, 1H).

Preparation P18
N-[(4aR,6S,8aR)-8a-(4-Bromo-1,3-thiazol-2-yl)-6-(methoxymethyl)-6-methyl-4,4a,5,6,8,8a-hexahydropyrano[3,4-d][1,3]thiazin-2-yl]benzamide (P18)
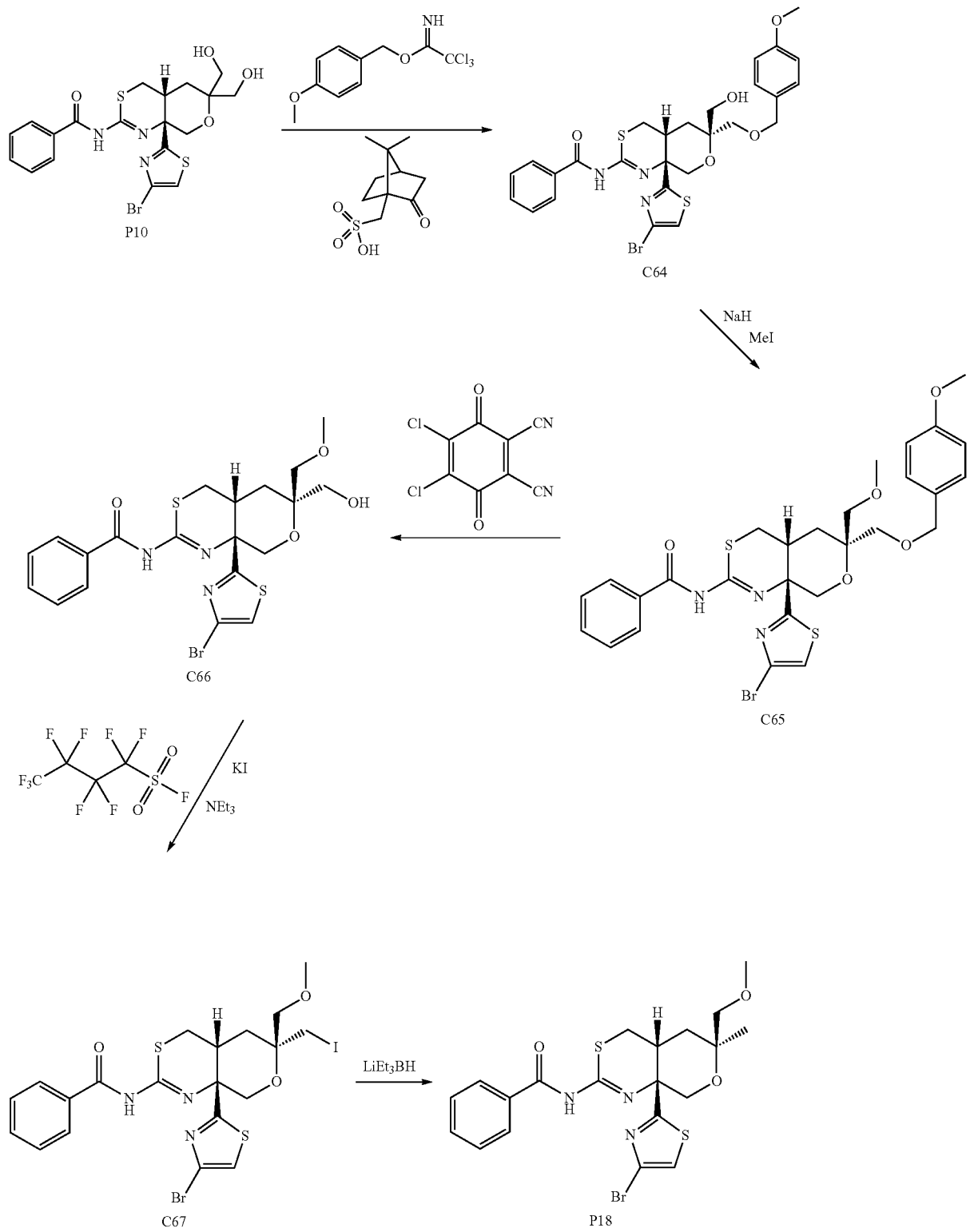

Step 1. Synthesis of N-[(4aR,6S,8aR)-8a-(4-bromo-1,3-thiazol-2-yl)-6-(hydroxymethyl)-6-{[(4-methoxybenzyl)oxy]methyl}-4,4a,5,6,8,8a-hexahydropyrano[3,4-d][1,3]thiazin-2-yl]benzamide (C64)

(7,7-Dimethyl-2-oxobicyclo[2.2.1]hept-1-yl)methanesulfonic acid (camphorsulfonic acid; 9.3 mg, 0.04 mmol) was added to a mixture of P10 (200 mg, 0.40 mmol) and 4-methoxybenzyl-2,2,2-trichloroacetimidate (162 mg, 0.56 mmol) in dichloromethane (15 mL). After stirring at room temperature for 5 hours, the reaction mixture was diluted with saturated aqueous sodium bicarbonate solution (15 mL) and extracted with ethyl acetate (3×15 mL). The combined organic layers were dried over sodium sulfate, filtered, and concentrated under reduced pressure; silica gel chromatography (Gradient: 0% to 100% ethyl acetate in heptane) provided the product as a white solid. Yield: 96 mg, 0.16 mmol 39%. LCMS m/z 620.2 [M+H]$^+$. $^1$H NMR (400 MHz, CDCl$_3$) δ 8.05 (br s, 2H), 7.53-7.60 (m, 1H), 7.44-7.51 (m, 2H), 7.20-7.25 (m, 3H), 6.79-6.87 (m, 2H), 4.40-4.57 (m, 2H), 4.13-4.20 (m, 2H), 3.80-3.88 (m, 1H), 3.77 (d, J=12.1 Hz, 1H), 3.75 (s, 3H), 3.58 (d, J=9.4 Hz, 1H), 3.43 (d, J=9.4 Hz, 1H), 3.12-3.23 (m, 2H), 2.57 (dd, J=12.7, 2.2 Hz, 1H), 1.96 (t, J=13.7 Hz, 1H), 1.66 (dd, J=13.9, 4.5 Hz, 1H).

Step 2. Synthesis of N-[(4aR,6S,8aR)-8a-(4-bromo-1,3-thiazol-2-yl)-6-{[(4-methoxybenzyl)oxy]methyl}-6-(methoxymethyl)-4,4a,5,6,8,8a-hexahydropyrano[3,4-d][1,3]thiazin-2-yl]benzamide (C65)

A solution of C64 (438 mg, 0.71 mmol) in tetrahydrofuran (5 mL) was added drop-wise to a stirring suspension of sodium hydride (60% dispersion in mineral oil, 70.8 mg, 1.77 mmol) in tetrahydrofuran (10 mL) at 0° C. The ice bath was removed and the mixture was stirred at room temperature for 20 minutes, whereupon it was cooled to 0° C. Iodomethane (66.1 μL, 1.06 mmol) was added, and the ice bath was removed. After the reaction mixture had stirred at room temperature for 3 hours, it was diluted with saturated aqueous ammonium chloride solution (25 mL) and water (10 mL). The resulting mixture was extracted with diethyl ether (3×35 mL), and the combined organic layers were dried over sodium sulfate, filtered, and concentrated in vacuo. Silica gel chromatography (Gradient: 0% to 90% ethyl acetate in heptane) afforded the product as a white solid. Yield: 356 mg, 0.563 mmol, 80%. LCMS m/z 634.3 [M+H]$^+$. $^1$H NMR (400 MHz, CDCl$_3$) δ 7.90 (br s, 2H), 7.36-7.41 (m, 1H), 7.27-7.33 (m, 2H), 7.04-7.08 (m, 3H), 6.61-6.65 (m, 2H), 4.27-4.37 (m, 2H), 4.03 (d, J=12.1 Hz, 1H), 3.59-3.69 (m, 2H), 3.55 (s, 3H), 3.36 (d, J=9.8 Hz, 1H), 3.26 (s, 3H), 3.24 (s, 1H), 3.22 (d, J=3.1 Hz, 1H), 3.10 (dd, J=9.9, 5.3 Hz, 1H), 3.00 (dd, J=12.9, 4.3 Hz, 1H), 2.43 (dd, J=12.9, 2.3 Hz, 1H), 1.87 (t, J=13.7 Hz, 1H), 1.57 (dd, J=14.1, 4.7 Hz, 1H).

Step 3. Synthesis of N-[(4aR,6R,8aR)-8a-(4-bromo-1,3-thiazol-2-yl)-6-(hydroxymethyl)-6-(methoxymethyl)-4,4a,5,6,8,8a-hexahydropyrano[3,4-d][1,3]thiazin-2-yl]benzamide (C66)

2,3-Dichloro-5,6-dicyano-1,4-benzoquinone (151 mg, 0.65 mmol) was added to a mixture of C65 (343 mg, 0.54 mmol) in a mixture of dichloromethane and water (19:1, 15 mL). After 2.2 hours, the reaction mixture was diluted with dichloromethane (30 mL) and filtered through diatomaceous earth. The filtrate was concentrated in vacuo and subjected to silica gel chromatography (Gradient: 0% to 95% ethyl acetate in heptane) to provide the product as a white solid. Yield: 242 mg, 0.47 mmol, 87%. LCMS m/z 514.1 [M+H]$^+$. $^1$H NMR (400 MHz, CDCl$_3$) δ 8.08 (br s, 2H), 7.53-7.60 (m, 1H), 7.44-7.52 (m, 2H), 7.26 (s, 1H), 4.15-4.23 (m, 1H), 3.77-3.83 (m, 2H), 3.65-3.74 (m, 2H), 3.42-3.55 (m, 1H), 3.47 (s, 3H), 3.25-3.32 (m, 1H), 3.19 (dd, J=12.9, 4.3 Hz, 1H), 2.64 (d, J=12.9 Hz, 1H), 2.12 (d, J=13.3 Hz, 1H), 1.73 (dd, J=13.9, 4.1 Hz, 1H).

Step 4. Synthesis of N-[(4aR,6S,8aR)-8a-(4-bromo-1,3-thiazol-2-yl)-6-(iodomethyl)-6-(methoxymethyl)-4,4a,5,6,8,8a-hexahydropyrano[3,4-d][1,3]thiazin-2-yl]benzamide (C67)

1,1,2,2,3,3,4,4,4-Nonafluorobutane-1-sulfonyl fluoride (0.326 mL, 1.85 mmol) was added drop-wise to a solution of triethylamine (295 μL, 2.12 mmol) and C66 (271 mg, 0.53 mmol) in acetonitrile (7.5 mL). After the reaction mixture had stirred at room temperature for 70 minutes, potassium iodide (878 mg, 5.29 mmol) was added, and the reaction mixture was heated at 45° C. for 16 hours. After cooling to room temperature, it was diluted with water (30 mL) and extracted with diethyl ether (3×30 mL). The combined organic layers were washed with saturated aqueous sodium thiosulfate solution (20 mL), dried over sodium sulfate, filtered, and concentrated in vacuo. Silica gel chromatography (Gradient: 0% to 80% ethyl acetate in heptane) provided the product as a white solid. Yield: 200 mg, 0.32 mmol, 61%. LCMS m/z 624.0 [M+H]$^+$. $^1$H NMR (400 MHz, CDCl$_3$) 7.98 (br s, 2H), 7.45-7.62 (m, 3H), 7.26 (s, 1H), 4.10-4.20 (m, 1H), 3.74-3.90 (m, 3H), 3.48 (s, 3H), 3.37-3.45 (m, 2H), 3.14-3.27 (m, 2H), 2.63 (d, J=12.9 Hz, 1H), 2.02-2.14 (m, 1H), 1.91 (dd, J=13.3, 3.5 Hz, 1H).

Step 5. Synthesis of N-[(4aR,6S,8aR)-8a-(4-bromo-1,3-thiazol-2-yl)-6-(methoxymethyl)-6-methyl-4,4a,5,6,8,8a-hexahydropyrano[3,4-d][1,3]thiazin-2-yl]benzamide (P18)

A solution of lithium triethylborohydride in tetrahydrofuran (1.0 M, 3.46 mL, 3.46 mmol) was added drop-wise to a 0° C. solution of C67 (196 mg, 0.32 mmol) in tetrahydrofuran (6 mL). The ice bath was removed upon completion of the addition, and the reaction mixture was allowed to warm to room temperature over 10 minutes. The reaction mixture was then heated at reflux for 5.5 hours, whereupon it was allowed to cool to room temperature, and carefully diluted with saturated aqueous sodium bicarbonate solution (25 mL). The resulting mixture was extracted with ethyl acetate (3×25 mL), and the combined organic layers were dried over sodium sulfate, filtered and concentrated in vacuo. The residue was dissolved in methanol and heated at reflux for 1.2 hours, allowed to cool to ambient temperature, and then concentrated under reduced pressure. Purification via silica gel chromatography (Gradient: 0% to 100% ethyl acetate in heptane) afforded the product as a colorless solid. Yield: 52.2 mg, 0.11 mmol, 33%. LCMS m/z 498.2 [M+H]$^+$. $^1$H NMR (400 MHz, CDCl$_3$) δ 7.90-8.25 (br m, 2H), 7.42-7.58 (m, 3H), 7.22 (s, 1H), 4.10-4.30 (br m, 1H), 3.73 (d, J=12.1 Hz, 1H), 3.61-3.65 (m, 2H), 3.45 (s, 3H), 3.10-3.31 (m, 2H), 2.58 (d, J=12.9 Hz, 1H), 1.86-2.01 (m, 1H), 1.74 (d, J=11.4 Hz, 1H), 1.29 (s, 3H).

Preparation P19

5-(Difluoromethoxy)pyridine-2-carboxylic acid (P19)

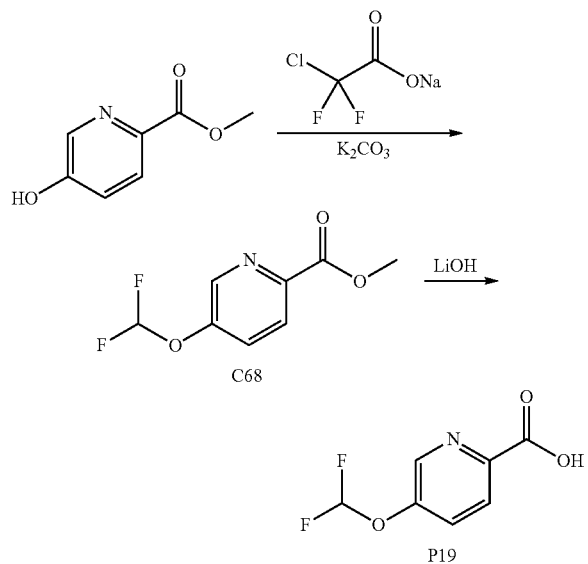

vacuo. Silica gel chromatography (Eluent: 5:1 petroleum ether/ethyl acetate) afforded the product as a pale yellow oil. Yield: 17 g, 84 mmol, 65%. $^1$H NMR (400 MHz, CDCl$_3$) δ 8.56 (s, 1H), 8.17 (d, J=8.7 Hz, 1H), 7.59 (br d, J=8.7 Hz, 1H), 6.64 (t, $J_{HF}$=71.9 Hz, 1H), 4.00 (s, 3H).

Step 2. Synthesis of 5-(difluoromethoxy)pyridine-2-carboxylic acid (P19)

A solution of C68 (17 g, 84 mmol) in tetrahydrofuran (100 mL) and water (50 mL) was cooled to 0° C. and treated with lithium hydroxide (6.0 g, 250 mmol). After the reaction mixture had stirred at room temperature for 2 hours, it was acidified to a pH of 3 with 1 M aqueous hydrochloric acid. The aqueous layer was extracted with ethyl acetate (3×100 mL), and the combined organic layers were washed with saturated aqueous sodium chloride solution (100 mL), dried, filtered, and concentrated under reduced pressure to provide the product as a white solid. Yield: 13 g, 69 mmol, 82%. LCMS m/z 189.8 [M+H]$^+$. $^1$H NMR (400 MHz, CDCl$_3$) δ 8.52 (d, J=2.4 Hz, 1H), 8.29 (d, J=8.5 Hz, 1H), 7.73 (dd, J=8.6, 2.4 Hz, 1H), 6.68 (t, $J_{HF}$=71.5 Hz, 1H).

Preparation P20

5-(Difluoromethoxy)-3-methylpyridine-2-carboxylic acid (P20)

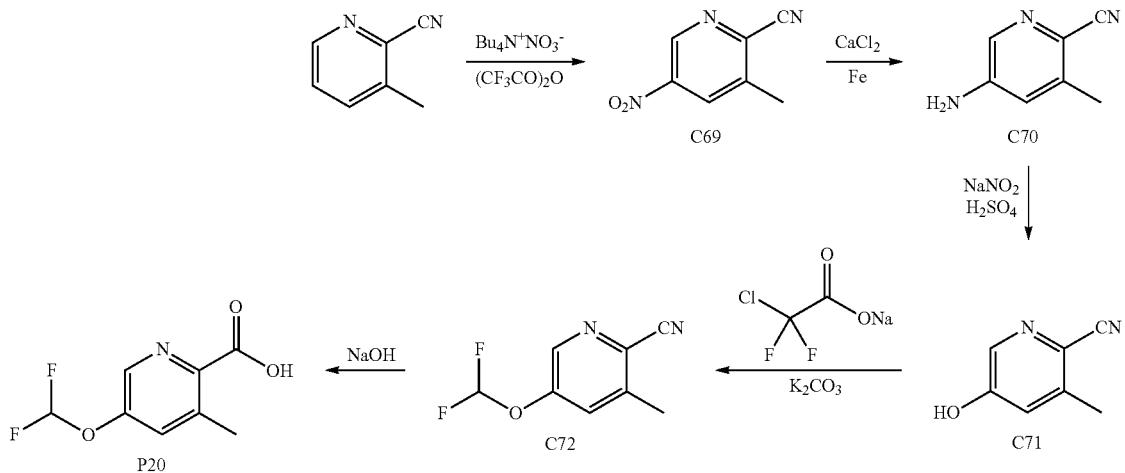

Step 1. Synthesis of methyl 5-(difluoromethoxy)pyridine-2-carboxylate (C68)

Potassium carbonate (45.1 g, 326 mmol) was added to a solution of methyl 5-hydroxypyridine-2-carboxylate (20 g, 130 mmol) in N,N-dimethylformamide (500 mL), and the reaction mixture was stirred at room temperature for 0.5 hours. Sodium chloro(difluoro)acetate (63.7 g, 418 mmol) was introduced, and the resulting mixture was heated at 100° C. for 5 hours, whereupon it was partitioned between saturated aqueous sodium chloride solution (300 mL) and ethyl acetate (300 mL). The aqueous layer was extracted with ethyl acetate (3×200 mL), and the combined organic layers were washed with saturated aqueous sodium chloride solution (2×200 mL), dried, filtered, and concentrated in Step 1. Synthesis of 3-methyl-5-nitropyridine-2-carbonitrile (C69)

A mixture of 3-methylpyridine-2-carbonitrile (128 g, 1.08 mol) and tetrabutylammonium nitrate (363 g, 1.19 mol) in tert-butyl methyl ether (1.3 L) was cooled to 4° C. Trifluoroacetic anhydride (171 mL, 1.21 mol) was added, and the reaction mixture was allowed to stir at room temperature for 60 hours. It was then adjusted to a pH of approximately 7 by addition of 20% aqueous sodium hydroxide solution, and extracted with dichloromethane (3×1 L). The combined organic layers were dried, filtered, and concentrated in vacuo; purification via silica gel chromatography (Gradient: 0% to 10% ethyl acetate in petroleum ether) afforded the product as a yellow solid. Yield: 70 g, 0.43 mmol, 40%. $^1$H NMR (400 MHz, CDCl$_3$) δ 9.31-9.36 (m, 1H), 8.47-8.52 (m, 1H), 2.74 (s, 3H).

Step 2. Synthesis of 5-amino-3-methylpyridine-2-carbonitrile (C70)

To a solution of C69 (40.0 g, 245 mmol) in ethanol (630 mL) and water (70 mL) was added calcium chloride (13.6 g, 123 mmol), followed by iron powder (123 g, 2.20 mol), and the reaction mixture was stirred overnight at room temperature. After filtration of the reaction mixture, the filtrate was concentrated in vacuo, and the residue was purified by chromatography on silica gel (Gradient: 10% to 50% ethyl acetate in petroleum ether). The product was obtained as a yellow solid. Yield: 20.0 g, 150 mmol, 61%. $^1$H NMR (400 MHz, CDCl$_3$) δ 7.94 (d, J=2.5 Hz, 1H), 6.81 (d, J=2.5 Hz, 1H), 4.07-4.19 (br s, 2H), 2.45 (s, 3H).

Step 3. Synthesis of 5-hydroxy-3-methylpyridine-2-carbonitrile (C71)

Sodium nitrite (1.6 M aqueous solution containing 10.3 g of sodium nitrite, 149 mmol) was slowly added to a 0° C. solution of C70 (18.0 g, 135 mmol) in water (243 mL) and concentrated sulfuric acid (67.5 mL). The reaction mixture was warmed to room temperature and then stirred at 100° C. for 3 hours, whereupon it was cooled and extracted with ethyl acetate (3×75 mL). The combined organic layers were washed with water (2×75 mL) and with saturated aqueous sodium chloride solution (2×75 mL), dried, filtered, and concentrated under reduced pressure to afford the product as a yellow solid. Yield: 16 g, 120 mmol, 89%. $^1$H NMR (400 MHz, DMSO-d$_6$) δ 11.07 (br s, 1H), 8.08 (d, J=2.6 Hz, 1H), 7.20 (d, J=2.3 Hz, 1H), 2.40 (s, 3H).

solution (3×200 mL). The combined aqueous layers were extracted with ethyl acetate (200 mL), and the combined organic layers were dried over sodium sulfate, filtered, and concentrated in vacuo. Silica gel chromatography (Gradient: 5% to 15% ethyl acetate in petroleum ether) provided the product as a colorless oil. Yield: 3.9 g, 21 mmol, 49%. $^1$H NMR (400 MHz, CDCl$_3$) δ 8.39 (br d, J=2.1 Hz, 1H), 7.47-7.43 (m, 1H), 6.64 (t, J$_{HF}$=71.5 Hz, 1H), 2.59 (s, 3H).

Step 5. Synthesis of 5-(difluoromethoxy)-3-methylpyridine-2-carboxylic acid (P20)

Aqueous sodium hydroxide solution (1 M, 124 mL, 124 mmol) was added to a solution of C72 (7.60 g, 41.3 mmol) in ethanol (200 mL), and the reaction mixture was stirred for 16 hours at 70° C. It was then diluted with tert-butyl methyl ether (200 mL) and extracted with water (2×100 mL). The combined aqueous layers were washed with tert-butyl methyl ether (100 mL), acidified to pH 2 with 1 M aqueous hydrochloric acid, and extracted with tert-butyl methyl ether (2×200 mL). The combined organic extracts were dried over sodium sulfate, filtered, and concentrated in vacuo to afford the product as a white solid. Yield: 6.6 g, 32 mmol, 77%. LCMS m/z 203.7 [M+H]$^+$. $^1$H NMR (400 MHz, CD$_3$OD) δ 8.32 (br d, J=2.1 Hz, 1H), 7.58-7.62 (m, 1H), 7.06 (t, J$_{HF}$=72.7 Hz, 1H), 2.64 (s, 3H).

Preparation P21

3-Chloro-5-(difluoromethoxy)pyridine-2-carboxylic acid (P21)

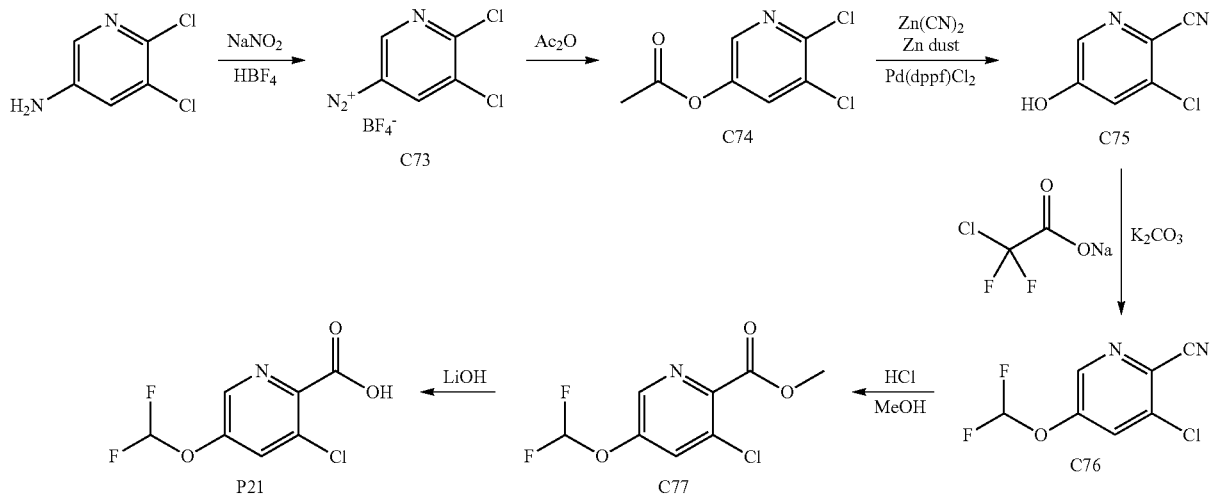

Step 4. Synthesis of 5-(difluoromethoxy)-3-methyl-pyridine-2-carbonitrile (C72)

A mixture of C71 (5.70 g, 42.5 mmol), sodium chlorodifluoroacetate (13.0 g, 85.3 mmol), and potassium carbonate (17.6 g, 127 mmol) in N,N-dimethylformamide (175 mL) was stirred for 30 minutes at 100° C. The reaction mixture was then diluted with ethyl acetate (400 mL), and sequentially washed with saturated aqueous ammonium chloride solution (3×200 mL) and saturated aqueous sodium chloride

Step 1. Synthesis of 5, 6-dichloropyridine-3-diazonium tetrafluoroborate (C73)

To a 0° C. solution of 5,6-dichloropyridin-3-amine (15 g, 92 mmol) in tetrafluoroboric acid (~45% in water; 150 mL) was added a solution of sodium nitrite (6.67 g, 96.6 mmol) in water (90 mL) in a drop-wise manner, during which time the diazonium salt precipitated. After completion of the addition, the reaction mixture was stirred at 0° C. for 1 hour.

It was then filtered; the filter cake was washed with petroleum ether (3×200 mL) to afford the product (25.8 g) as a pale red solid. This material was used directly in the next step.

Step 2. Synthesis of 5, 6-dichloropyridin-3-yl acetate (C74)

Compound C73 (from the previous step; 25.8 g, ≤92 mmol) was dissolved in acetic anhydride (75 mL) and slowly warmed to 70° C. When nitrogen evolution had ceased, stirring was continued for 1 hour at 70° C., whereupon the solvent was evaporated. The residue was dissolved in tert-butyl methyl ether (100 mL) and washed with water (4×40 mL). The combined aqueous layers were extracted with additional tert-butyl methyl ether (3×50 mL), and the combined organic layers were washed with saturated aqueous sodium chloride solution (5×20 mL), dried over sodium sulfate, filtered, and concentrated in vacuo. Silica gel chromatography (Gradient: 0% to 25% ethyl acetate in petroleum ether) afforded the product as a yellow oil. Yield: 9.7 g, 47 mmol, 51% over 2 steps. $^1$H NMR (400 MHz, DMSO-d$_6$) δ 8.33 (d, J=2.5 Hz, 1H), 8.18 (d, J=2.5 Hz, 1H), 2.32 (s, 3H).

Step 3. Synthesis of 3-chloro-5-hydroxypyridine-2-carbonitrile (C75)

Zinc cyanide (2.6 g, 22 mmol), zinc dust (145 mg, 2.21 mmol), and [1,1'-bis(diphenylphosphino)ferrocene]dichloropalladium(II) (1.72 g, 2.35 mmol) were added to a room temperature solution of C74 (9.7 g, 47 mmol) in N,N-dimethylformamide (60 mL). The reaction mixture was stirred at 140° C. for 13 hours, whereupon it was diluted with tert-butyl methyl ether (200 mL) and water (150 mL) and filtered through a pad of diatomaceous earth. The aqueous layer of the filtrate was extracted with additional tert-butyl methyl ether (3×50 mL), and the combined organic layers were washed with saturated aqueous sodium chloride solution (8×50 mL), dried over sodium sulfate, filtered, and concentrated in vacuo to provide the product as a brown solid. Yield: 6.8 g, 44 mmol, 94%. $^1$H NMR (400 MHz, CD$_3$OD) δ 8.16 (d, J=2.5 Hz, 1H), 7.38 (d, J=2.5 Hz, 1H).

Step 4. Synthesis of 3-chloro-5-(difluoromethoxy)pyridine-2-carbonitrile (C76)

A mixture of C75 (6.8 g, 44 mmol), sodium chloro(difluoro)acetate (20 g, 180 mmol) and potassium carbonate (36.5 g, 264 mmol) in N,N-dimethylformamide (70 mL) was stirred at 100° C. for 40 minutes (until no gas evolution could be seen). The reaction mixture was diluted with tert-butyl methyl ether (200 mL) and water (150 mL), and the aqueous layer was extracted with additional tert-butyl methyl ether (3×100 mL). The combined organic layers were washed with saturated aqueous sodium chloride solution (8×50 mL), dried over sodium sulfate, filtered, and concentrated under reduced pressure. Chromatography on silica gel (Gradient: 0% to 20% ethyl acetate in petroleum ether) afforded the product as a yellow oil. Yield: 5.55 g, 27.1 mmol, 62%. $^1$H NMR (400 MHz, CDCl$_3$) δ 8.52-8.45 (m, 1H), 7.73-7.65 (m, 1H), 6.68 (t, J$_{HF}$=70.8 Hz, 1H).

Step 5. Synthesis of methyl 3-chloro-5-(difluoromethoxy)pyridine-2-carboxylate (C77)

Compound C76 (4.82 g, 23.6 mmol) was dissolved in a solution of hydrogen chloride in methanol (4 M; 75 mL), and the reaction mixture was stirred at 60° C. for 13 hours. It was then diluted with water (50 mL) and stirred at room temperature for 30 minutes. The mixture was concentrated under reduced pressure and the residual aqueous phase was neutralized via addition of saturated aqueous sodium bicarbonate solution (200 mL) and then extracted with ethyl acetate (3×60 mL). The combined organic layers were washed with saturated aqueous sodium chloride solution (30 mL), dried over sodium sulfate, filtered, and concentrated in vacuo. The resulting material was combined with the crude product from a similar reaction carried out using C76 (500 mg, 2.4 mmol), and the mixture was subjected to silica gel chromatography (Gradient: 0% to 20% ethyl acetate in petroleum ether), providing the product as a yellow oil, which solidified upon standing at room temperature. Yield: 3.4 g, 14 mmol, 54%. $^1$H NMR (400 MHz, CDCl$_3$) δ 8.50-8.43 (m, 1H), 7.68-7.62 (m, 1H), 6.64 (t, J$_{HF}$=71.3 Hz, 1H), 4.02 (s, 3H).

Step 6. Synthesis of 3-chloro-5-(difluoromethoxy)pyridine-2-carboxylic acid (P21)

Lithium hydroxide monohydrate (279 mg, 6.31 mmol) was added to a solution of C77 (1.0 g, 4.2 mmol) in tetrahydrofuran (40 mL) and water (20 mL). The reaction mixture was stirred at room temperature for 3 hours, whereupon it was concentrated in vacuo, and the residual aqueous phase was adjusted to a pH of 2-3 via addition of 2 M aqueous hydrochloric acid. The resulting mixture was extracted with ethyl acetate (7×20 mL), and the combined organic layers were dried over sodium sulfate, filtered, and concentrated under reduced pressure to afford the product as a pale yellow solid. Yield: 720 mg, 3.22 mmol, 77%. LCMS m/z 222.0 (chlorine isotope pattern observed) [M−H$^+$]. $^1$H NMR (400 MHz, DMSO-d$_6$) δ 8.51 (d, J=2.0 Hz, 1H), 8.06 (d, J=2.0 Hz, 1H), 7.44 (t, J$_{HF}$=72.8 Hz, 1H).

Preparation P22

2-(Fluoromethyl)-1,3-oxazole-4-carboxylic acid (P22)

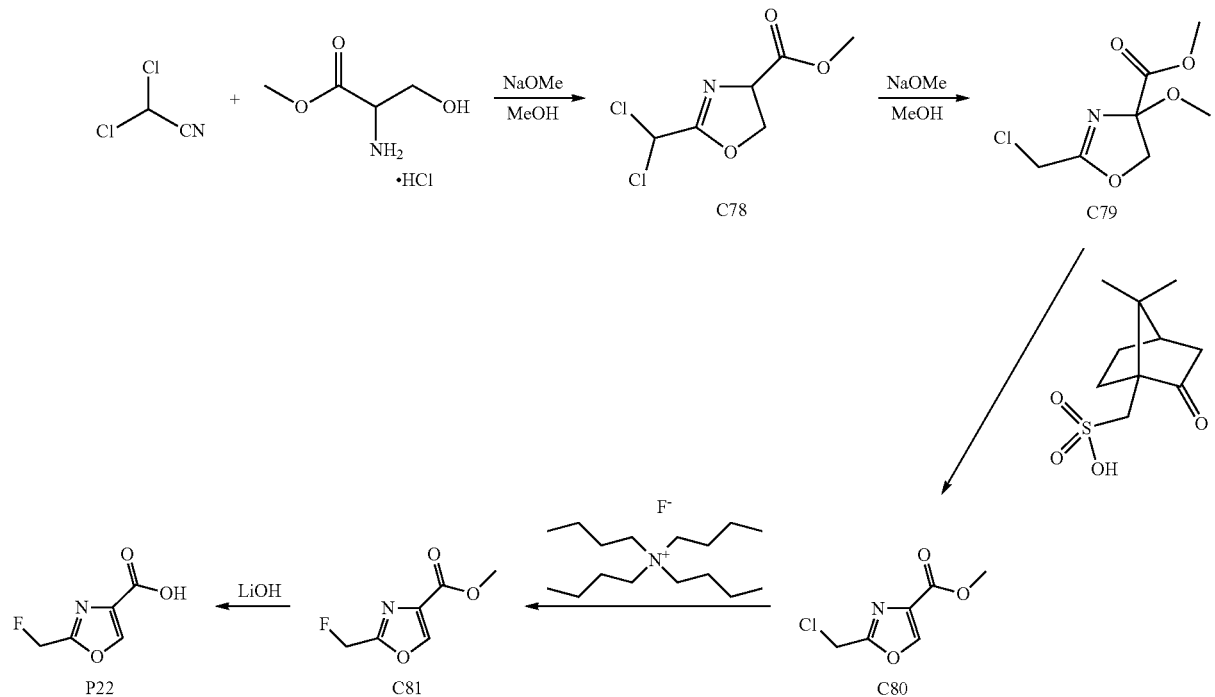

Step 1. Synthesis of methyl 2-(dichloromethyl)-4,5-dihydro-1,3-oxazole-4-carboxylate (C78)

A solution of dichloroacetonitrile (215 g, 1.96 mol) in methanol (200 mL) was added drop-wise to a −5° C. solution of sodium methoxide (15.4 g, 0.285 mol) in methanol (500 mL). A solution of methyl 2-amino-3-hydroxypropanoate, hydrochloride salt (382 g, 2.45 mol) in methanol (300 mL) was then added to the −5° C. reaction mixture, which was subsequently allowed to stir at room temperature for 16 hours. Dichloromethane (1 L) and water (800 mL) were added, and the aqueous layer was extracted with dichloromethane (1 L); the combined organic layers were concentrated in vacuo to provide the product as a yellow oil, which was used in the next step without further purification. Yield: 300 g, 1.4 mol, 71%. $^1$H NMR (400 MHz, CDCl$_3$) δ 6.29 (s, 1H), 4.90 (dd, J=10.8, 8.3 Hz, 1H), 4.74 (dd, J=8.8, 8.3 Hz, 1H), 4.66 (dd, J=10.8, 8.9 Hz, 1H), 3.82 (s, 3H).

Step 2. Synthesis of methyl 2-(chloromethyl)-4-methoxy-4, 5-dihydro-1,3-oxazole-4-carboxylate (C79)

A solution of C78 (205 g, 0.967 mol) in methanol (700 mL) was added drop-wise to a cooled solution of sodium methoxide (52.2 g, 0.966 mol) in methanol (300 mL), at a rate sufficient to maintain the reaction temperature below 10° C. The reaction mixture was then stirred at room temperature for 16 hours, whereupon it was diluted with dichloromethane (1 L) and water (800 mL). The aqueous layer was extracted with dichloromethane (2×500 mL), and the combined organic layers were concentrated in vacuo to afford the product as a yellow oil. This material was used in the next step without additional purification. Yield: 200 g, 0.96 mol, 99%.

Step 3. Synthesis of methyl 2-(chloromethyl)-1,3-oxazole-4-carboxylate (C80)

(7,7-Dimethyl-2-oxobicyclo[2.2.1]hept-1-yl)methanesulfonic acid (camphorsulfonic acid, 45.9 g, 0.198 mol) was added to a solution of C79 (193 g, 0.930 mol) in toluene (700 mL), and the reaction mixture was heated at 70° C. for 1 hour. Water (1 L) was added, and the mixture was extracted with ethyl acetate (2×1 L); the combined organic layers were sequentially washed with aqueous potassium carbonate solution (10%, 500 mL), water (800 mL), and saturated aqueous sodium chloride solution (0.8 L), dried, and concentrated in vacuo. Silica gel chromatography (Gradient: 5% to 25% ethyl acetate in petroleum ether) provided the product as a white solid. Yield: 55 g, 0.31 mol, 33%. $^1$H NMR (400 MHz, CDCl$_3$) δ 8.26 (s, 1H), 4.65 (s, 2H), 3.93 (s, 3H).

Step 4. Synthesis of methyl 2-(fluoromethyl)-1,3-oxazole-4-carboxylate (C81)

To a suspension of C80 (40 g, 0.23 mol) in acetonitrile (1 L) was added tetrabutylammonium fluoride (357 g, 1.36 mol), and the reaction mixture was stirred at 25° C. for 16 hours. After removal of solvent in vacuo, the residue was diluted with water (1 L) and extracted with ethyl acetate (4×1 L). The combined organic layers were dried over sodium sulfate, filtered, and concentrated under reduced pressure. Chromatography on silica gel (Gradient: 17% to 23% ethyl acetate in petroleum ether) afforded the product as a yellow solid. Yield: 8.7 g, 55 mmol, 24%. $^1$H NMR (400 MHz, CDCl$_3$) δ 8.31 (d, J=1.2 Hz, 1H), 5.43 (d, $J_{HF}$=47.2 Hz, 2H), 3.94 (s, 3H).

Step 5. Synthesis of 2-(fluoromethyl)-1,3-oxazole-4-carboxylic acid (P22)

To a solution of C81 (18 g, 110 mmol) in tetrahydrofuran (150 mL) was added a solution of lithium hydroxide (5.42 g, 226 mmol) in a mixture of methanol and water (1:1, 500 mL). The reaction mixture was stirred at room temperature for 1 hour, whereupon it was concentrated in vacuo. After the residue had been dissolved in water (500 mL), it was acidified by addition of 2 M aqueous hydrochloric acid until it reached a pH of 2. The aqueous layer was then extracted with ethyl acetate (2×100 mL), and the combined organic layers were dried over sodium sulfate, filtered, and concentrated under reduced pressure, providing the product as a yellow solid. Yield: 13 g, 90 mmol, 82%. LCMS m/z 144.0 [M−H$^+$]. $^1$H NMR (400 MHz, CD$_3$OD) δ 8.61 (s, 1H), 5.47 (d, $J_{HF}$=47 Hz, 2H).

Examples 1 and 2

N-{2-[(4aS,8aS)-2-Amino-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (1) and N-{2-[(4aR,8aR)-2-Amino-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (2)

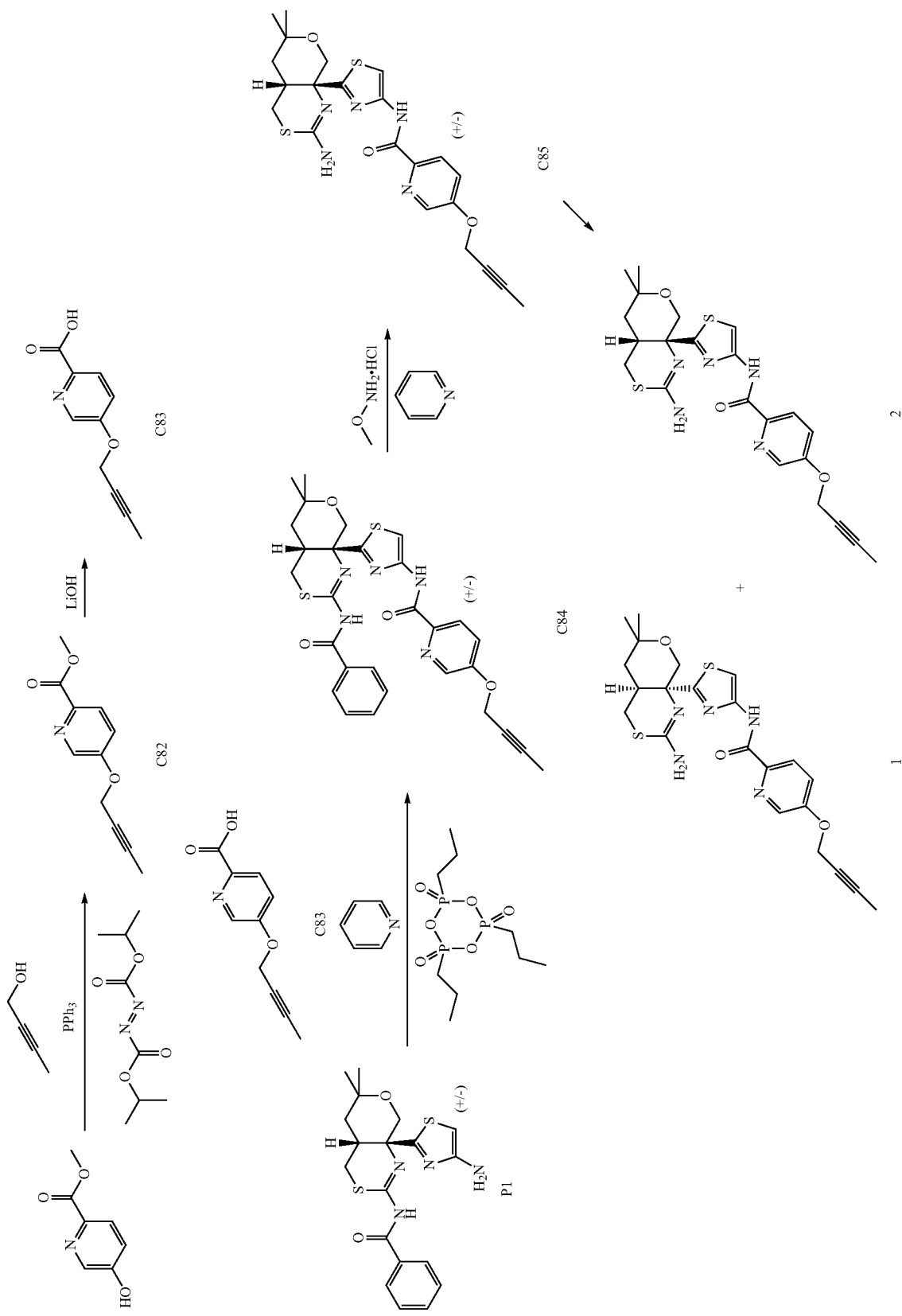

Step 1. Synthesis of methyl 5-(but-2-yn-1-yloxy) pyridine-2-carboxylate (C82)

To a 0° C. solution of but-2-yn-1-ol (0.645 mL, 8.62 mmol) in tetrahydrofuran 30 mL) were added methyl 5-hydroxypyridine-2-carboxylate (1.30 g, 8.49 mmol), triphenylphosphine (3.34 g, 12.7 mmol), and diisopropyl azodicarboxylate (2.50 mL, 12.7 mmol). The reaction mixture was then warmed to room temperature (18° C.) and stirred for 48 hours, whereupon it was concentrated in vacuo. Silica gel chromatography (Gradient: 15% to 50% ethyl acetate in petroleum ether) afforded the product as a yellow solid. Yield: 1.1 g, 5.4 mmol, 64%. $^1$H NMR (400 MHz, CDCl$_3$) δ 8.46 (d, J=2.9 Hz, 1H), 8.13 (d, J=8.8 Hz, 1H), 7.37 (dd, J=8.8, 2.9 Hz, 1H), 4.77 (q, J=2.3 Hz, 2H), 3.99 (s, 3H), 1.86 (t, J=2.3 Hz, 3H).

Step 2. Synthesis of 5-(but-2-yn-1-yloxy)pyridine-2-carboxylic acid (C83)

A solution of lithium hydroxide monohydrate (975 mg, 23.2 mmol) in water (7 mL) was added drop-wise to a room temperature (15° C.) solution of C82 (1.59 g, 7.75 mmol) in tetrahydrofuran (20 mL), and the reaction mixture was stirred at room temperature for 1 hour. It was then acidified to pH 2 via addition of 2 M aqueous hydrochloric acid, and extracted with ethyl acetate (2×100 mL). The combined organic layers were washed with saturated aqueous sodium chloride solution (2×100 mL), dried over sodium sulfate, filtered, and concentrated under reduced pressure to provide the product as a yellow solid. Yield: 1.0 g, 5.2 mmol, 67%. LCMS m/z 192.1 [M+H]$^+$. $^1$H NMR (400 MHz, CD$_3$OD) δ 8.35 (d, J=2.9 Hz, 1H), 8.14 (d, J=8.7 Hz, 1H), 7.57 (dd, J=8.7, 2.8 Hz, 1H), 4.87 (q, J=2.3 Hz, 2H), 1.84 (t, J=2.3 Hz, 3H).

Step 3. Synthesis of N-{2-[cis-2-(benzoylamino)-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (C84)

Pyridine (114 mg, 1.44 mmol) and 2,4,6-tripropyl-1,3,5,2,4,6-trioxatriphosphinane 2,4,6-trioxide (50% solution in ethyl acetate; 690 mg, 1.08 mmol) were added to a mixture of P1 (150 mg, 0.37 mmol) and C83 (87 mg, 0.46 mmol) in ethyl acetate (20 mL). The reaction mixture was stirred at 40° C. for 16 hours, whereupon it was concentrated under reduced pressure to provide the product as a yellow oil, which was used directly in the next step without additional purification. LCMS m/z 576.1 [M+H]$^+$.

Step 4. Synthesis of N-{2-[cis-2-amino-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (C85)

A mixture of C84 (from the previous step; ≤50.37 mmol), methoxylamine hydrochloride (301 mg, 3.60 mmol), and pyridine (2.85 g, 36.0 mmol) in ethanol (25 mL) was stirred at 60° C. for 16 hours. The reaction mixture was then concentrated in vacuo and purified by reversed phase HPLC (Column: Phenomenex Gemini C18, 8 μm; Mobile phase A: aqueous ammonia, pH 10; Mobile phase B: acetonitrile; Gradient: 36% to 56% B), affording the product as a white solid. Yield: 69 mg, 0.15 mmol, 40% over 2 steps. LCMS m/z 472.1 [M+H]$^+$.

Step 5. Isolation of N-{2-[(4aS,8aS)-2-amino-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (1) and N-{2-[(4aR,8aR)-2-amino-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (2)

Racemic C85 (from the previous step, 69 mg) was separated into its component enantiomers via two separations using supercritical fluid chromatography [Column: Chiral Technologies Chiralpak AD, 10 μm; Mobile phase: 55:45 carbon dioxide/(ethanol containing 0.1% ammonium hydroxide)]. The first-eluting enantiomer was 1, isolated as a white solid. Yield: 19 mg, 28% from the supercritical fluid chromatography. LCMS m/z 472.0 [M+H]$^+$. $^1$H NMR (400 MHz, CDCl$_3$) δ 10.41 (br s, 1H), 8.35 (d, J=2.4 Hz, 1H), 8.24 (d, J=8.3 Hz, 1H), 7.68 (s, 1H), 7.45 (dd, J=8.4, 2.6 Hz, 1H), 4.81-4.77 (m, 2H), 4.10 (d, J=11.7 Hz, 1H), 3.73 (d, J=11.7 Hz, 1H), 3.21 (dd, J=12, 4 Hz, 1H), 3.03-2.94 (m, 1H), 2.55 (br d, J=12.5 Hz, 1H), 1.96 (dd, J=13.6, 13.3 Hz, 1H), 1.90-1.86 (m, 3H), 1.46 (s, 3H), 1.38 (dd, J=13.5, 4 Hz, 1H), 1.33 (s, 3H).

The second-eluting enantiomer, also obtained as a white solid, was 2. Yield: 21 mg, 30% from the supercritical fluid chromatography. LCMS m/z 472.0 [M+H]$^+$. $^1$H NMR (400 MHz, CDCl$_3$) δ 10.41 (br s, 1H), 8.35 (d, J=2.5 Hz, 1H), 8.24 (d, J=8.6 Hz, 1H), 7.68 (s, 1H), 7.45 (dd, J=8.5, 2.5 Hz, 1H), 4.81-4.77 (m, 2H), 4.10 (d, J=11.6 Hz, 1H), 3.73 (d, J=11.4 Hz, 1H), 3.21 (dd, J=12, 4 Hz, 1H), 3.03-2.94 (m, 1H), 2.55 (brd, J=12.3 Hz, 1H), 1.96 (dd, J=13.3, 13.3 Hz, 1H), 1.91-1.86 (m, 3H), 1.46 (s, 3H), 1.38 (dd, J=13, 3.5 Hz, 1H), 1.33 (s, 3H).

The absolute configuration of the more potent enantiomer 2 (see Table 2) was assigned in analogy with the work reported by C. R. Butler et al., *J. Med. Chem.* 2015, 58, 2678-2702, and M. A. Brodney, *J. Med. Chem.* 2015, 58, 3223-3252. This rationale was applied in assigning absolute stereochemistry to all of the enantiomer pairs obtained herein.

Alternate Synthesis of Example 2

N-{2-[(4aR,8aR)-2-Amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyridine-2-carboxamide (2)

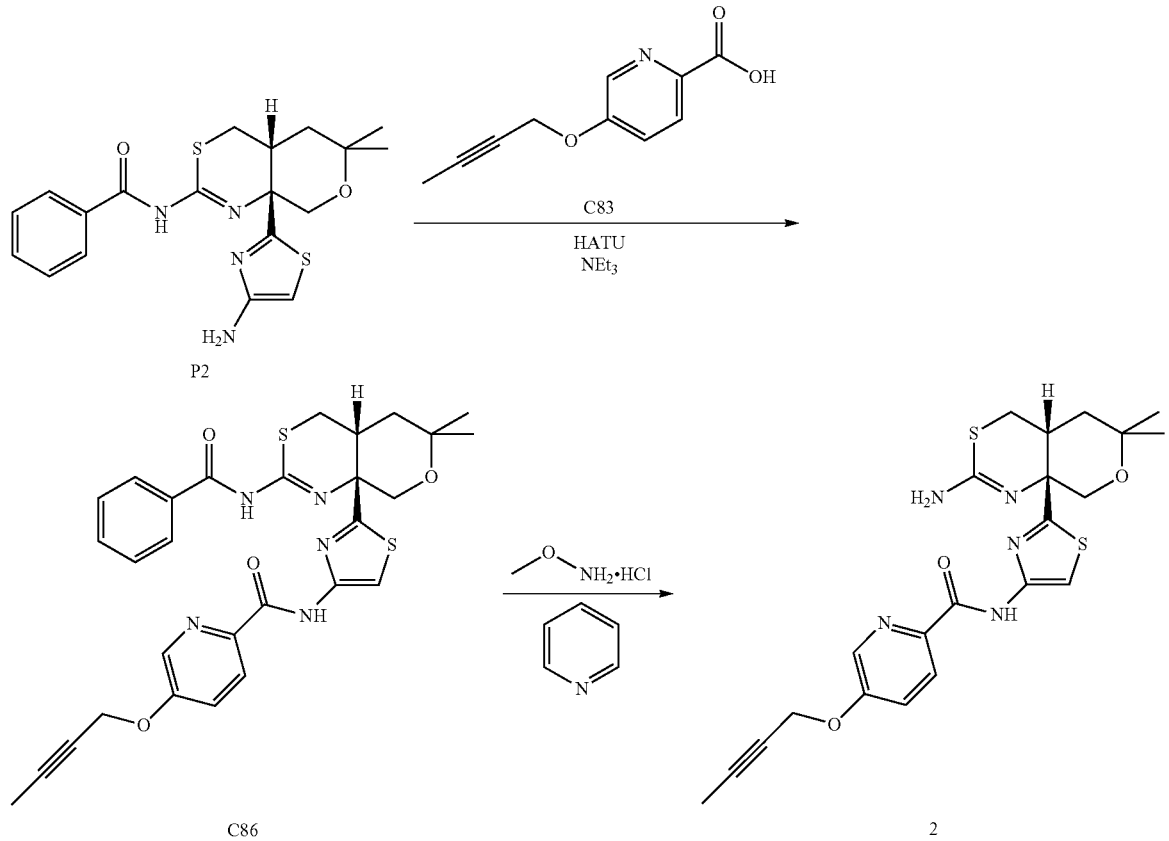

Step 1. Synthesis of N-{2-[(4aR,8aR)-2-(benzoylamino)-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (C86)

To a solution of C83 (40 mg, 0.21 mmol) in dichloromethane (15 mL) were added O-(7-azabenzotriazol-1-yl)-N,N,N',N'-tetramethyluronium hexafluorophosphate (HATU; 92 mg, 0.24 mmol) and triethylamine (32 mg, 0.32 mmol) at room temperature (~17° C.). After the reaction mixture had stirred at room temperature for 30 minutes, P2 (86% purity; 80 mg, 0.17 mmol) was added in one portion, and stirring was continued for 18 hours at 25° C. The reaction mixture was combined with material from a similar reaction carried out using P2 (20 mg of 86% purity; 43 μmol), and the resulting solution was diluted with dichloromethane (50 mL) and washed with saturated aqueous sodium chloride solution (2×30 mL). The combined aqueous layers were extracted with dichloromethane (30 mL); the combined organic layers were dried over sodium sulfate, filtered, and concentrated in vacuo to afford the product as a yellow solid. This material was taken directly to the following step, without additional purification. LCMS m/z 576.1 [M+H]$^+$.

Step 2. Synthesis of N-{2-[(4aR,8aR)-2-amino-6,6-dimethyl-4,4a,5,6-tetrahydropyrano[3,4-d][1,3]thiazin-8a (8H)-yl]-1,3-thiazol-4-yl}-5-(but-2-yn-1-yloxy)pyridine-2-carboxamide (2)

Methoxylamine hydrochloride (179 mg, 2.14 mmol) and pyridine (1.69 g, 21.4 mmol) were added to a suspension of C86 (from the previous step; ≤0.21 mmol) in ethanol (25 mL), and the reaction mixture was stirred at 60° C. for 12 hours. After the reaction mixture had been concentrated in vacuo, the residue was purified via reversed phase HPLC (Column: Phenomenex Gemini C18, 5 μm; Mobile phase A: 0.05% ammonia in water; Mobile phase B: acetonitrile; Gradient: 42% to 62% B), providing the product as an off-white solid. Yield: 63 mg, 0.13 mmol, 62% over 2 steps. LCMS m/z 472.0 [M+H]$^+$. $^1$H NMR (400 MHz, CDCl$_3$) δ 10.41 (br s, 1H), 8.35 (d, J=2.5 Hz, 1H), 8.24 (d, J=8.7 Hz, 1H), 7.68 (s, 1H), 7.45 (dd, J=8.8, 2.8 Hz, 1H), 4.9-4.3 (br s, 2H), 4.79 (br q, J=2 Hz, 2H), 4.10 (d, J=11.5 Hz, 1H), 3.73 (d, J=11.5 Hz, 1H), 3.21 (dd, J=12.7, 4.1 Hz, 1H), 3.02-2.94 (m, 1H), 2.54 (dd, J=12.4, 2.5 Hz, 1H), 1.96 (dd, J=13.4, 13.4 Hz, 1H), 1.88 (t, J=2.2 Hz, 3H), 1.45 (s, 3H), 1.38 (dd, J=13.4, 4.1 Hz, 1H), 1.33 (s, 3H).

Examples 3, 4, and 5

N-{2-[cis-2'-Amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (3), N-{2-[(4a'S,8a'S)-2'-Amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (4), and N-{2-[(4a'R,8a'R)-2'-Amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (5)

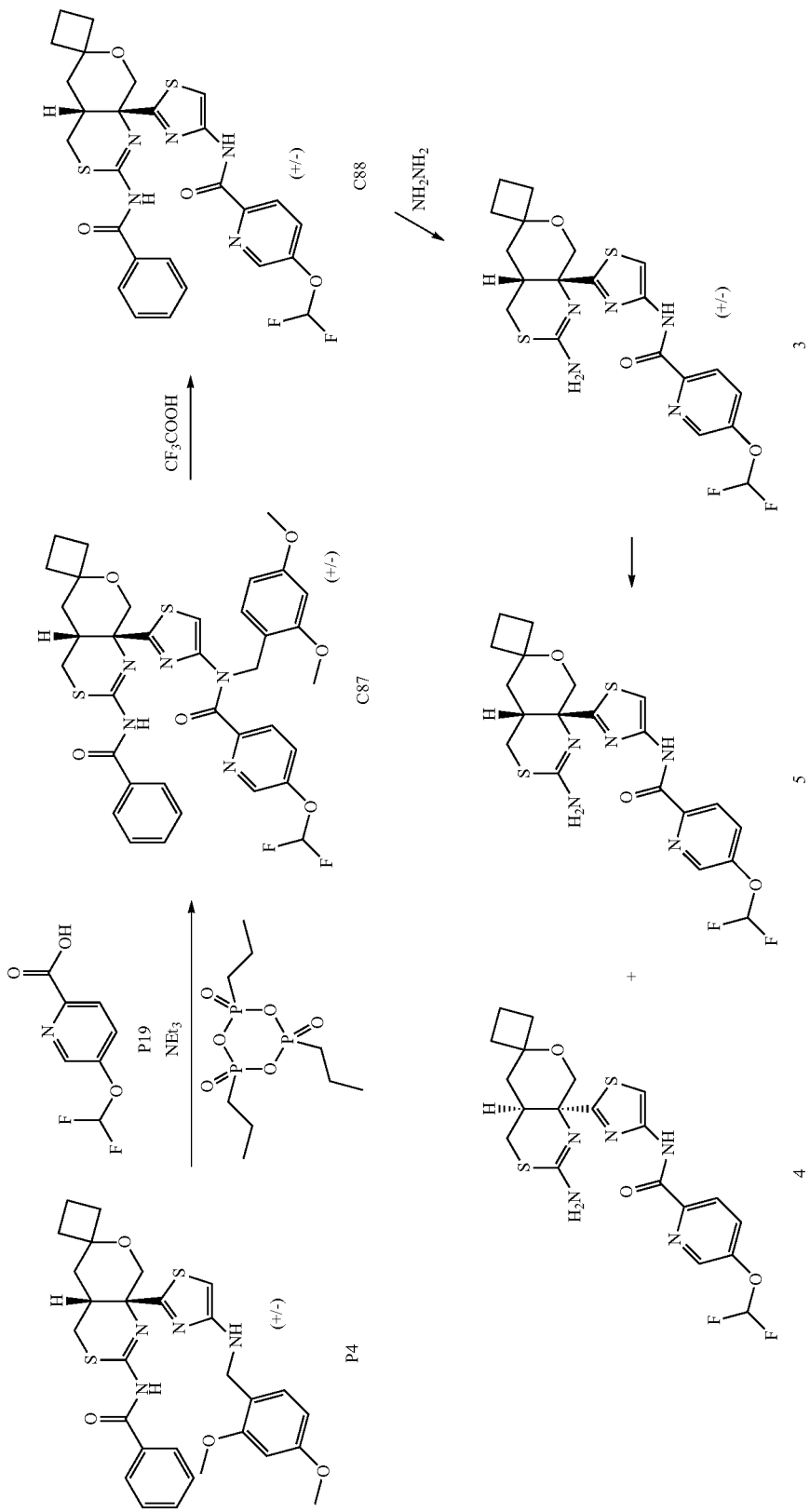

Step 1. Synthesis of N-{2-[cis-2'-(benzoylamino)-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)-N-(2,4-dimethoxybenzyl)pyridine-2-carboxamide (C87)

Triethylamine (0.295 mL, 2.12 mmol) was added to a mixture of P19 (0.161 g, 0.851 mmol) in ethyl acetate (1 mL). The resulting solution was treated with 2,4,6-tripropyl-1,3,5,2,4,6-trioxatriphosphinane 2,4,6-trioxide (50% solution in ethyl acetate; 3.48 mL, 5.85 mmol), and the reaction mixture was heated at 65° C. for 20 minutes. Compound P4 (300 mg, 0.531 mmol) was then added, and stirring was continued for 16 hours at 65° C. After the reaction mixture had cooled to room temperature, it was diluted with ethyl acetate (100 mL) and washed with water (2×150 mL). The organic layer was then sequentially washed with saturated aqueous sodium bicarbonate solution (250 mL; the resulting aqueous wash was found to exhibit a pH of 8) and saturated aqueous sodium chloride solution (250 mL), dried over sodium sulfate, filtered, and concentrated in vacuo. Silica gel chromatography (Gradient: 0% to 100% ethyl acetate in heptane) afforded the product as a yellow solid. Yield: 248 mg, 0.337 mmol, 63%. $^1$H NMR (400 MHz, CDCl$_3$), characteristic peaks: β 7.79 (d, J=8.6 Hz, 1H), 7.58-7.49 (m, 2H), 7.49-7.40 (m, 2H), 6.59 (t, $J_{HF}$=72.0 Hz, 1H), 6.47-6.35 (m, 2H), 5.25-5.04 (m, 2H), 3.79 (s, 3H), 3.70 (s, 3H), 2.89 (br d, J=12 Hz, 1H), 2.46 (br d, J=13 Hz, 1H).

Step 2. Synthesis of N-{2-[cis-2'-(benzoylamino)-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (C88)

Trifluoroacetic acid (1.3 mL, 17 mmol) was added to a solution of C87 (247 mg, 0.336 mmol) in dichloromethane (17 mL), and the reaction mixture was allowed to stir at room temperature for 16 hours, whereupon it was partitioned between aqueous sodium bicarbonate solution (100 mL) and dichloromethane (50 mL). The aqueous layer was extracted with dichloromethane (2×50 mL), and the combined organic layers were washed with saturated aqueous sodium chloride solution (150 mL), dried over sodium sulfate, and filtered. The filtrate was adsorbed onto silica gel and subjected to silica gel chromatography (Gradient: 0% to 80% ethyl acetate in heptane), providing the product as a white solid. Yield: 158 mg, 0.270 mmol, 80%. $^1$H NMR (400 MHz, CDCl$_3$) δ 10.43 (br s, 1H), 8.50 (d, J=2.6 Hz, 1H), 8.33 (d, J=8.6 Hz, 1H), 8.15-8.07 (m, 2H), 7.77 (s, 1H), 7.69 (dd, J=8.6, 2.6 Hz, 1H), 7.57-7.51 (m, 1H), 7.50-7.43 (m, 2H), 6.66 (t, $J_{HF}$=71.9 Hz, 1H), 3.85 (AB quartet, upfield doublet is broadened, $J_{AB}$=12.1 Hz, $\Delta v_{AB}$=81 Hz, 2H), 3.22 (dd, J=12.5, 4 Hz, 1H), 3.09-3.00 (m, 1H), 2.61 (dd, J=13, 2 Hz, 1H), 2.32-1.97 (m, 5H), 1.94-1.82 (m, 2H), 1.77-1.63 (m, 1H).

Step 3. Synthesis of N-{2-[cis-2'-amino-4a',5'-dihydro-4'H-spiro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (3)

To a solution of C88 (158 mg, 0.270 mmol) in dichloromethane (5 mL) was added ethanol (0.158 mL, 2.71 mmol), followed by hydrazine monohydrate (0.143 mL, 2.95 mmol), and the reaction mixture was allowed to stir at room temperature for 16 hours. It was then concentrated under reduced pressure, dissolved in dichloromethane (10 mL), and adsorbed onto silica gel after addition of a small amount of methanol and ethyl acetate. Silica gel chromatography (Gradient: 0% to 10% methanol in dichloromethane) afforded a white solid, which was triturated with dichloromethane (5 mL) to provide, after washing with dichloromethane (2×3 mL), the product as a white solid (40 mg). The filtrate from the trituration was concentrated in vacuo and triturated with dichloromethane (3 mL), providing additional product as a white solid. Combined yield: 75 mg, 0.16 mmol, 59%. LCMS m/z 482.3 [M+H]$^+$. $^1$H NMR (400 MHz, CDCl$_3$) δ 10.40 (br s, 1H), 8.49 (dd, J=2.7, 0.5 Hz, 1H), 8.32 (dd, J=8.6, 0.6 Hz, 1H), 7.73 (s, 1H), 7.68 (br dd, J=8.6, 2.6 Hz, 1H), 6.66 (t, $J_{HF}$=71.9 Hz, 1H), 3.83 (AB quartet, upfield doublet is broadened, $J_{AB}$=11.4 Hz, $\Delta v_{AB}$=43 Hz, 2H), 3.22 (dd, J=12.6, 4.1 Hz, 1H), 2.93-2.85 (m, 1H), 2.61 (dd, J=12.5, 2.7 Hz, 1H), 2.33-2.14 (m, 3H), 2.04-1.95 (m, 2H), 1.92-1.81 (m, 1H), 1.75 (dd, J=13.4, 4.0 Hz, 1H), 1.73-1.61 (m, 1H).

Step 4. Isolation of N-{2-[(4a'S,8a'S)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (4) and N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide (5)

Racemic 3 (from the previous step, 75 mg) was separated into its component enantiomers via supercritical fluid chromatography [Column: Chiral Technologies Chiralcel OJ-H, 5 μm; Mobile phase: 9:1 carbon dioxide/(methanol containing 0.2% ammonium hydroxide)]. The first-eluting enantiomer was 4. Yield: 21 mg, 28% from the supercritical fluid chromatography. LCMS m/z 482.3 [M+H]$^+$. $^1$H NMR (400 MHz, CDCl$_3$) δ 10.40 (br s, 1H), 8.49 (dd, J=2.6, 0.5 Hz, 1H), 8.32 (dd, J=8.6, 0.6 Hz, 1H), 7.76 (s, 1H), 7.68 (br dd, J=8.6, 2.7 Hz, 1H), 6.66 (t, $J_{HF}$=71.9 Hz, 1H), 3.92-3.82 (m, 2H), 3.25 (dd, J=12.7, 4.2 Hz, 1H), 3.02-2.92 (m, 1H), 2.66 (br d, J=12.8 Hz, 1H), 2.35-2.14 (m, 3H), 2.09-1.75 (m, 4H), 1.74-1.61 (m, 1H).

The second-eluting enantiomer was 5. Yield: 14 mg, 19% from the supercritical fluid chromatography. LCMS m/z 482.1 [M+H]$^+$. $^1$H NMR (400 MHz, CDCl$_3$) δ 10.40 (br s, 1H), 8.49 (dd, J=2.6, 0.5 Hz, 1H), 8.32 (dd, J=8.6, 0.6 Hz, 1H), 7.73 (s, 1H), 7.68 (br dd, J=8.6, 2.7 Hz, 1H), 6.66 (t, $J_{HF}$=72.0 Hz, 1H), 3.84 (AB quartet, upfield doublet is broadened, $J_{AB}$=11.4 Hz, $\Delta v_{AB}$=35 Hz, 2H), 3.23 (dd, J=12.5, 4.0 Hz, 1H), 2.96-2.86 (m, 1H), 2.62 (dd, J=12.7, 2.4 Hz, 1H), 2.34-2.14 (m, 3H), 2.04-1.94 (m, 2H), 1.93-1.81 (m, 1H), 1.76 (dd, J=13.5, 3.8 Hz, 1H), 1.74-1.61 (m, 1H).

The absolute configuration of the more potent enantiomer 5 (see Table 2) was assigned in analogy with the work reported by C. R. Butler et al., *J. Med. Chem.* 2015, 58, 2678-2702, and M. A. Brodney, *J. Med. Chem.* 2015, 58, 3223-3252. The same rationale was used in assigning the absolute stereochemistry of all subsequent separated pairs of enantiomers.

Example 6

N-{2-[(4a'R,8a'R)-2'-Amino-4a',5'-dihydro-4'H-spiro[cyclobutane-1,6'-pyrano[3,4-d][1,3]thiazin]-8a'(8'H)-yl]-1,3-thiazol-4-yl}-5-chloropyridine-2-carboxamide (6)

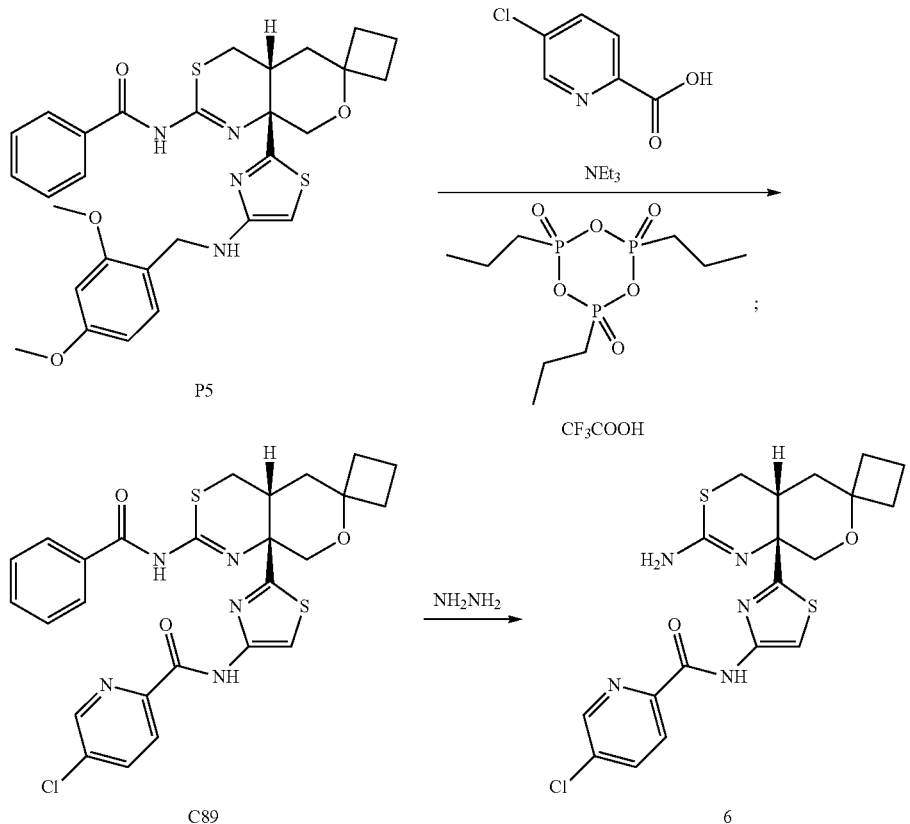

Step 1. Synthesis of N-{2-[(4a'R,8a'R)-2'-(benzoylamino)-4a',5'-dihydro-4'H-spiro[cyclobutane-1,6'-pyrano[3,4-d][1,3]thiazin]-8a'(8'H)-yl]-1,3-thiazol-4-yl}-5-chloropyridine-2-carboxamide (C89)

Triethylamine (98 μL, 0.70 mmol) was added to a mixture of 5-chloropyridine-2-carboxylic acid (44.6 mg, 0.283 mmol) in ethyl acetate (5 mL). The resulting solution was treated with 2,4,6-tripropyl-1,3,5,2,4,6-trioxatriphosphinane 2,4,6-trioxide (50% solution in ethyl acetate; 0.169 mL, 0.284 mmol), and the reaction mixture was heated at 65° C. for 20 minutes, whereupon P5 (100 mg, 0.177 mmol) was added and stirring was continued for 16 hours at 65° C. After cooling to room temperature, the reaction mixture was diluted with ethyl acetate (100 mL) and washed sequentially with water (2×150 mL), saturated aqueous sodium bicarbonate solution (250 mL), and saturated aqueous sodium chloride solution (250 mL), dried over sodium sulfate, filtered, and concentrated in vacuo. The residue was dissolved in dichloromethane (3 mL) and treated with trifluoroacetic acid (0.68 mL, 8.8 mmol). After the reaction mixture had stirred at room temperature for 16 hours, dichloromethane (100 mL) was added, and the resulting solution was treated with saturated aqueous sodium bicarbonate solution (350 mL). The organic layer was washed with saturated aqueous sodium chloride solution (250 mL), dried over sodium sulfate, filtered, and concentrated under reduced pressure. Chromatography on silica gel (Gradient: 0% to 100% ethyl acetate in heptane) afforded the product as a yellow solid. Yield: 61.2 mg, 0.110 mmol, 62%. $^1$H NMR (400 MHz, CDCl$_3$) δ 10.42 (br s, 1H), 8.60 (dd, J=2.4, 0.6 Hz, 1H), 8.25 (dd, J=8.4, 0.6 Hz, 1H), 8.17-8.05 (m, 2H), 7.91 (dd, J=8.3, 2.4 Hz, 1H), 7.78 (s, 1H), 7.57-7.51 (m, 1H), 7.46 (br dd, J=7.7, 7.0 Hz, 2H), 3.85 (AB quartet, J$_{AB}$=11.9 Hz, Δv$_{AB}$=80.9 Hz, 2H), 3.22 (dd, J=12.9, 4.1 Hz, 1H), 3.09-3.00 (m, 1H), 2.61 (dd, J=13.1, 2.7 Hz, 1H), 2.32-1.97 (m, 5H), 1.95-1.82 (m, 2H), 1.77-1.64 (m, 1H).

Step 2. Synthesis of N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-chloropyridine-2-carboxamide (6)

Conversion of C89 to 6 was carried out according to the procedure described for synthesis of 3 from C88 in Examples 3, 4, and 5. In this case, the material obtained from the silica gel chromatographic purification was triturated with diethyl ether (5 mL) to provide the product as a white solid. Yield: 26 mg, 58 μmol, 53%. LCMS m/z 450.3 [M+H]$^+$. $^1$H NMR (400 MHz, CDCl$_3$) δ 10.39 (br s, 1H), 8.59 (dd, J=2.3, 0.7 Hz, 1H), 8.24 (dd, J=8.3, 0.6 Hz, 1H), 7.90 (dd, J=8.4, 2.3 Hz, 1H), 7.71 (s, 1H), 4.59-4.47 (br s, 2H), 3.80 (AB quartet, J$_{AB}$=11.2 Hz, Δv$_{AB}$=61.7 Hz, 2H), 3.21 (dd, J=12.6, 4.1 Hz, 1H), 2.88-2.81 (m, 1H), 2.59 (dd, J=12.5, 2.7 Hz, 1H), 2.32-2.15 (m, 3H), 2.05-1.95 (m, 2H), 1.92-1.81 (m, 1H), 1.74-1.60 (m, 1H), 1.73 (dd, J=13.3, 4.1 Hz, 1H).

Example 7

N-{2-[(4aR,8aR)-2-Amino-6,6-dimethyl-4,4a,5,6-tetrahydropyrano[3,4-d][1,3]thiazin-8a(8H)-yl]-1,3-thiazol-4-yl}-5-(difluoromethoxy)pyridine-2-carboxamide (7)

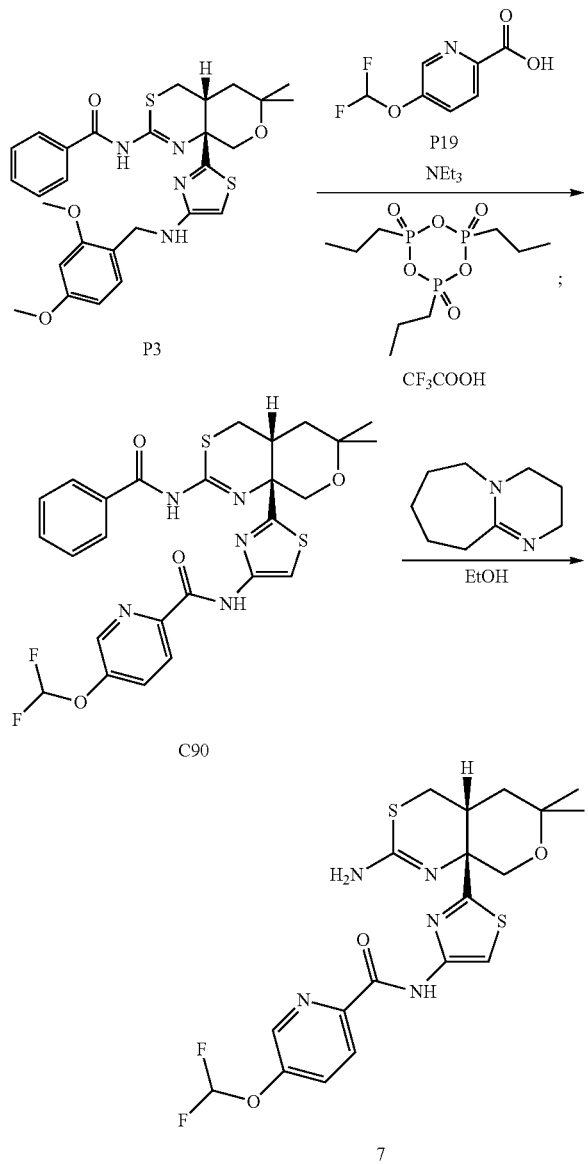

Step 1. Synthesis of N-{2-[(4aR,8aR)-2-(benzoylamino)-6,6-dimethyl-4,4a,5,6-tetrahydropyrano[3,4-d][1,3]thiazin-8a (8H)-yl]-1,3-thiazol-4-yl}-5-(difluoromethoxy)pyridine-2-carboxamide (C90)

Triethylamine (7.0 mL, 50 mmol) was added to a mixture of P19 (3.83 g, 20.3 mmol) in ethyl acetate (63 mL). To the resulting solution was added 2,4,6-tripropyl-1,3,5,2,4,6-trioxatriphosphinane 2,4,6-trioxide (50% solution in ethyl acetate; 30.2 mL, 50.7 mmol), and the reaction mixture was heated at 65° C. for 20 minutes. A solution of P3 (7.0 g, 13 mmol) in ethyl acetate (25 mL) was added, and the reaction mixture was stirred at 65° C. for 1 hour. After cooling to room temperature, the reaction mixture was diluted with ethyl acetate and washed sequentially with water (twice), saturated aqueous sodium bicarbonate solution (until the resulting aqueous wash reached a pH of 8), and saturated aqueous sodium chloride solution. It was then dried over sodium sulfate, filtered, and concentrated in vacuo; the resulting solid was dissolved in dichloromethane (700 mL), treated with trifluoroacetic acid (49 mL, 640 mmol), and allowed to stir at room temperature overnight. The reaction mixture was then diluted with dichloromethane and basified via addition of 1 M aqueous sodium hydroxide solution. The aqueous layer was extracted twice with dichloromethane, and the combined organic layers were washed with saturated aqueous sodium chloride solution, dried over sodium sulfate, filtered, and concentrated under reduced pressure. Silica gel chromatography (Gradient: 0% to 100% ethyl acetate in heptane) provided a residue, which was triturated for an hour in heptane containing a small amount of ethyl acetate. The product was obtained as a yellow solid. Yield: 3.70 g, 6.45 mmol, 50%. LCMS m/z 574.3 [M+H]$^+$. $^1$H NMR (400 MHz, CDCl$_3$), characteristic peaks: δ 12.50-12.35 (br s, 1H), 10.44 (br s, 1H), 8.50 (dd, J=2.6, 0.6 Hz, 1H), 8.33 (dd, J=8.6, 0.6 Hz, 1H), 7.78 (br s, 1H), 7.69 (dd, J=8.6, 2.6 Hz, 1H), 7.61-7.40 (br m, 3H), 6.66 (t, J$_{HF}$=71.9 Hz, 1H), 4.25-4.13 (m, 1H), 3.76 (d, J=12.5 Hz, 1H), 3.30-3.11 (m, 2H), 2.63-2.52 (m, 1H), 2.16-1.99 (m, 1H), 1.57-1.49 (m, 1H), 1.48 (s, 3H), 1.34 (s, 3H).

Step 2. Synthesis of N-{2-[(4aR,8aR)-2-amino-6,6-dimethyl-4,4a,5,6-tetrahydropyrano[3,4-d][1,3]thiazin-8a (8H)-yl]-1,3-thiazol-4-yl}-5-(difluoromethoxy)pyridine-2-carboxamide (7)

A mixture of C90 (3.70 g, 6.45 mmol) and 1,8-diazabicyclo[5.4.0]undec-7-ene (95%, 1.02 mL, 6.48 mmol) in methanol (104 mL) was heated to 70° C. Additional methanol (500 mL) and dichloromethane (100 mL) were added to fully solubilize the reagents, and the reaction mixture was stirred overnight at 70° C. After the reaction mixture had cooled, it was added to ethyl acetate, and the mixture was washed sequentially with aqueous sodium bicarbonate solution and saturated aqueous sodium chloride solution, dried over sodium sulfate, filtered, and concentrated in vacuo. Silica gel chromatography (Gradient: 0% to 5% methanol in dichloromethane), followed by trituration in heptane containing a small amount of dichloromethane, provided the product as a white solid. This material proved to be crystalline via powder X-ray diffraction. Yield: 2.15 g, 4.58 mmol, 71%. LCMS m/z 470.3 [M+H]$^+$. $^1$H NMR (400 MHz, CDCl$_3$) δ 10.40 (br s, 1H), 8.49 (dd, J=2.6, 0.5 Hz, 1H), 8.32 (dd, J=8.7, 0.5 Hz, 1H), 7.71 (s, 1H), 7.68 (br dd, J=8.6, 2.6 Hz, 1H), 6.66 (t, J$_{HF}$=71.9 Hz, 1H), 4.56 (br s, 2H), 4.10 (d, J=11.5 Hz, 1H), 3.73 (d, J=11.5 Hz, 1H), 3.21 (dd, J=12.5, 4.1 Hz, 1H), 2.98 (dddd, J=13, 4, 4, 3 Hz, 1H), 2.55 (dd, J=12.5, 2.7 Hz, 1H), 1.96 (dd, J=13.3, 13.2 Hz, 1H), 1.46 (s, 3H), 1.38 (dd, J=13.4, 4.1 Hz, 1H), 1.33 (s, 3H).

Example 8

N-{2-[(4aR,6S,8aR)-2-Amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide (8)

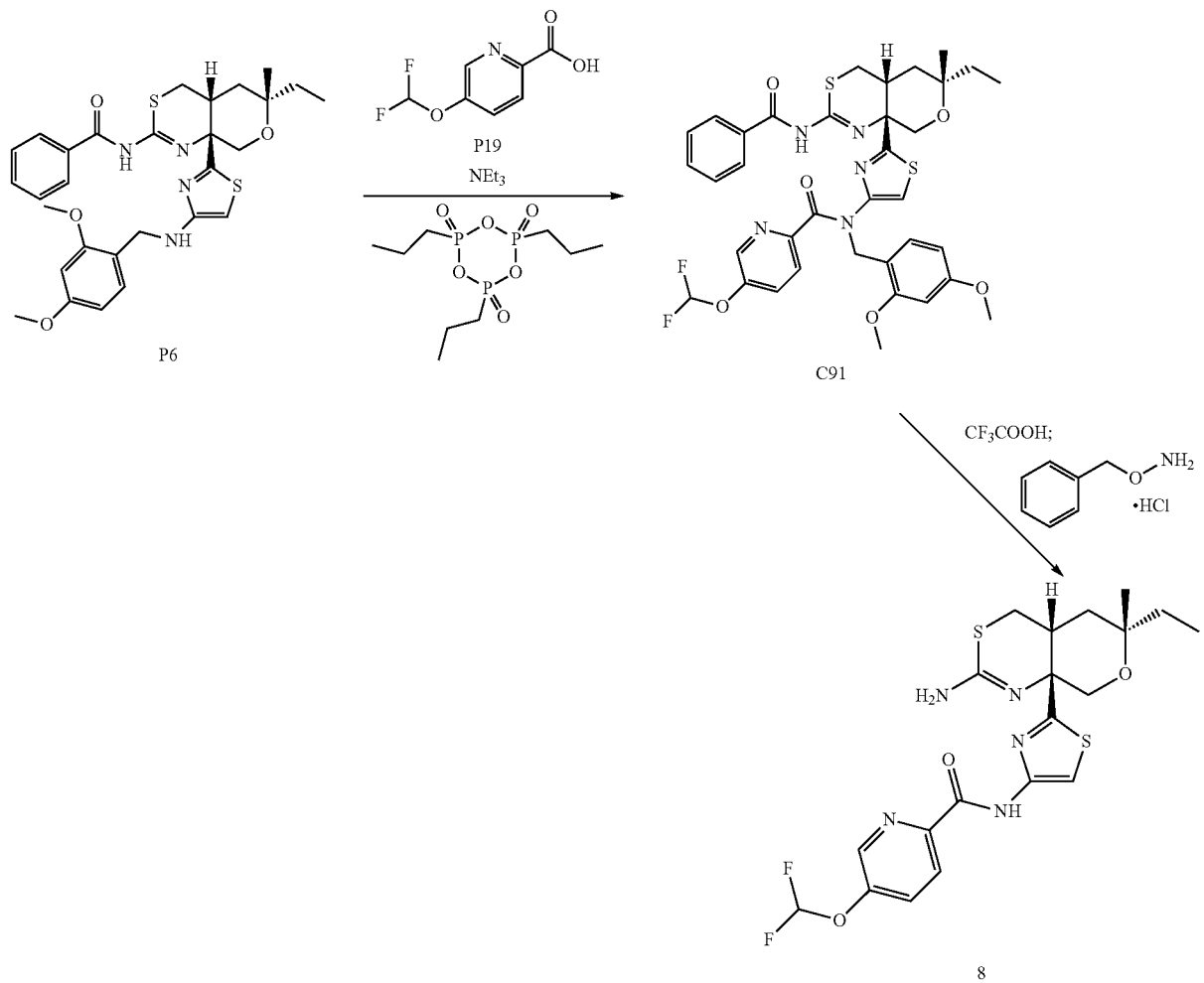

Step 1. Synthesis of N-{2-[(4aR,6S,8aR)-2-(benzoylamino)-6-ethyl-6-methyl-4,4a,5,6-tetrahydropyrano[3,4-d][1,3]thiazin-8a(8H)-yl]-1,3-thiazol-4-yl)}-5-(difluoromethoxy)-N-(2,4-dimethoxybenzyl)pyridine-2-carboxamide (C91)

2,4,6-Tripropyl-1,3,5,2,4,6-trioxatriphosphinane 2,4,6-trioxide (50% solution in ethyl acetate, 0.25 mL, 0.42 mmol) was added to a mixture of P19 (32.0 mg, 0.169 mmol) and triethylamine (59 μL, 0.42 mmol) in ethyl acetate (0.2 mL). The reaction mixture was heated to 60° C. for 20 minutes, whereupon P6 (60.0 mg, 0.106 mmol) was added, and stirring was continued at 60° C. for 1 hour. The reaction mixture was then diluted with ethyl acetate and water. The aqueous layer was extracted twice with ethyl acetate, and the combined organic layers were washed twice with saturated aqueous sodium bicarbonate solution and once with saturated aqueous sodium chloride solution, dried over sodium sulfate, filtered, and concentrated in vacuo. LCMS m/z 738.5 [M+H]$^+$. This residue was subjected to chromatography on silica gel (Gradient: 0% to 60% ethyl acetate in heptane) to afford the product (77 mg), which was taken directly to the following step.

Step 2. Synthesis of N-{2-[(4aR,6S,8aR)-2-amino-6-ethyl-6-methyl-4,4a,5,6-tetrahydropyrano[3,4-d][1,3]thiazin-8a (8H)-yl]-1,3-thiazol-4-yl}-5-(difluoromethoxy)pyridine-2-carboxamide (8)

Trifluoroacetic acid (0.2 mL) was added to a solution of C91 (from the previous step; 77 mg, 0.10 mmol) in dichloromethane (0.5 mL), and the reaction mixture was stirred at room temperature for 45 minutes. It was then concentrated under reduced pressure, and the residue was partitioned between ethyl acetate and saturated aqueous sodium bicarbonate solution. The aqueous layer was extracted three times with ethyl acetate, and the combined organic layers were dried over sodium sulfate, filtered, and concentrated in vacuo. The resulting material (60 mg) was dissolved in ethanol (1 mL), treated with pyridine (0.16 mL) and O-benzylhydroxylamine hydrochloride (155 mg, 0.970 mmol), and heated at 50° C. for 3 hours. After the reaction mixture had been concentrated in vacuo, the residue was partitioned between diethyl ether and 0.25 M aqueous hydrochloric acid. The aqueous layer was washed six times with diethyl ether, whereupon it was adjusted to a pH of approximately 12 via slow addition of 1 M aqueous sodium hydroxide solution. The aqueous layer was then extracted three times with dichloromethane, and the combined dichloromethane extracts were dried over sodium sulfate, filtered, and concentrated in vacuo. Silica gel chromatography (Gradient: 0% to 50% ethyl acetate in heptane) provided the product. Yield: 17.4 mg, 36 μmol, 34% over 2 steps. LCMS m/z 484.4 [M+H]$^+$. $^1$H NMR (400 MHz, CDCl$_3$) δ 10.40 (br s, 1H), 8.49 (d, J=2.7 Hz, 1H), 8.32 (d, J=8.6 Hz, 1H), 7.70 (s, 1H), 7.68 (br dd, J=8.6, 2.7 Hz, 1H), 6.65 (t, J$_{HF}$=72.0 Hz, 1H), 5.0-4.2 (v br s, 2H), 4.08 (d, J=11.5 Hz, 1H), 3.71 (d, J=11.5 Hz, 1H), 3.22 (dd, J=12.5, 4.2 Hz, 1H), 3.03-2.95 (m, 1H), 2.55 (dd, J=12.5, 2.7 Hz, 1H), 1.91 (dd, J=13.3, 13.2 Hz, 1H), 1.68-1.51 (m, 2H), 1.39 (s, 3H), 1.33 (dd, J=13.4, 4.2 Hz, 1H), 0.95 (t, J=7.5 Hz, 3H).

The absolute and relative stereochemistry of 8 and its isomers in Examples 26, 27, and 28 were assigned on the basis of the stereodefined synthesis of 8 carried out in Alternate Synthesis of Example 8 below, NMR work, and the biological activity of these compounds. From the $^1$H NMR spectra, 8 and 28 are enantiomers of one another; 26 and 27 are also enantiomers of one another. This information, in conjunction with the stereodefined synthesis of Example 8 below, allowed assignment of the configuration at the quaternary centers bearing the methyl and ethyl groups of 8 and 28. Examination of the biological activity of the four compounds (see Table 2), in conjunction with consideration of the remaining stereochemical possibilities, provided the absolute configurations at the ring fusion and the quaternary center for 26 and 27 (see discussion under Isolation of C9 and C10 in Preparation P2 above).

Alternate Synthesis of Example 8

N-{2-[(4aR,6S,8aR)-2-Amino-6-ethyl-6-methyl-4, 4a,5,6-tetrahydropyrano[3,4-d][1,3]thiazin-8a(8H)-yl]-1,3-thiazol-4-yl}-5-(difluoromethoxy)pyridine-2-carboxamide (8)

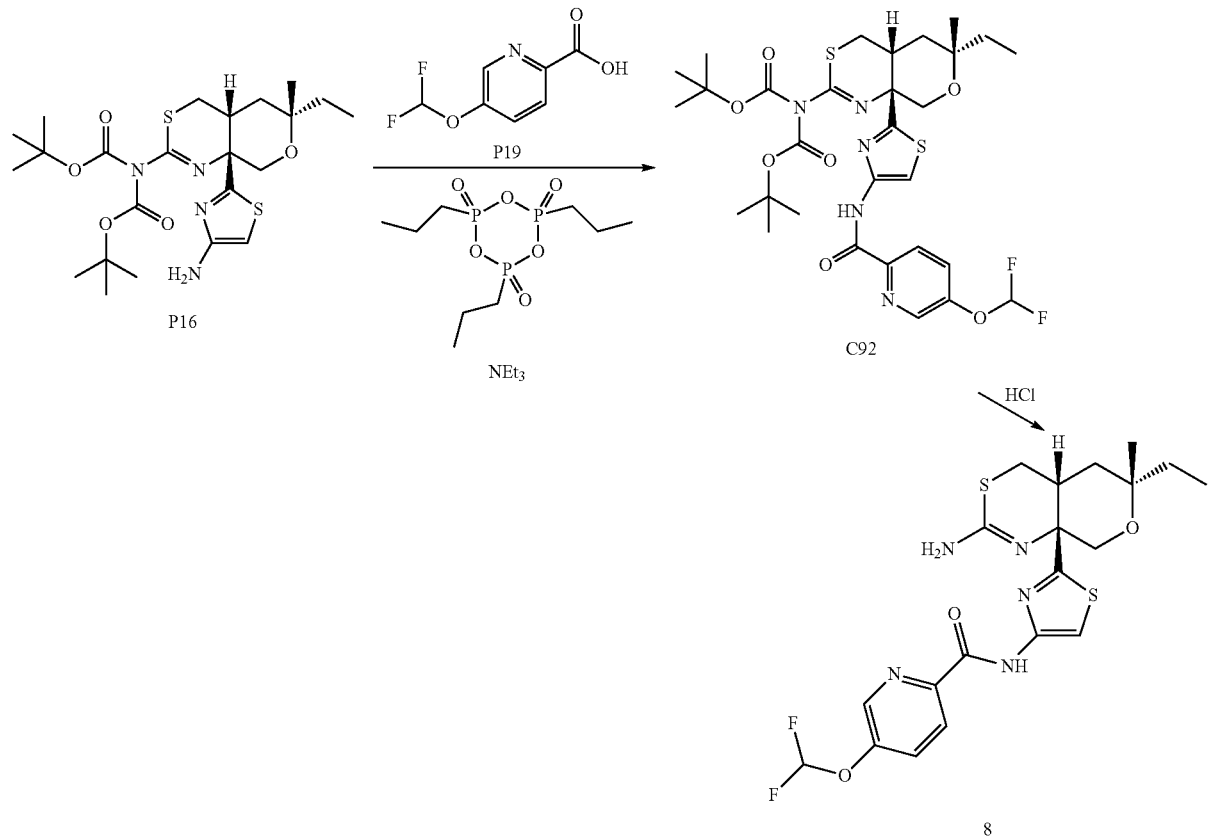

Step 1. Synthesis of di-tert-butyl {(4aR,6S,8aR)-8a-[4-({[5-(difluoromethoxy) pyridin-2-yl]carbonyl}amino)-1,3-thiazol-2-yl]-6-ethyl-6-methyl-4,4a,5,6,8,8a-hexahydropyrano[3,4-d][1,3]thiazin-2-yl}imidodicarbonate (C92)

A mixture of P19 (18.1 mg, 95.7 μmol), triethylamine (44.5 μL, 0.319 mmol), and 2,4,6-tripropyl-1,3,5,2,4,6-trioxatriphosphinane 2,4,6-trioxide (50% solution in ethyl acetate; 190 μL, 0.319 mmol) in ethyl acetate (1 mL) was heated at 55° C. for 20 minutes. The reaction mixture was then allowed to cool to 45° C., whereupon P16 (41 mg, 80 μmol) was added, and heating was continued at 45° C. for 1 hour. After the reaction mixture had cooled to room temperature, it was partitioned between ethyl acetate (15 mL) and saturated aqueous sodium bicarbonate solution (10 mL). The aqueous layer was then extracted with ethyl acetate (15 mL), and the combined organic layers were dried over sodium sulfate, filtered, and concentrated in vacuo. Chromatography on silica gel (Gradient: 0% to 90% ethyl acetate in heptane) afforded the product as a white solid. Yield: 26.4 mg, 38.6 μmol, 48%. $^1$H NMR (400 MHz, CDCl$_3$) δ 10.41 (br s, 1H), 8.50 (br d, J=2.3 Hz, 1H), 8.32 (br d, J=8.6 Hz, 1H), 7.75 (s, 1H), 7.68 (br dd, J=8.6, 2.6 Hz, 1H), 6.66 (t, $J_{HF}$=72.0 Hz, 1H), 3.97 (AB quartet, $J_{AB}$=11.7 Hz, $\Delta v_{AB}$=60.3 Hz, 2H), 3.37 (dd, J=12.8, 4.0 Hz, 1H), 3.22-3.13 (m, 1H), 2.63 (dd, J=12.7, 2.7 Hz, 1H), 2.05 (dd, J=13.4, 13.4 Hz, 1H), 1.68-1.54 (m, 2H), 1.54 (s, 18H), 1.43-1.36 (m, 1H), 1.39 (s, 3H), 0.95 (t, J=7.5 Hz, 3H).

Step 2. Synthesis of N-{2-[(4aR,6S,8aR)-2-amino-6-ethyl-6-methyl-4,4a,5,6-tetrahydropyrano[3,4-d][1,3]thiazin-8a (8H)-yl]-1,3-thiazol-4-yl}-5-(difluoromethoxy)pyridine-2-carboxamide (8)

A mixture of C92 (26 mg, 38 μmol) and a solution of hydrogen chloride in 1,4-dioxane (4 M, 1 mL) was stirred at 51° C. for 7 hours. After the reaction mixture had cooled to room temperature, it was concentrated in vacuo, and the residue was treated with aqueous sodium bicarbonate solution (5 mL) and extracted with ethyl acetate (4×7.5 mL). The combined organic layers were dried over sodium sulfate, filtered, and concentrated in vacuo. Silica gel chromatography (Gradient: 0% to 100% ethyl acetate in heptane) provided the product as a white solid. Yield: 15.8 mg, 32.6 μmol, 86%. LCMS m/z 484.3 [M+H]$^+$. $^1$H NMR (400 MHz, CDCl$_3$) δ 10.40 (br s, 1H), 8.49 (d, J=2.5 Hz, 1H), 8.32 (d, J=8.6 Hz, 1H), 7.71 (s, 1H), 7.68 (dd, J=8.6, 2.5 Hz, 1H), 6.66 (t, $J_{HF}$=71.9 Hz, 1H), 5.0-4.2 (v br s, 2H), 4.08 (d, J=11.5 Hz, 1H), 3.72 (d, J=11.5 Hz, 1H), 3.22 (dd, J=12.5, 4.1 Hz, 1H), 3.03-2.95 (m, 1H), 2.55 (dd, J=12.5, 2.7 Hz, 1H), 1.91 (dd, J=13.3, 13.3 Hz, 1H), 1.68-1.52 (m, 2H), 1.40 (s, 3H), 1.34 (dd, J=13.3, 4.1 Hz, 1H), 0.95 (t, J=7.5 Hz, 3H).

Example 9

N-{2-[(4aR,6R,8aR)-2-Amino-6-(methoxymethyl)-6-methyl-4,4a,5,6-tetrahydropyrano [3,4-d][1,3]thiazin-8a (8H)-yl]-1,3-thiazol-4-yl}-5-(difluoromethoxy)pyridine-2-carboxamide (9)

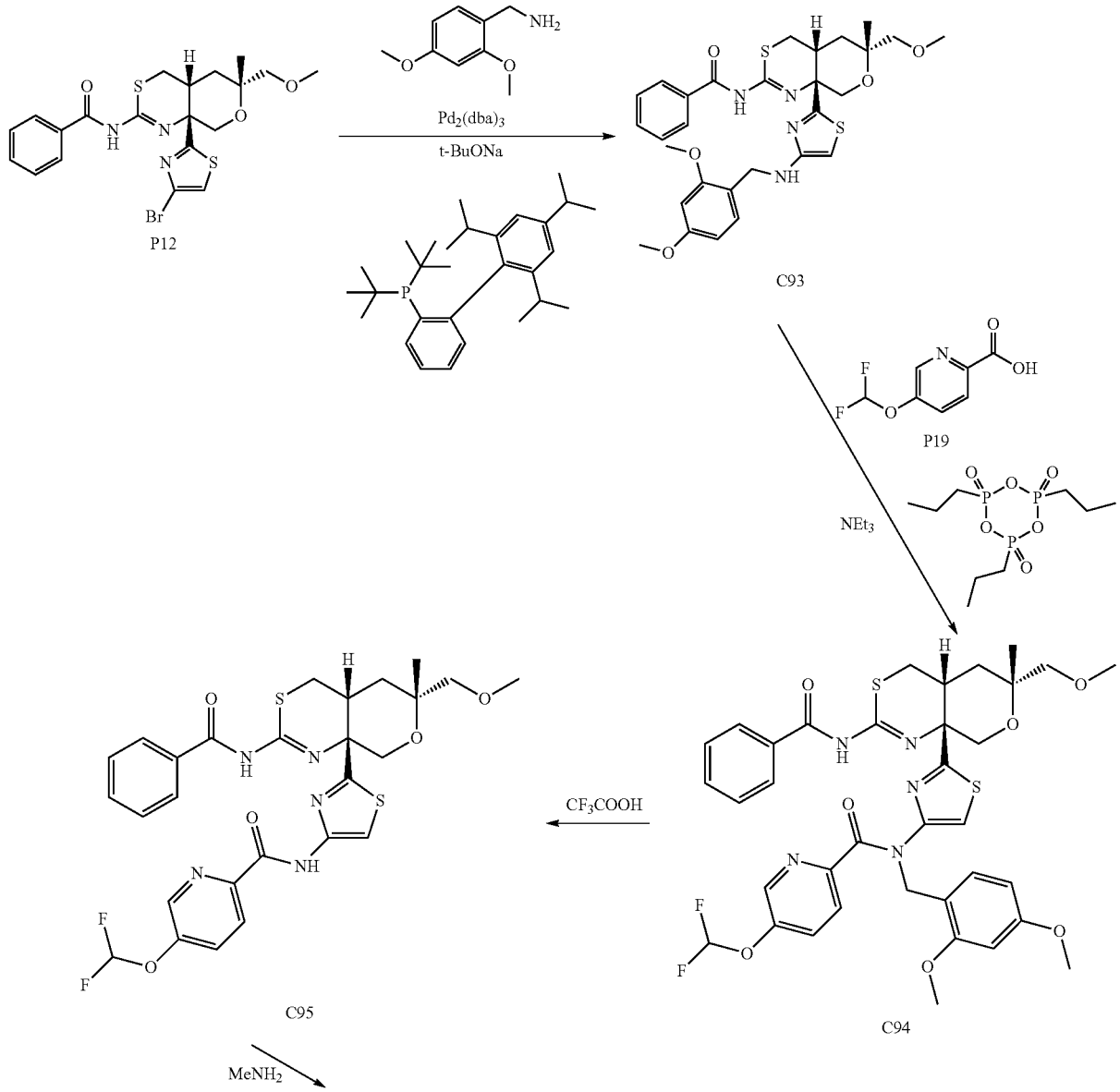

-continued

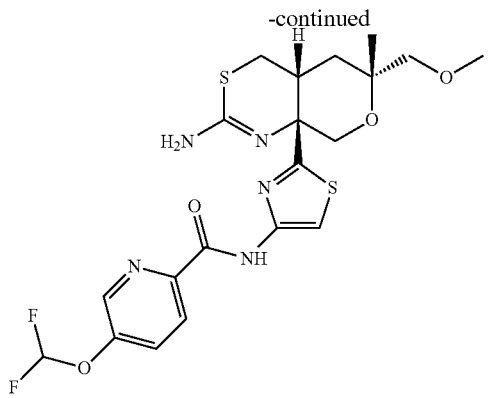

9

Step 1. Synthesis of N-[(4aR,6R,8aR)-8a-{4-[(2,4-dimethoxybenzyl)amino]-1,3-thiazol-2-yl}-6-(methoxymethyl)-6-methyl-4,4a,5,6,8,8a-hexahydro-pyrano[3,4-d][1,3]thiazin-2-yl]benzamide (C93)

A mixture of tris(dibenzylideneacetone)dipalladium(0) (4.7 mg, 5.1 µmol), di-tert-butyl[2',4',6'-tri(propan-2-yl)biphenyl-2-yl]phosphane (95%, 6.7 mg, 15 µmol), and sodium tert-butoxide (22 mg, 0.23 mmol) was purged in three cycles of evacuation followed by argon fill. 1,4-Dioxane (1.0 mL, which had been sparged with argon) was added, and the reaction mixture was stirred at 85° C. for 10 minutes. A solution of P12 (50 mg, 0.10 mmol) and 1-(2,4-dimethoxyphenyl)methanamine (27 µL, 0.18 mmol) in 1,4-dioxane (1.0 mL, which had been sparged with argon) was then added, and heating was continued at 95° C. for 30 minutes. After the reaction mixture had cooled nearly to room temperature, it was poured into saturated aqueous sodium bicarbonate solution (7 mL) and extracted with ethyl acetate (3×7 mL). The combined organic layers were dried over sodium sulfate, filtered, and concentrated in vacuo; silica gel chromatography (Gradient: 10% to 100% ethyl acetate in heptane) provided the product as a light orange-white solid. Yield: 37.8 mg, 64.8 µmol, 65%. $^1$H NMR (400 MHz, CDCl$_3$) δ 8.31-8.07 (br s, 2H), 7.55-7.48 (m, 1H), 7.48-7.41 (m, 2H), 7.21 (d, J=8.2 Hz, 1H), 6.48 (d, half of AB quartet, J=2.3 Hz, 1H), 6.45 (dd, half of ABX pattern, J=8.2, 2.4 Hz, 1H), 5.73 (s, 1H), 4.68 (br t, J=6 Hz, 1H), 4.24-4.15 (m, 3H), 3.85 (s, 3H), 3.81 (s, 3H), 3.73 (d, J=12.5 Hz, 1H), 3.38 (s, 3H), 3.32 (AB quartet, J$_{AB}$=9.4 Hz, Δv$_{AB}$=27.4 Hz, 2H), 3.31-3.24 (m, 1H), 3.24-3.15 (m, 1H), 2.54 (dd, J=12.9, 2.5 Hz, 1H), 2.11-2.00 (m, 1H), 1.51-1.44 (m, 1H), 1.46 (s, 3H).

Step 2. Synthesis of N-{2-[(4aR,6R,8aR)-2-(benzoylamino)-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy)-N-(2,4-dimethoxybenzyl)pyridine-2-carboxamide (C94)

Conversion of C93 to C94 was effected using the method described for synthesis of C87 from P4 in Examples 3, 4 and 5. The product was isolated as a yellow-orange-white solid. Yield: 27 mg, 36 µmol, 57%. LCMS m/z 754.5 [M+H]$^+$. $^1$H NMR (400 MHz, CDCl$_3$), characteristic peaks: δ 7.80 (d, J=8.5 Hz, 1H), 7.57-7.49 (m, 2H), 7.45 (br dd, J=8, 7 Hz, 2H), 6.57 (t, J$_{HF}$=71.9 Hz, 1H), 6.47-6.35 (m, 2H), 5.28-5.03 (m, 2H), 3.78 (s, 3H), 3.70 (s, 3H), 3.63-3.53 (m, 1H), 3.37 (s, 3H), 3.28 (AB quartet, J$_{AB}$=9.4 Hz, Δv$_{AB}$=22.3 Hz, 2H), 2.95-2.73 (m, 2H), 2.43 (dd, J=12.9, 2.4 Hz, 1H), 1.97 (dd, J=13, 13 Hz, 1H), 1.44-1.36 (m, 1H), 1.35 (br s, 3H).

Step 3. Synthesis of N-{2-[(4aR,6R,8aR)-2-(benzoylamino)-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide (C95)

A mixture of C94 (27 mg, 36 µmol), dichloromethane (250 µL), and trifluoroacetic acid (69 µL, 0.90 mmol) was stirred at room temperature for 2.5 hours, whereupon the reaction mixture was concentrated under reduced pressure, diluted with saturated aqueous sodium bicarbonate solution (4 mL), and extracted with ethyl acetate (4×5 mL). The combined organic layers were dried over sodium sulfate, filtered, and concentrated in vacuo, providing a residue (23 mg) that was taken directly to the following step. LCMS m/z 604.5 [M+H]$^+$. $^1$H NMR (400 MHz, CDCl$_3$), characteristic peaks: δ 8.46 (d, J=2.5 Hz, 1H), 8.25 (d, J=8.6 Hz, 1H), 8.03 (br d, J=7.6 Hz, 2H), 7.71 (s, 1H), 7.65 (dd, J=8.7, 2.6 Hz, 1H), 7.56-7.48 (m, 1H), 7.44 (br dd, J=8, 7 Hz, 2H), 6.66 (t, J$_{HF}$=72.0 Hz, 1H), 4.14 (d, J=11.9 Hz, 1H), 3.35 (s, 3H), 3.29 (AB quartet, J$_{AB}$=9.6 Hz, Δv$_{AB}$=18.3 Hz, 2H), 2.05-1.94 (m, 1H), 1.50-1.41 (m, 1H), 1.45 (s, 3H).

Step 4. Synthesis of N-{2-[(4aR,6R,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide (9)

A solution of C95 (from the previous step; 23 mg, ≤36 µmol) and methylamine (33% solution in ethanol; 0.4 mL) in ethanol (0.4 mL) was stirred at room temperature overnight. Removal of solvent in vacuo provided a solid, which was subjected to chromatography on silica gel (Gradient: 20% to 100% ethyl acetate in heptane). The product was isolated as a white solid. Yield: 14 mg, 28 µmol, 78% over 2 steps. LCMS m/z 500.4 [M+H]$^+$. $^1$H NMR (400 MHz, CDCl$_3$) δ 10.40 (br s, 1H), 8.49 (d, J=2.5 Hz, 1H), 8.32 (d, J=8.7 Hz, 1H), 7.71 (s, 1H), 7.68 (dd, J=8.6, 2.6 Hz, 1H), 6.65 (t, J$_{HF}$=72.0 Hz, 1H), 4.11 (d, J=11.5 Hz, 1H), 3.76 (d, J=11.5 Hz, 1H), 3.42 (s, 3H), 3.34 (AB quartet, J$_{AB}$=9.3 Hz, Δv$_{AB}$=18.4 Hz, 2H), 3.22 (dd, J=12.5, 4.1 Hz, 1H), 3.06-2.98 (m, 1H), 2.57 (dd, J=12.5, 2.7 Hz, 1H), 1.98 (dd, J=13.4, 13.3 Hz, 1H), 1.49 (s, 3H), 1.38 (dd, J=13.4, 4.1 Hz, 1H).

Example 10

N-{2-[(4aR,8aR)-2-Amino-6,6-bis(fluoromethyl)-4,4a,5,6-tetrahydropyrano[3,4-d][1,3]thiazin-8a(8H)-yl]-1,3-thiazol-4-yl}-5-(difluoromethoxy)pyridine-2-carboxamide (10)

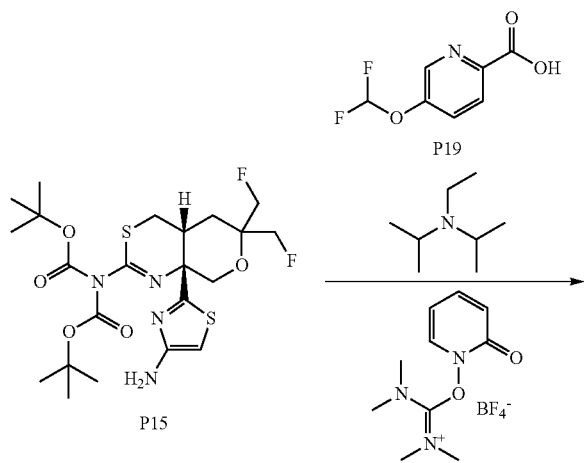

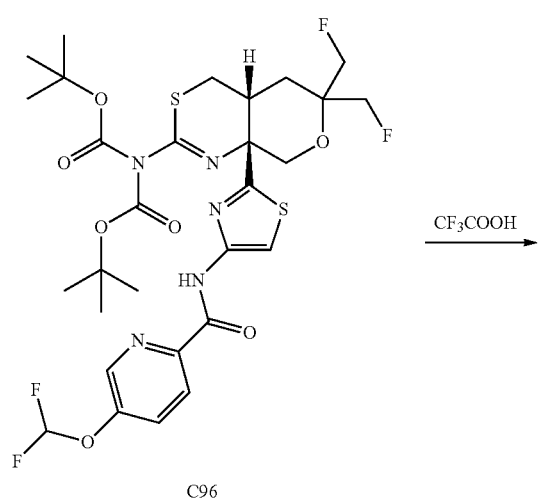

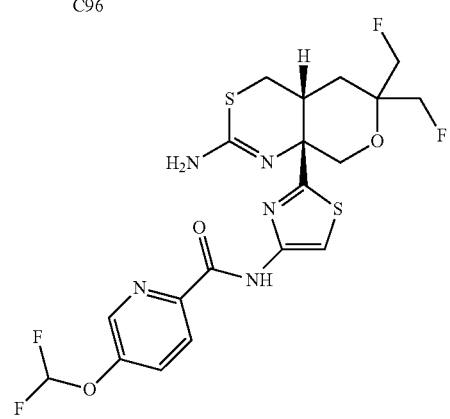

Step 1. Synthesis of di-tert-butyl [(4aR,8aR)-8a-[4-({[5-(difluoromethoxy)pyridin-2-yl]carbonyl}amino)-1,3-thiazol-2-yl]-6,6-bis(fluoromethyl)-4,4a,5,6,8,8a-hexahydropyrano[3,4-d][1,3]thiazin-2-yl]imidodicarbonate (C96)

A mixture of P19 (2.48 mg, 13.1 µmol), N,N-diisopropylethylamine (4.3 µL 25 µmol), and 2-[2-oxo-1(2H)-pyridyl]-1,1,3,3-tetramethyluronium tetrafluoroborate (TPTU; 4.28 mg, 14.4 µmol) in N,N-dimethylformamide (100 µL) was stirred for 20 minutes, whereupon additional TPTU (0.1 equivalent) was added. After another 10 minutes, a solution of P15 (7 mg, 0.01 mmol) in N,N-dimethylformamide (114 µL) was added in one portion to the reaction mixture, and stirring was continued for 24 hours. Aqueous sodium bicarbonate solution and ethyl acetate were then added, and the aqueous layer was extracted twice with ethyl acetate. The combined organic layers were washed with saturated aqueous sodium chloride solution, dried over sodium sulfate, filtered, and concentrated in vacuo; silica gel chromatography was carried out twice (Column #1 gradient: 0% to 100% ethyl acetate in heptane; Column #2 gradient: 0% to 50% ethyl acetate in heptane) to provide the product. Yield: 2 mg, 3 µmol, 30%. $^1$H NMR (400 MHz, CDCl$_3$) δ 10.43 (br s, 1H), 8.50 (d, J=2.4 Hz, 1H), 8.32 (d, J=8.6 Hz, 1H), 7.78 (s, 1H), 7.69 (dd, J=8.6, 2.5 Hz, 1H), 6.66 (t, $J_{HF}$=72.0 Hz, 1H), 4.98-4.72 (m, 2H), 4.55-4.27 (m, 2H), 4.05 (AB quartet, $J_{AB}$=11.7 Hz, $\Delta v_{AB}$=49.3 Hz, 2H), 3.35 (dd, J=13.0, 3.9 Hz, 1H), 3.25-3.15 (m, 1H), 2.70 (dd, J=12.9, 2.7 Hz, 1H), 2.21-2.09 (m, 1H), 1.75-1.67 (m, 1H), 1.55 (s, 18H).

Step 2. Synthesis of N-{2-[(4aR,8aR)-2-amino-6,6-bis(fluoromethyl)-4,4a,5,6-tetrahydropyrano[3,4-d][1,3]thiazin-8a(8H)-yl]-1,3-thiazol-4-yl}-5-(difluoromethoxy) pyridine-2-carboxamide (10)

Trifluoroacetic acid (0.1 mL) was added drop-wise to a 0° C. solution of C96 (2 mg, 3 µmol) in dichloromethane (0.4 mL). The cooling bath was removed, and the reaction mixture was stirred for 1.25 hours, whereupon 10% aqueous sodium bicarbonate solution and dichloromethane were added. The aqueous layer was extracted with dichloromethane (3×25 mL), and the combined organic layers were washed with saturated aqueous sodium chloride solution, dried over sodium sulfate, filtered, and concentrated in vacuo. Silica gel chromatography (Gradient: 0% to 10% methanol in dichloromethane) provided the product. Yield: 0.5 mg, 0.9 µmol, 30%. LCMS m/z 506.3 [M+H]$^+$. $^1$H NMR (400 MHz, CDCl$_3$), characteristic peaks: δ 10.43 (br s, 1H), 8.50 (d, J=2.4 Hz, 1H), 8.32 (br d, J=8.6 Hz, 1H), 7.72-7.66 (m, 1H), 6.67 (t, $J_{HF}$=71.9 Hz, 1H), 4.98-4.71 (m, 2H), 4.52-4.23 (m, 3H), 3.34 (dd, J=13, 4 Hz, 1H), 2.79 (br d, J=13 Hz, 1H).

TABLE 1

*Method of Preparation, Structure, and Physicochemical Properties for Examples 11-41.*

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 11 | Examples 1 and 2[1,2]; P1 | 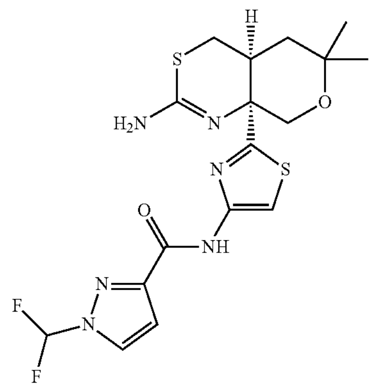 [SMILES: CC1(C)C[C@@H]2CSC(N)=N[C@]2(c2nc(NC(=O)c3ccn(C(F)F)n3)cs2)CO1] | 9.36 (br s, 1H), 7.90 (d, J = 2.5 Hz, 1H), 7.64 (s, 1H), 7.24 (t, J$_{HF}$ = 60.2 Hz, 1H), 7.08 (d, J = 2.4 Hz, 1H), 4.75-4.52 (br s, 2H), 4.07 (d, J = 11.5 Hz, 1H), 3.71 (d, J = 11.5 Hz, 1H), 3.19 (dd, J = 12.6, 3.8 Hz, 1H), 2.98-2.89 (m, 1H), 2.54 (br dd, J = 12.4, 2 Hz, 1H), 1.95 (dd, J = 13.2, 13.2 Hz, 1H), 1.44 (s, 3H), 1.37 (dd, J = 13.6, 3.8 Hz, 1H), 1.32 (s, 3H); 442.9 |
| 12 | Examples 1 and 2[1,2]; P1 | 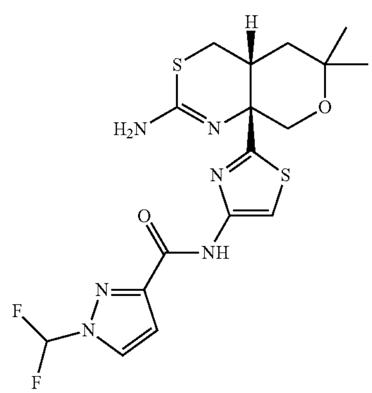 [SMILES: CC1(C)C[C@H]2CSC(N)=N[C@@]2(c2nc(NC(=O)c3ccn(C(F)F)n3)cs2)CO1] | 9.36 (br s, 1H), 7.90 (d, J = 2.5 Hz, 1H), 7.64 (s, 1H), 7.24 (t, J$_{HF}$ = 60.2 Hz, 1H), 7.08 (d, J = 2.6 Hz, 1H), 4.75-4.51 (br s, 2H), 4.07 (d, J = 11.4 Hz, 1H), 3.72 (d, J = 11.4 Hz, 1H), 3.19 (dd, J = 12.4, 4.1 Hz, 1H), 2.99-2.90 (m, 1H), 2.54 (br dd, J = 12.4, 2 Hz, 1H), 1.96 (dd, J = 13.3, 13.2 Hz, 1H), 1.44 (s, 3H), 1.38 (dd, J = 13.3, 3.9 Hz, 1H), 1.32 (s, 3H); 442.9 |
| 13 | Examples 1 and 2[3,4]; P1 | 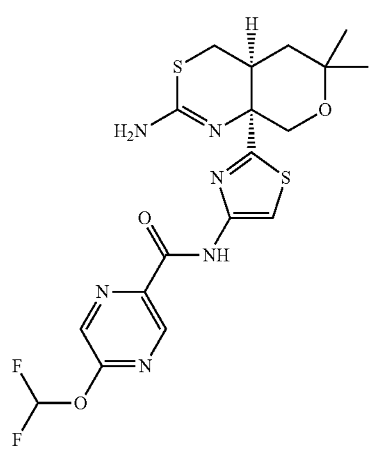 [SMILES: CC1(C)C[C@@H]2CSC(N)=N[C@]2(c2nc(NC(=O)c3cnc(OC(F)F)cn3)cs2)CO1] | 10.11 (s, 1H), 9.08 (s, 1H), 8.37 (s, 1H), 7.72 (s, 1H), 7.52 (t, J$_{HF}$ = 71.5 Hz, 1H), 4.08 (d, J = 11 Hz, 1H), 3.72 (d, J = 11 Hz, 1H), 3.19 (d, J = 11 Hz, 1H), 3.02-2.89 (m, 1H), 2.55 (d, J = 11 Hz, 1H), 1.96 (dd, J = 13, 13 Hz, 1H), 1.45 (s, 3H), 1.43-1.34 (m, 1H), 1.33 (s, 3H); 470.9 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 14 | Examples 1 and 2[3,4]; P1 | 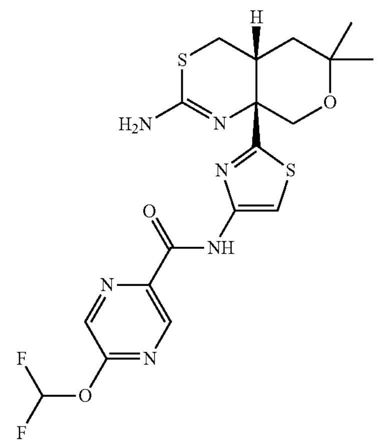 [SMILES: CC1(C)C[C@H]2CSC(N)=N[C@@]2(c2nc(NC(=O)c3cnc(OC(F)F)cn3)cs2)CO1] | 10.11 (s, 1H), 9.07 (s, 1H), 8.37 (s, 1H), 7.71 (s, 1H), 7.52 (t, J$_{HF}$ = 71.4 Hz, 1H), 4.08 (d, J = 11.5 Hz, 1H), 3.72 (d, J = 11.5 Hz, 1H), 3.19 (dd, J = 12.6, 3.9 Hz, 1H), 3.01-2.90 (m, 1H), 2.55 (br d, J = 12.4 Hz, 1H), 1.96 (dd, J = 13.4, 13.3 Hz, 1H), 1.45 (s, 3H), 1.38 (dd, J = 13.4, 3.8 Hz, 1H), 1.32 (s, 3H); 470.9 |
| 15 | Examples 1 and 2[5]; P1, P19 | 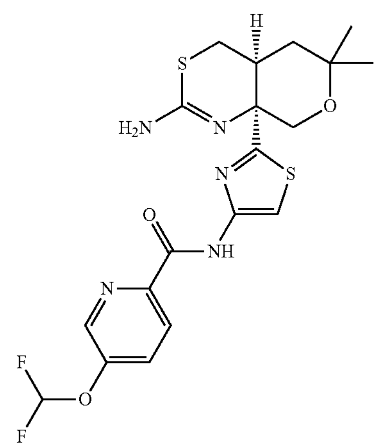 [SMILES: CC1(C)C[C@@H]2CSC(N)=N[C@]2(c2nc(NC(=O)c3ccc(OC(F)F)cn3)cs2)CO1] | 10.40 (br s, 1H), 8.49 (br s, 1H), 8.32 (d, J = 8.8 Hz, 1H), 7.73-7.64 (m, 1H), 7.70 (s, 1H), 6.66 (t, J$_{HF}$ = 71.9 Hz, 1H), 4.90-4.35 (br s, 2H), 4.09 (d, J = 11.5 Hz, 1H), 3.72 (d, J = 11.5 Hz, 1H), 3.20 (dd, J = 12.4, 3.6 Hz, 1H), 3.03-2.92 (m, 1H), 2.54 (br d, J = 12.3 Hz, 1H), 1.96 (dd, J = 13.6, 13.0 Hz, 1H), 1.45 (s, 3H), 1.38 (dd, J = 13, 4 Hz, 1H), 1.32 (s, 3H); 469.9 |
| 16 | Examples 1 and 2[6,7]; P1 | 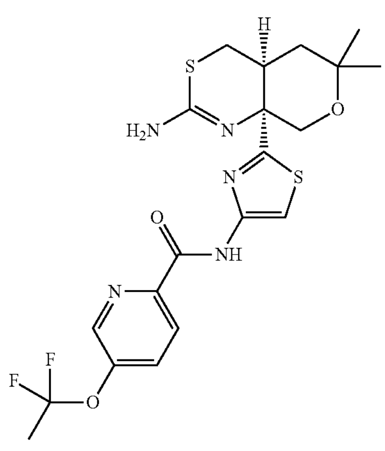 [SMILES: CC(F)(F)Oc1ccc(C(=O)Nc2csc([C@@]34COC(C)(C)C[C@@H]3CSC(N)=N4)n2)nc1] | 10.43 (s, 1H), 8.49 (s, 1H), 8.28 (d, J = 8 Hz, 1H), 7.79-7.64 (m, 2H), 4.85-4.43 (br s, 2H), 4.09 (d, J = 11 Hz, 1H), 3.72 (d, J = 11 Hz, 1H), 3.20 (br d, J = 11 Hz, 1H), 3.04-2.90 (m, 1H), 2.54 (d, J = 12 Hz, 1H), 2.12-1.89 (m, 4H), 1.46 (s, 3H), 1.42-1.33 (m, 1H), 1.32 (s, 3H); 483.9 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 17 | Examples 1 and 2[6,7]; P1 | 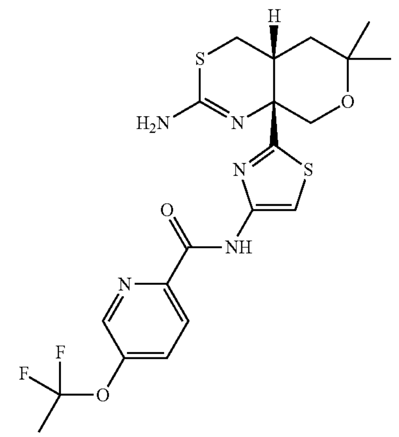 [SMILES: CC(F)(F)Oc1ccc(C(=O)Nc2csc([C@]34COC(C)(C)C[C@H]3CSC(N)=N4)n2)nc1] | 10.43 (s, 1H), 8.49 (s, 1H), 8.28 (d, J = 8.5 Hz, 1H), 7.78-7.66 (m, 2H), 5.0-4.3 (br s, 2H), 4.09 (d, J = 11 Hz, 1H), 3.72 (d, J = 11 Hz, 1H), 3.20 (br d, J = 12 Hz, 1H), 3.03-2.92 (m, 1H), 2.54 (d, J = 12 Hz, 1H), 2.09-1.89 (m, 4H), 1.45 (s, 3H), 1.42-1.34 (m, 1H), 1.32 (s, 3H); 483.9 |
| 18 | Examples 1 and 2[1,8,9]; P1 | 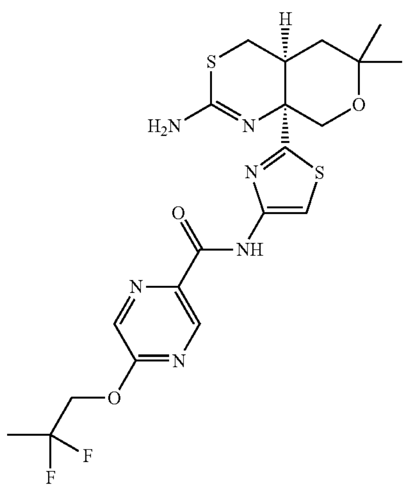 [SMILES: CC(F)(F)COc1cnc(C(=O)Nc2csc([C@@]34COC(C)(C)C[C@@H]3CSC(N)=N4)n2)cn1] | 10.12 (s, 1H), 9.02 (s, 1H), 8.30 (s, 1H), 7.70 (s, 1H), 4.80-4.42 (br s, 2H), 4.62 (t, J$_{HF}$ = 11.9 Hz, 2H), 4.09 (d, J = 11.8 Hz, 1H), 3.73 (d, J = 11.8 Hz, 1H), 3.20 (br d, J = 12 Hz, 1H), 3.01-2.92 (m, 1H), 2.55 (br d, J = 12 Hz, 1H), 1.96 (dd, J = 13, 13 Hz, 1H), 1.79 (t, J$_{HF}$ = 18.7 Hz, 3H), 1.45 (s, 3H), 1.38 (br d, J = 13 Hz, 1H), 1.33 (s, 3H); 499.0 |
| 19 | Examples 1 and 2[1,8,9]; P1 | 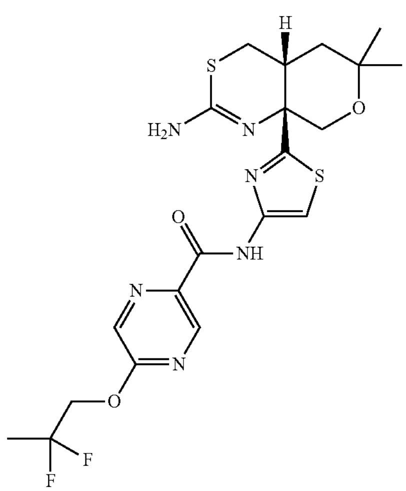 [SMILES: CC(F)(F)COc1cnc(C(=O)Nc2csc([C@]34COC(C)(C)C[C@H]3CSC(N)=N4)n2)cn1] | 10.12 (s, 1H), 9.01 (s, 1H), 8.30 (s, 1H), 7.70 (s, 1H), 4.8-4.5 (br s, 2H), 4.62 (t, J$_{HF}$ = 11.9 Hz, 2H), 4.08 (d, J = 11.3 Hz, 1H), 3.73 (d, J = 11.5 Hz, 1H), 3.20 (dd, J = 12, 3 Hz, 1H), 3.02-2.92 (m, 1H), 2.55 (br d, J = 12 Hz, 1H), 1.96 (dd, J = 13, 13 Hz, 1H), 1.79 (t, J$_{HF}$ = 18.6 Hz, 3H), 1.45 (s, 3H), 1.38 (dd, J = 13, 3 Hz, 1H), 1.33 (s, 3H); 499.0 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 20 | Examples 1 and 2[1,10,11]; P1 | 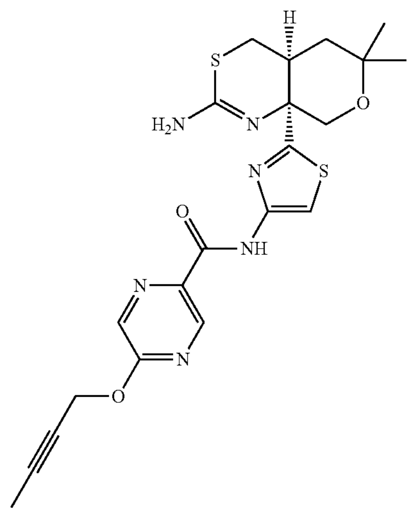 [SMILES: CC#CCOc1cnc(C(=O)Nc2csc([C@@]34COC(C)(C)C[C@@H]3CSC(N)=N4)n2)cn1] | 10.12 (s, 1H), 9.03 (s, 1H), 8.23 (s, 1H), 7.70 (s, 1H), 5.08-5.04 (m, 2H), 4.09 (d, J = 11.4 Hz, 1H), 3.73 (d, J = 11.4 Hz, 1H), 3.20 (dd, J = 12, 4 Hz, 1H), 3.00-2.92 (m, 1H), 2.54 (br d, J = 12 Hz, 1H), 1.96 (dd, J = 13, 13 Hz, 1H), 1.92-1.88 (m, 3H), 1.45 (s, 3H), 1.38 (dd, J = 13, 3.5 Hz, 1H), 1.33 (s, 3H); 472.9 |
| 21 | Examples 1 and 2[1,10,11]; P1 | 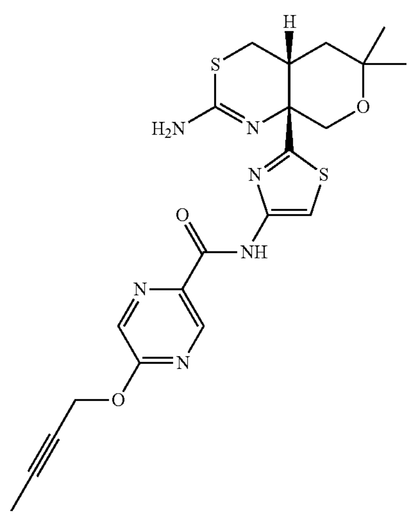 [SMILES: CC#CCOc1cnc(C(=O)Nc2csc([C@]34COC(C)(C)C[C@H]3CSC(N)=N4)n2)cn1] | 10.12 (s, 1H), 9.02 (s, 1H), 8.23 (s, 1H), 7.69 (s, 1H), 5.06 (s, 2H), 4.08 (d, J = 12 Hz, 1H), 3.76 (br d, J = 12 Hz, 1H), 3.20 (dd, J = 12, 4 Hz, 1H), 3.03-2.93 (m, 1H), 2.55 (br d, J = 13 Hz, 1H), 1.96 (dd, J = 13, 13 Hz, 1H), 1.90 (br s, 3H), 1.45 (s, 3H), 1.42-1.35 (m, 1H), 1.33 (s, 3H); 472.9 |
| 22 | Examples 1 and 2[1,12]; P1, P22 | 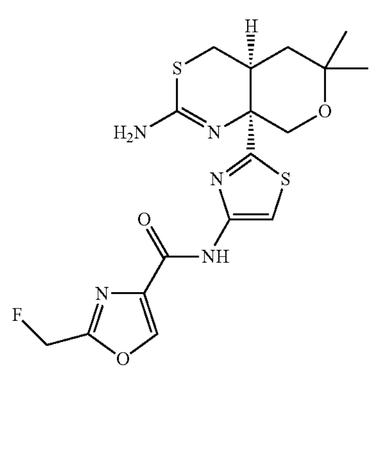 [SMILES: CC1(C)C[C@@H]2CSC(N)=N[C@]2(c2nc(NC(=O)c3coc(CF)n3)cs2)CO1] | 9.39 (br s, 1H), 8.37 (d, J = 1.3 Hz, 1H), 7.63 (s, 1H), 5.45 (d, J$_{HF}$ = 47.1 Hz, 2H), 4.77-4.55 (br s, 2H), 4.06 (d, J = 11.6 Hz, 1H), 3.70 (d, J = 11.5 Hz, 1H), 3.18 (dd, J = 12.5, 4.1 Hz, 1H), 2.98-2.90 (m, 1H), 2.54 (dd, J = 12.5, 2.6 Hz, 1H), 1.95 (dd, J = 13.4, 13.4 Hz, 1H), 1.44 (s, 3H), 1.38 (dd, J = 13.4, 4.0 Hz, 1H), 1.32 (s, 3H); 425.9 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 23 | Examples 1 and 2[1,12]; P1, P22 | 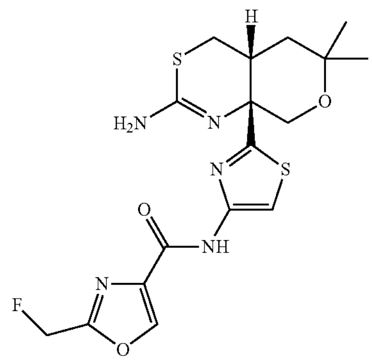 [SMILES: CC1(C)C[C@H]2CSC(N)=N[C@@]2(c2nc(NC(=O)c3coc(CF)n3)cs2)CO1] | 9.39 (br s, 1H), 8.37 (d, J = 1.4 Hz, 1H), 7.63 (s, 1H), 5.45 (d, J$_{HF}$ = 47.2 Hz, 2H), 4.78-4.59 (br s, 2H), 4.06 (d, J = 11.6 Hz, 1H), 3.70 (d, J = 11.5 Hz, 1H), 3.17 (dd, J = 12.5, 4.1 Hz, 1H), 2.97-2.89 (m, 1H), 2.54 (dd, J = 12.6, 2.8 Hz, 1H), 1.95 (dd, J = 13.4, 13.2 Hz, 1H), 1.44 (s, 3H), 1.37 (dd, J = 13.3, 4.1 Hz, 1H), 1.32 (s, 3H); 425.9 |
| 24 | Example 7; P3, P20 | 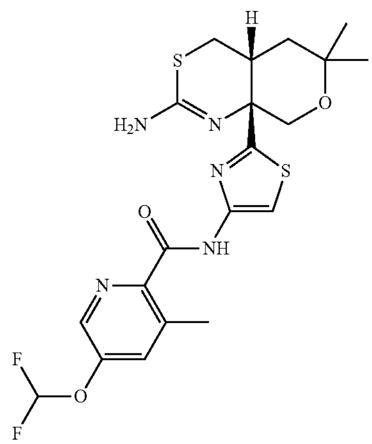 [SMILES: Cc1cc(OC(F)F)cnc1C(=O)Nc1csc([C@]23COC(C)(C)C[C@H]2CSC(N)=N3)n1] | 10.57 (br s, 1H), 8.35 (br d, J = 2.6 Hz, 1H), 7.67 (s, 1H), 7.43-7.41 (m, 1H), 6.63 (t, J$_{HF}$ = 72.2 Hz, 1H), 4.58-4.50 (br s, 2H), 4.10 (d, J = 11.5 Hz, 1H), 3.72 (d, J = 11.5 Hz, 1H), 3.21 (dd, J = 12.5, 4.1 Hz, 1H), 3.02-2.94 (m, 1H), 2.84 (s, 3H), 2.54 (dd, J = 12.5, 2.6 Hz, 1H), 1.96 (dd, J = 13.3, 13.3 Hz, 1H), 1.46 (s, 3H), 1.38 (dd, J = 13.4, 4.0 Hz, 1H), 1.33 (s, 3H); 484.3 |
| 25 | Examples 1 and 2[13]; P1, P20 | 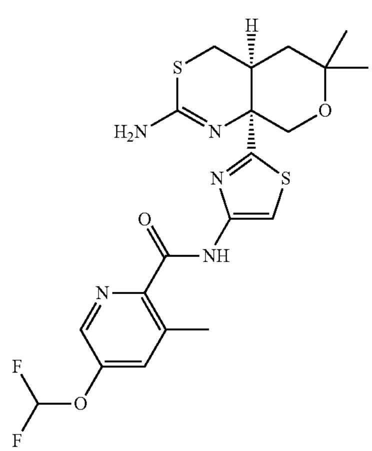 [SMILES: Cc1cc(OC(F)F)cnc1C(=O)Nc1csc([C@@]23COC(C)(C)C[C@@H]2CSC(N)=N3)n1] | 10.58 (br s, 1H), 8.37-8.33 (m, 1H), 7.67 (s, 1H), 7.45-7.40 (m, 1H), 6.64 (t, J$_{HF}$ = 72.1 Hz, 1H), 4.87-4.40 (v br s, 2H), 4.10 (d, J = 11.5 Hz, 1H), 3.73 (d, J = 11.5 Hz, 1H), 3.21 (dd, J = 12.4, 4.0 Hz, 1H), 3.02-2.94 (m, 1H), 2.84 (s, 3H), 2.58-2.51 (m, 1H), 1.96 (dd, J = 13.3, 13.2 Hz, 1H), 1.46 (s, 3H), 1.38 (dd, J = 13.5, 4 Hz, 1H), 1.33 (s, 3H); 484.0 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 26 | Example 8; P7, P19 | 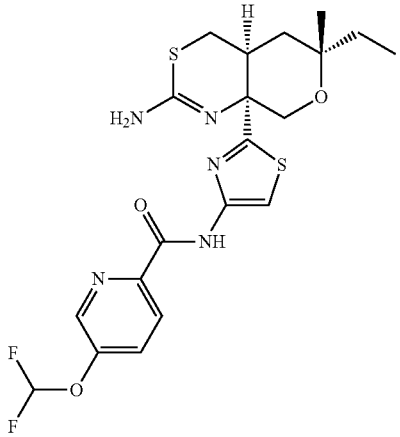 [SMILES: CC[C@@]1(C)C[C@@H]2CSC(N)=N[C@]2(c2nc(NC(=O)c3ccc(OC(F)F)cn3)cs2)CO1] | 10.39 (br s, 1H), 8.49 (d, J = 2.7 Hz, 1H), 8.32 (d, J = 8.6 Hz, 1H), 7.70 (s, 1H), 7.68 (br dd, J = 8.6, 2.7 Hz, 1H), 6.66 (t, J$_{HF}$ = 72.0 Hz, 1H), 4.91-4.42 (br s, 2H), 3.98 (d, J = 11.5 Hz, 1H), 3.67 (d, J = 11.5 Hz, 1H), 3.19 (dd, J = 12.5, 4.1 Hz, 1H), 3.00-2.92 (m, 1H), 2.53 (dd, J = 12.5, 2.7 Hz, 1H), 2.19-2.07 (m, 1H), 1.93 (dd, J = 13.4, 13.4 Hz, 1H), 1.66-1.55 (m, 1H), 1.44 (dd, J = 13.6, 4.1 Hz, 1H), 1.23 (s, 3H), 0.95 (t, J = 7.4 Hz, 3H); 484.4 |
| 27 | Example 8; P8, P19 | 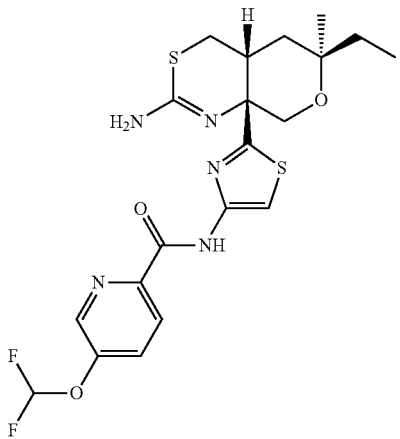 [SMILES: CC[C@]1(C)C[C@H]2CSC(N)=N[C@@]2(c2nc(NC(=O)c3ccc(OC(F)F)cn3)cs2)CO1] | 10.40 (br s, 1H), 8.49 (br d, J = 2.6 Hz, 1H), 8.32 (d, J = 8.6 Hz, 1H), 7.70 (s, 1H), 7.68 (br dd, J = 8.6, 2.7 Hz, 1H), 6.66 (t, J$_{HF}$ = 72.0 Hz, 1H), 4.85-4.50 (br s, 2H), 3.98 (d, J = 11.5 Hz, 1H), 3.67 (d, J = 11.5 Hz, 1H), 3.19 (dd, J = 12.5, 4.1 Hz, 1H), 3.00-2.92 (m, 1H), 2.53 (dd, J = 12.5, 2.7 Hz, 1H), 2.19-2.07 (m, 1H), 1.93 (dd, J = 13.4, 13.4 Hz, 1H), 1.66-1.55 (m, 1H), 1.44 (dd, J = 13.6, 4.1 Hz, 1H), 1.23 (s, 3H), 0.95 (t, J = 7.4 Hz, 3H); 484.2 |
| 28 | Example 8; P9, P19 | 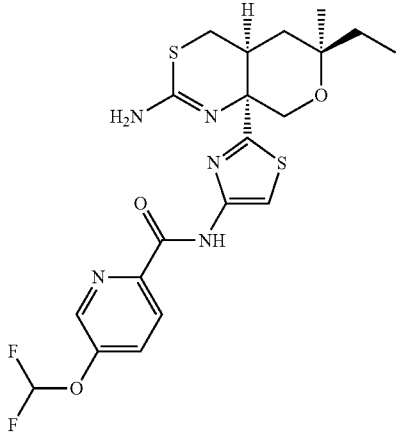 [SMILES: CC[C@]1(C)C[C@@H]2CSC(N)=N[C@]2(c2nc(NC(=O)c3ccc(OC(F)F)cn3)cs2)CO1] | Somewhat impure; characteristic product peaks: 10.41 (br s, 1H), 8.50 (d, J = 2.8 Hz, 1H), 8.32 (d, J = 8.7 Hz, 1H), 7.76 (s, 1H), 6.66 (t, J$_{HF}$ = 72.0 Hz, 1H), 4.10 (d, J = 12.1 Hz, 1H), 3.88 (br d, J = 12 Hz, 1H), 3.26 (dd, J = 12.4, 4.2 Hz, 1H), 2.62 (dd, J = 12.6, 2.6 Hz, 1H), 1.90 (dd, J = 13, 13 Hz, 1H), 1.67-1.56 (m, 2H), 1.40 (s, 3H), 1.39 (dd, J = 13, 4 Hz, 1H), 0.96 (t, J = 7.6 Hz, 3H); 484.4 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 29 | Example 8; P11, P19 | 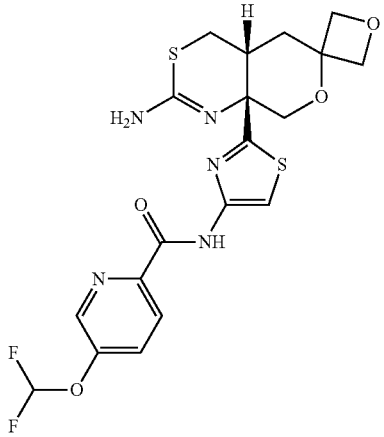 [SMILES: NC1=N[C@@]2(c3nc(NC(=O)c4ccc(OC(F)F)cn4)cs3)COC3(COC3)C[C@H]2CS1] | 10.38 (br s, 1H), 8.48 (dd, J = 2.7, 0.5 Hz, 1H), 8.32 (dd, J = 8.6, 0.6 Hz, 1H), 7.72 (s, 1H), 7.68 (br dd, J = 8.6, 2.7 Hz, 1H), 6.66 (t, J$_{HF}$ = 71.9 Hz, 1H), 4.87 (br d, J = 6.2 Hz, 1H), 4.73 (d, J = 6.6 Hz, 1H), 4.68 (d, J = 6.4 Hz, 1H), 4.44 (d, J = 6.6 Hz, 1H), 3.84 (AB quartet, J$_{AB}$ = 11.5 Hz, Δv$_{AB}$ = 20.6 Hz, 2H), 3.21 (dd, J = 12.6, 4.1 Hz, 1H), 2.86-2.79 (m, 1H), 2.65 (dd, J = 12.7, 2.7 Hz, 1H), 2.25-2.16 (m, 1H), 2.10 (dd, half of ABX pattern, J = 13.6, 4.3 Hz, 1H); 484.2 |
| 30 | Examples 1 and 2; P2, P21 | 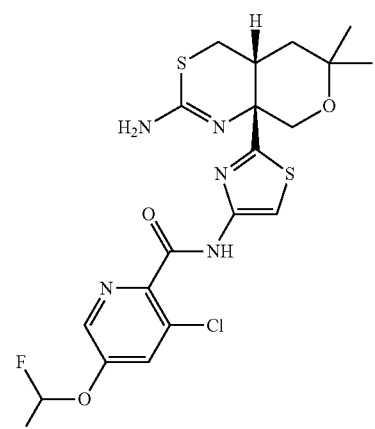 | 10.35 (br s, 1H), 8.44 (d, J = 2.4 Hz, 1H), 7.73 (s, 1H), 7.70 (d, J = 2.4 Hz, 1H), 6.67 (t, J$_{HF}$ = 71.3 Hz, 1H), 4.09 (d, J = 11.5 Hz, 1H), 3.73 (d, J = 11.4 Hz, 1H), 3.20 (dd, J = 12.5, 4.1 Hz, 1H), 3.00-2.92 (m, 1H), 2.54 (dd, J = 12.6, 2.6 Hz, 1H), 1.96 (dd, J = 13.4, 13.3 Hz, 1H), 1.45 (s, 3H), 1.38 (dd, J = 13.4, 4.0 Hz, 1H), 1.32 (s, 3H); 504.1 (chlorine isotope pattern observed) |
| 31 | Examples 1 and 2; P2 | 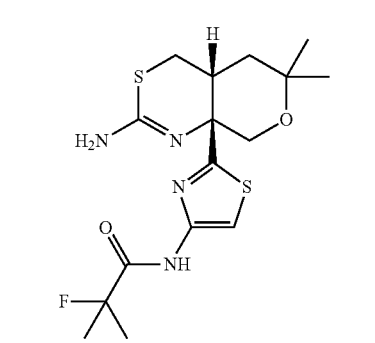 [SMILES: CC1(C)C[C@H]2CSC(N)=N[C@@]2(c2nc(NC(=O)C(C)(C)F)cs2)CO1] | 8.85 (br s, 1H), 7.54 (s, 1H), 4.90-4.43 (br s, 2H), 4.04 (d, J = 11 Hz, 1H), 3.69 (d, J = 11 Hz, 1H), 3.17 (d, J = 11 Hz, 1H), 2.99-2.83 (m, 1H), 2.53 (d, J = 12 Hz, 1H), 1.94 (dd, J = 12.5, 12.5 Hz, 1H), 1.67 (d, J$_{HF}$ = 22.1 Hz, 6H), 1.43 (s, 3H), 1.4-1.3 (m, 1H), 1.31 (s, 3H); 387.0 |
| 32 | Examples 1 and 2; P2 | 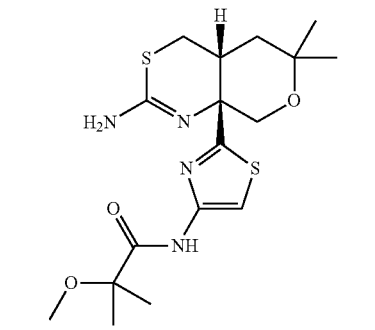 | 9.18 (br s, 1H), 7.54 (s, 1H), 4.06 (d, J = 11.5 Hz, 1H), 3.70 (d, J = 11.8 Hz, 1H), 3.38 (s, 3H), 3.18 (dd, J = 12.4, 4.1 Hz, 1H), 2.97-2.89 (m, 1H), 2.53 (dd, J = 12.4, 2.4 Hz, 1H), 1.95 (dd, J = 13.3, 13.3 Hz, 1H), 1.48 (s, 6H), 1.44 (s, 3H), 1.37 (dd, J = 13.2, 3.9 Hz, 1H), 1.32 (s, 3H); 399.0 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 33 | Examples 1 and 2; P2 | 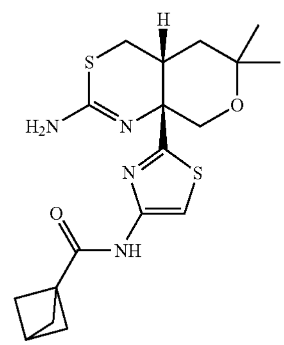 [SMILES: CC1(C)C[C@H]2CSC(N)=N[C@@]2(c2nc(NC(=O)C34CC(C3)C4)cs2)CO1] | 7.99 (br s, 1H), 7.53 (s, 1H), 4.03 (d, J = 11.8 Hz, 1H), 3.72 (d, J = 11.8 Hz, 1H), 3.16 (dd, J = 12, 4 Hz, 1H), 2.95-2.86 (m, 1H), 2.57-2.51 (m, 1H), 2.55 (s, 1H), 2.17 (s, 6H), 1.94 (dd, J = 13, 13 Hz, 1H), 1.43 (s, 3H), 1.37 (dd, J = 13, 4 Hz, 1H), 1.32 (s, 3H); 393.0 |
| 34 | Example 9; P13, P19 | 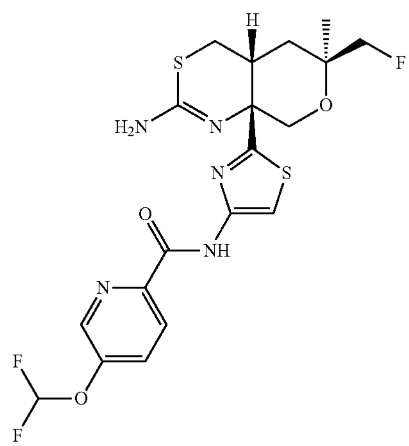 [SMILES: C[C@@]1(CF)C[C@H]2CSC(N)=N[C@@]2(c2nc(NC(=O)c3ccc(OC(F)F)cn3)cs2)CO1] | 10.39 (br s, 1H), 8.49 (d, J = 2.2 Hz, 1H), 8.31 (d, J = 8.6 Hz, 1H), 7.71 (s, 1H), 7.68 (dd, J = 8.6, 2.2 Hz, 1H), 6.66 (t, J$_{HF}$ = 72.0 Hz, 1H), 4.96-4.38 (v br s, 2H), 4.68 (d of AB quartets, J$_{HF}$ = 47 Hz, J$_{AB}$ = 9.6 Hz, Δv$_{AB}$ = 10 Hz, 2H), 4.14 (d, J = 11.9 Hz, 1H), 3.77 (d, J = 11.5 Hz, 1H), 3.20 (dd, J = 12.6, 4.0 Hz, 1H), 3.05-2.96 (m, 1H), 2.58 (dd, J = 12.6, 2.2 Hz, 1H), 1.98 (ddd, J = 13.7, 13.7, 3.1 Hz, 1H), 1.66 (dd, J = 14, 4 Hz, 1H), 1.32 (br s, 3H); 488.3 |
| 35 | Alternate synthesis of Example 8$^{14}$; P14, P19 | 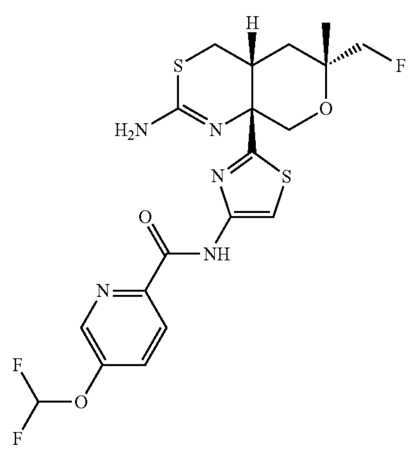 [SMILES: C[C@]1(CF)C[C@H]2CSC(N)=N[C@@]2(c2nc(NC(=O)c3ccc(OC(F)F)cn3)cs2)CO1] | 10.40 (br s, 1H), 8.49 (br s, 1H), 8.32 (d, J = 8.5 Hz, 1H), 7.72 (s, 1H), 7.68 (br d, J = 8.6 Hz, 1H), 6.66 (t, J$_{HF}$ = 71.9 Hz, 1H), 4.9-4.4 (v br s, 2H), 4.27 (d of AB quartets, J$_{HF}$ = 47.5 Hz, J$_{AB}$ = 9 Hz, Δv$_{AB}$ = 10.5 Hz, 2H), 4.11 (d, J = 11.6 Hz, 1H), 3.78 (d, J = 11.4 Hz, 1H), 3.23 (dd, J = 12.6, 3.9 Hz, 1H), 3.08-2.99 (m, 1H), 2.58 (br d, J = 12.6 Hz, 1H), 2.03 (dd, J = 13, 13 Hz, 1H), 1.51 (br s, 3H), 1.42-1.34 (m, 1H); 488.3 |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 36 | Alternate synthesis of Example 8; P16, P20 | 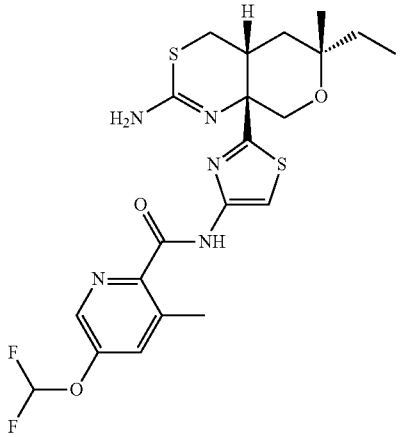 [SMILES: CC[C@@]1(C)C[C@H]2CSC(N)=N[C@@]2(c2nc(NC(=O)c3ncc(OC(F)F)cc3C)cs2)CO1] | 10.57 (br s, 1H), 8.36-8.33 (m, 1H), 7.67 (s, 1H), 7.43-7.40 (m, 1H), 6.63 (t, $J_{HF}$ = 72.2 Hz, 1H), 4.80-4.35 (v br s, 2H), 4.08 (d, J = 11.5 Hz, 1H), 3.72 (d, J = 11.5 Hz, 1H), 3.22 (dd, J = 12.2, 4.0 Hz, 1H), 3.03-2.95 (m, 1H), 2.84 (s, 3H), 2.55 (dd, J = 12.5, 2.5 Hz, 1H), 1.90 (dd, J = 13.3, 13.3 Hz, 1H), 1.68-1.51 (m, 2H), 1.39 (s, 3H), 1.33 (dd, J = 13.3, 4.1 Hz, 1H), 0.95 (t, J = 7.4 Hz, 3H); 498.4 |
| 37 | Alternate synthesis of Example 8; P16 | 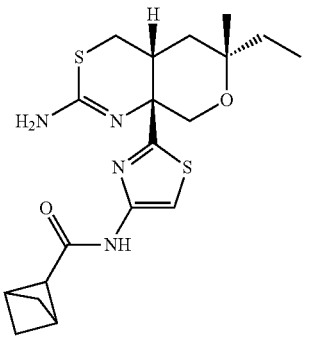 [SMILES: CC[C@@]1(C)C[C@H]2CSC(N)=N[C@@]2(c2nc(NC(=O)C3C4CC3C4)cs2)CO1] | 7.96 (br s, 1H), 7.52 (s, 1H), 4.80-4.27 (v br s, 2H), 4.02 (d, J = 11.5 Hz, 1H), 3.68 (d, J = 11.4 Hz, 1H), 3.17 (dd, J = 12.4, 4.1 Hz, 1H), 2.94-2.86 (m, 1H), 2.55 (s, 1H), 2.53 (dd, J = 12.4, 2.6 Hz, 1H), 2.18 (s, 6H), 1.89 (dd, J = 13.3, 13.3 Hz, 1H), 1.67-1.50 (m, 2H), 1.37 (s, 3H), 1.32 (dd, J = 13.3, 4.2 Hz, 1H), 0.94 (t, J = 7.5 Hz, 3H); 407.4 |
| 38 | Examples 3, 4, and 5[15]; P17, P19 | 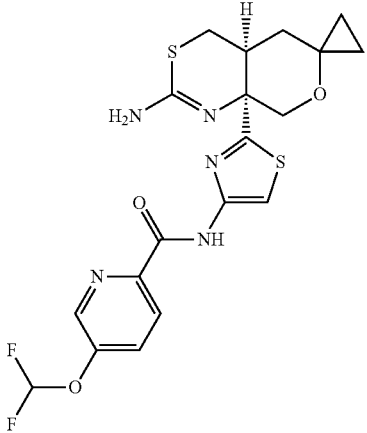 [SMILES: NC1=N[C@]2(c3nc(NC(=O)c4ccc(OC(F)F)cn4)cs3)COC3(CC3)C[C@@H]2CS1] | 10.42 (br s, 1H), 8.48 (br d, J = 2.7 Hz, 1H), 8.32 (br d, J = 8.6 Hz, 1H), 7.73 (s, 1H), 7.68 (dd, J = 8.6, 2.6 Hz, 1H), 6.66 (t, $J_{HF}$ = 72.0 Hz, 1H), 4.63-4.49 (br s, 2H), 3.90 (AB quartet, $J_{AB}$ = 10.8 Hz, $\Delta v_{AB}$ = 50.6 Hz, 2H), 3.21 (dd, J = 12.6, 4.0 Hz, 1H), 3.05-2.97 (m, 1H), 2.72-2.63 (m, 1H), 2.61 (dd, J = 12.6, 2.7 Hz, 1H), 1.04-0.95 (m, 2H), 0.88-0.81 (m, 1H), 0.66-0.58 (m, 1H), 0.56-0.49 (m, 1H); 468.3[16] |

TABLE 1-continued

Method of Preparation, Structure, and Physicochemical Properties for Examples 11-41.

| Example Number | Method of Preparation; Non-commercial starting materials | Structure | $^1$H NMR (400 MHz, CHCl$_3$) δ; Mass spectrum, observed ion m/z [M + H]$^+$ (unless otherwise indicated) |
|---|---|---|---|
| 39 | Examples 3, 4, and 5[15]; P17, P19 | 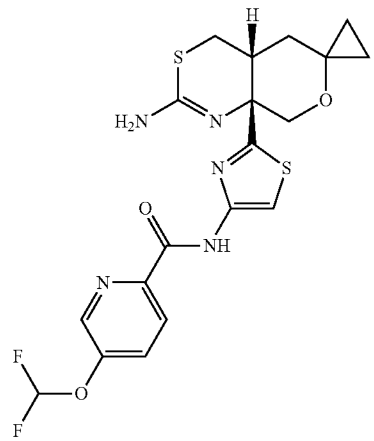 [SMILES: NC1=N[C@@]2(c3nc(NC(=O)c4ccc(OC(F)F)cn4)cs3)COC3(CC3)C[C@H]2CS1] | 10.42 (br s, 1H), 8.48 (br d, J = 2.5 Hz, 1H), 8.32 (br d, J = 8.6 Hz, 1H), 7.73 (s, 1H), 7.68 (br dd, J = 8.6, 2.7 Hz, 1H), 6.66 (t, J$_{HF}$ = 71.9 Hz, 1H), 4.66-4.50 (br s, 2H), 3.90 (AB quartet, J$_{AB}$ = 10.7 Hz, Δν$_{AB}$ = 50.6 Hz, 2H), 3.21 (dd, J = 12.6, 4.1 Hz, 1H), 3.04-2.97 (m, 1H), 2.72-2.63 (m, 1H), 2.60 (dd, J = 12.6, 2.8 Hz, 1H), 1.04-0.95 (m, 2H), 0.89-0.80 (m, 1H), 0.66-0.57 (m, 1H), 0.56-0.49 (m, 1H); 468.3[16] |
| 40 | Example 9; P18, P19 | 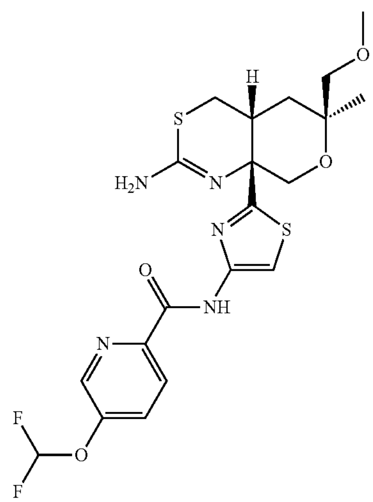 [SMILES: COC[C@]1(C)C[C@H]2CSC(N)=N[C@@]2(c2nc(NC(=O)c3ccc(OC(F)F)cn3)cs2)CO1] | 10.40 (br s, 1H), 8.50 (br d, J = 2.3 Hz, 1H), 8.33 (br d, J = 8.6 Hz, 1H), 7.71 (s, 1H), 7.68 (br dd, J = 8.6, 2.6 Hz, 1H), 6.66 (t, J$_{HF}$ = 71.9 Hz, 1H), 4.77-4.45 (br s, 2H), 4.11 (d, J = 11.6 Hz, 1H), 3.75 (d, J = 11.6 Hz, 1H), 3.68 (s, 2H), 3.49 (s, 3H), 3.19 (dd, J = 12.5, 4.1 Hz, 1H), 3.01-2.93 (m, 1H), 2.57 (dd, J = 12.6, 2.6 Hz, 1H), 1.89 (dd, J = 13.6, 13.6 Hz, 1H), 1.62 (dd, J = 13.8, 4.2 Hz, 1H), 1.31 (s, 3H); 500.4 |
| 41 | Example 6; P5 | 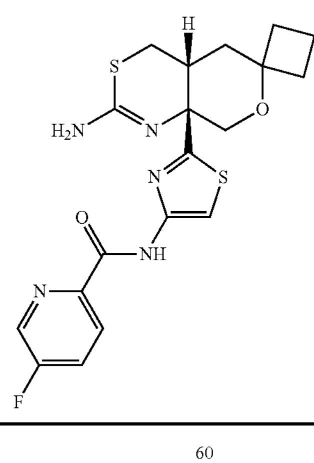 | 10.37 (br s, 1H), 8.49 (d, J = 2.7 Hz, 1H), 8.33 (dd, J = 8.7, 4.6 Hz, 1H), 7.71 (s, 1H), 7.61 (ddd, J = 8.6, 8.1, 2.8 Hz, 1H), 4.76-4.35 (br s, 2H), 3.80 (AB quartet, upfield doublet is broadened, J$_{AB}$ = 11.3 Hz, Δν$_{AB}$ = 57.1 Hz, 2H), 3.21 (dd, J = 12.6, 4.1 Hz, 1H), 2.90-2.81 (m, 1H), 2.59 (dd, J = 12.6, 2.7 Hz, 1H), 2.32-2.14 (m, 3H), 2.05-1.95 (m, 2H), 1.92-1.81 (m, 1H), 1.74 (dd, J = 13.3, 4.0 Hz, 1H), 1.74-1.63 (m, 1H); 434.3 |

1. In this case, the final deprotection was carried out using hydrazine monohydrate, rather than methoxylamine hydrochloride.

2. Examples 11 and 12 were isolated from the corresponding racemic material via supercritical fluid chromatography [Column: Chiral Technologies Chiralpak AD, 10 µm; Mobile phase: 7:3 carbon dioxide/(ethanol containing 0.1% ammonium hydroxide)]. The individual enantiomers were then purified using reversed phase HPLC (Column: Phenomenex Gemini C18, 10 µm; Mobile phase A: aqueous ammonia, pH 10; Mobile phase B: acetonitrile; Gradient: 26% to 46% B). The first-eluting enantiomer from the supercritical fluid chromatography was Example 11; the later-eluting enantiomer was Example 12. The absolute configuration of the more potent enantiomer (see Table 2), for this and all subsequent separated pairs of enantiomers, was assigned in analogy with the work reported by C. R. Butler et al., *J. Med. Chem.* 2015, 58, 2678-2702, and M. A. Brodney, *J. Med. Chem.* 2015, 58, 3223-3252.

3. The requisite 5-(difluoromethoxy)pyrazine-2-carboxylic acid was synthesized from methyl 5-hydroxypyrazine-2-carboxylate using the general procedure described for conversion of C71 to P20 in Preparation P20.

4. Examples 13 and 14 were isolated from the corresponding racemic material via supercritical fluid chromatography [Column: Chiral Technologies Chiralpak AD, 10 µm; Mobile phase: 65:35 carbon dioxide/(methanol containing 0.1% ammonium hydroxide)]. The first-eluting enantiomer from the supercritical fluid chromatography was Example 13; the later-eluting enantiomer was Example 14.

5. Example 15 was isolated from the corresponding racemic material via supercritical fluid chromatography [Column: Chiral Technologies Chiralpak AD, 10 µm; Mobile phase: 65:35 carbon dioxide/(methanol containing 0.1% ammonium hydroxide)]. Example 15 was the first-eluting enantiomer; the second-eluting enantiomer was identical to Example 7.

6. Potassium hydroxide-mediated reaction of 5-hydroxypyridine-2-carbonitrile with 2-bromo-1,1-difluoroethene provided 5-(2-bromo-1,1-difluoroethoxy)pyridine-2-carbonitrile, which was subjected to the action of hydrogen chloride in methanol to afford methyl 5-(2-bromo-1,1-difluoroethoxy)pyridine-2-carboxylate. Reductive removal of the bromide was effected via hydrogenation over palladium on carbon; subsequent ester hydrolysis with lithium hydroxide provided the requisite 5-(1,1-difluoroethoxy)pyridine-2-carboxylic acid.

7. Examples 16 and 17 were isolated from the corresponding racemic material via supercritical fluid chromatography [Column: Chiral Technologies Chiralpak AD, 10 µm; Mobile phase: 65:35 carbon dioxide/(methanol containing 0.1% ammonium hydroxide)]. The first-eluting enantiomer was Example 16; the later-eluting enantiomer was Example 17.

8. Methyl 5-chloropyrazine-2-carboxylate was reacted with cesium carbonate and 2,2-difluoropropan-1-ol to provide methyl 5-(2,2-difluoropropoxy)pyrazine-2-carboxylate; ester hydrolysis was effected with lithium hydroxide to afford the requisite 5-(2,2-difluoropropoxy)pyrazine-2-carboxylic acid.

9. Examples 18 and 19 were isolated from the corresponding racemic material via supercritical fluid chromatography [Column: Chiral Technologies Chiralpak AD, 10 µm; Mobile phase: 7:3 carbon dioxide/(ethanol containing 0.1% ammonium hydroxide)]. The first-eluting enantiomer was Example 18; the later-eluting enantiomer was Example 19.

10. Reaction of methyl 5-chloropyrazine-2-carboxylate with but-2-yn-1-ol and potassium tert-butoxide, followed by ester hydrolysis with lithium hydroxide, afforded the requisite 5-(but-2-yn-1-yloxy)pyrazine-2-carboxylic acid.

11. Examples 20 and 21 were isolated from the corresponding racemic material via supercritical fluid chromatography [Column: Chiral Technologies Chiralpak AD, 10 µm; Mobile phase: 7:3 carbon dioxide/(ethanol containing 0.1% ammonium hydroxide)]. The first-eluting enantiomer was Example 20; the later-eluting enantiomer was Example 21.

12. Examples 22 and 23 were isolated from the corresponding racemic material via supercritical fluid chromatography [Column: Chiral Technologies Chiralpak AD, 10 µm; Mobile phase: 7:3 carbon dioxide/(ethanol containing 0.1% ammonium hydroxide)]. The individual enantiomers were then purified using reversed phase HPLC (Column: Phenomenex Gemini C18, 10 µm; Mobile phase A: aqueous ammonia, pH 10; Mobile phase B: acetonitrile; Gradient: 22% to 42% B). The first-eluting enantiomer from the supercritical fluid chromatography was Example 22; the later-eluting enantiomer was Example 23.

13. Example 25 was isolated from the corresponding racemic material via supercritical fluid chromatography [Column: Chiral Technologies Chiralpak AD, 5 µm; Mobile phase: 7:3 carbon dioxide/(ethanol containing 0.1% ammonium hydroxide)]. Example 25 was the first-eluting enantiomer; the second-eluting enantiomer was identical to Example 24.

14. Conversion of P14 to the requisite di-tert-butyl [(4aR,6R,8aR)-8a-(4-amino-1,3-thiazol-2-yl)-6-(fluoromethyl)-6-methyl-4,4a,5,6,8,8a-hexahydropyrano[3,4-d][1,3]thiazin-2-yl]imidodicarbonate was effected using the method described for synthesis of P15 from C52 in Preparation P15.

15. Examples 38 and 39 were isolated from the corresponding racemic material via supercritical fluid chromatography [Column: Chiral Technologies Chiralpak AS-H, 5 µm; Mobile phase: 85:15 carbon dioxide/(methanol containing 0.2% ammonium hydroxide)]. Each enantiomer was then individually purified via silica gel chromatography (Gradient: 0% to 10% methanol in dichloromethane). The first-eluting enantiomer from the supercritical fluid chromatography was Example 38; the later-eluting enantiomer was Example 39.

16. This LCMS data comes from the crude product of the final reaction; the major component exhibited m/z 468.3 $[M+H]^+$.

Biological Assays

BACE1 Cell-Free Assay: Beta-secretase (BACE) is one of the enzymes involved in the generation of the amyloid beta peptide found in the amyloid plaques of Alzheimer's disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a ½ log dose response curve from a top concentration of 100 µM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 µL assay buffer [100 mM sodium acetate, pH 4.5 (brought to pH with acetic acid), and 0.001% Tween-20]. Plates are covered and incubated for 3 hours at 37° C. The reaction is stopped with the addition of 30 µL of 1.5 µM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

TABLE 2

Biological activity and IUPAC name for Examples 1-41

| Example Number | BACE1 Cell-free Assay IC$_{50}$ (µM)[a] | IUPAC Name |
|---|---|---|
| 1 | 31.0 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(but-2-yn-1-yloxy)pyridine-2-carboxamide |
| 2 | 0.088[b] | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(but-2-yn-1-yloxy)pyridine-2-carboxamide |
| 3 | 0.252 | N-{2-[cis-2'-amino-4a',5'-dihydro-4'H-spiro[cyclobutane-1,6'-pyrano[3,4-d][1,3] thiazin]-8a'(8'H)-yl]-1,3-thiazol-4-yl}-5-(difluoromethoxy)pyridine-2-carboxamide |
| 4 | >21.1 | N-{2-[(4a'S,8a'S)-2'-amino-4a',5'-dihydro-4'H-spiro[cyclobutane-1,6'-pyrano[3,4-d] [1,3]thiazin]-8a'(8'H)-yl]-1,3-thiazol-4-yl}-5-(difluoromethoxy)pyridine-2-carboxamide |
| 5 | 0.138[b] | N-{2-[(4a'R,8a'R)-2'-amino-4a',5'-dihydro-4'H-spiro[cyclobutane-1,6'-pyrano[3,4-d] [1,3]thiazin]-8a'(8'H)-yl]-1,3-thiazol-4-yl}-5-(difluoromethoxy)pyridine-2-carboxamide |
| 6 | 0.088 | N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-chloropyridine-2-carboxamide |
| 7 | 0.116[b] | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(difluoromethoxy)pyridine-2-carboxamide |
| 8 | 0.041 | N-{2-[(4aR,6S,8aR)-2-amino-6-ethyl-6-methyl-4,4a,5,6-tetrahydropyrano[3,4-d] [1,3]thiazin-8a(8H)-yl]-1,3-thiazol-4-yl}-5-(difluoromethoxy)pyridine-2-carboxamide |
| 9 | 0.105 | N-{2-[(4aR,6R,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide |
| 10 | 0.565 | N-{2-[(4aR,8aR)-2-amino-6,6-bis(fluoromethyl)-4,4a,5,6-tetrahydro pyrano[3,4-d][1,3]thiazin-8a(8H)-yl]-1,3-thiazol-4-yl}-5-(difluoromethoxy)pyridine-2-carboxamide |
| 11 | 6.96 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-1-(difluoromethyl)-1H-pyrazole-3-carboxamide |
| 12 | 0.022 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-1-(difluoromethyl)-1H-pyrazole-3-carboxamide |
| 13 | 7.95 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(difluoromethoxy)pyrazine-2-carboxamide |
| 14 | 0.167 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(difluoromethoxy)pyrazine-2-carboxamide |
| 15 | 22.2 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(difluoromethoxy)pyridine-2-carboxamide |
| 16 | 28.5 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(1,1-difluoroethoxy)pyridine-2-carboxamide |
| 17 | 0.416 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(1,1-difluoroethoxy)pyridine-2-carboxamide |
| 18 | 61.7 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(2,2-difluoropropoxy)pyrazine-2-carboxamide |
| 19 | 0.421 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(2,2-difluoropropoxy)pyrazine-2-carboxamide |

TABLE 2-continued

Biological activity and IUPAC name for Examples 1-41

| Example Number | BACE1 Cell-free Assay IC$_{50}$ (μM)[a] | IUPAC Name |
|---|---|---|
| 20 | 15.5 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(but-2-yn-1-yloxy)pyrazine-2-carboxamide |
| 21 | 0.041 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(but-2-yn-1-yloxy)pyrazine-2-carboxamide |
| 22 | 15.1 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-2-(fluoromethyl)-1,3-oxazole-4-carboxamide |
| 23 | 0.017 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-2-(fluoromethyl)-1,3-oxazole-4-carboxamide |
| 24 | 0.047[b] | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-5-(difluoromethoxy)-3-methylpyridine-2-carboxamide |
| 25 | 14.8 | N-{2-[(4aS,8aS)-2-amino-6,6-dimethyl-4,4a,5,6-tetrahydropyrano[3,4-d][1,3] thiazin-8a(8H)-yl]-1,3-thiazol-4-yl}-5-(difluoromethoxy)-3-methylpyridine-2-carboxamide |
| 26 | 0.406 | N-{2-[(4aS,6S,8aS)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide |
| 27 | 1.83 | N-{2-[(4aR,6R,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide |
| 28 | 14.8 | N-{2-[(4aS,6R,8aS)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide |
| 29 | 0.675 | N-{2-[(4a'R,8a'R)-2'-amino-4a',5'-dihydro-4'H-spiro[oxetane-3,6'-pyrano[3,4-d][1,3] thiazin]-8a'(8'H)-yl]-1,3-thiazol-4-yl}-5-(difluoromethoxy)pyridine-2-carboxamide |
| 30 | 0.059 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-3-chloro-5-(difluoromethoxy)pyridine-2-carboxamide |
| 31 | 0.911 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-2-fluoro-2-methylpropanamide |
| 32 | 1.69 | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}-2-methoxy-2-methylpropanamide |
| 33 | 0.734[c] | N-{2-[(4aR,8aR)-2-amino-6,6-dimethyl-4,4a,5,6-tetrahydropyrano[3,4-d][1,3] thiazin-8a(8H)-yl]-1,3-thiazol-4-yl}bicyclo[1.1.1]pentane-1-carboxamide |
| 34 | 0.194 | N-{2-[(4aR,6S,8aR)-2-amino-6-(fluoromethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide |
| 35 | 0.176 | N-{2-[(4aR,6R,8aR)-2-amino-6-(fluoromethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide |
| 36 | 0.060 | N-{2-[(4aR,6S,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide |
| 37 | 0.177 | N-{2-[(4aR,6S,8aR)-2-amino-6-ethyl-6-methyl-4,4a,5,6-tetrahydropyrano[3,4-d][1,3]thiazin-8a(8H)-yl]-1,3-thiazol-4-yl}bicyclo[1.1.1]pentane-2-carboxamide |
| 38 | 34.5 | N-{2-[(4a'S,8a'S)-2'-amino-4a',5'-dihydro-4'H-spiro[cyclopropane-1,6'-pyrano[3,4-d][1,3]thiazin]-8a'(8'H)-yl]-1,3-thiazol-4-yl}-5-(difluoromethoxy)pyrazine-2-carboxamide |
| 39 | 0.314 | N-{2-[(4a'R,8a'R)-2'-amino-4a',5'-dihydro-4'H-spiro[cyclopropane-1,6'-pyrano[3,4-d] [1,3]thiazin]-8a'(8'H)-yl]-1,3-thiazol-4-yl}-5-(difluoromethoxy)pyridine-2-carboxamide |
| 40 | 2.08 | N-{2-[(4aR,6S,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide |
| 41 | 0.714 | N-{2-[(4a'R,8a'R)-2'-amino-4a',5'-dihydro-4'H-spiro[cyclobutane-1,6'-pyrano[3,4-d] [1,3]thiazin]-8a'(8'H)-yl]-1,3-thiazol-4-yl}-5-fluoropyridine-2-carboxamide |

[a]Reported IC$_{50}$ values are the geometric mean of 2-4 determinations, unless otherwise indicated.
[b]The reported IC$_{50}$ value is the geometric mean of ≥5 determinations.
[c]The IC$_{50}$ value is from a single determination.

We claim:
1. A compound of Formula I

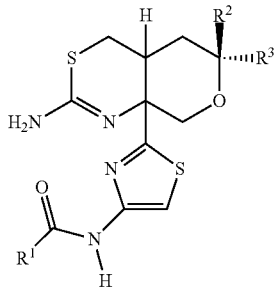

wherein
R¹ is selected from the group consisting of:
C$_{1-6}$alkyl optionally substituted with one to three fluoro or C$_{1-3}$alkoxy;
C$_{5-9}$bicycloalkyl optionally substituted with one to three R⁴; and
a 5- to 6-membered heteroaryl, having one to four heteroatoms independently selected from N, O or S, wherein at least one of the heteroatoms is N and wherein said N is optionally substituted with R⁵; and wherein said 5- to 6-membered heteroaryl is optionally substituted on carbon with one to three R⁴;
R² and R³ are each independently selected from C$_{1-6}$alkyl or C$_{3-7}$cycloalkyl; wherein the C$_{1-6}$alkyl is optionally substituted with one to three fluoro or C$_{1-3}$alkoxy; or R² and R³ taken together with the carbon to which they are attached form a C$_{3-6}$cycloalkyl ring or a 4- to 6-membered heterocycloalkyl ring, each of which is optionally and independently substituted with one to three fluoro, C$_{1-3}$alkyl or C$_{1-3}$alkoxy;
R⁴ at each occurrence is independently selected from the group consisting of halogen, hydroxy, cyano, C$_{1-6}$alkyl, C$_{1-6}$alkoxy, C$_{3-6}$alkenyl, C$_{3-6}$alkenyloxy, C$_{3-6}$alkynyl, C$_{3-6}$alkynyloxy, C$_{1-6}$alkoxy-C$_{1-6}$alkyl, C$_{3-6}$cycloalkoxy, C$_{3-6}$cycloalkyl, C$_{3-6}$cycloalkyl-C$_{1-6}$alkyl, C$_{3-6}$cycloalkyl-C$_{1-6}$alkoxy, 4- to 6-membered heterocycloalkyl and 4- to 6-membered heterocycloalkyl-C$_{1-6}$alkyl; wherein said C$_{1-6}$alkyl, C$_{1-6}$alkoxy, C$_{3-6}$alkenyl, C$_{3-6}$alkenyloxy, C$_{3-6}$alkynyl, C$_{3-6}$alkynyloxy, C$_{1-6}$alkoxy-C$_{1-6}$alkyl, C$_{3-6}$ cycloalkoxy, C$_{3-6}$cycloalkyl, C$_{3-6}$cycloalkyl-C$_{1-6}$alkyl, C$_{3-6}$cycloalkyl-C$_{1-6}$alkoxy, 4- to 6-membered heterocycloalkyl and 4- to 6-membered heterocycloalkyl-C$_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; and
R⁵ is hydrogen, C$_{1-6}$alkyl, C$_{3-6}$alkenyl, C$_{3-6}$alkynyl, C$_{1-6}$alkoxy-C$_{1-6}$alkyl, C$_{3-6}$cycloalkyl, C$_{3-6}$cycloalkyl-C$_{1-6}$alkyl, 4- to 6-membered heterocycloalkyl and 4- to 6 membered heterocycloalkyl-C$_{1-6}$alkyl; wherein said C$_{1-6}$alkyl, C$_{3-6}$alkenyl, C$_{3-6}$alkynyl, C$_{1-6}$alkoxy-C$_{1-6}$alkyl, C$_{3-6}$cycloalkyl, C$_{3-6}$cycloalkyl-C$_{1-6}$alkyl, 4- to 6-membered heterocycloalkyl and 4-to 6-membered heterocycloalkyl-C$_{1-6}$alkyl are each optionally substituted with one to three substituents independently selected from fluoro, chloro, hydroxy, cyano, methyl, fluoromethyl, difluoromethyl, trifluoromethyl, methoxy, fluoromethoxy, difluoromethoxy and trifluoromethoxy; or R⁴ and R⁵ taken together can be a C$_{3-5}$alkylene;
or a tautomer thereof or a pharmaceutically acceptable salt of said compound or tautomer.

2. The compound of claim 1 of Formula 1a

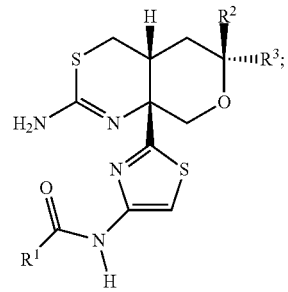

or a tautomer thereof or a pharmaceutically acceptable salt of said compound or tautomer.

3. The compound of claim 1 of Formula 1b

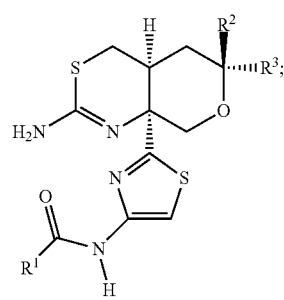

or a tautomer thereof or a pharmaceutically acceptable salt of said compound or tautomer.

4. The compound of claim 1 wherein R¹ is a 5-membered heteroaryl selected from the group consisting of pyrazolyl and oxazolyl; each optionally substituted on carbon with one to two R⁴; and wherein said pyrazolyl is substituted on N with R⁵;
R⁴ at each occurrence is independently selected from the group consisting of halogen, C$_{1-3}$alkyl, C$_{3-6}$cycloalkyl, and C$_{1-3}$alkoxy-C$_{1-3}$alkyl; wherein said C$_{1-3}$alkyl is optionally substituted with one to three fluoro; and
R⁵ is C$_{1-3}$alkyl or C$_{3-6}$cycloalkyl, wherein said C$_{1-3}$alkyl is optionally substituted with one to three fluoro;
or a tautomer thereof or a pharmaceutically acceptable salt of said compound or tautomer.

5. The compound of claim 4 wherein R¹ is selected from the group consisting of

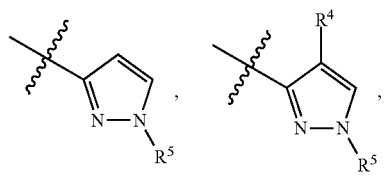

-continued

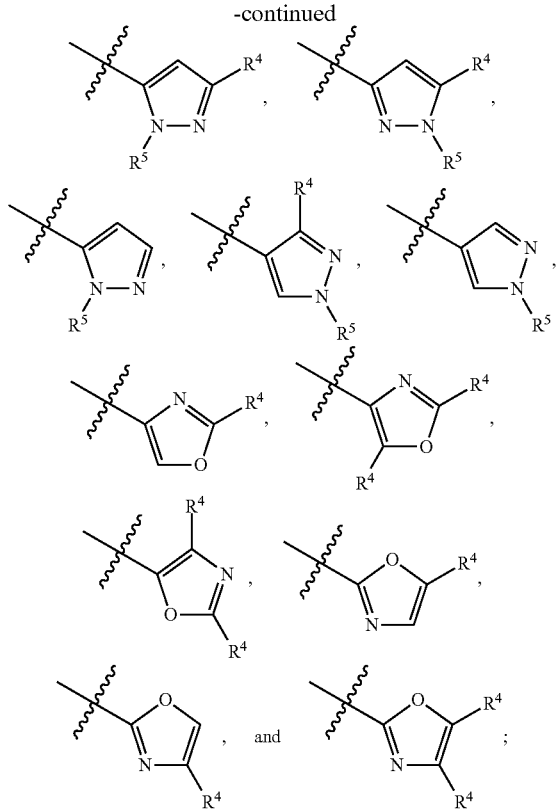

R⁴ at each occurrence is independently selected from the group consisting of chloro, methyl, ethyl, isopropyl, isobutyl, fluoromethyl, difluoromethyl, trifluoromethyl, cyclopropyl, cyclobutyl and methoxymethyl; and R⁵ is methyl, ethyl, isopropyl, difluoromethyl, cyclopropyl or cyclobutyl;

or a tautomer thereof or a pharmaceutically acceptable salt of said compound or tautomer.

6. The compound according to claim 5 wherein $R^1$ is selected from the group consisting of

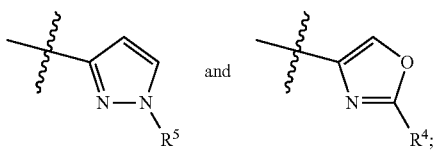

$R^2$ and $R^3$ are each methyl;
$R^4$ is fluoromethyl; and
$R^5$ is difluoromethyl;
or a tautomer thereof or a pharmaceutically acceptable salt of said compound or tautomer.

7. The compound according to claim 1 wherein $R^1$ is a 6-membered heteroaryl selected from the group consisting of pyridinyl and pyrazinyl; each optionally substituted on carbon with one to two $R^4$; and $R^4$ at each occurrence is independently selected from the group consisting of halogen, $C_{1-6}$alkyl, $C_{1-6}$alkoxy and $C_{3-6}$alkynyloxy; wherein said $C_{1-6}$alkyl and $C_{1-6}$alkoxy are optionally substituted with one to three fluoro;
or a tautomer thereof or a pharmaceutically acceptable salt of said compound or tautomer.

8. The compound according to claim 7 wherein $R^1$ is selected from the group consisting of

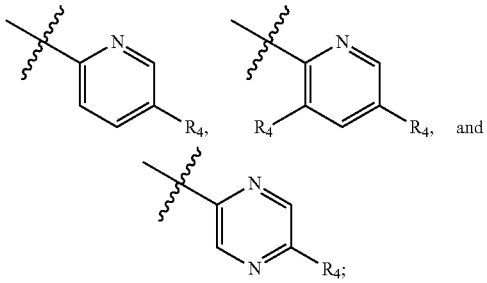

and
$R^4$ at each occurrence is independently selected from the group consisting of fluoro, chloro, methyl, fluoromethyl, difluoromethyl, trifluoromethyl, methoxy, fluoromethoxy, difluoromethoxy, 1,1-difluoroethoxy, trifluoromethoxy, difluoropropoxy and butynyloxy;
or a tautomer thereof or pharmaceutically acceptable salt of said compound or tautomer.

9. The compound according to claim 8 wherein $R^1$ is

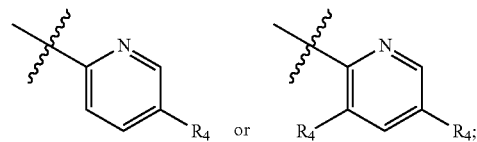

and
$R^4$ at each occurrence is independently selected from the group consisting of chloro, fluoro, methyl, but-2-ynyloxy, difluoromethoxy and 1,1-difluoroethoxy;
or a tautomer thereof or a pharmaceutically acceptable salt of said compound or tautomer.

10. The compound according to claim 9 wherein $R^2$ and $R^3$ are each independently selected from the group consisting of methyl, fluoromethyl, methoxymethyl, ethyl and cyclopropyl;
or a tautomer thereof or a pharmaceutically acceptable salt of said compound or tautomer.

11. The compound according to claim 9 wherein $R^2$ and $R^3$ taken together with the carbon to which they are attached form a cyclopropyl, cyclobutyl or oxetanyl ring;
or a tautomer thereof or a pharmaceutically acceptable salt of said compound or tautomer.

12. The compound according to claim 8 wherein $R^1$ is

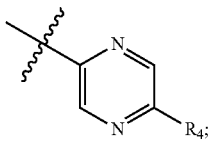

and
$R^4$ is selected from the group consisting of difluoromethoxy, 2,2-difluoropropoxy and but-2-ynyloxy;

or a tautomer thereof or a pharmaceutically acceptable salt of said compound or tautomer.

13. The compound according to claim 12 wherein
R$^2$ and R$^3$ are each methyl;
or a tautomer thereof or a pharmaceutically acceptable salt of said compound or tautomer.

14. The compound according to claim 2 wherein
R$^1$ is C$_{1-6}$alkyl optionally substituted with one to three fluoro or C$_{1-3}$alkoxy;
or a tautomer thereof or a pharmaceutically acceptable salt of said compound or tautomer.

15. The compound according to claim 14 wherein
R$^1$ is 2-fluoropropan-2-yl or 2-methoxypropan-2-yl; and
R$^2$ and R$^3$ are each methyl;
or a tautomer thereof or a pharmaceutically acceptable salt of said compound or tautomer.

16. The compound according to claim 1 selected from the group consisting of:
N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyridine-2-carboxamide;
N-{2-[(4aR,8aR)-2-amino-6,6-dimethyl-4,4a,5,6-tetrahydropyrano[3,4-][1,3]thiazin-8a(8H)-yl]-1,3-thiazol-4-yl}-5-(but-2-yn-1-yloxy)pyridine-2-carboxamide;
N-{2-[cis-2'-amino-4a', 5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide;
N-{2-[(4a'S,8a'S)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide;
N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide;
N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-chloropyridine-2-carboxamide;
N-{2-[(4aR,8aR)-2-amino-6,6-dimethyl-4,4a,5,6-tetrahydropyrano[3,4-][1,3]thiazin-8a(8H)-yl]-1,3-thiazol-4-yl}-5-(difluoromethoxy)pyridine-2-carboxamide;
N-{2-[(4aR,6S,8aR)-2-amino-6-ethyl-6-methyl-4,4a,5,6-tetrahydropyrano[3,4-d ][1,3]thiazin-8a(8H)-yl]-1,3-thiazol-4-yl}-5-(difluoromethoxy)pyridine-2-carboxamide;
N-{2-[(4aR,6R,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide;
N-{2-[(4aR,8aR)-2-amino-6,6-bis(fluoromethyl)-4,4a,5,6-tetrahydropyrano[3,4-d][1,3]thiazin-8a(8H)-yl]-1,3-thiazol-4-yl}-5-(difluoromethoxy)pyridine-2-carboxamide;
N-{2-[(4aS,8aS)-2-amino-6,6-dimethyl-4,4a, 5,6-tetrahydropyrano[3,4-d][1,3]thiazin-8a(8H)-yl]-1,3-thiazol-4-yl}-1-(difluoromethyl)-1H-pyrazole-3-carboxamide;
N-{2-[(4aR,8aR)-2-amino-6,6-dimethyl-4,4a,5,6-tetrahydropyrano[3,4-d][1,3]thiazin-8a(8H)-yl]-1,3-(difluoromethyl)-1H-pyrazole-3-carboxamide;
N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyrazine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyrazine-2-carboxamide;
N-{2-[(4aS,8aS)-2-amino-6,6-dimethyl-4,4a, 5,6-tetrahydropyrano[3,4d][1,3]thiazin-8a(8H)-yl]-1,3-thiazol-4-yl}-5-(difluoromethoxy)pyridine-2-carboxamide;
N-{2-[(4aS,8aS)-2-amino-6,6-dimethyl-4,4a, 5,6-tetrahydropyrano[3,4-d][1,3]thiazin-8a(8H)-yl]-1,3-thiazol-4-yl}-5-(1,1-difluoroethoxy)pyridine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(1,1-difluoroethoxy)pyridine-2-carboxamide;
N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(2,2-difluoropropoxy)pyrazine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(2,2-difluoropropoxy)pyrazine-2-carboxamide;
N-{2-[(4aS,8aS)-2-amino-6,6-dimethyl-4,4a,5,6-tetrahydropyrano[3,4-d ][1,3]thiazin-8a(8H)-yl]-1,3-thiazol-4-yl}-5-(but-2-yn-1-yloxy)pyrazine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(but-2-yn-1-yloxy)pyrazine-2-carboxamide;
N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-2-(fluoromethyl)-1,3-oxazole-4-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;
N-{2-[(4aS,8aS)-2-amino-6,6-dimethyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;
N-{2-[(4aS,6S,8aS)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide;
N-{2-[(4aR,6R,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide;
N-{2-[(4aS,6R,8aS)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide;
N-{2-[(4a'R,8a'R)-2'-amino-4a',5'-dihydro-4'H-spiro[oxetane-3,6'-pyrano[3,4-d][1,3]thiazin]-8a'(8'H)-yl]-1,3-thiazol-4-yl}-5-(difluoromethoxy)pyridine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-3-chloro-5-(difluoromethoxy)pyridine-2-carboxamide;
N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-2-fluoro-2-methylpropanamide;
N-{2-[(4aR,8aR)-2-amino-6,6-dimethyl-4,4a,5,6-tetrahydropyrano[3,4-d ][1,3]thiazin-8a(8H)-yl]-1,3-thiazol-4-yl}-2-methoxy-2-methylpropanamide;
N-{2-[(4aR,6S,8aR)-2-amino-6-(fluoromethyl)-6-methyl-4,4a,5,6-tetrahydropyrano [3,4-d][1,3]thiazin-8a(8H)-yl]-1,3-thiazol-4-yl}-5-(difluoromethoxy) pyridine-2-carboxamide;

N-{2-[(4aR,6R,8aR)-2-amino-6-(fluoromethyl)-6-methyl-4,4a,5,6-tetrahydropyrano [3,4-d][1,3]thiazin-8a(8H)-yl]-1,3-thiazol-4-yl}-5-(difluoromethoxy) pyridine-2-carboxamide;

N-{2-[(4aR,6S,8aR)-2-amino-6-ethyl-6-methyl-4,4a,5,6-tetrahydropyrano[3,4-d][1,3]thiazin-8a(8H)-yl]-1,3-thiazol-4-yl}-5-(difluoromethoxy)-3-methylpyridine-2-carboxamide;

N-{2-[(4a'S,8a'S)-2'-amino-4a',5'-dihydro-4'H-spiro[cyclopropane-1,6'-pyrano[3,4-d][1,3]thiazin]-8a'(8'H)-yl]-1,3-thiazol-4-yl}-5-(difluoromethoxy)pyridine-2-carboxamide;

N-{2-[(4a'R,8a'R)-2'-amino-4a',5'-dihydro-4'H-spiro[cyclopropane-1,6'-pyrano[3,4-d][1,3]thiazin]-8a'(8'H)-yl]-1,3-thiazol-4-yl}-5-(difluoromethoxy)pyridine-2-carboxamide;

N-{2-[(4aR,6S,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy)pyridine-2-carboxamide; and N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-fluoropyridine-2-carboxamide;

or a tautomer thereof or a pharmaceutically acceptable salt of said compound or tautomer.

17. The compound of claim 16 which is N-{2-[(4a'R,8a'R)-2'-amino-4a',5'-dihydro-4'H-spiro[cyclobutane-1,6'-pyrano[3,4-d][1,3]thiazin]-8a'(8'H)-yl]-1,3-thiazol-4-yl}-5-(difluoromethoxy)pyridine-2-carboxamide; or a tautomer thereof or a pharmaceutically acceptable salt of said compound or tautomer.

18. The compound of claim 16 which is N-{2-[(4aR,8aR)-2-amino-6,6-dimethyl-4,4a,5,6-tetrahydropyrano[3,4-d][1,3]thiazin-8a(8H)-yl]-1,3-thiazol-4-yl}-5-(difluoromethoxy)pyridine-2-carboxamide; or a tautomer thereof or a pharmaceutically acceptable salt of said compound or tautomer.

19. The compound of claim 16 which is N-{2-[(4aR,6S,8aR)-2-amino-6-ethyl-6-methyl-4,4a,5,6-tetrahydropyrano [3,4-d][1,3]thiazin-8a(8H)-yl]-1,3-thiazol-4-yl}-5-(difluoromethoxy) pyridine-2-carboxamide; or a tautomer thereof or a pharmaceutically acceptable salt of said compound or tautomer.

20. The compound of claim 16 which is N-{2-[(4aR,6R,8aR)-2-amino-6-(methoxymethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide; or a tautomer thereof or a pharmaceutically acceptable salt of said compound or tautomer.

21. The compound of claim 16 which is N-{2-[(4aS,6S,8aS)-2-amino-6-ethyl-6-methyl-4,4a,5,6-tetrahydropyrano [3,4-d][1,3]thiazin-8a(8H)-yl]-1,3-thiazol-4-yl}-5-(difluoromethoxy) pyridine-2-carboxamide; or a tautomer thereof or a pharmaceutically acceptable salt of said compound or tautomer.

22. The compound of claim 16 which is N-{2-[(4aR,6R,8aR)-2-amino-6-(fluoromethyl)-6-methyl-4,4a,5,6-tetrahydropyrano[3,4-d][1,3]thiazin-8a(8H)-yl]-1,3-thiazol-4-yl}-5-(difluoromethoxy) pyridine-2-carboxamide; or a tautomer thereof or a pharmaceutically acceptable salt of said compound or tautomer.

23. A pharmaceutical composition comprising a therapeutically effective amount of a compound of claim 1, or a tautomer thereof or a pharmaceutically acceptable salt of said compound or tautomer, and a pharmaceutically acceptable vehicle, diluent or carrier.

24. A method for treating Alzheimer's disease, treating Type 2 diabetes, of inhibiting production of amyloid-β protein or of inhibiting beta-site amyloid precursor protein cleaving enzyme 1 (BACE1) in a patient, the method comprising administering a therapeutically effective amount of a compound according to claim 1, or a tautomer thereof or a pharmaceutically acceptable salt of said compound or tautomer, to a patient in need of treatment of Alzheimer's disease, treatment of Type 2 diabetes, inhibition of production of amyloid-β protein or inhibition of beta-site amyloid precursor protein cleaving enzyme 1 (BACE1).

25. The method of claim 24 wherein Alzheimer's disease is treated.

26. The method of claim 24 wherein the diabetes is treated and the diabetes is Type 2 diabetes.

27. The method of claim 24 wherein the production of amyloid-β protein is inhibited.

28. The method of claim 24 wherein beta-site amyloid precursor protein cleaving enzyme 1 (BACE1) is inhibited.

* * * * *